(12) United States Patent
Holman et al.

(10) Patent No.: US 9,947,167 B2
(45) Date of Patent: *Apr. 17, 2018

(54) TREATMENT SYSTEM AND METHOD FOR INGESTIBLE PRODUCT DISPENSING SYSTEM AND METHOD

(75) Inventors: Paul Holman, Seattle, WA (US); Royce A. Levien, Lexington, MA (US); Mark A. Malamud, Seattle, WA (US); Neal Stephenson, Seattle, WA (US); Christopher Charles Young, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/200,906

(22) Filed: Oct. 3, 2011

(65) Prior Publication Data

US 2013/0054019 A1  Feb. 28, 2013

Related U.S. Application Data

(63) Continuation-in-part of application No. 13/200,106, filed on Sep. 16, 2011, now Pat. No. 8,989,895, and
(Continued)

(51) Int. Cl.
    G07F 17/00    (2006.01)
    G06Q 50/00    (2012.01)
    G06Q 50/28    (2012.01)

(52) U.S. Cl.
    CPC ......... G07F 17/0064 (2013.01); G06Q 50/00 (2013.01); G06Q 50/28 (2013.01)

(58) Field of Classification Search
    CPC .. G06F 19/3462; G06F 17/0092; G06Q 50/22
(Continued)

(56) References Cited

U.S. PATENT DOCUMENTS 1,570,405 A    1/1926  Salerno
3,040,935 A    6/1962  Lopata
(Continued)

FOREIGN PATENT DOCUMENTS

EP    1469431 B1 *  9/2009  ............... A23N 4/14
NL    2003661 C       4/2011
(Continued)

OTHER PUBLICATIONS

Poulter, Sean, "Medicine vending machines that dispense prescriptions 24 hours a day go on trial," Daily Mail Online, Jun. 22, 2010 (Year: 2010).*
(Continued)

*Primary Examiner* — Jonathan Ng
*Assistant Examiner* — John P Go

(57) ABSTRACT

A computationally implemented system and method that is designed to, but is not limited to: electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being. In addition to the foregoing, other method aspects are described in the claims, drawings, and text forming a part of the present disclosure.

57 Claims, 71 Drawing Sheets

Related U.S. Application Data a continuation-in-part of application No. 13/200,113, filed on Sep. 16, 2011, now Pat. No. 8,892,249, and a continuation-in-part of application No. 13/200,829, filed on Sep. 30, 2011, now abandoned, and a continuation-in-part of application No. 13/200,830, filed on Sep. 30, 2011, now abandoned, and a continuation-in-part of application No. 13/199,361, filed on Aug. 26, 2011, and a continuation-in-part of application No. 13/199,481, filed on Aug. 30, 2011, now Pat. No. 9,600,850, and a continuation-in-part of application No. 13/199,544, filed on Aug. 31, 2011, and a continuation-in-part of application No. 13/199,545, filed on Aug. 31, 2011, now Pat. No. 9,240,028, and a continuation of application No. 13/200,907, filed on Oct. 3, 2011.

(58) Field of Classification Search
USPC .......................................................... 705/2, 3
See application file for complete search history.

(56) References Cited

U.S. PATENT DOCUMENTS

| | | |
|---|---|---|
| 3,702,583 A | 11/1972 | Rullman |
| 3,859,904 A | 1/1975 | Carriazo |
| 4,076,846 A | 2/1978 | Nakatsuka et al. |
| 4,135,077 A | 1/1979 | Wills |
| 4,293,296 A | 10/1981 | Caiello et al. |
| 4,452,132 A | 6/1984 | Miller et al. |
| 4,634,597 A | 1/1987 | Spiel et al. |
| 4,666,204 A | 5/1987 | Reinholtz |
| 4,681,000 A | 7/1987 | Wolters |
| 4,723,614 A | 2/1988 | Lahti |
| 4,797,818 A | 1/1989 | Cotter |
| 4,974,747 A | 12/1990 | Ahlstrom |
| 5,121,677 A | 6/1992 | Le Claire et al. |
| 5,132,914 A | 7/1992 | Cahlander et al. |
| 5,176,922 A | 1/1993 | Balsano et al. |
| 5,197,376 A | 3/1993 | Bird et al. |
| 5,228,382 A | 7/1993 | Hayashi et al. |
| 5,261,150 A | 11/1993 | Grube et al. |
| 5,408,443 A | 4/1995 | Weinberger |
| 5,417,989 A | 5/1995 | Atwood et al. |
| 5,511,594 A | 4/1996 | Brennan et al. |
| 5,522,309 A | 6/1996 | Mizobuchi et al. |
| 5,522,310 A | 6/1996 | Black, Sr. et al. |
| 5,540,943 A | 7/1996 | Naramura |
| 5,583,129 A | 12/1996 | Spona et al. |
| 5,598,947 A | 2/1997 | Smith |
| 5,615,778 A | 4/1997 | Kaiser et al. |
| 5,697,043 A | 12/1997 | Baskaran et al. |
| 5,731,020 A | 3/1998 | Russo |
| 5,736,940 A | 4/1998 | Burgener |
| 5,762,971 A | 6/1998 | Schirmer |
| 5,820,906 A | 10/1998 | Akesson et al. |
| 6,032,574 A | 3/2000 | Brayton et al. |
| 6,048,191 A | 4/2000 | Beltrami |
| 6,105,818 A | 8/2000 | Speranza |
| 6,112,182 A | 8/2000 | Akers et al. |
| 6,137,686 A | 10/2000 | Saye |
| 6,194,017 B1 | 2/2001 | Woodward et al. |
| 6,200,125 B1 | 3/2001 | Akutagawa |
| 6,202,923 B1 | 3/2001 | Boyer et al. |
| 6,236,974 B1 | 5/2001 | Kolawa et al. |
| 6,245,556 B1 | 6/2001 | Sako et al. |
| 6,251,456 B1 | 6/2001 | Maul et al. |
| 6,268,004 B1 | 7/2001 | Hayashi |
| 6,280,784 B1 | 8/2001 | Yang et al. |
| 6,280,785 B1 | 8/2001 | Yang et al. |
| 6,280,786 B1 | 8/2001 | Williams et al. |
| 6,317,686 B1 | 11/2001 | Ran |
| 6,376,000 B1 | 4/2002 | Waters |
| 6,415,555 B1 | 7/2002 | Montague |
| 6,490,870 B1 | 12/2002 | Efremkine |
| 6,618,062 B1 | 9/2003 | Brown et al. |
| 6,622,064 B2 | 9/2003 | Bartholomew et al. |
| 6,637,432 B2 * | 10/2003 | Wakefield ......... A61M 15/0025 128/200.14 |
| 6,644,359 B1 | 11/2003 | Wertheim |
| 6,646,659 B1 | 11/2003 | Brown et al. |
| 6,658,990 B1 | 12/2003 | Henning et al. |
| 6,660,317 B1 | 12/2003 | Akutagawa |
| 6,660,982 B2 | 12/2003 | Thorneywork |
| 6,711,460 B1 | 3/2004 | Reese |
| 6,802,433 B2 | 10/2004 | Leykin et al. |
| 6,843,166 B1 | 1/2005 | Li |
| 6,859,215 B1 | 2/2005 | Brown et al. |
| 6,865,261 B1 | 3/2005 | Rao et al. |
| 6,998,087 B1 | 2/2006 | Hanson et al. |
| 7,006,893 B2 * | 2/2006 | Hart ...................... G06F 19/322 700/231 |
| 7,027,996 B2 | 4/2006 | Levinson |
| 7,054,909 B1 * | 5/2006 | Ohkubo et al. ................ 709/208 |
| 7,080,597 B2 | 7/2006 | Ando |
| 7,098,794 B2 | 8/2006 | Lindsay et al. |
| 7,110,964 B2 | 9/2006 | Tengler et al. |
| 7,183,518 B2 | 2/2007 | Near et al. |
| 7,187,960 B2 | 3/2007 | Abreu |
| 7,188,082 B2 | 3/2007 | Keane et al. |
| 7,200,644 B1 | 4/2007 | Flanagan |
| 7,231,917 B2 | 6/2007 | Frederiksen |
| 7,243,789 B2 * | 7/2007 | Discko, Jr. ................ A61C 5/06 206/15.3 |
| 7,281,468 B2 | 10/2007 | Frem |
| 7,286,258 B2 | 10/2007 | Schnoebelen et al. |
| 7,295,889 B2 | 11/2007 | Lähteenmäki |
| 7,299,982 B2 | 11/2007 | Kreiner et al. |
| 7,319,780 B2 | 1/2008 | Fedorovskaya et al. |
| 7,343,174 B2 | 3/2008 | Suryanarayana et al. |
| 7,364,068 B1 | 4/2008 | Strubbe et al. |
| 7,392,193 B2 | 6/2008 | Mault |
| 7,395,134 B2 | 7/2008 | Bartholomew et al. |
| 7,415,375 B2 | 8/2008 | Shakman et al. |
| 7,451,015 B2 | 11/2008 | Mazur et al. |
| 7,457,685 B2 | 11/2008 | D'Silva |
| 7,555,360 B1 | 6/2009 | Green et al. |
| 7,571,586 B1 | 8/2009 | Morales |
| 7,625,198 B2 | 12/2009 | Lipson et al. |
| 7,630,790 B2 | 12/2009 | Handfield et al. |
| 7,680,690 B1 | 3/2010 | Catalano |
| 7,698,566 B1 | 4/2010 | Stone |
| 7,747,345 B2 * | 6/2010 | Ohmura ............... G06F 19/3462 700/231 |
| 7,762,181 B2 | 7/2010 | Boland et al. |
| 7,783,379 B2 * | 8/2010 | Beane et al. ................... 700/237 |
| 7,818,089 B2 | 10/2010 | Hanna et al. |
| 7,842,323 B1 | 11/2010 | White |
| 7,884,953 B1 | 2/2011 | Willcocks et al. |
| 7,961,916 B2 | 6/2011 | Wang et al. |
| 7,974,873 B2 | 7/2011 | Simmons et al. |
| 8,007,847 B2 | 8/2011 | Biderman et al. |
| 8,027,748 B2 | 9/2011 | Handfield et al. |
| 8,085,135 B2 | 12/2011 | Cohen Alloro et al. |
| 8,173,186 B2 | 5/2012 | Kuwabara et al. |
| 8,190,447 B2 | 5/2012 | Hungerford et al. |
| 8,204,757 B2 | 6/2012 | Carlson et al. |
| 8,249,946 B2 | 8/2012 | Froseth et al. |
| 8,306,655 B2 | 11/2012 | Newman |
| 8,370,176 B2 | 2/2013 | Vespasiani |
| 8,412,369 B2 | 4/2013 | Ames, II et al. |
| 8,504,440 B1 | 8/2013 | Kolawa et al. |
| 8,521,326 B1 | 8/2013 | Holtje |
| 8,583,511 B2 | 11/2013 | Hendrickson |
| 8,594,838 B2 | 11/2013 | Selker et al. |
| 8,594,935 B2 | 11/2013 | Cioffi et al. |
| 8,688,277 B2 | 4/2014 | Studor et al. |
| 8,744,618 B2 | 6/2014 | Peters et al. |
| 8,793,588 B2 | 7/2014 | DiPietro |
| 2001/0005830 A1 | 6/2001 | Kuroyanagi |
| 2001/0028308 A1 | 10/2001 | De La Huerga |
| 2001/0036495 A1 | 11/2001 | Ganan-Calvo |
| 2002/0029149 A1 | 3/2002 | Nishina |

(56) References Cited

U.S. PATENT DOCUMENTS

| | | |
|---|---|---|
| 2002/0049652 A1 | 4/2002 | Moore et al. |
| 2002/0055878 A1 | 5/2002 | Burton et al. |
| 2002/0069097 A1 | 6/2002 | Conrath |
| 2002/0081356 A1 | 6/2002 | Bebiak et al. |
| 2002/0116634 A1 | 8/2002 | Okubo |
| 2002/0138201 A1 | 9/2002 | Greensides |
| 2002/0156682 A1 | 10/2002 | DiPietro |
| 2002/0192572 A1 | 12/2002 | Lau |
| 2003/0017248 A1 | 1/2003 | Gray |
| 2003/0024946 A1* | 2/2003 | Severino .............. G07F 13/08 222/2 |
| 2003/0050854 A1 | 3/2003 | Showghi et al. |
| 2003/0051606 A1 | 3/2003 | Cusenza et al. |
| 2003/0069745 A1 | 4/2003 | Zenko |
| 2003/0071806 A1 | 4/2003 | Annand |
| 2003/0079612 A1* | 5/2003 | Con ....................... 99/275 |
| 2003/0099157 A1 | 5/2003 | Quine |
| 2003/0105555 A1 | 6/2003 | Lunak et al. |
| 2003/0121929 A1 | 7/2003 | Liff et al. |
| 2003/0125836 A1* | 7/2003 | Chirnomas ............ G07F 9/02 700/236 |
| 2003/0125963 A1 | 7/2003 | Haken |
| 2003/0125986 A1 | 7/2003 | Collosi |
| 2003/0185948 A1 | 10/2003 | Garwood |
| 2003/0197005 A1 | 10/2003 | Huegerich et al. |
| 2003/0208113 A1 | 11/2003 | Mault et al. |
| 2003/0208409 A1 | 11/2003 | Mault |
| 2003/0219527 A1 | 11/2003 | Sasaki et al. |
| 2003/0236682 A1 | 12/2003 | Heyer |
| 2003/0236706 A1 | 12/2003 | Weiss |
| 2004/0025701 A1 | 2/2004 | Colston et al. |
| 2004/0044469 A1 | 3/2004 | Bender et al. |
| 2004/0045579 A1* | 3/2004 | Miki et al. ............... 134/1.3 |
| 2004/0049407 A1 | 3/2004 | Rosenberg |
| 2004/0054554 A1 | 3/2004 | Barts et al. |
| 2004/0073448 A1 | 4/2004 | Barts et al. |
| 2004/0073449 A1 | 4/2004 | Yang |
| 2004/0091843 A1 | 5/2004 | Albro et al. |
| 2004/0093265 A1 | 5/2004 | Ramchandani et al. |
| 2004/0093268 A1 | 5/2004 | Ramchandani et al. |
| 2004/0103033 A1 | 5/2004 | Reade et al. |
| 2004/0117205 A1 | 6/2004 | Reardan et al. |
| 2004/0131659 A1 | 7/2004 | Gibson et al. |
| 2004/0143503 A1 | 7/2004 | Suthar |
| 2004/0151820 A1 | 8/2004 | Harris |
| 2004/0158350 A1 | 8/2004 | Ostergaard et al. |
| 2004/0158499 A1 | 8/2004 | Dev et al. |
| 2004/0172169 A1* | 9/2004 | Wright, IV ............ A61J 3/074 700/265 |
| 2004/0193495 A1 | 9/2004 | Kim |
| 2004/0214597 A1 | 10/2004 | Suryanarayana et al. |
| 2004/0226775 A1 | 11/2004 | Takatama et al. |
| 2004/0238555 A1 | 12/2004 | Parks |
| 2004/0246819 A1 | 12/2004 | Quine |
| 2004/0250842 A1* | 12/2004 | Adams ................ B08B 9/0321 134/169 C |
| 2004/0263319 A1 | 12/2004 | Huomo |
| 2005/0023710 A1 | 2/2005 | Brodkin et al. |
| 2005/0038719 A1 | 2/2005 | Young et al. |
| 2005/0048461 A1* | 3/2005 | Lahteenmaki .......... A61J 3/002 435/3 |
| 2005/0059849 A1 | 3/2005 | Liu |
| 2005/0060063 A1* | 3/2005 | Reichelt ................. G07F 5/18 700/244 |
| 2005/0065640 A1 | 3/2005 | Mallett et al. |
| 2005/0079257 A1 | 4/2005 | Neto |
| 2005/0080520 A1 | 4/2005 | Kline et al. |
| 2005/0080650 A1 | 4/2005 | Noel |
| 2005/0090425 A1 | 4/2005 | Reardan et al. |
| 2005/0098169 A1 | 5/2005 | Frederiksen |
| 2005/0113968 A1* | 5/2005 | Williams .............. G07F 11/44 700/236 |
| 2005/0114149 A1 | 5/2005 | Rodriguez et al. |
| 2005/0131738 A1 | 6/2005 | Morris |
| 2005/0157148 A1 | 7/2005 | Baker et al. |
| 2005/0160052 A1 | 7/2005 | Schneider et al. |
| 2005/0171663 A1 | 8/2005 | Mittelsteadt et al. |
| 2005/0193901 A1 | 9/2005 | Buehler |
| 2005/0209915 A1 | 9/2005 | Saluccio |
| 2005/0226975 A1 | 10/2005 | Droulllard |
| 2005/0230472 A1 | 10/2005 | Chang |
| 2005/0233011 A1 | 10/2005 | Beavers |
| 2005/0241497 A1 | 11/2005 | Cantu |
| 2005/0251289 A1* | 11/2005 | Bonney ................ A61M 15/00 700/244 |
| 2005/0267811 A1 | 12/2005 | Almblad |
| 2005/0280544 A1 | 12/2005 | Mishelevich |
| 2006/0015289 A1 | 1/2006 | Shakman et al. |
| 2006/0053184 A1 | 3/2006 | Grana |
| 2006/0064037 A1 | 3/2006 | Shalon et al. |
| 2006/0081653 A1* | 4/2006 | Boland ................... A47J 31/40 222/243 |
| 2006/0108415 A1 | 5/2006 | Thomas et al. |
| 2006/0111976 A1 | 5/2006 | Pompushko |
| 2006/0147581 A1 | 7/2006 | Svendsen et al. |
| 2006/0161453 A1 | 7/2006 | Kost et al. |
| 2006/0178943 A1 | 8/2006 | Rollinson et al. |
| 2006/0182240 A1 | 8/2006 | Schelberg, Jr. et al. |
| 2006/0191885 A1 | 8/2006 | Near et al. |
| 2006/0224419 A1 | 10/2006 | Servizio et al. |
| 2006/0237523 A1 | 10/2006 | Carlson et al. |
| 2006/0259188 A1* | 11/2006 | Berg ....................... 700/231 |
| 2006/0260601 A1 | 11/2006 | Schedeler et al. |
| 2006/0263501 A1 | 11/2006 | Oghafua et al. |
| 2006/0277066 A1 | 12/2006 | Hungerford et al. |
| 2006/0278093 A1 | 12/2006 | Biderman et al. |
| 2006/0286218 A1 | 12/2006 | Salzman |
| 2007/0027432 A1 | 2/2007 | Radford et al. |
| 2007/0037567 A1 | 2/2007 | Ungless et al. |
| 2007/0038727 A1 | 2/2007 | Bailey et al. |
| 2007/0048407 A1 | 3/2007 | Collins et al. |
| 2007/0055550 A1 | 3/2007 | Courtney et al. |
| 2007/0055694 A1 | 3/2007 | Ruge et al. |
| 2007/0057039 A1 | 3/2007 | Carlson et al. |
| 2007/0061170 A1 | 3/2007 | Lorsch |
| 2007/0061209 A1 | 3/2007 | Jackson |
| 2007/0062156 A1* | 3/2007 | Kim ..................... B65B 57/00 53/131.5 |
| 2007/0083494 A1 | 4/2007 | Carlson et al. |
| 2007/0092614 A1 | 4/2007 | Waldock |
| 2007/0150371 A1 | 6/2007 | Gangji |
| 2007/0150375 A1 | 6/2007 | Yang |
| 2007/0151984 A1 | 7/2007 | Baker et al. |
| 2007/0168205 A1 | 7/2007 | Carlson et al. |
| 2007/0170049 A1* | 7/2007 | Mansur ................. B01D 1/0017 202/160 |
| 2007/0170195 A1* | 7/2007 | Segiet ..................... G07F 9/105 221/15 |
| 2007/0183633 A1 | 8/2007 | Hoffmann |
| 2007/0185615 A1 | 8/2007 | Bossi et al. |
| 2007/0185785 A1 | 8/2007 | Carlson et al. |
| 2007/0191689 A1 | 8/2007 | Elitok |
| 2007/0192715 A1* | 8/2007 | Kataria et al. .............. 715/764 |
| 2007/0208454 A1 | 9/2007 | Forrester et al. |
| 2007/0231435 A1 | 10/2007 | Ream et al. |
| 2007/0260487 A1 | 11/2007 | Bartfeld et al. |
| 2007/0267441 A1 | 11/2007 | van Opstal et al. |
| 2007/0271001 A1 | 11/2007 | Ratnakar |
| 2007/0275690 A1 | 11/2007 | Hunter et al. |
| 2007/0292573 A1 | 12/2007 | Smith |
| 2007/0294129 A1 | 12/2007 | Froseth et al. |
| 2008/0059226 A1* | 3/2008 | Melker et al. ................. 705/2 |
| 2008/0077440 A1* | 3/2008 | Doron ..................... A61B 5/076 705/2 |
| 2008/0084450 A1 | 4/2008 | Silverbrook |
| 2008/0114678 A1 | 5/2008 | Bennett et al. |
| 2008/0124433 A1 | 5/2008 | Yelden et al. |
| 2008/0125897 A1 | 5/2008 | DiGianfilippo et al. |
| 2008/0126220 A1 | 5/2008 | Baril et al. |
| 2008/0126985 A1 | 5/2008 | Baril et al. |
| 2008/0141315 A1 | 6/2008 | Ogilvie |
| 2008/0162181 A1 | 7/2008 | Ben-Haim et al. |
| 2008/0172261 A1 | 7/2008 | Albertson et al. |

(56) References Cited

U.S. PATENT DOCUMENTS

| | | | | |
|---|---|---|---|---|
| 2008/0173711 | A1* | 7/2008 | Handfield | A61J 7/0084 235/385 |
| 2008/0195247 | A1* | 8/2008 | Mallett | A61L 11/00 700/225 |
| 2008/0224823 | A1 | 9/2008 | Lawson et al. | |
| 2008/0249859 | A1 | 10/2008 | Angell et al. | |
| 2008/0249865 | A1 | 10/2008 | Angell et al. | |
| 2008/0260918 | A1 | 10/2008 | Lai et al. | |
| 2008/0272138 | A1* | 11/2008 | Ross | G06F 19/3462 221/1 |
| 2008/0281915 | A1 | 11/2008 | Elad et al. | |
| 2008/0288287 | A1 | 11/2008 | Stanners | |
| 2008/0314918 | A1 | 12/2008 | Nuriely | |
| 2009/0012433 | A1 | 1/2009 | Fernstrom et al. | |
| 2009/0029016 | A1 | 1/2009 | Pfister et al. | |
| 2009/0043176 | A1 | 2/2009 | Nakajima et al. | |
| 2009/0087819 | A1 | 4/2009 | Adachi et al. | |
| 2009/0099944 | A1 | 4/2009 | Robinson et al. | |
| 2009/0105875 | A1 | 4/2009 | Wiles | |
| 2009/0106313 | A1 | 4/2009 | Boldyga | |
| 2009/0106316 | A1 | 4/2009 | Kubono et al. | |
| 2009/0106826 | A1 | 4/2009 | Palestrant | |
| 2009/0112683 | A1 | 4/2009 | Hamilton, II et al. | |
| 2009/0112754 | A1 | 4/2009 | Seifert et al. | |
| 2009/0112782 | A1 | 4/2009 | Cross et al. | |
| 2009/0130449 | A1 | 5/2009 | El-Siblani | |
| 2009/0132379 | A1 | 5/2009 | Baril et al. | |
| 2009/0142223 | A1* | 6/2009 | Hyde | A61L 2/24 422/1 |
| 2009/0149717 | A1 | 6/2009 | Brauer et al. | |
| 2009/0161907 | A1 | 6/2009 | Healey et al. | |
| 2009/0164897 | A1 | 6/2009 | Amer-Yahia et al. | |
| 2009/0167553 | A1 | 7/2009 | Hong et al. | |
| 2009/0192898 | A1 | 7/2009 | Baril | |
| 2009/0198547 | A1 | 8/2009 | Sudak | |
| 2009/0199105 | A1 | 8/2009 | Kamada et al. | |
| 2009/0218363 | A1* | 9/2009 | Terzini | 221/4 |
| 2009/0234712 | A1 | 9/2009 | Kolawa et al. | |
| 2009/0236333 | A1 | 9/2009 | Ben-Shmuel et al. | |
| 2009/0236334 | A1 | 9/2009 | Ben-Shmuel et al. | |
| 2009/0236335 | A1 | 9/2009 | Ben-Shmuel et al. | |
| 2009/0242620 | A1 | 10/2009 | Sahuguet | |
| 2009/0254531 | A1 | 10/2009 | Walker et al. | |
| 2009/0259559 | A1 | 10/2009 | Carroll et al. | |
| 2009/0259688 | A1 | 10/2009 | Do et al. | |
| 2009/0261175 | A1 | 10/2009 | Kauppinen et al. | |
| 2009/0267895 | A1 | 10/2009 | Bunch | |
| 2009/0294521 | A1 | 12/2009 | de la Huerga | |
| 2009/0295569 | A1 | 12/2009 | Corwin et al. | |
| 2009/0295575 | A1 | 12/2009 | Kennedy | |
| 2009/0297668 | A1 | 12/2009 | Cantu | |
| 2009/0299645 | A1 | 12/2009 | Colby et al. | |
| 2009/0313125 | A1 | 12/2009 | Roh et al. | |
| 2009/0317519 | A1 | 12/2009 | Lavie et al. | |
| 2009/0326516 | A1 | 12/2009 | Bangera et al. | |
| 2010/0017296 | A1 | 1/2010 | Spignesi, Jr. et al. | |
| 2010/0038416 | A1 | 2/2010 | Canora | |
| 2010/0038594 | A1 | 2/2010 | Bohlig et al. | |
| 2010/0042427 | A1 | 2/2010 | Graham et al. | |
| 2010/0043834 | A1 | 2/2010 | Scheringer | |
| 2010/0045705 | A1 | 2/2010 | Vertegaal et al. | |
| 2010/0047410 | A1 | 2/2010 | Lichtenstein | |
| 2010/0052900 | A1 | 3/2010 | Covannon et al. | |
| 2010/0055257 | A1 | 3/2010 | Hervig | |
| 2010/0062169 | A1* | 3/2010 | Pierre | B05B 13/0221 427/388.1 |
| 2010/0063889 | A1 | 3/2010 | Proctor, Jr. et al. | |
| 2010/0087155 | A1 | 4/2010 | Dubost | |
| 2010/0097180 | A1 | 4/2010 | Cardullo | |
| 2010/0100237 | A1 | 4/2010 | Ratnakar | |
| 2010/0106523 | A1 | 4/2010 | Kalamas | |
| 2010/0106607 | A1 | 4/2010 | Riddiford et al. | |
| 2010/0121156 | A1* | 5/2010 | Yoo | 600/300 |
| 2010/0121669 | A1 | 5/2010 | Madigan | |
| 2010/0121722 | A1 | 5/2010 | Vawter | |
| 2010/0125362 | A1 | 5/2010 | Canora et al. | |
| 2010/0136666 | A1 | 6/2010 | Kobayashi et al. | |
| 2010/0139992 | A1 | 6/2010 | Delia et al. | |
| 2010/0145506 | A1* | 6/2010 | Waugh | G06F 19/3462 700/231 |
| 2010/0160745 | A1 | 6/2010 | Hills et al. | |
| 2010/0161345 | A1 | 6/2010 | Cain et al. | |
| 2010/0161600 | A1 | 6/2010 | Higgins et al. | |
| 2010/0167648 | A1 | 7/2010 | Doutriaux | |
| 2010/0189842 | A1 | 7/2010 | Toren | |
| 2010/0204676 | A1 | 8/2010 | Cardullo | |
| 2010/0206765 | A1 | 8/2010 | Fonte | |
| 2010/0235201 | A1 | 9/2010 | McEvoy | |
| 2010/0250384 | A1 | 9/2010 | Bhargava | |
| 2010/0256993 | A1 | 10/2010 | Vespasiani | |
| 2010/0259719 | A1 | 10/2010 | Sabeta | |
| 2010/0268378 | A1 | 10/2010 | Sharpley | |
| 2010/0268380 | A1* | 10/2010 | Waugh | G07F 11/44 700/239 |
| 2010/0275625 | A1 | 11/2010 | Lowenstein | |
| 2010/0286632 | A1 | 11/2010 | Dos Santos | |
| 2010/0291515 | A1 | 11/2010 | Pinnisi et al. | |
| 2010/0292998 | A1 | 11/2010 | Bodlaender et al. | |
| 2010/0299158 | A1 | 11/2010 | Siegel | |
| 2010/0303972 | A1 | 12/2010 | Srivastava | |
| 2010/0305974 | A1 | 12/2010 | Patch et al. | |
| 2010/0310737 | A1 | 12/2010 | Someya et al. | |
| 2010/0312143 | A1 | 12/2010 | Kim | |
| 2010/0312385 | A1 | 12/2010 | Deuber | |
| 2010/0312601 | A1 | 12/2010 | Lin | |
| 2010/0320189 | A1 | 12/2010 | Buchheit | |
| 2010/0332140 | A1 | 12/2010 | Joyce et al. | |
| 2010/0332250 | A1 | 12/2010 | Simpson et al. | |
| 2011/0000923 | A1 | 1/2011 | Morales | |
| 2011/0004624 | A1 | 1/2011 | Bansai et al. | |
| 2011/0009715 | A1 | 1/2011 | O'Reilly et al. | |
| 2011/0022225 | A1 | 1/2011 | Rothschild | |
| 2011/0022298 | A1 | 1/2011 | Kronberg | |
| 2011/0027432 | A1 | 2/2011 | Loeser | |
| 2011/0031236 | A1 | 2/2011 | Ben-Shmuel et al. | |
| 2011/0035338 | A1 | 2/2011 | Kagan et al. | |
| 2011/0040660 | A1 | 2/2011 | Allison et al. | |
| 2011/0054678 | A1 | 3/2011 | Thompson | |
| 2011/0055044 | A1 | 3/2011 | Wiedl | |
| 2011/0060457 | A1 | 3/2011 | De Vrught et al. | |
| 2011/0076349 | A1 | 3/2011 | Yoshihara et al. | |
| 2011/0087076 | A1 | 4/2011 | Brynelsen et al. | |
| 2011/0124996 | A1 | 5/2011 | Reinke et al. | |
| 2011/0133005 | A1 | 6/2011 | Chesack | |
| 2011/0160902 | A1 | 6/2011 | Postins | |
| 2011/0166881 | A1 | 7/2011 | Brazzo et al. | |
| 2011/0173062 | A1 | 7/2011 | Chen et al. | |
| 2011/0180441 | A1 | 7/2011 | Bach | |
| 2011/0186624 | A1 | 8/2011 | Wagner et al. | |
| 2011/0208617 | A1 | 8/2011 | Weiland | |
| 2011/0218839 | A1 | 9/2011 | Shamaiengar | |
| 2011/0231212 | A1 | 9/2011 | Hurley et al. | |
| 2011/0231266 | A1 | 9/2011 | Baril | |
| 2011/0282712 | A1 | 11/2011 | Amos et al. | |
| 2011/0289572 | A1 | 11/2011 | Skeel et al. | |
| 2011/0300270 | A1 | 12/2011 | Koppens | |
| 2011/0307316 | A1 | 12/2011 | Peters et al. | |
| 2011/0313867 | A9 | 12/2011 | Silver | |
| 2011/0318717 | A1 | 12/2011 | Adamowicz | |
| 2011/0320037 | A1 | 12/2011 | Frugone | |
| 2012/0004770 | A1 | 1/2012 | Ooyen et al. | |
| 2012/0016745 | A1 | 1/2012 | Hendrickson | |
| 2012/0016754 | A1 | 1/2012 | Jackson | |
| 2012/0041770 | A1 | 2/2012 | Philippe | |
| 2012/0041778 | A1 | 2/2012 | Kraft | |
| 2012/0088023 | A1 | 4/2012 | Begun | |
| 2012/0088212 | A1 | 4/2012 | Knaan | |
| 2012/0089249 | A1 | 4/2012 | Rosenblum | |
| 2012/0101914 | A1 | 4/2012 | Kumar et al. | |
| 2012/0131619 | A1 | 5/2012 | Ogilvie | |
| 2012/0136731 | A1 | 5/2012 | Kidron et al. | |
| 2012/0137325 | A1 | 5/2012 | Ogilvie | |
| 2012/0152125 | A1 | 6/2012 | Yoakim et al. | |

(56) References Cited

U.S. PATENT DOCUMENTS

| | | | |
|---|---|---|---|
| 2012/0156337 A1 | 6/2012 | Studor et al. |
| 2012/0168985 A1 | 7/2012 | Kläber |
| 2012/0173271 A1 | 7/2012 | Omidi |
| 2012/0179665 A1 | 7/2012 | Baarman et al. |
| 2012/0196011 A1 | 8/2012 | Felix |
| 2012/0214140 A1 | 8/2012 | Brynelsen et al. |
| 2012/0233002 A1 | 9/2012 | Abujbara |
| 2012/0246004 A1 | 9/2012 | Book et al. |
| 2012/0251688 A1 | 10/2012 | Zimmerman et al. |
| 2012/0251689 A1 | 10/2012 | Batchelder |
| 2012/0258216 A1 | 10/2012 | Wessels |
| 2012/0262039 A1 | 10/2012 | Daugbjerg et al. |
| 2012/0268259 A1 | 10/2012 | Igel et al. |
| 2012/0284126 A1 | 11/2012 | Giraud et al. |
| 2012/0290412 A1 | 11/2012 | Marovets |
| 2012/0310760 A1 | 12/2012 | Phillips et al. |
| 2012/0323208 A1 | 12/2012 | Bochenko et al. |
| 2012/0323707 A1 | 12/2012 | Urban |
| 2013/0006415 A1 | 1/2013 | Paydar et al. |
| 2013/0011529 A1 | 1/2013 | Belzowski et al. |
| 2013/0018356 A1 | 1/2013 | Prince et al. |
| 2013/0034633 A1 | 2/2013 | von Hasseln |
| 2013/0089642 A1 | 4/2013 | Lipson et al. |
| 2013/0151268 A1 | 6/2013 | Fletcher |
| 2013/0158705 A1 | 6/2013 | Levy et al. |
| 2013/0171304 A1 | 7/2013 | Huntley |
| 2013/0189405 A1 | 7/2013 | Filliol et al. |
| 2013/0196035 A1 | 8/2013 | Passet et al. |
| 2013/0238118 A1 | 9/2013 | Haas |
| 2013/0273217 A1 | 10/2013 | Minvielle |
| 2013/0304529 A1 | 11/2013 | Phalake et al. |
| 2014/0013962 A1 | 1/2014 | Lipton et al. |
| 2014/0050811 A1 | 2/2014 | Lipton et al. |
| 2014/0304055 A1 | 10/2014 | Faith |

FOREIGN PATENT DOCUMENTS

| | | |
|---|---|---|
| WO | WO 03/056493 A1 | 7/2003 |
| WO | WO 2006/095212 A1 | 9/2006 |

OTHER PUBLICATIONS

"Scientests create 'inhalable' food?"; bearing a date of Aug. 29, 2012; snapshot taken Apr. 12, 2009; available at http://web.archive.org/web/20090412131937/http://chowhound.chow.com/topics/611174.

"Transdermal Nutrient Delivery System"; U.S. Army Soldier and Biological Chemical Command; snapshot taken Jul. 21, 2004; available at http://web.archive.org/web/20040721134210 http://archives.tproc.org/www.sbccom.army.mil/products/food/tdnds.pdf.

U.S. Appl. No. 13/435,591, Holman et al.
U.S. Appl. No. 13/435,550, Holman et al.
U.S. Appl. No. 13/432,525, Holman et al.
U.S. Appl. No. 13/432,507, Holman et al.
U.S. Appl. No. 13/385,690, Holman et al.
U.S. Appl. No. 13/385,687, Holman et al.
U.S. Appl. No. 13/385,129, Holman et al.
U.S. Appl. No. 13/385,128, Holman et al.
U.S. Appl. No. 13/373,847, Holman et al.
U.S. Appl. No. 13/373,846, Holman et al.
U.S. Appl. No. 13/373,675, Holman et al.
U.S. Appl. No. 13/373,674, Holman et al.
U.S. Appl. No. 13/317,979, Holman et al.
U.S. Appl. No. 13/317,978, Holman et al.
U.S. Appl. No. 13/317,546, Holman et al.
U.S. Appl. No. 13/317,545, Holman et al.
U.S. Appl. No. 13/200,907, Holman et al.
U.S. Appl. No. 13/200,830, Holman et al.
U.S. Appl. No. 13/200,829, Holman et al.
U.S. Appl. No. 13/200,113, Holman et al.
U.S. Appl. No. 13/200,106, Holman et al.
U.S. Appl. No. 13/199,545, Holman et al.
U.S. Appl. No. 13/199,544, Holman et al.
U.S. Appl. No. 13/199,481, Holman et al.
U.S. Appl. No. 13/199,361, Holman et al.

"3D food printing"; PharmacyEscrow.com; printed on Apr. 4, 2012; 2 pages.

Blain, Loz; "Cornucopia: Digital Gastronomy—could 3D printing be the next revolution in cooking?"; Gizmag; Jan. 14, 2010; 4 pages.

Broomfield, Mark; "The Future of Food Printing"; Fab@Home; Aug. 20, 2009; 1 page.

Coelho, Marcelo; "Cornucopia"; printed on Apr. 4, 2012; 1 page; located at fluid.media.mut.edu.

Cohen et al.; "Hydrocolloid Printing: A Novel Platform for Customized Food Production"; Twentieth Annual International Solid Freeform Fabrication Symposium, Austin, Texas; bearing a date of 2009; cover page and pp. 807-818.

Fawkes, Piers; "3D Food Printing", PSFK; Jan. 17, 2008; 8 pages.

Flatley, Joseph L.; "Ikea's kitchen of the future: 3D food printing, mood lighting, virtual Gordon Ramsay"; Engadget; printed on Apr. 4, 2012; 4 pages; AOL Inc.

McKendrick, Joe; "3D food 'printing': coming to a kitchen near you"; Smartplanet; Dec. 27, 2010; 6 pages; located at www.smartplanet.com/business/blog/business-brains.

Periard et al.; "Printing Food"; Cornell University; printed on Apr. 6, 2012; 11 pages; located at www.creativemachines.cornell.edu/papers/SFF07_Periard2.pdf.

"Printed Meats!"; Fabbaloo; Aug. 23, 2010; 5 pages; Fabbaloo.

"Prototypes and Concept Designs for a Digital Gastronomy"; Cornucopia; printed on Apr. 4, 2012; 5 pages.

Sandhana, Lakshmi; "The printed future of Christmas dinner"; BBC News Technology; Dec. 24, 2010; 4 pages; MMXI.

Seth, Radhika; "Printing My Food by the Molecule"; Yanko Design; Mar. 2, 2010; 7 pages.

Seth, Radhika; "Surreal Food Is Real and Printed"; Yanko Design; Aug. 26, 2009; 6 pages.

"The CandyFab 6000"; Evil Mad Scientist Laboratories; bearing a date of 2011; 7 pages; Evil Mad Scientist Laboratories.

"Welcome to The CandyFabProject"; CandyFab.org; Jan. 22, 2011; 3 pages; The CandyFab Project.

American Society of Hospital Pharmacists; "ASHP Technical Assistance Bulleting on Compounding Nonsterile Products in Pharmacies"; Am. J. Hosp. Pharm.; bearing a date of 1994, approved Apr. 27, 1994; pp. 73-79; vol. 51, No. 1441-8; American Society of Hospital Pharmacists, Inc.

"Airline Tickets and Airline Reservations from American Airlines"; AA.com; 1 page; retrieved from the internet wayback machine on Oct. 27, 2011; located at http://web.archieve.org/web.20101027131457/http://www.aa.com.

Williams, N.T.; "Medication administration through enteral feeding tubes"; Am J Health Syst Pharm.; bearing a date of Dec. 15, 2008; 2 pages (abstract only); vol. 65, No. 24; located at http://www.ncbi.nlm.nih.gov/pubmed/19052281.

McDonald's; sample restaurant menu; Feb. 10, 2014; 1 page; located at: http://www.burgerbusiness.com/wp-content/uploads/McD_Calor . . . .

Indiana State Excise Police; "Alcohol Laws"; snapshot taken Oct. 22, 2010; pp. 1-2; located at http://web.archive.org/web/20101122202431/http://www.in.gov/atc/isep/2384.htm.

Valuevapor.com; "Starter Kits"; printed on Sep. 22, 2014; pp. 1-2; located at http://web.archive.org/web/20100610083606/http://www.valuevapor.com/VV/store/index.php?main_page=index&cPath=10.

"Easy Delft Blue Eggs"; The Sweet Adventures of Sugarbelle Blog; Mar. 25, 2012; pp. 1-7; located at: www.sweetsugarbelle.com/2012/03/simple-delft-blue-easter-egg-cookies (best copy available).

Fiore et al; "Effects of Imagery Copy and Product Samples on Responses Toward the Product"; Journal of Interactive Marketing; bearing a date of Spring 2001; pp. 36-46; vol. 15, No. 2.

McDonagh-Philp, Deana; "Using Focus Groups to Support New Product Development"; Institution of Engineering Designers Journal; Sep. 2000; pp. 1-6.

Shimmura et al.; "Analysis of Eating Behavior in Restaurants Based on Leftover Food"; 2010; pp. 956-960; IEEE.

(56) References Cited

OTHER PUBLICATIONS

"Toddlers at the Table: Avoiding Power Struggles," located at https://archive.org/web/20101012173406/http://kidshealth.org/parent/nutrition_center/staying_fit/toddler_meals.html; KidsHealth; 2010; pp. 1-2; The Nemours Foundation.

Connors et al.; "Using a Visual Plate Waste Study to Monitor Menu Performance"; Journal of the American Dietetic Association; 2004, created on Oct. 18, 2016; pp. 94-96; vol. 104; American Dietetic Association.

\* cited by examiner

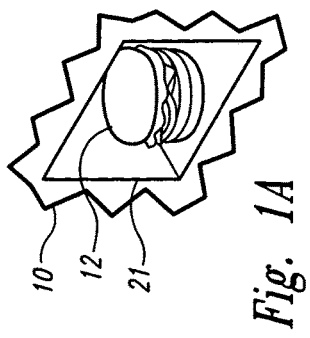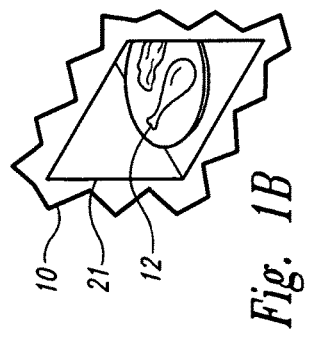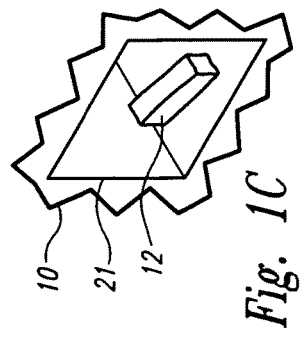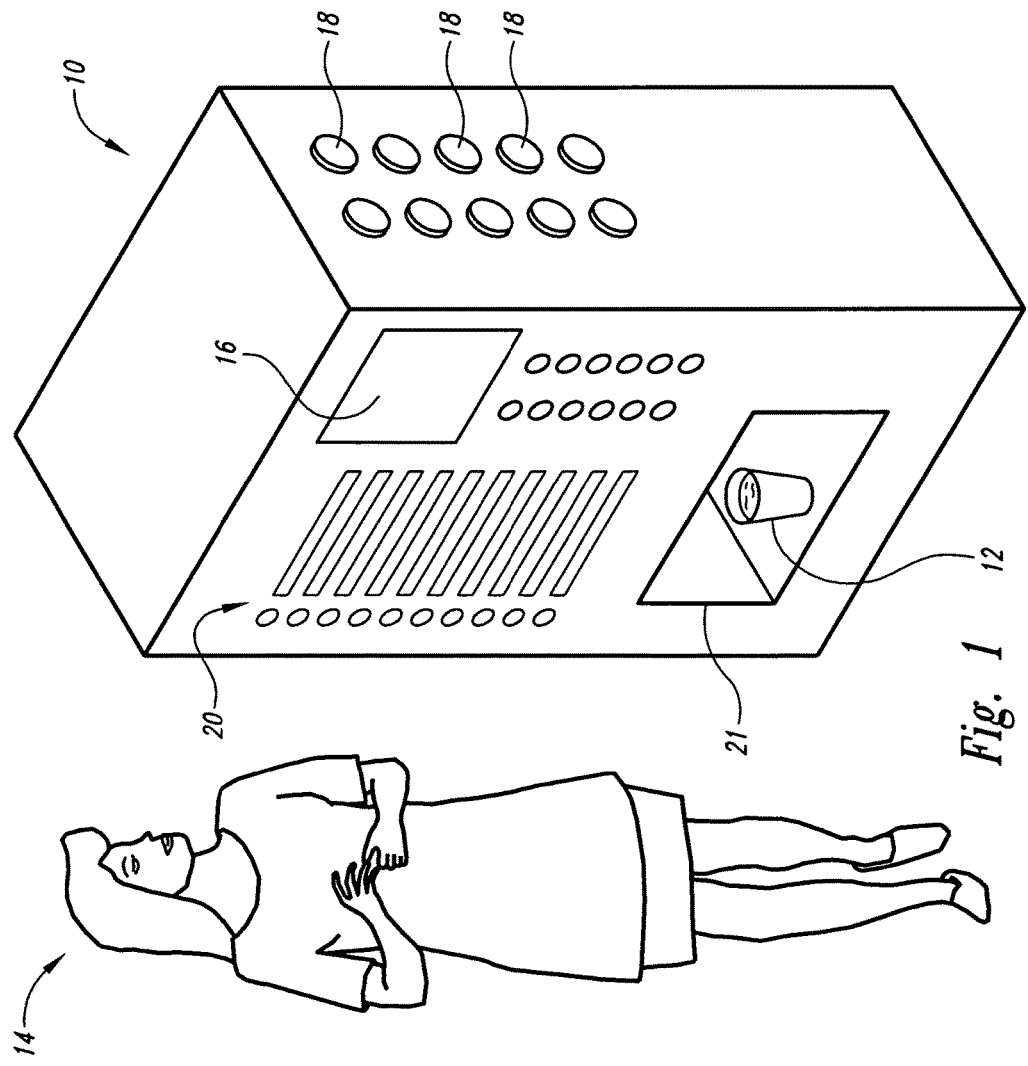

Last Action Performed and Option to Treat Machine    Today's Date: 8-15-2011

| Date / Time | Action | Product | Portion | Ingredients | Controlled Substance | Amount |
|---|---|---|---|---|---|---|
| 8-14-2011 3:25 pm | Material Dispersed | Smoothie | 12 oz. | Raspberry Sugar Lemon Juice | Aspirin Lovastatin | 325 mg. 10 mg. |

Clean Machine Before Proceeding ?

YES    NO

VIEW ACTION LOG

*Fig. 3*

Action Log ⌐16

Today's Date: 8-15-2011    12:24 pm

| Date / Time | Action | Product | Portion | Ingredients | Controlled Substance | Amount |
|---|---|---|---|---|---|---|
| 8-14-2011 3:25 pm | Material Dispensed | Smoothie | 12 oz. | Raspberry Sugar Lemon Juice | Aspirin Lovastatin | 325 mg. 10 mg. |
| 8-12-2011 11:45 am | Machine Treated | X | X | X | X | X |
| 8-12-2011 9:27 am | Material Dispensed | Snack Bar | 3 oz. | Chocolate Peanut Dairy Cream | Hydrocodone | 15 mg. |
| 8-9-2011 1:18 pm | Material Dispensed | Pudding | 6 oz. | Vanilla Lactose Sugar Milk | Diazepam Retinol | 15 mg. 500 mg. |
| 8-9-2011 1:17 pm | Machine Treated | X | X | X | X | X |
| 8-14-2011 3:25 pm | Material Dispensed | Jello | 4 oz. | Strawberry Gelatin Sugar | Fluoxetine | 20 mg. |
| ... | ... | ... | ... | ... | ... | ... |

Selection of Known Allergies — Today's Date: 8-15-2011  12:24 pm

| Peanut | Wheat | Cephalosporins |
| Tree Nuts | Egg | Sulfonamides |
| Milk / Dairy | Vinegar | Anti-inflammitories |
| Corn | Sulphites | Codeine / Opiates |
| Garlic | Tetracycline | Phenytoin |
| Fruit | Dilantin | Sulfa Drugs |
| Shellfish | Tegretol | Other.... |
| Soy | Penicillin | OK |

*Fig. 5*

Selection of Controlled Substance    Today's Date: 8-15-2011  12:24 pm

| Abacavir Sulphate | Atorvastin | Cipro |
| --- | --- | --- |
| Abarelix | A, Vitamin | C, Vitamin |
| Acyclovir | Bupropion | Diazepam |
| Adderall | Calcium | Dopamine |
| Amino Acids | Carbatrol | Doxycycline |
| Amoxicillin | Codeine | D, Vitamin |
| Aspirin | Celebrex | OK |

10 ingestible product dispensing system

- e1140 substance mixtures elec circ arrange
- e1141 treating cellular elec circ arrange
- e1142 treating network elec circ arrange
- e1143 treating circuitry elec circ arrange
- e1144 treating wireless elec circ arrange
- e1145 treating microprocessor elec circ arrange
- e1146 treating memory elec circ arrange
- e1147 treating servers elec circ arrange
- e1148 treating card elec circ arrange
- e1149 treating blowing elec circ arrange
- e1150 treating compressed elec circ arrange
- e1151 treating vacuum elec circ arrange
- e1152 treating ultrasonic elec circ arrange
- e1153 treating electromagnetic elec circ arrange
- e1154 treating abrasives elec circ arrange
- e1155 treating brush elec circ arrange
- e1156 treating chemical elec circ arrange
- e1157 treating tubes elec circ arrange
- e1158 treating nozzles elec circ arrange
- e1159 treating heating elec circ arrange

Fig. 22

10 ingestible product dispensing system

| e1220 treating agitator elec circ arrange | e1221 treating syringe elec circ arrange | e1222 treating head elec circ arrange | e1223 treating replacement elec circ arrange | e1224 treating exchange elec circ arrange |
| e1225 treating other elec circ arrange | e1226 treating includes elec circ arrange | e1227 treating first elec circ arrange | e1228 treating combination elec circ arrange | e1229 treating mixture elec circ arrange |
| e1230 treating nutraceuticals elec circ arrange | e1231 treating organic elec circ arrange | e1232 treating fluids elec circ arrange | e1233 treating powders elec circ arrange | e1234 treating allergens elec circ arrange |
| e1235 treating agents elec circ arrange | e1236 treating regions elec circ arrange | e1237 treating authoritative elec circ arrange | e1238 treating designated elec circ arrange | e1239 treating reactive elec circ arrange |

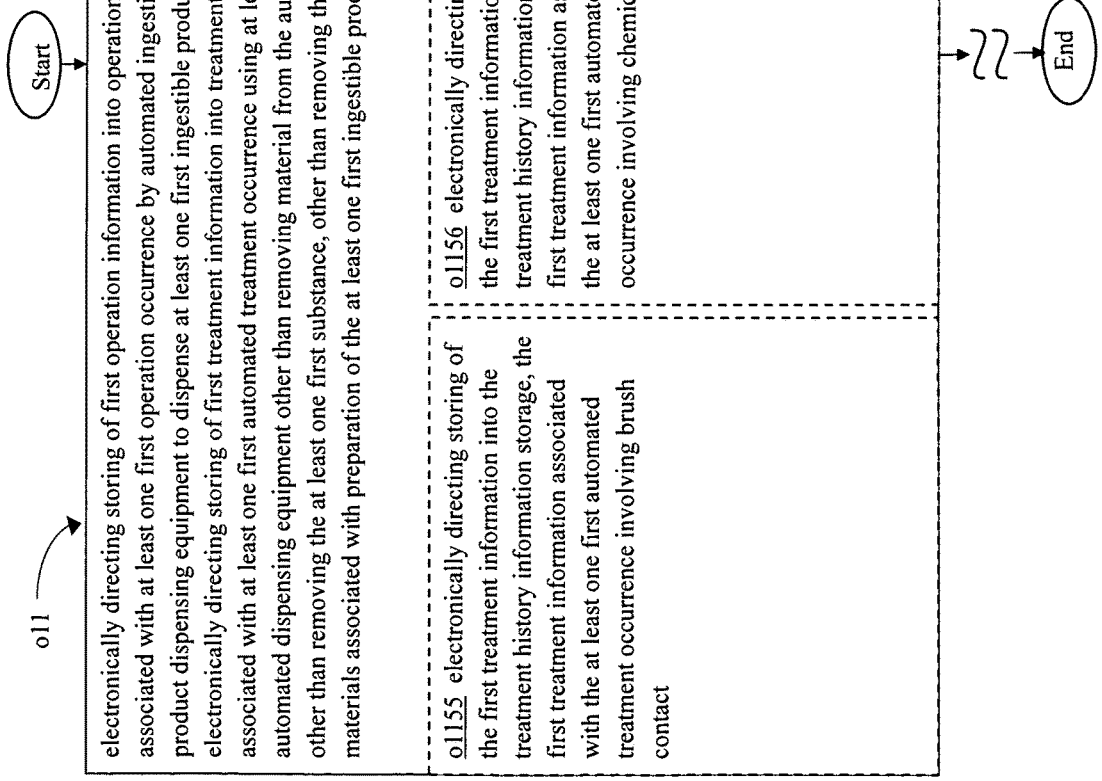

*Fig. 51* o11 electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage , the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product o1158 electronically directing storing of the first treatment information into the treatment history information storage, the first treatment information associated with the at least one first automated treatment occurrence to treat at least a portion of the automated ingestible product dispensing equipment as one or more nozzles o1159 electronically directing storing of the first treatment information into the treatment history information storage, the first treatment information associated with the at least one first automated treatment occurrence to treat at least a portion of the automated ingestible product dispensing equipment as one or more heating chambers o1160 electronically directing storing of the first treatment information into the treatment history information storage, the first treatment information associated with the at least one first automated treatment occurrence to treat at least a portion of the automated ingestible product dispensing equipment as one or more blender compartments

*Fig. 59*

(Start) → o12 electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input o1216 electronically directing the at least one second automated treatment occurrence of the at least one automated device to treat at least a portion of the automated ingestible product dispensing equipment as one or more nozzles o1217 electronically directing the at least one second automated treatment occurrence of the at least one automated device to treat at least a portion of the automated ingestible product dispensing equipment as one or more heating chambers o1218 electronically directing the at least one second automated treatment occurrence of the at least one automated device to treat at least a portion of the automated ingestible product dispensing equipment as one or more blender compartments (End)

Fig. 69

(Start) → o12 electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input o1246 electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more sound sensing components o1247 electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more computer networks o1248 electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more cellular networks (End)

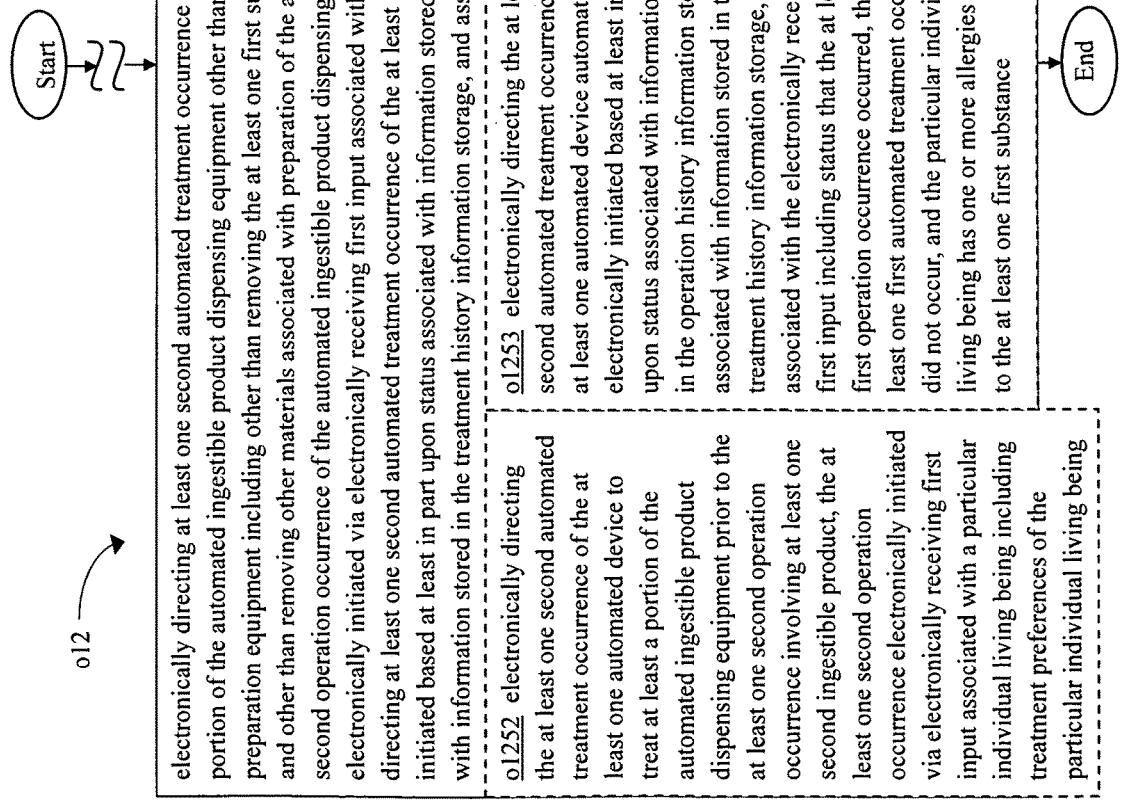

TREATMENT SYSTEM AND METHOD FOR INGESTIBLE PRODUCT DISPENSING SYSTEM AND METHOD

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/200,106, entitled SUBSTANCE CONTROL SYSTEM AND METHOD FOR DISPENSING SYSTEMS, naming Paul Holman, Royce A. Levien, Mark A. Malamud, Neal Stephenson, and Christopher Charles Young as inventors, filed 16 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,113, entitled SUBSTANCE CONTROL SYSTEM AND METHOD FOR DISPENSING SYSTEMS, naming Paul Holman, Royce A. Levien, Mark A. Malamud, Neal Stephenson, and Christopher Charles Young as inventors, filed 16 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,829, entitled CLEANING SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, CHRISTOPHER CHARLES Young as inventors, filed 30 Sep. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/200,830, entitled CLEANING SYSTEM AND METHOD FOR INGESTIBLE PRODUCT PREPARATION SYSTEM AND METHOD, naming PAUL HOLMAN, ROYCE A. LEVIEN, MARK A. MALAMUD, NEAL STEPHENSON, CHRISTOPHER CHARLES YOUNG as inventors, filed 30 Sep. 2011, which is currently co-pending or is an application of which a currently co-pending application is entitled to the benefit of the filing date.

For purposes of the USPTO extra-statutory requirements, the present application constitutes a continuation of U.S. patent application Ser. No. 13/200,907, entitled TREATMENT SYSTEM AND METHOD FOR INGESTIBLE PRODUCT DISPENSING SYSTEM AND METHOD, naming PAUL HOLMAN, ROYCE A. LEVIEN, MARK A. MALAMUD, NEAL STEPHENSON, CHRISTOPHER CHARLES YOUNG as inventors, filed 3 Oct. 2011, which is currently co-pending or is an application of which a currently co-pending application is entitled to the benefit of the filing date.

For purposes of the USPTO extra-statutory requirements, the present application constitutes a continuation-in-part U.S. patent application Ser. No. 13/199,361, entitled CONTROLLED SUBSTANCE AUTHORIZATION SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 26 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,481, entitled CONTROLLED SUBSTANCE AUTHORIZATION SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 30 Aug. 2011, which is currently co-pending or is an application of which a currently co-pending application is entitled to the benefit of the filing date.

For purposes of the USPTO extra-statutory requirements, the present application constitutes a continuation-in-part U.S. patent application Ser. No. 13/199,544, entitled REPORTING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 31 Aug. 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/199,545, entitled REPORTING SYSTEM AND METHOD FOR INGESTIBLE PRODUCT PREPARATION SYSTEM AND METHOD, naming Paul Holman, Royce A. Levien, Mark A. Malamud, Neal Stephenson, and Christopher Charles Young as inventors, filed 31 Aug. 2011, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

A method includes, but is not limited to electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product; and electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input.

In one or more various aspects, related machines, compositions of matter, or manufactures of systems may include, but are not limited to, virtually any combination of hardware, software, and/or firmware configured to effect the herein-referenced method aspects depending upon the design choices of the system designer (limited to patentable subject matter under 35 USC 101).

A system includes, but is not limited to: means for electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product; and means for electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input. In addition to the foregoing, other system aspects are described in the claims, drawings, and text forming a part of the present disclosure.

A system includes, but is not limited to a store and first treating electrical circuitry arrangement for electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product; and a second treating electrical circuitry arrangement for electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input. In addition to the foregoing, other system aspects are described in the claims, drawings, and text forming a part of the present disclosure.

An article of manufacture including a non-transitory signal-bearing storage medium bearing one or more instructions for electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product; and one or more instructions for electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input. In addition to the foregoing, other computer program product aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 is a schematic diagram depicting a first exemplary implementation of a ingestible product dispensing system 10 including a treatment system therefor.

FIG. 1A is a schematic diagram depicting a dispensing portion of a second version of the first exemplary implementation of the ingestible product dispensing system 10 dispensing a second ingestible product therefrom.

FIG. 1B is a schematic diagram depicting a dispensing portion of a third version of the first exemplary implementation of the ingestible product dispensing system 10 dispensing a third ingestible product therefrom.

FIG. 1C is a schematic diagram depicting a dispensing portion of a fourth version of the first exemplary implementation of the ingestible product dispensing system 10 dispensing a fourth ingestible product therefrom.

FIG. 3 is a schematic view of a display screen of an exemplary implementation of the ingestible product dispensing system 10 in FIG. 1 displaying first content.

FIG. 4 is a schematic view of a display screen of an exemplary implementation of the ingestible product dispensing system 10 in FIG. 1 displaying second content.

FIG. 5 is a schematic view of a display screen of the first exemplary implementation of the ingestible product dispensing system 10 in FIG. 1 displaying third content.

FIG. 7 is a schematic view of a display screen of the first exemplary implementation of the ingestible product dispensing system 10 in FIG. 1 displaying fifth content.

FIG. 19 is a block diagram depicting one or more exemplary electrical circuitry arrangements of the ingestible product dispensing system 10 of FIG. 1.

FIG. 22 is a block diagram depicting one or more exemplary electrical circuitry arrangements of the ingestible product dispensing system 10 of FIG. 1.

FIG. 50 is a high-level flowchart including exemplary implementations of operation O11 of FIG. 31.

FIG. 51 is a high-level flowchart including exemplary implementations of operation O11 of FIG. 31.

FIG. 59 is a high-level flowchart including exemplary implementations of operation O12 of FIG. 31.

FIG. 69 is a high-level flowchart including exemplary implementations of operation O12 of FIG. 31.

FIG. 71 is a high-level flowchart including exemplary implementations of operation O12 of FIG. 31.

DETAILED DESCRIPTION

Figure 2:
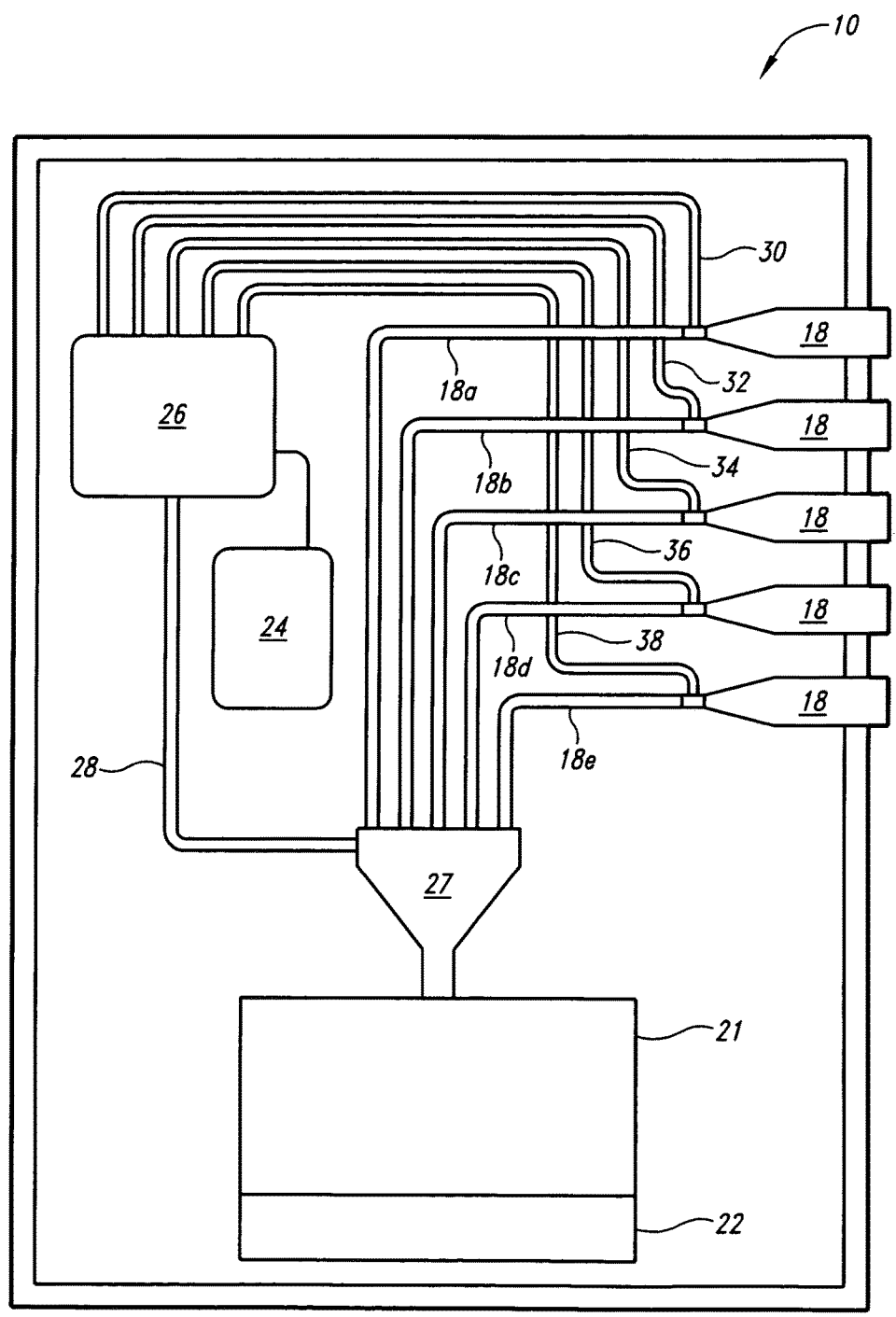
FIG. 2 is a cross-sectional schematic view of the first exemplary implementation of the ingestible product dispensing system 10 in FIG. 1.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, automated and semi-automated machines to make, manufacture, fabricate, or otherwise prepare and/or dispense ingestible products to be ingested by living beings such as humans, animals, plants, etc are known to a degree with interest existing for future development as well. Automated and semi-automated preparation of the ingestible products can incorporate all known forms of preparation of food and other ingestible products including but not limited to all known forms of energy addition to one or more ingredients of the ingestible products (such as through various forms of thermal heating or adding microwave, infrared, or ultrasonic energy), extracting energy from one or more ingredients of the ingestible products (such as through thermodynamic-cycle based cooling or peltier cooling), deposition methods (including deposition by layering or at the pixel level), and combinational methods (such as blending, mixing, ingredient injection, kneading, stirring, ultrasonic agitation, other agitational methods, etc.), etc.

Although ingestible products made, fabricated, or otherwise prepared and/or dispensed by semi-automated and automated machines are presently limited in scope to a degree, it is envisioned that with future development, this will change. Ingestible products can take many forms including, but not limited to, solids, semi-solids, liquids, gases, dispersions (such as true solutions, colloid dispersions, emulsions, foams, and gels) and vast combinations thereof. Ingestion by the living beings can occur through many pathways including, but not limited to, oral ingestion, transdermal ingestion, peg-tube ingestion, nasal ingestion, anal ingestion, injectable ingestion, tear-duct ingestion, and respiratory ingestion.

As depicted in FIG. 1, an exemplary implementation of an ingestible product dispensing system 10 is shown to dispense (including in some implementations preparation) of ingestible products such as a liquid drink 12 to be consumed by a particular individual living being, such as a human being 14 shown. Other sorts of ingestible products can include but are not limited to sandwiches (as shown, for example, in FIG. 1A), full meals (as shown, for example, in FIG. 1B), food bars (as shown, for example, in FIG. 1C), meal replacements, snacks, plant and/or animal based products, nutraceuticals, pharmaceuticals, smoothies, etc. The ingestible product dispensing system 10 is further depicted as showing display screen 16 and selection indicators 20 configured to provide information to users, such as the human being 14, what ingestible products are available to be dispensed (in some implementations prepared such as from ingredient containers 18) and to provide other sorts of information discussed herein. The display screen 16 can display textual and graphic information such as including but not limited to menu screens allowing users to select various dispensing (including in some implementations preparation) options and information requests. Other implementations can include other devices and methods for information input and output including those further discussed below. The selection indicators 20 or other display devices can display selection information including origin, type, certification, classification, etc. of ingestible ingredients and/or products available including information related to various implementations of substance control methods, systems, and articles of manufacture disclosed herein and discussed further below. Device treatment methods and systems can be included with operation of the ingestible product dispensing system 10 to allow for choice, at least to a degree, by users regarding the extent and manner that devices and components of the ingestible product dispensing system 10 are to be treated prior to preparation of one or more ingestible products. The display screen 16 can also inform users of previously executed treatment procedures and/or prior digestible product preparations. Treatment procedures can include, but are not limited to, various sanitizing, de-odorizing, hygienic, energizing, sterilizing, de-gassing, quarantining, etc. Treatment procedures can also include, but are not limited to, various cleaning procedures directed to other than removing ingestible product and ingredients left behind from previous preparation operations so that the treatment procedures discussed herein address concerns other than typical cleaning procedures involved with cleaning after an ingestible product has been prepared.

For instance, FIG. 2 is an exemplary cross-sectional schematic view of internal construction for the first version of the first exemplary implementation of the ingestible product dispensing system 10 in FIG. 1. As shown in FIG. 2, system fixtures (e.g. tubing 18a-18e, 28, and 30-38, manifolds 26 and dispensing area surfaces 21 and 22) can provide surfaces that may harbor certain undesirable materials, viruses, bacteria, other micro-organisms, chemicals, odors, etc before, during, or subsequent to dispensing of digestible products to be removed by various treatments.

For instance, FIG. 3 depicts the display screen 16 showing content 40 as to a last ingestible product preparation performed immediately before in sequence to a current instance of ingestible product preparation selection. The content 40 includes date/time of the previous preparation, the action that was performed, name, size, ingredients, name and amount of controlled substances involved with the previously prepared product. The content 40 also includes a user selectable option to have treatment performed before ingestible product dispensing (including in some implementations preparation) by selecting "yes" or to opt out by selecting "no." There is also a user selectable option to have an action log of a chronological series of ingestible product dispensing (including in some implementations preparation) instances displayed such as shown with content 42 in FIG. 4.

For instance, FIG. 5 depicts the display screen 16 showing content 44 having user selectable options to indicate what sorts of ingredients or general categories my cause problems, such as allergies, for the user. This information inputted by the user can then be used by the ingestible product dispensing system 10 to assist in determining if one or more portions of the ingestible product dispensing system 10 should be treated, such as by automated treatment procedures performed thereby, prior to further one or more instances of ingestible product preparation.

Figure 6:
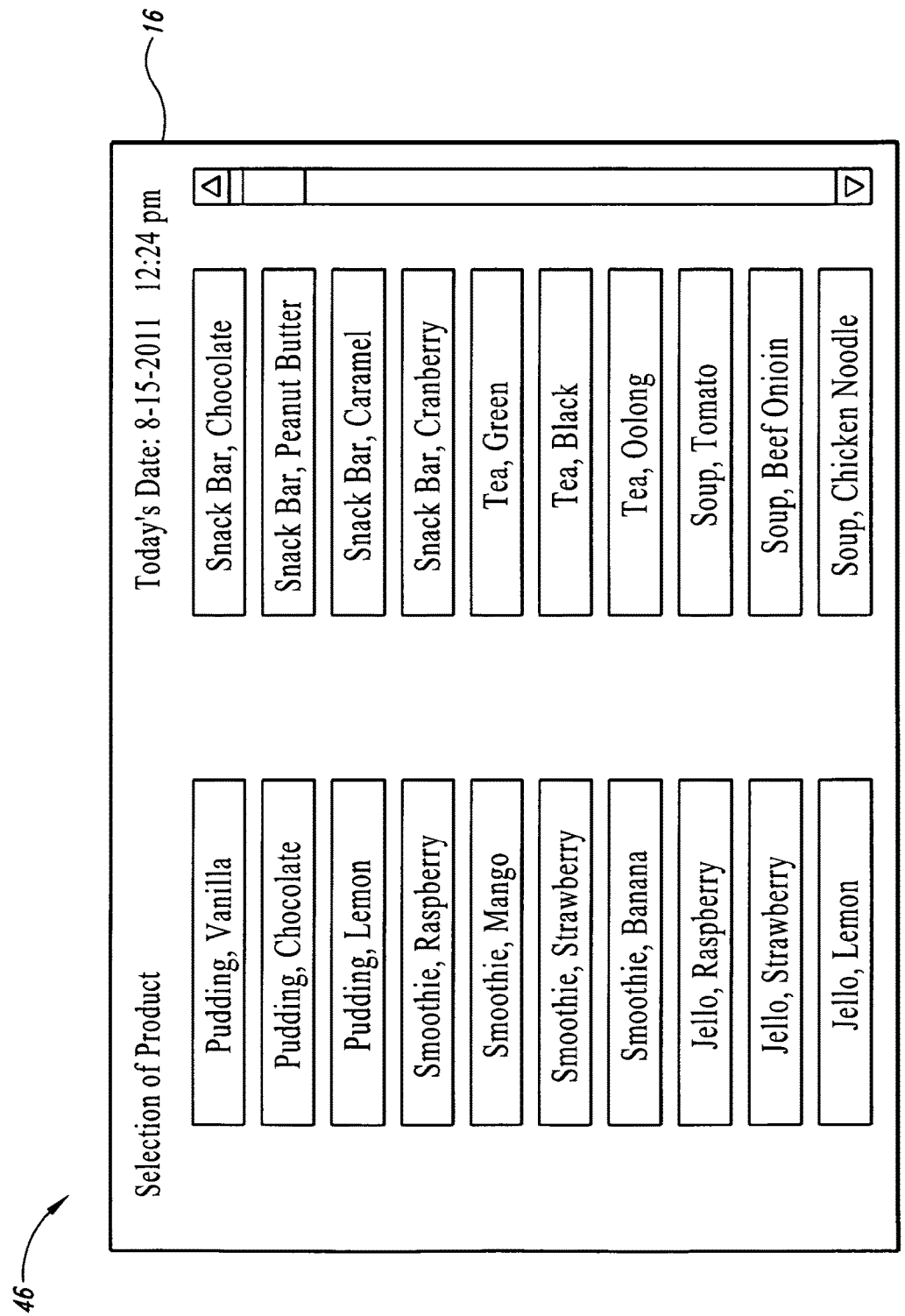
FIG. 6 is a schematic view of a display screen of the first exemplary implementation of the ingestible product dispensing system 10 in FIG. 1 displaying fourth content.

For instance, FIG. 6 depicts the display screen 16 showing content 46 having user selectable options to indicate what one or more ingestible products are desired for the ingestible product dispensing system 10 to dispense (in some implementations including preparation). For instance, FIG. 7 depicts the display screen 16 showing content 48 having user selectable options to indicate what one or more controlled substances are desired for inclusion by the ingestible product dispensing system 10 in ingestible product dispensing (in some implementations including preparation). In some implementations, this information can also be used by the ingestible product dispensing system 10 to determine if one or more treatment procedures should be executed prior to further ingestible product dispensing (in some implementations including preparation).

Figure 8:
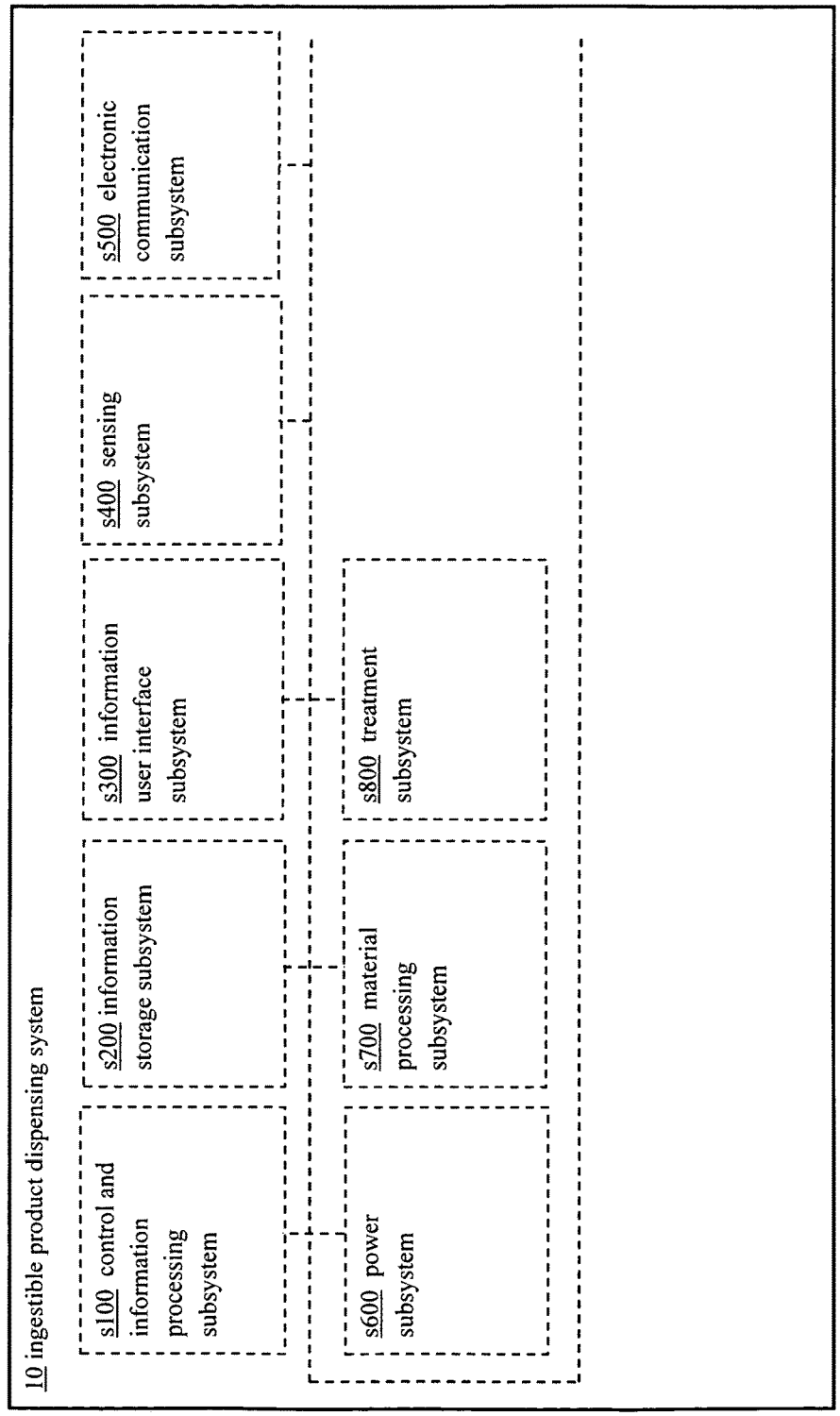
FIG. 8 is a block diagram depicting an exemplary implementation of the ingestible product dispensing system 10 of FIG. 1 including exemplary subsystems.

An exemplary version of the ingestible product dispensing system 10 is shown in FIG. 8 to optionally include various subsystems such as control and information processing subsystem s100, information storage subsystem s200, information user interface subsystem s300, sensing subsystem s400, electronic communication subsystem s500, power subsystem s600, material processing subsystem s700, and treatment subsystem s800.

Figure 9:
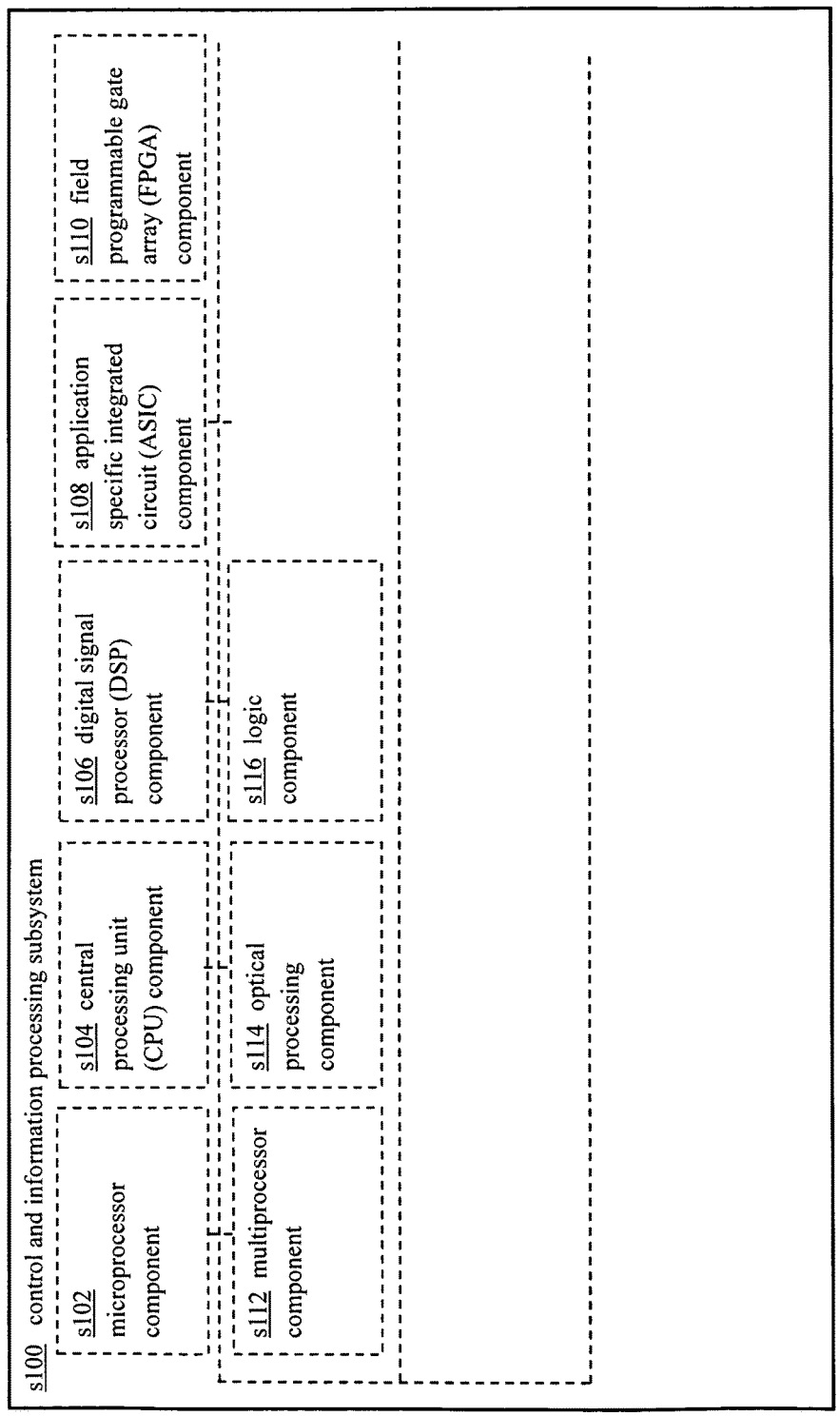
FIG. 9 is a block diagram depicting a control and information processing subsystem s100 of an exemplary implementation of the ingestible product dispensing system 10 of FIG. 1.

An exemplary implementation of the control and information processing subsystem s100 is shown in FIG. 9 to optionally include various components such as microprocessor component s102, central processing unit (CPU) component s104, digital signal processor (DSP) component s106, application specific integrated circuit (ASIC) component s108, field programmable gate array (FPGA) component s110, multiprocessor component s112, and optical processing component s114.

Figure 10:
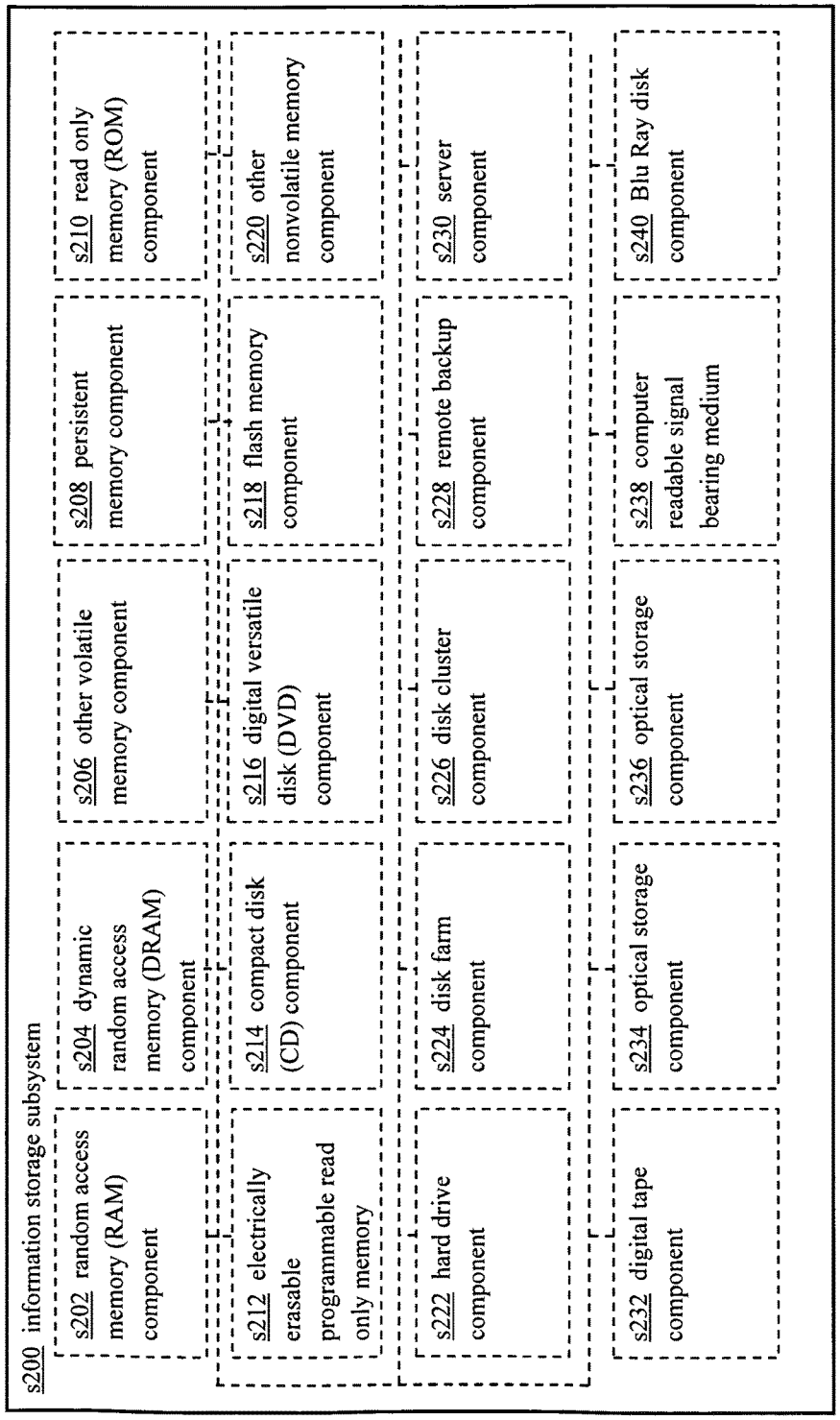
FIG. 10 is a block diagram depicting an information storage subsystem s200 of an exemplary implementation of the ingestible product dispensing system 10 of FIG. 1.

An exemplary implementation of the information storage subsystem s200 is shown in FIG. 10 to optionally include various components such as random access memory (RAM) component s202, dynamic random access memory (DRAM) component s204, other volatile memory component s206, persistent memory component s208, read only memory (ROM) component s210, electrically erasable programmable read only memory (EEPROM) component s212, compact disk (CD) component s214, digital versatile disk (DVD) component s216, flash memory component s218, other nonvolatile memory component s220, hard drive component s222, disk farm component s224, disk cluster component s226, remote backup component s228, server component s230, digital tape component s232, optical storage component s234, optical storage component s236, computer readable signal bearing medium s238, and Blu Ray disk component s240.

Figure 11:
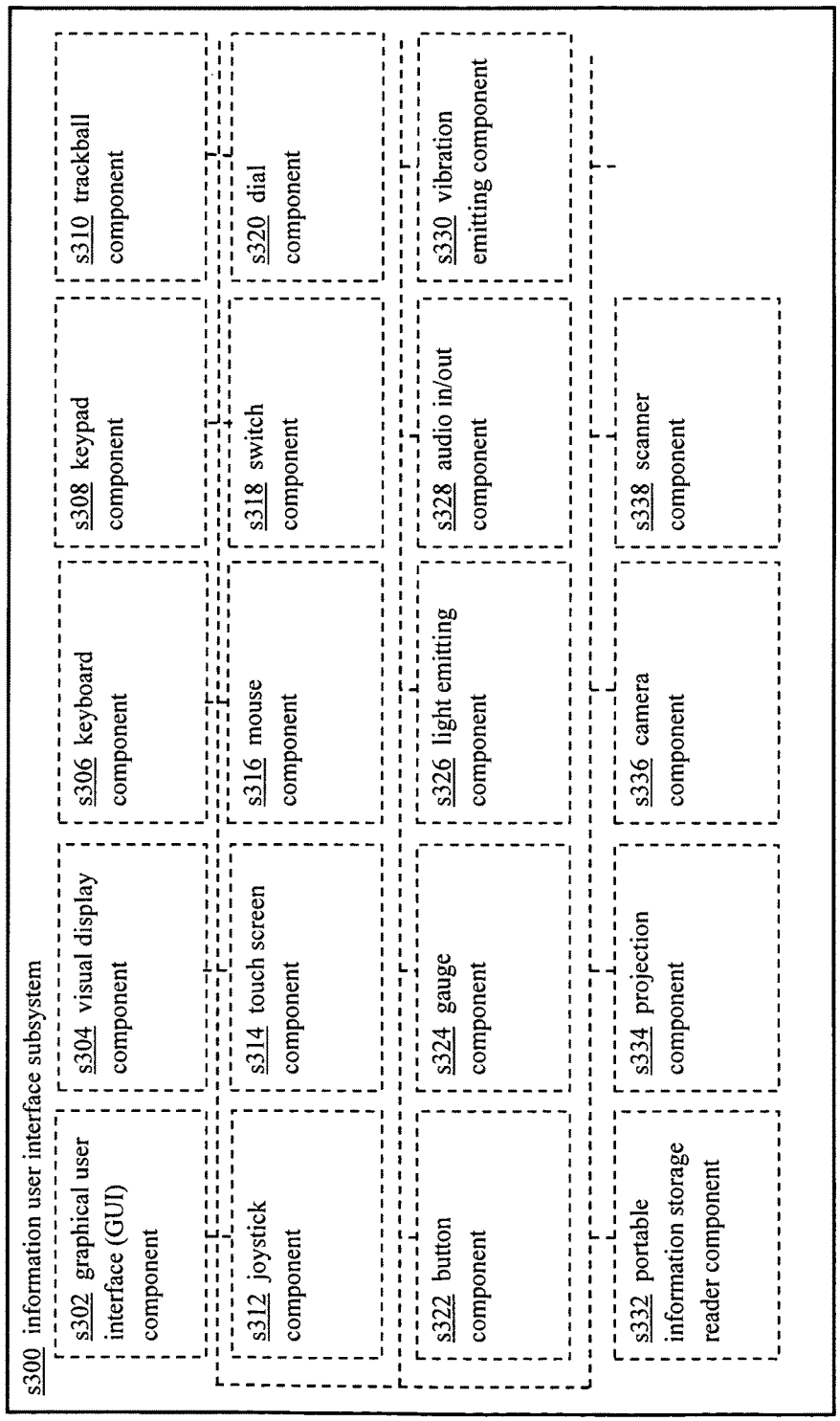
FIG. 11 is a block diagram depicting an information user interface subsystem s300 of an exemplary implementation of the ingestible product dispensing system 10 of FIG. 1.

An exemplary implementation of the information user interface subsystem s300 is shown in FIG. 11 to optionally include various components such as graphical user interface (GUI) component s302, visual display component s304, keyboard component s306, keypad component s308, trackball component s310, joystick component s312, touch screen component s314, mouse component s316, switch component s318, dial component s320, button component s322, gauge component s324, light emitting component s326, audio in/out component s328, vibration emitting component s330, portable information storage reader component s332, projection component s334, camera component s336, and scanner component s338.

Figure 12:
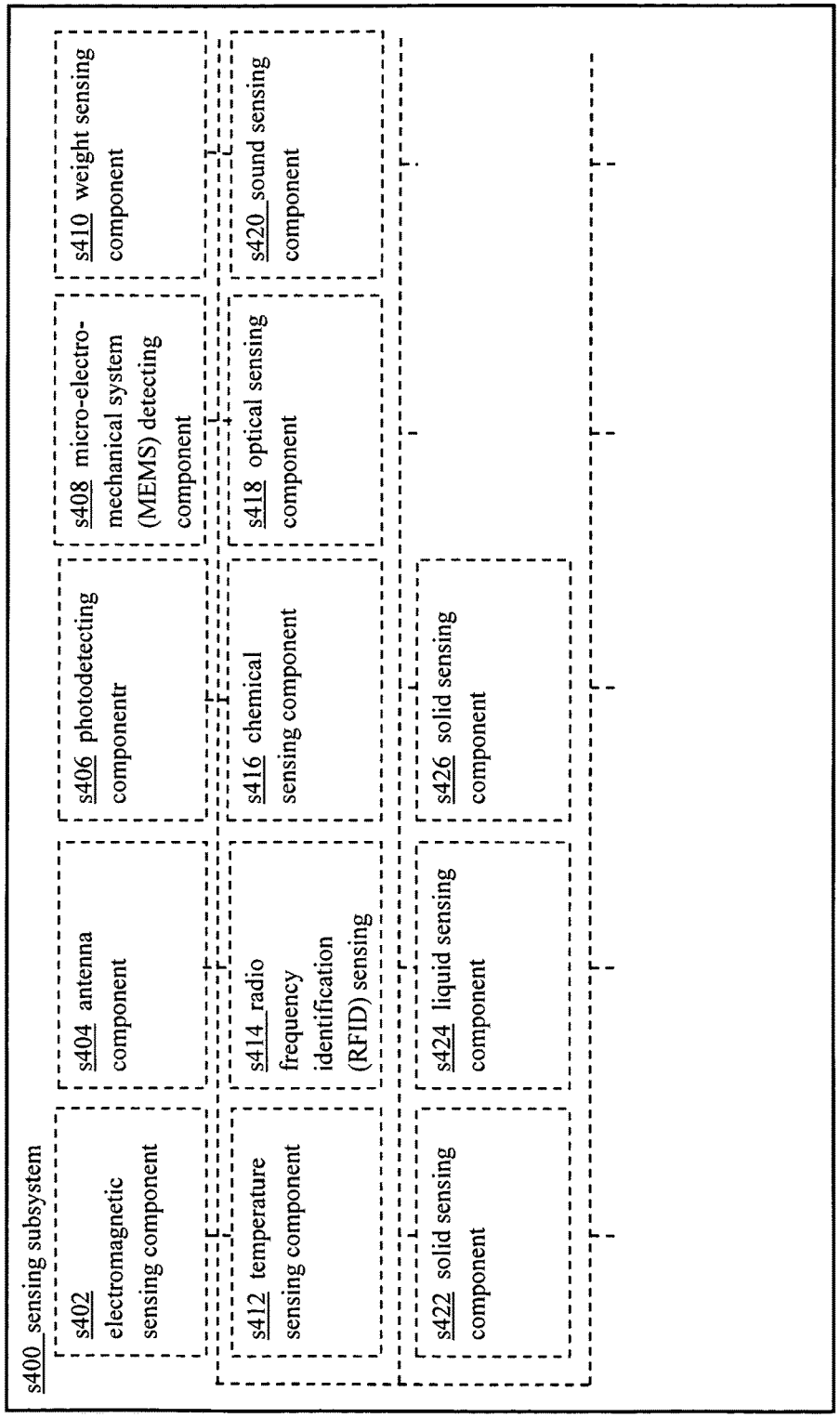
FIG. 12 is a block diagram depicting a sensing subsystem s400 of an exemplary implementation of the ingestible product dispensing system 10 of FIG. 1.

An exemplary implementation of the sensing subsystem s400 is shown in FIG. 12 to optionally include various components such as electromagnetic sensing component s402, antenna component s404, photodetecting component s406, micro-electro-mechanical system (MEMS) detecting component s408, weight sensing component s410, temperature sensing component s412, radio frequency identification (RFID) sensing component s414, chemical sensing component s416, optical sensing component s418, sound sensing component s420, solid sensing component s422, liquid sensing component s424, and solid sensing component s426.

Figure 13:
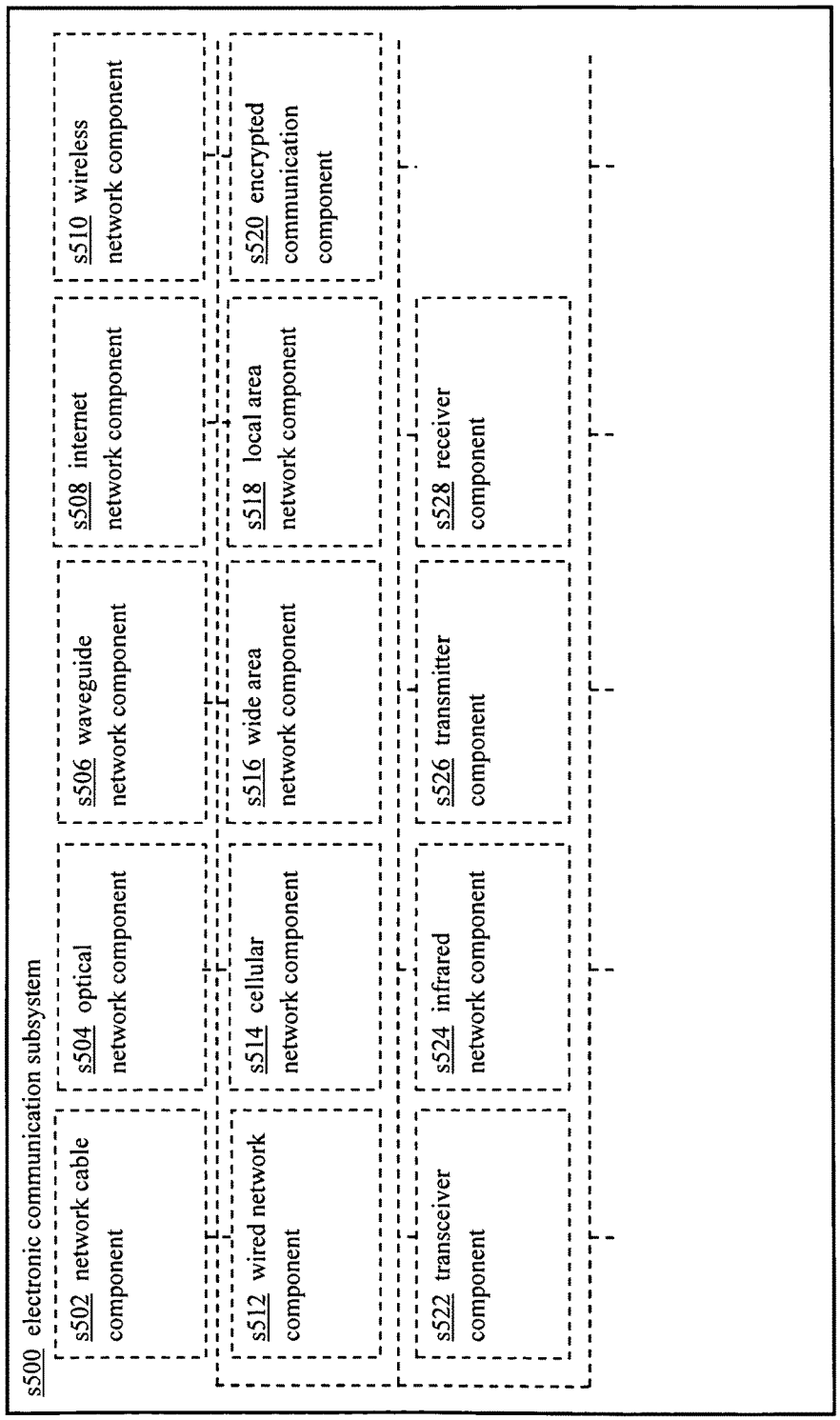
FIG. 13 is a block diagram depicting an electronic communication subsystem s500 of an exemplary implementation of the ingestible product dispensing system 10 of FIG. 1.

An exemplary implementation of the electronic communication subsystem s500 is shown in FIG. 13 to optionally include various components such as network cable component s502, optical network component s504, waveguide network component s506, internet network component s508, wireless network component s510, wired network component s512, cellular network component s514, wide area network component s516, local area network component s518, encrypted communication component s520, transceiver component s522, infrared network component s524, transmitter component s526, and receiver component s528.

Figure 14:
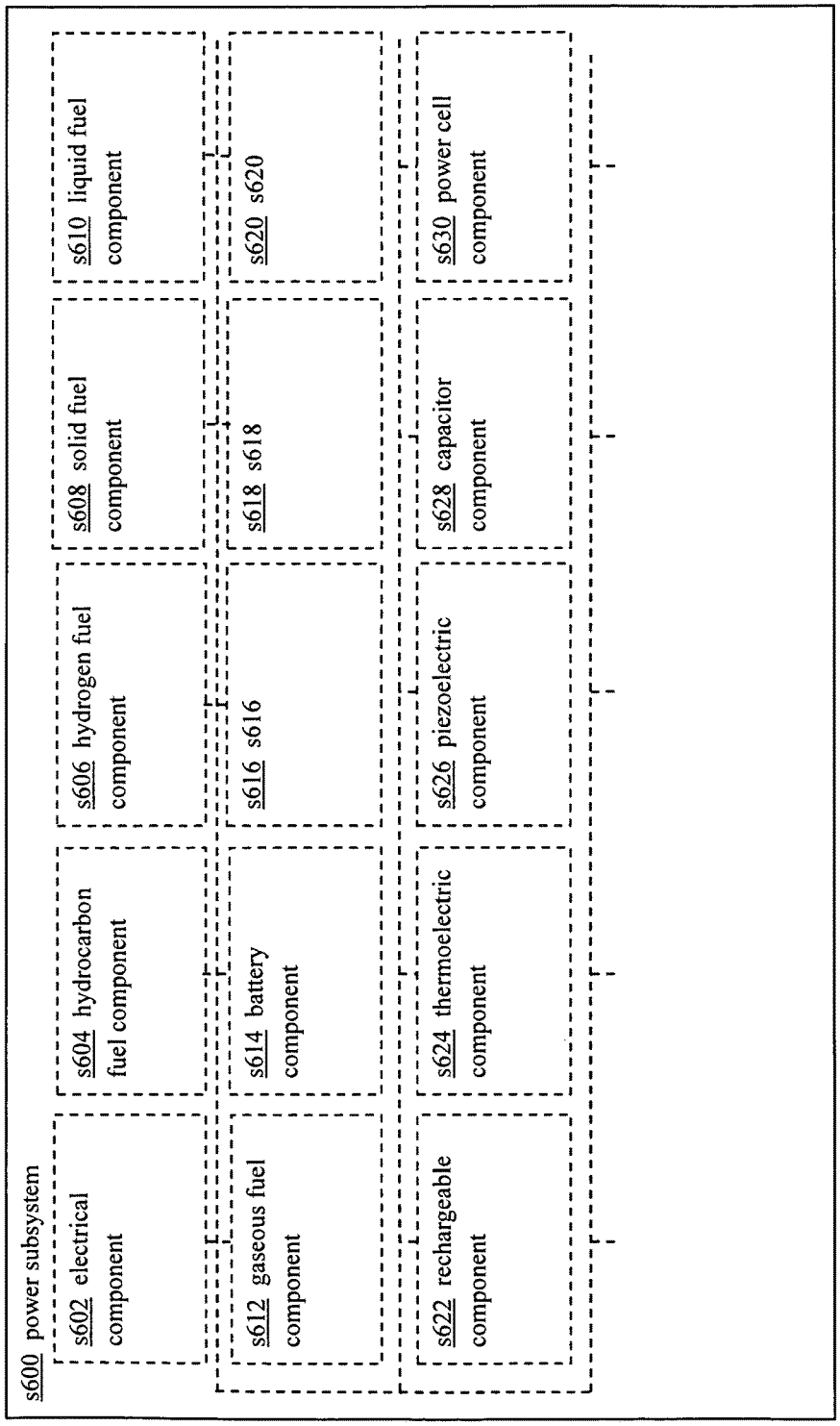
FIG. 14 is a block diagram depicting a power subsystem s600 of an exemplary implementation of the ingestible product dispensing system 10 of FIG. 1.

An exemplary implementation of the power subsystem s600 is shown in FIG. 14 to optionally include various components such as electrical component s602, hydrocarbon fuel component s604, hydrogen fuel component s606, solid fuel component s608, liquid fuel component s610, gaseous fuel component s612, and battery component s614.

Figure 15:
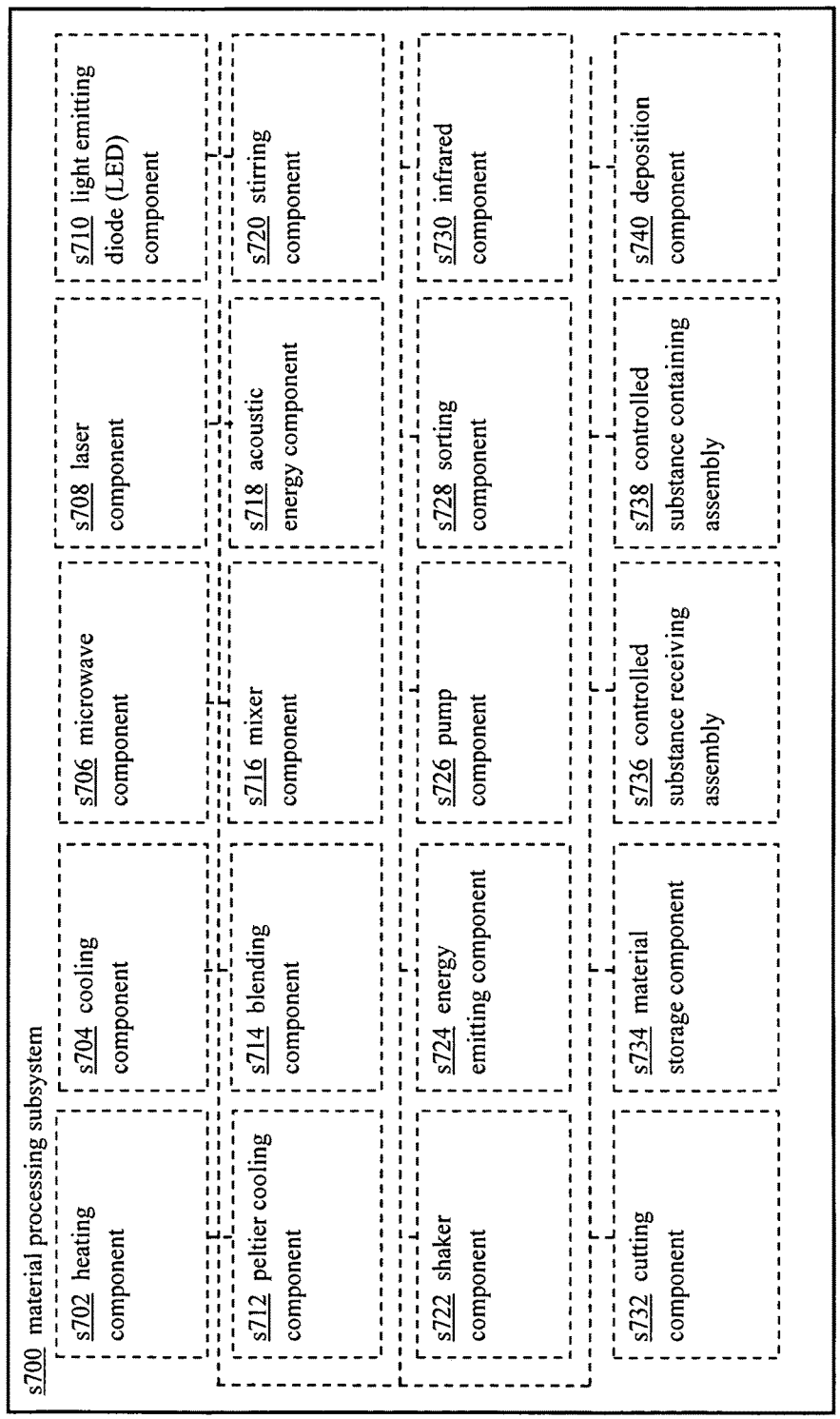
FIG. 15 is a block diagram depicting a material processing subsystem s700 of an exemplary implementation of the ingestible product dispensing system 10 of FIG. 1.

An exemplary implementation of the material processing subsystem s700 is shown in FIG. 15 to optionally include various components such as heating component s702, cooling component s704, microwave component s706, laser component s708, light emitting diode (LED) component s710, peltier cooling component s712, blending component s714, mixer component s716, acoustic energy component s718, stirring component s720, shaker component s722, energy emitting component s724, pump component s726, sorting component s728, infrared component s730, cutting component s732, material storage component s734, controlled substance receiving assembly s736, and controlled substance containing assembly s738.

Figure 16:
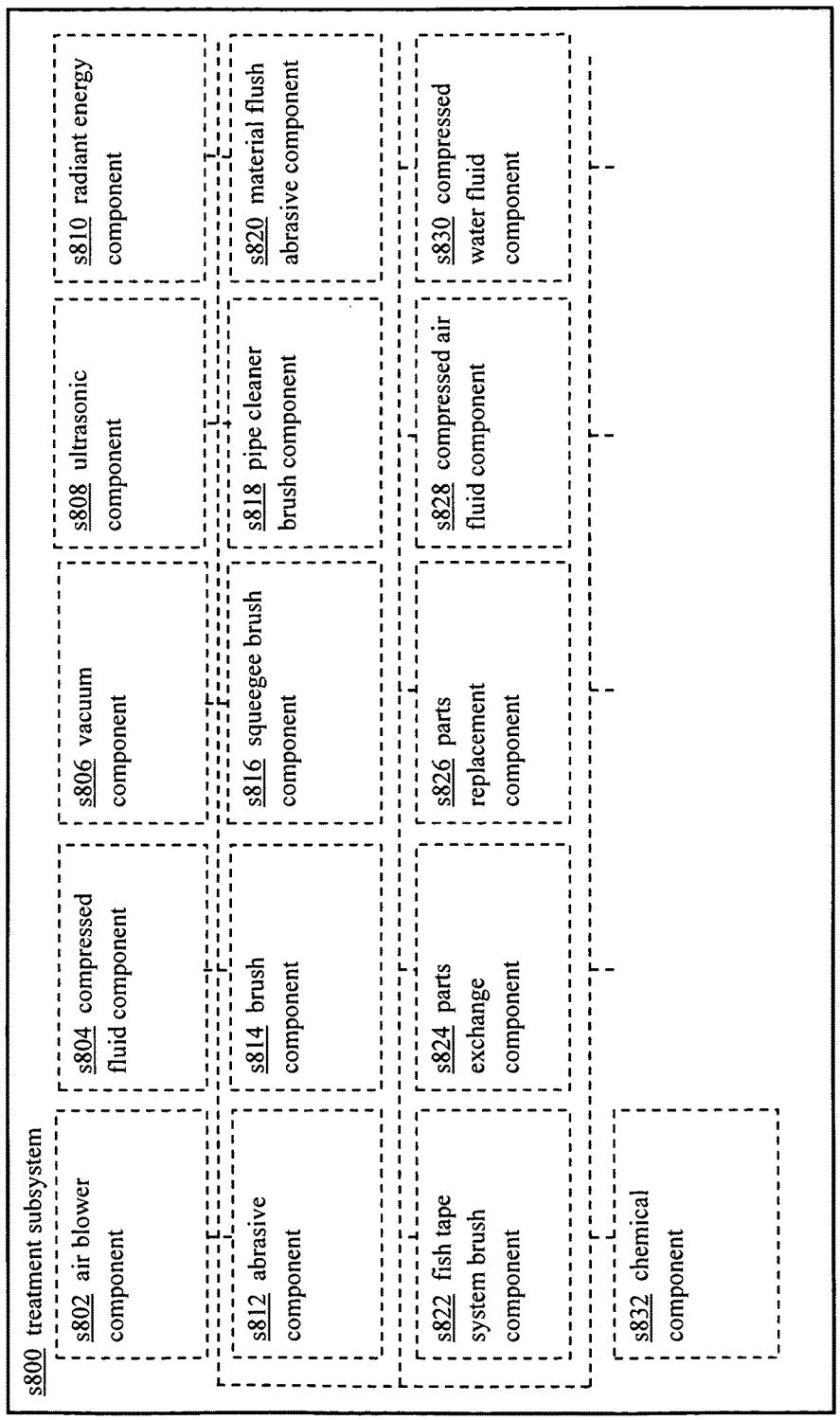
FIG. 16 is a block diagram depicting a treatment subsystem s800 of an exemplary implementation of the ingestible product dispensing system 10 of FIG. 1.

An exemplary implementation of the treatment subsystem s800 is shown in FIG. 16 to optionally include various components such as air blower component s802, compressed fluid component s804, vacuum component s806, ultrasonic component s808, radiant energy component s810, abrasive component s812, brush component s814, squeegee brush component s816, pipe cleaner brush component s818, material flush abrasive component s820, fish tape system brush component s822, parts exchange component s824, parts replacement component s826, compressed air fluid component s828, compressed water fluid component s830, and chemical component s832.

Figure 17:
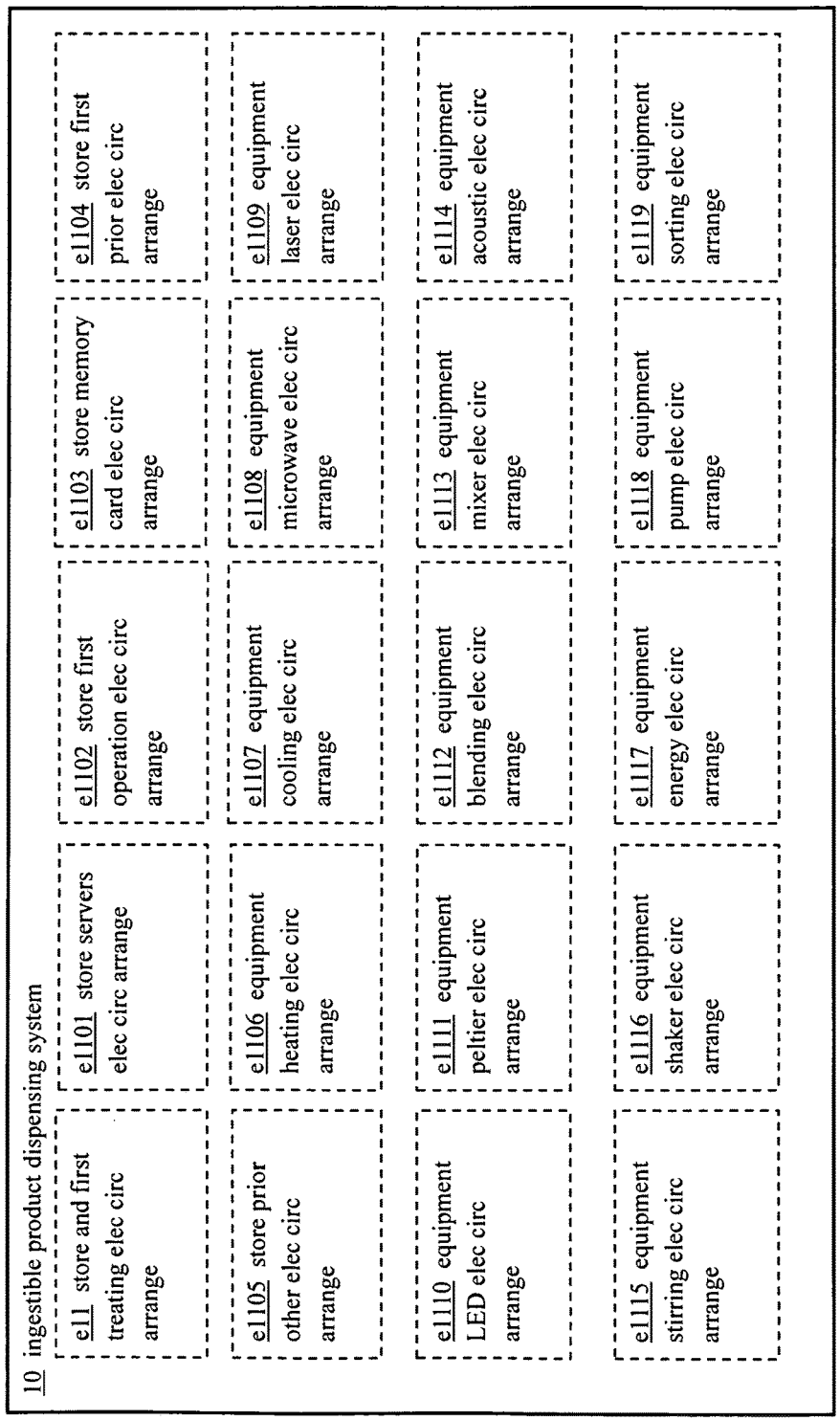
FIG. 17 is a block diagram depicting one or more exemplary electrical circuitry arrangements of the ingestible product dispensing system 10 of FIG. 1.

Implementations involve different combinations (otherwise known as "electrical circuitry arrangements") of components from the subsystems of the ingestible product dispensing system 10. Exemplary depictions of some of these electrical circuitry arrangements are shown in FIG. 17 to include store and first treating electrical circuitry arrangement e11, store servers electrical circuitry arrangement e1101, store first operation electrical circuitry arrangement e1102, store memory card electrical circuitry arrangement e1103, store first prior electrical circuitry arrangement e1104, store prior other electrical circuitry arrangement e1105, equipment heating electrical circuitry arrangement e1106, equipment cooling electrical circuitry arrangement e1107, equipment microwave electrical circuitry arrangement e1108, equipment laser electrical circuitry arrangement e1109, equipment LED electrical circuitry arrangement e1110, equipment peltier electrical circuitry arrangement e1111, equipment blending electrical circuitry arrangement e1112, equipment mixer electrical circuitry arrangement e1113, equipment acoustic electrical circuitry arrangement e1114, equipment stirring electrical circuitry arrangement e1115, equipment shaker electrical circuitry arrangement e1116, equipment energy electrical circuitry arrangement e1117, equipment pump electrical circuitry arrangement e1118, and equipment sorting electrical circuitry arrangement e1119.

Figure 18:
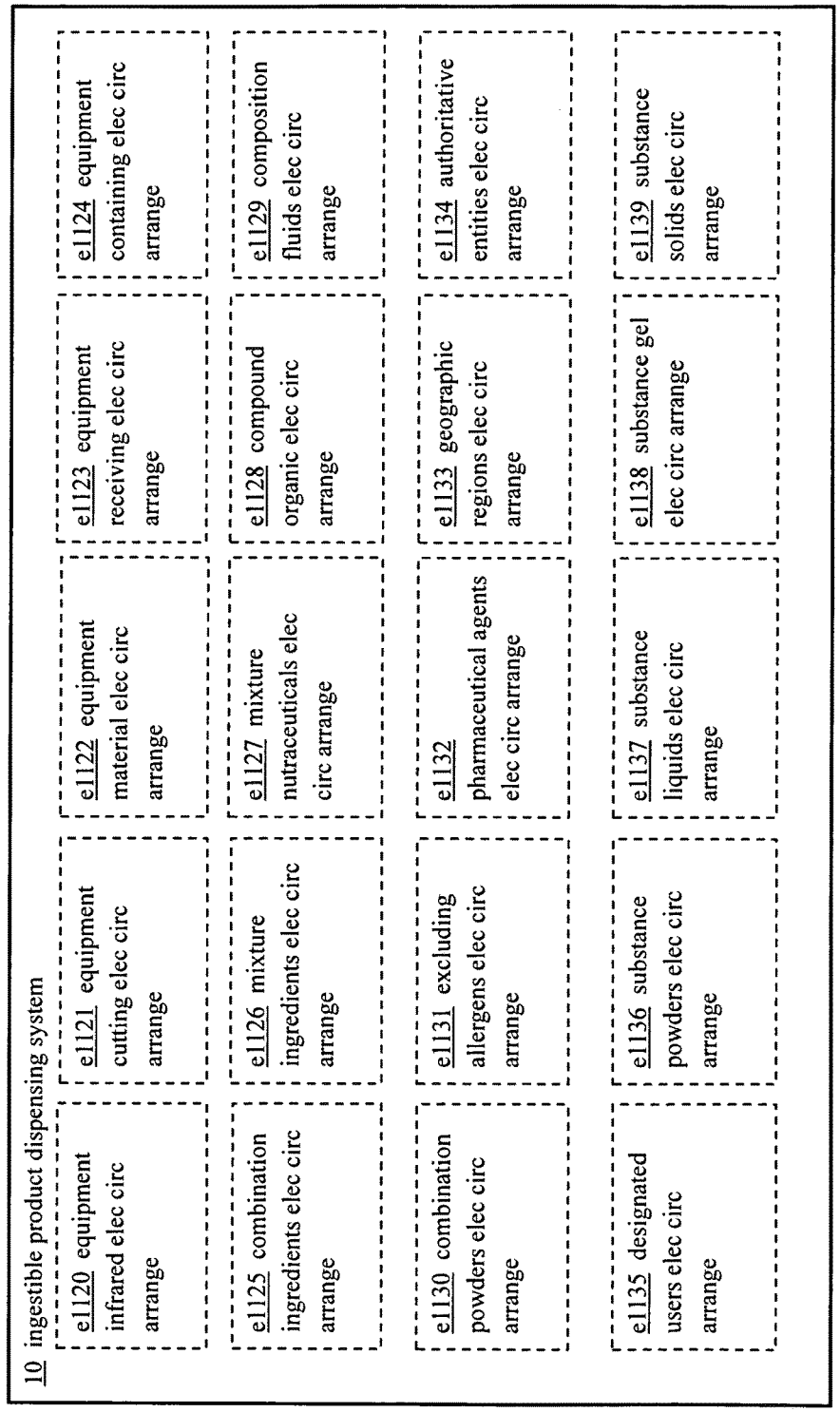
FIG. 18 is a block diagram depicting one or more exemplary electrical circuitry arrangements of the ingestible product dispensing system 10 of FIG. 1.

Some of these electrical circuitry arrangements are depicted in FIG. 18 to include equipment infrared electrical circuitry arrangement e1120, equipment cutting electrical circuitry arrangement e1121, equipment material electrical circuitry arrangement e1122, equipment receiving electrical circuitry arrangement e1123, equipment containing electrical circuitry arrangement e1124, combination ingredients electrical circuitry arrangement e1125, mixture ingredients electrical circuitry arrangement e1126, mixture nutraceuticals electrical circuitry arrangement e1127, compound organic electrical circuitry arrangement e1128, composition fluids electrical circuitry arrangement e1129, combination powders electrical circuitry arrangement e1130, excluding allergens electrical circuitry arrangement e113, pharmaceutical agents electrical circuitry arrangement e1132, geographic regions electrical circuitry arrangement e1133, authoritative entities electrical circuitry arrangement e1134, designated users electrical circuitry arrangement e1135, substance powders electrical circuitry arrangement e1136, substance liquids electrical circuitry arrangement e1137, substance gel electrical circuitry arrangement e1138, and substance solids electrical circuitry arrangement e1139.

Some of these electrical circuitry arrangements are depicted in FIG. 19 to include substance mixtures electrical circuitry arrangement e1140, treating cellular electrical circuitry arrangement e1141, treating network electrical circuitry arrangement e1142, treating circuitry electrical circuitry arrangement e1143, treating wireless electrical circuitry arrangement e1144, treating microprocessor electrical circuitry arrangement e1145, treating memory electrical circuitry arrangement e1146, treating servers electrical circuitry arrangement e1147, treating card electrical circuitry arrangement e1148, treating blowing electrical circuitry arrangement e1149, treating compressed electrical circuitry arrangement e1150, treating vacuum electrical circuitry arrangement e1151, treating ultrasonic electrical circuitry arrangement e1152, treating electromagnetic electrical circuitry arrangement e1153, treating abrasives electrical circuitry arrangement e1154, treating brush electrical circuitry arrangement e1155, treating chemical electrical circuitry arrangement e1156, treating tubes electrical circuitry arrangement e1157, treating nozzles electrical circuitry arrangement e1158, and treating heating electrical circuitry arrangement e1159.

Figure 20:
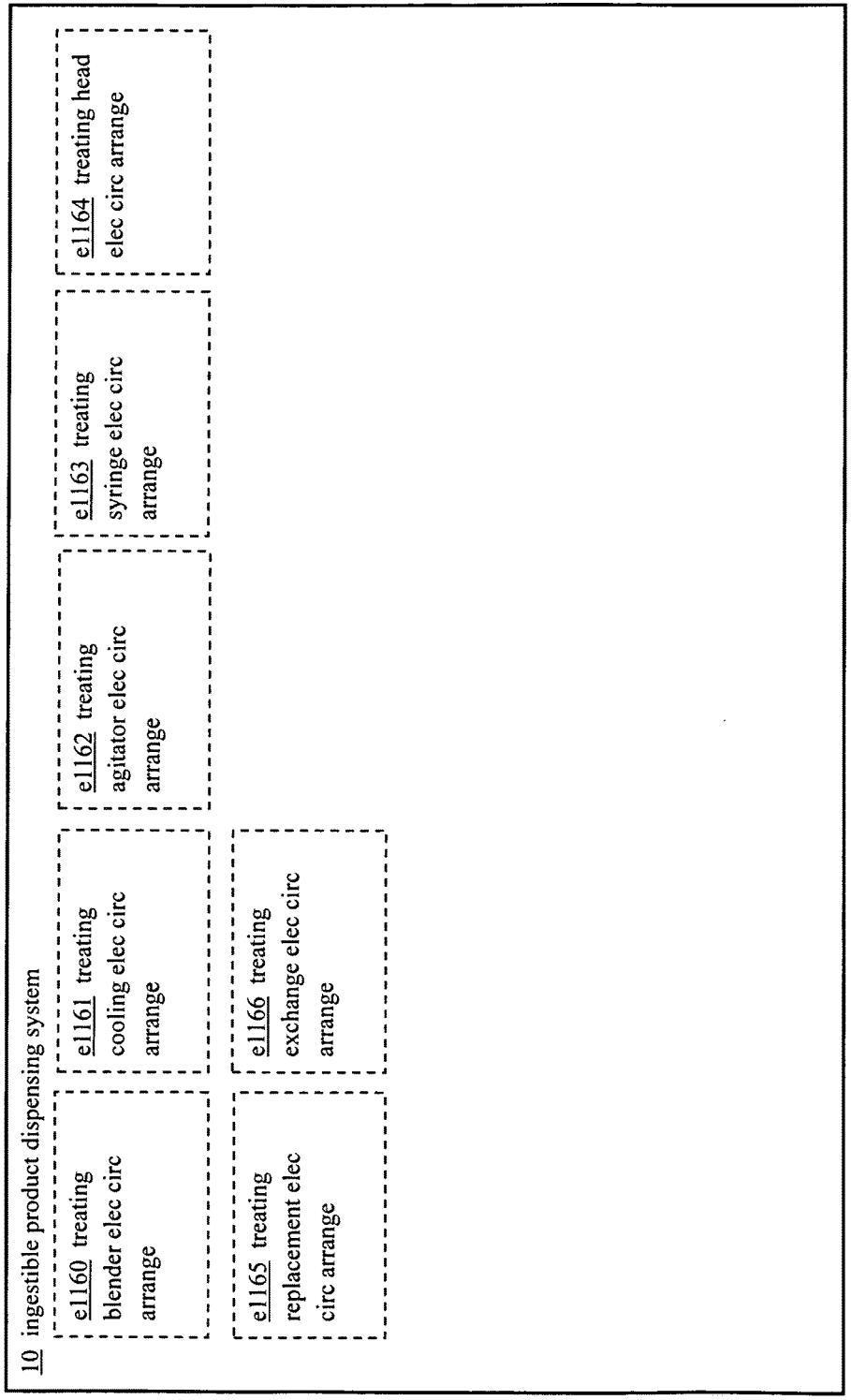
FIG. 20 is a block diagram depicting one or more exemplary electrical circuitry arrangements of the ingestible product dispensing system 10 of FIG. 1.

Some of these electrical circuitry arrangements are depicted in FIG. 20 to include treating blender electrical circuitry arrangement e1160, treating cooling electrical circuitry arrangement e1161, treating agitator electrical circuitry arrangement e1162, treating syringe electrical circuitry arrangement e1163, treating head electrical circuitry arrangement e1164, treating replacement electrical circuitry arrangement e1165, and treating exchange electrical circuitry arrangement e1166.

Figure 21:
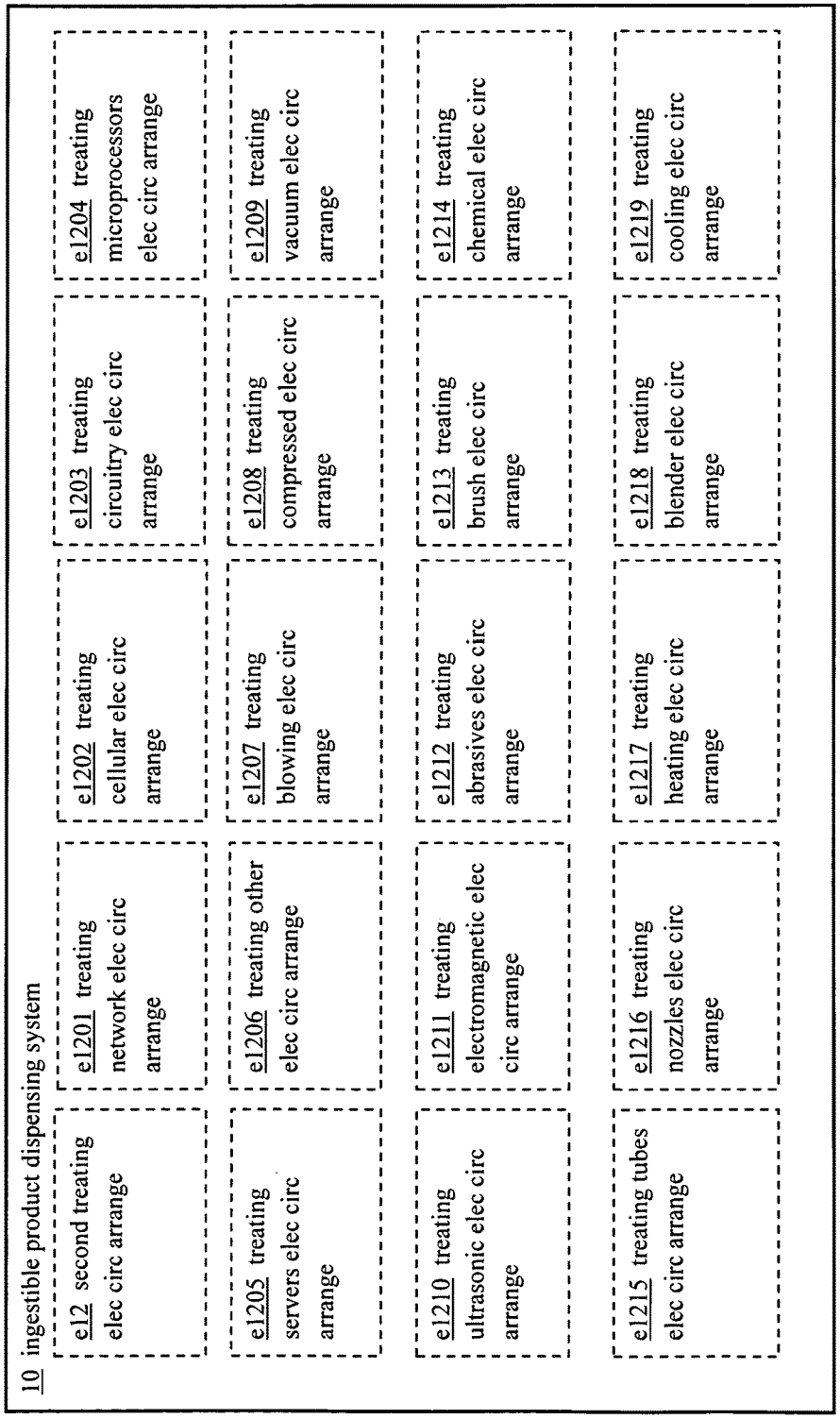
FIG. 21 is a block diagram depicting one or more exemplary electrical circuitry arrangements of the ingestible product dispensing system 10 of FIG. 1.

Some of these electrical circuitry arrangements are depicted in FIG. 21 to include second treating electrical circuitry arrangement e12, treating network electrical circuitry arrangement e1201, treating cellular electrical circuitry arrangement e1202, treating circuitry electrical circuitry arrangement e1203, treating microprocessors electrical circuitry arrangement e1204, treating servers electrical circuitry arrangement e1205, treating other electrical circuitry arrangement e1206, treating blowing electrical circuitry arrangement e1207, treating compressed electrical circuitry arrangement e1208, treating vacuum electrical circuitry arrangement e1209, treating ultrasonic electrical circuitry arrangement e1210, treating electromagnetic electrical circuitry arrangement e1211, and treating abrasives electrical circuitry arrangement e1212, treating brush electrical circuitry arrangement e1213, treating chemical electrical circuitry arrangement e1214, treating tubes electrical circuitry arrangement e1215, treating nozzles electrical circuitry arrangement e1216, treating heating electrical circuitry arrangement e1217, treating blender electrical circuitry arrangement e1218, and treating cooling electrical circuitry arrangement e1219.

Some of these electrical circuitry arrangements are depicted in FIG. 22 to include treating agitator electrical circuitry arrangement e1220, treating syringe electrical circuitry arrangement e1221, treating head electrical circuitry arrangement e1222, treating replacement electrical circuitry arrangement e1223, treating exchange electrical circuitry arrangement e1224, treating other electrical circuitry arrangement e1225, treating includes electrical circuitry arrangement e1226, treating first electrical circuitry arrangement e1227, treating combination electrical circuitry arrangement e1228, treating mixture electrical circuitry arrangement e1229, treating nutraceuticals electrical circuitry arrangement e1230, treating organic electrical circuitry arrangement e123, treating fluids electrical circuitry arrangement e1232, treating powders electrical circuitry arrangement e1233, treating allergens electrical circuitry arrangement e1234, treating agents electrical circuitry arrangement e1235, treating regions electrical circuitry arrangement e1236, treating authoritative electrical circuitry arrangement e1237, treating designated electrical circuitry arrangement e1238, and treating reactive electrical circuitry arrangement e1239.

Figure 23:
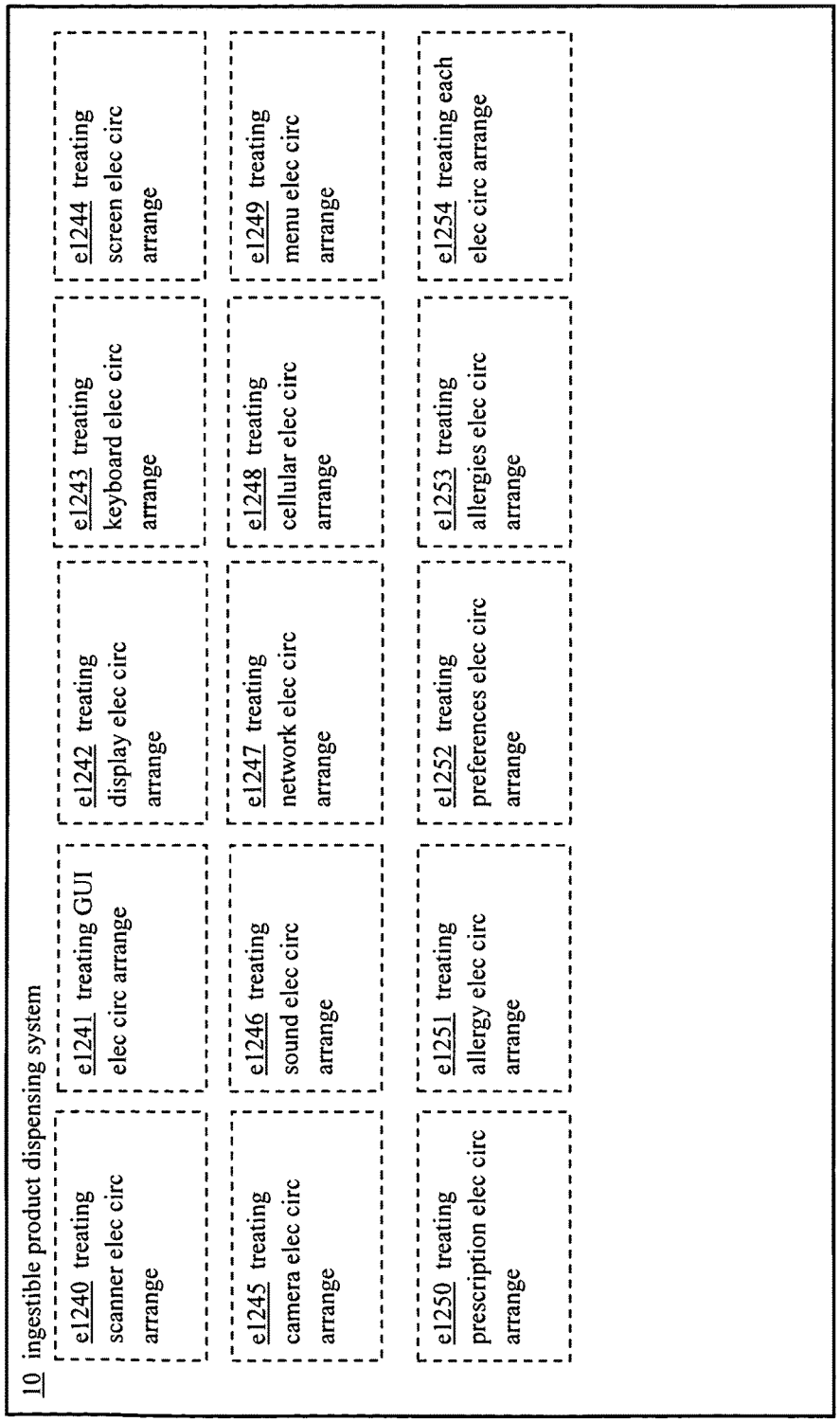
FIG. 23 is a block diagram depicting one or more exemplary electrical circuitry arrangements of the ingestible product dispensing system 10 of FIG. 1.

Some of these electrical circuitry arrangements are depicted in FIG. 23 to include treating scanner electrical circuitry arrangement e1240, treating GUI electrical circuitry arrangement e1241, treating display electrical circuitry arrangement e1242, treating keyboard electrical circuitry arrangement e1243, treating screen electrical circuitry arrangement e1244, treating camera electrical circuitry arrangement e1245, treating sound electrical circuitry arrangement e1246, treating network electrical circuitry arrangement e1247, treating cellular electrical circuitry arrangement e1248, treating menu electrical circuitry arrangement e1249, treating prescription electrical circuitry arrangement e1250, treating allergy electrical circuitry arrangement e1251, treating preferences electrical circuitry arrangement e1252, treating allergies electrical circuitry arrangement e1253, and treating each electrical circuitry arrangement e1254.

Figure 24:
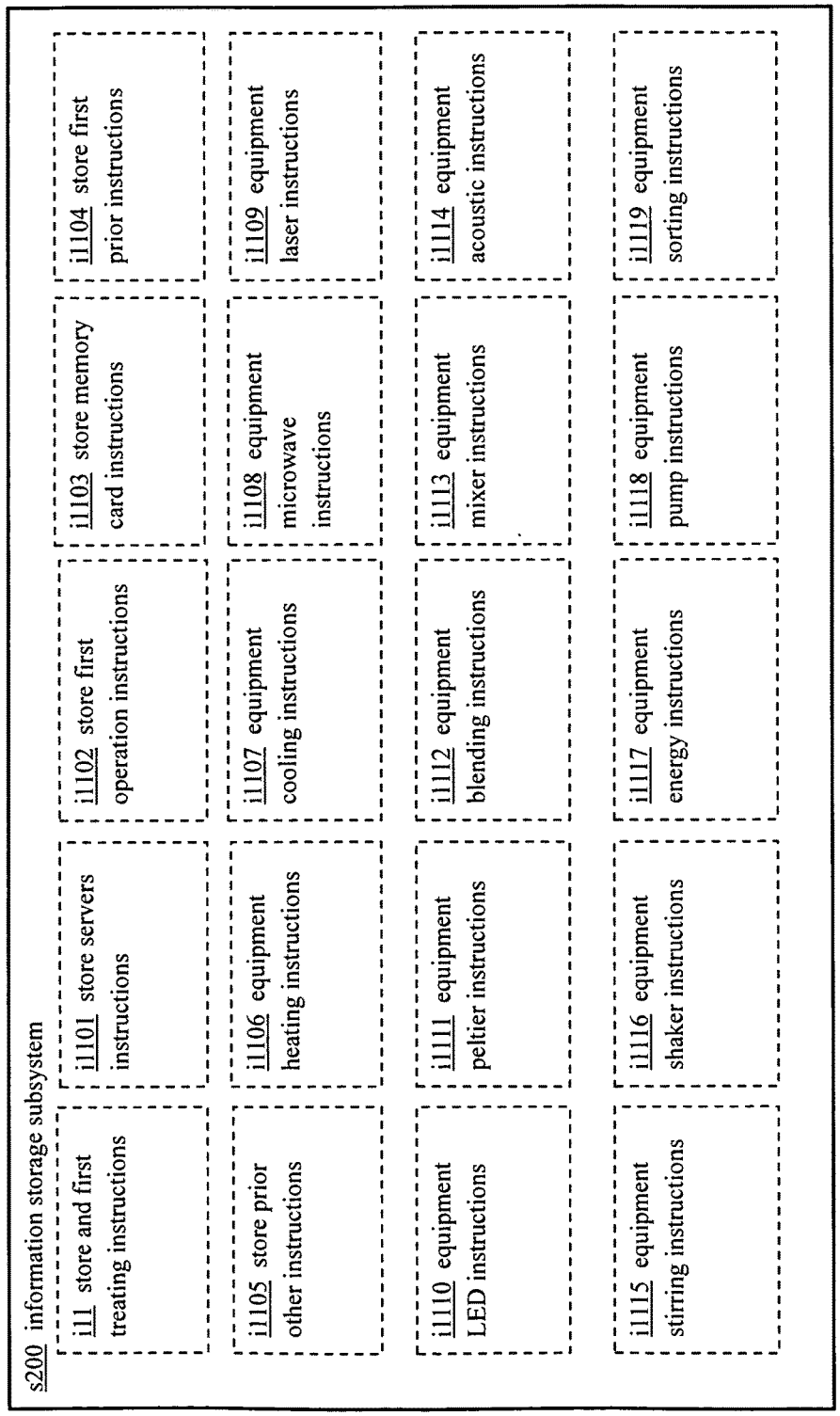
FIG. 24 is a block diagram depicting one or more exemplary instructions of the information storage subsystem s200 of the ingestible product dispensing system 10 of FIG. 1.

In implementations one or more instructions are stored and/or otherwise borne in various subsystems, components, and/or accessories of the ingestible product dispensing system 10 such as being borne in a non-transitory signal bearing medium of information storage subsystem s200. One or more exemplary instructions depicted in FIG. 24 as being borne in an exemplary version of a non-transitory signal bearing medium of information storage subsystem s200 include one or more store and first treating instructions i11, one or more store servers instructions i1101, one or more store first operation instructions i1102, one or more store memory card instructions i1103, one or more store first prior instructions i1104, one or more store prior other instructions i1105, one or more equipment heating instructions i1106, one or more equipment cooling instructions i1107, one or more equipment microwave instructions i1108, one or more equipment laser instructions i1109, one or more equipment LED instructions i1110, one or more equipment peltier instructions i1111, one or more equipment blending instructions i1112, one or more equipment mixer instructions i1113, one or more equipment acoustic instructions i1114, one or more equipment stirring instructions i1115, one or more equipment shaker instructions i1116, one or more equipment energy instructions i1117, one or more equipment pump instructions i1118, and one or more equipment sorting instructions i1119.

Figure 25:
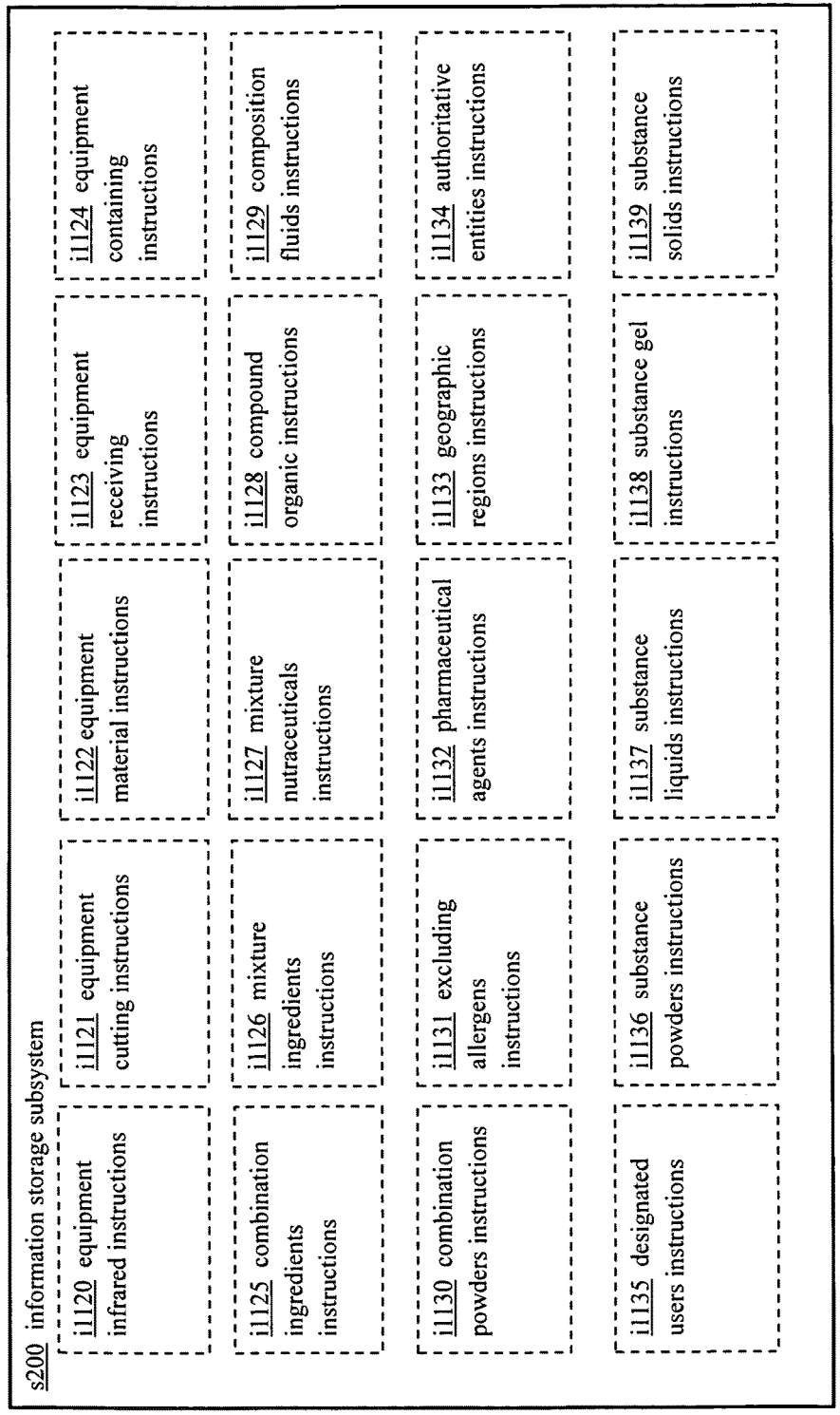
FIG. 25 is a block diagram depicting one or more exemplary instructions of the information storage subsystem s200 of the ingestible product dispensing system 10 of FIG. 1.

One or more exemplary instructions depicted in FIG. 25 as being borne in an exemplary version of a non-transitory signal bearing medium of information storage subsystem s200 include one or more equipment infrared instructions i1120, one or more equipment cutting instructions i1121, one or more equipment material instructions i1122, one or more equipment receiving instructions i1123, one or more equipment containing instructions i1124, one or more combination ingredients instructions i1125, one or more mixture ingredients instructions i1126, one or more mixture nutraceuticals instructions i1127, one or more compound organic instructions i1128, one or more composition fluids instructions i1129, one or more combination powders instructions i1130, one or more excluding allergens instructions i1131, one or more pharmaceutical agents instructions i1132, one or more geographic regions instructions i1133, one or more authoritative entities instructions i1134, one or more designated users instructions i1135, one or more substance powders instructions i1136, one or more substance liquids instructions i1137, one or more substance gel instructions i1138, and one or more substance solids instructions i1139.

Figure 26:
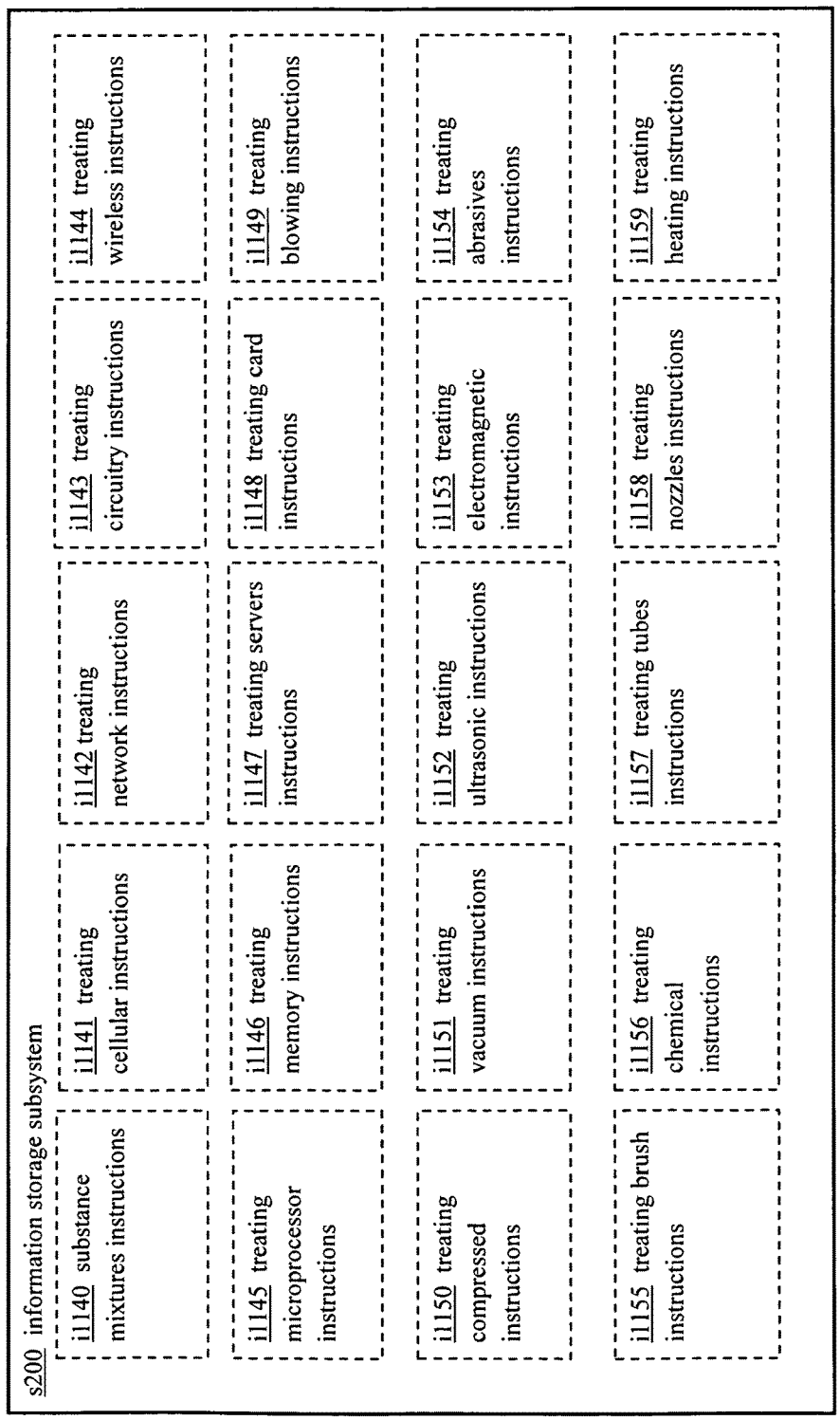
FIG. 26 is a block diagram depicting one or more exemplary instructions of the information storage subsystem s200 of the ingestible product dispensing system 10 of FIG. 1.

One or more exemplary instructions depicted in FIG. 26 as being borne in an exemplary version of a non-transitory signal bearing medium of information storage subsystem s200 include one or more substance mixtures instructions i1140, one or more treating cellular instructions i1141, one or more treating network instructions i1142, one or more treating circuitry instructions i1143, one or more treating wireless instructions i1144, one or more treating microprocessor instructions i1145, one or more treating memory instructions i1146, one or more treating servers instructions i1147, one or more treating card instructions i1148, one or more treating blowing instructions i1149, one or more treating compressed instructions i1150, one or more treating vacuum instructions i1151, one or more treating ultrasonic instructions i1152, one or more treating electromagnetic instructions i1153, one or more treating abrasives instructions i1154, one or more treating brush instructions i1155, one or more treating chemical instructions i1156, one or more treating tubes instructions i1157, one or more treating nozzles instructions i1158, and one or more treating heating instructions i1159.

Figure 27:
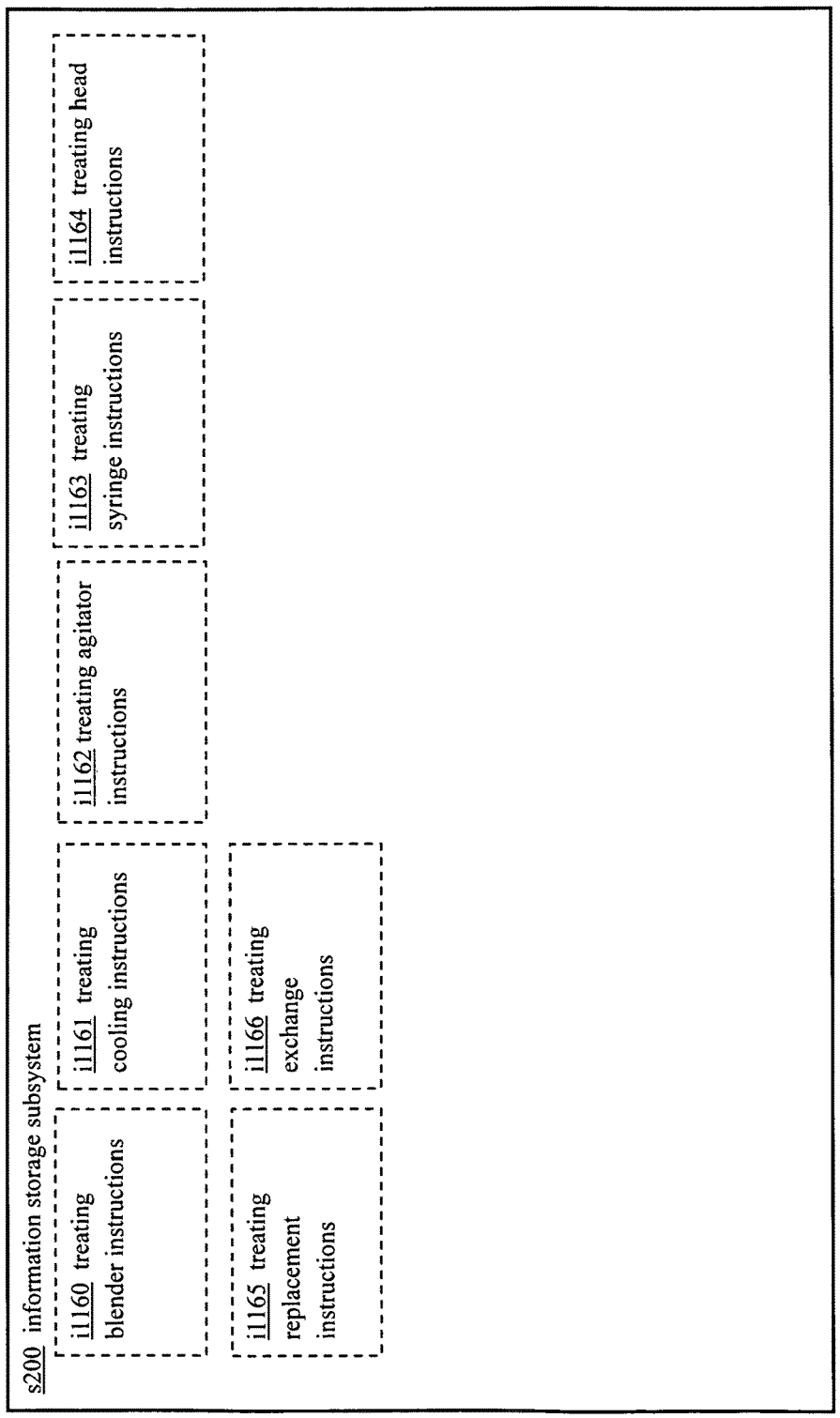
FIG. 27 is a block diagram depicting one or more exemplary instructions of the information storage subsystem s200 of the ingestible product dispensing system 10 of FIG. 1.

One or more exemplary instructions depicted in FIG. 27 as being borne in an exemplary version of a non-transitory signal bearing medium of information storage subsystem s200 include one or more treating blender instructions i1160, one or more treating cooling instructions i1161, one or more treating agitator instructions i1162, one or more treating syringe instructions i1163, one or more treating head instructions i1164, one or more treating replacement instructions i1165, and one or more treating exchange instructions i1166.

Figure 28:
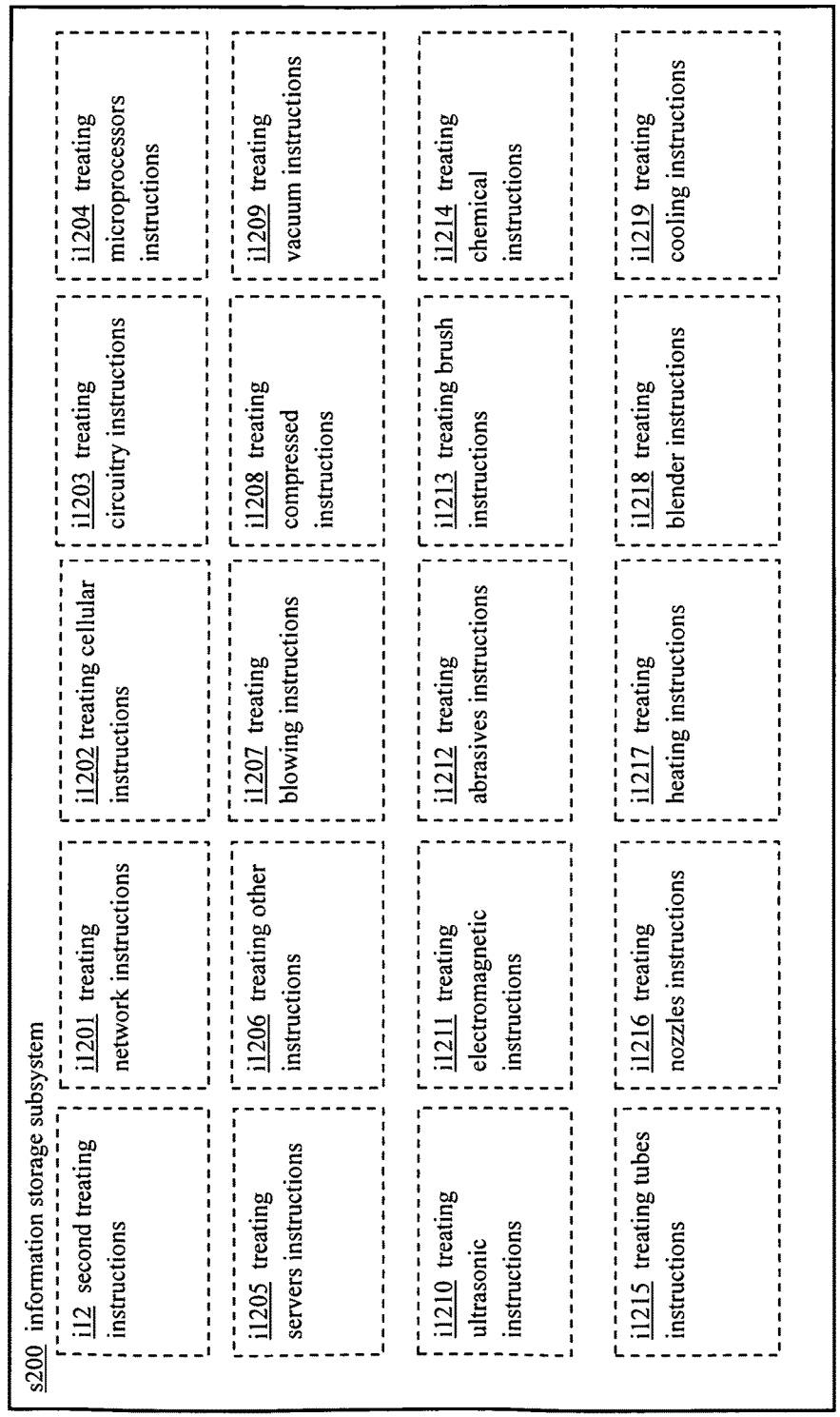
FIG. 28 is a block diagram depicting one or more exemplary instructions of the information storage subsystem s200 of the ingestible product dispensing system 10 of FIG. 1.

One or more exemplary instructions depicted in FIG. 28 as being borne in an exemplary version of a non-transitory signal bearing medium of information storage subsystem s200 include one or more second treating instructions i12, one or more treating network instructions i1201, one or more treating cellular instructions i1202, one or more treating circuitry instructions i1203, one or more treating microprocessors instructions i1204, one or more treating servers instructions i1205, one or more treating other instructions i1206, one or more treating blowing instructions i1207, one or more treating compressed instructions i1208, one or more treating vacuum instructions i1209, one or more treating ultrasonic instructions i1210, one or more treating electromagnetic instructions i1211, one or more treating abrasives instructions i1212, one or more treating brush instructions i1213, one or more treating chemical instructions i1214, one or more treating tubes instructions i1215, one or more treating nozzles instructions i1216, one or more treating heating instructions i1217, one or more treating blender instructions i1218, and one or more treating cooling instructions i1219.

Figure 29:
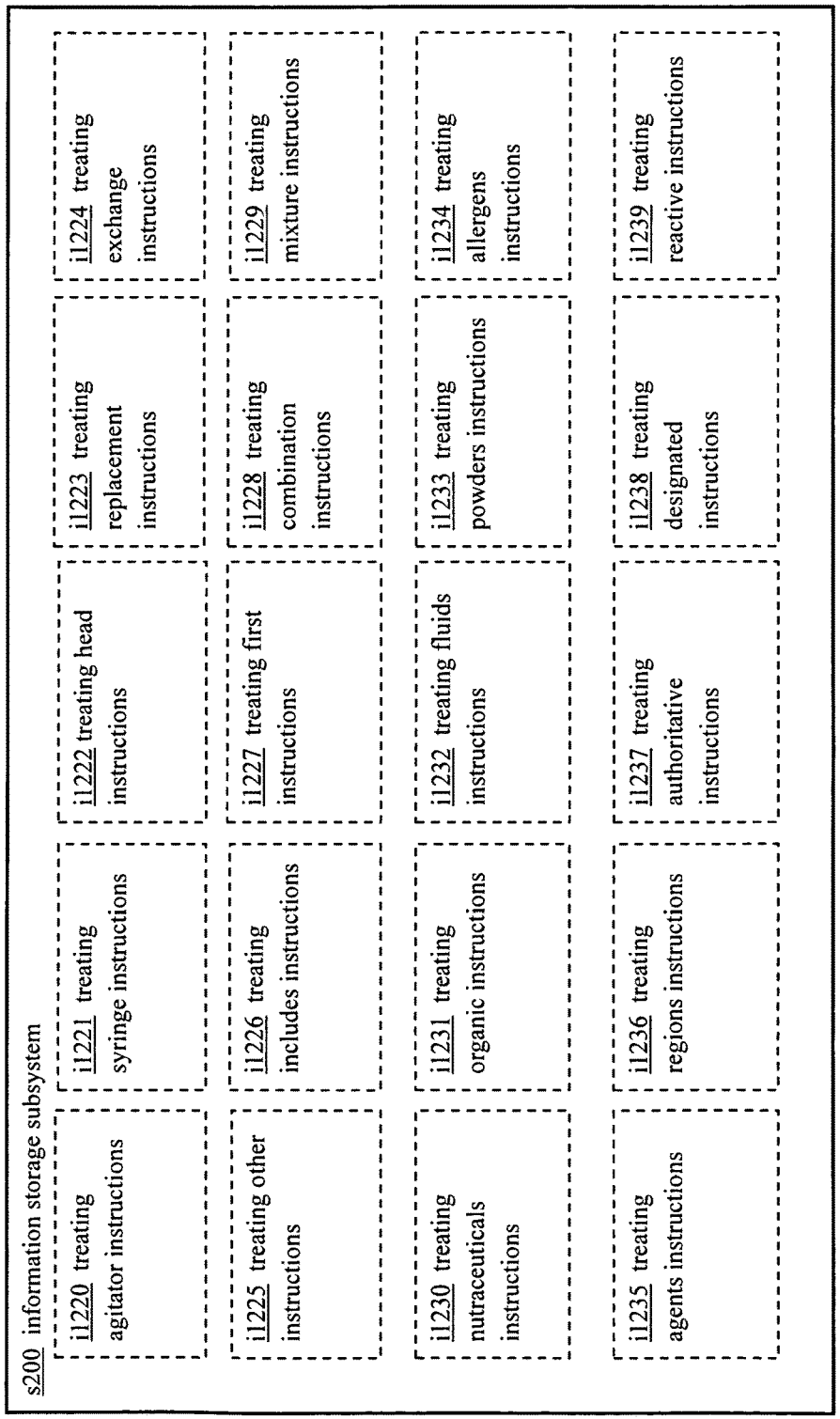
FIG. 29 is a block diagram depicting one or more exemplary instructions of the information storage subsystem s200 of the ingestible product dispensing system 10 of FIG. 1.

One or more exemplary instructions depicted in FIG. 29 as being borne in an exemplary version of a non-transitory signal bearing medium of information storage subsystem s200 include one or more treating agitator instructions i1220, one or more treating syringe instructions i1221, one or more treating head instructions i1222, one or more treating replacement instructions i1223, one or more treating exchange instructions i1224, one or more treating other instructions i1225, one or more treating includes instructions i1226, one or more treating first instructions i1227, one or more treating combination instructions i1228, one or more treating mixture instructions i1229, one or more treating nutraceuticals instructions i1230, one or more treating organic instructions i1231, one or more treating fluids instructions i1232, one or more treating powders instructions i1233, one or more treating allergens instructions i1234, one or more treating agents instructions i1235, one or more treating regions instructions i1236, one or more treating authoritative instructions i1237, one or more treating designated instructions i1238, and one or more treating reactive instructions i1239.

Figure 30:
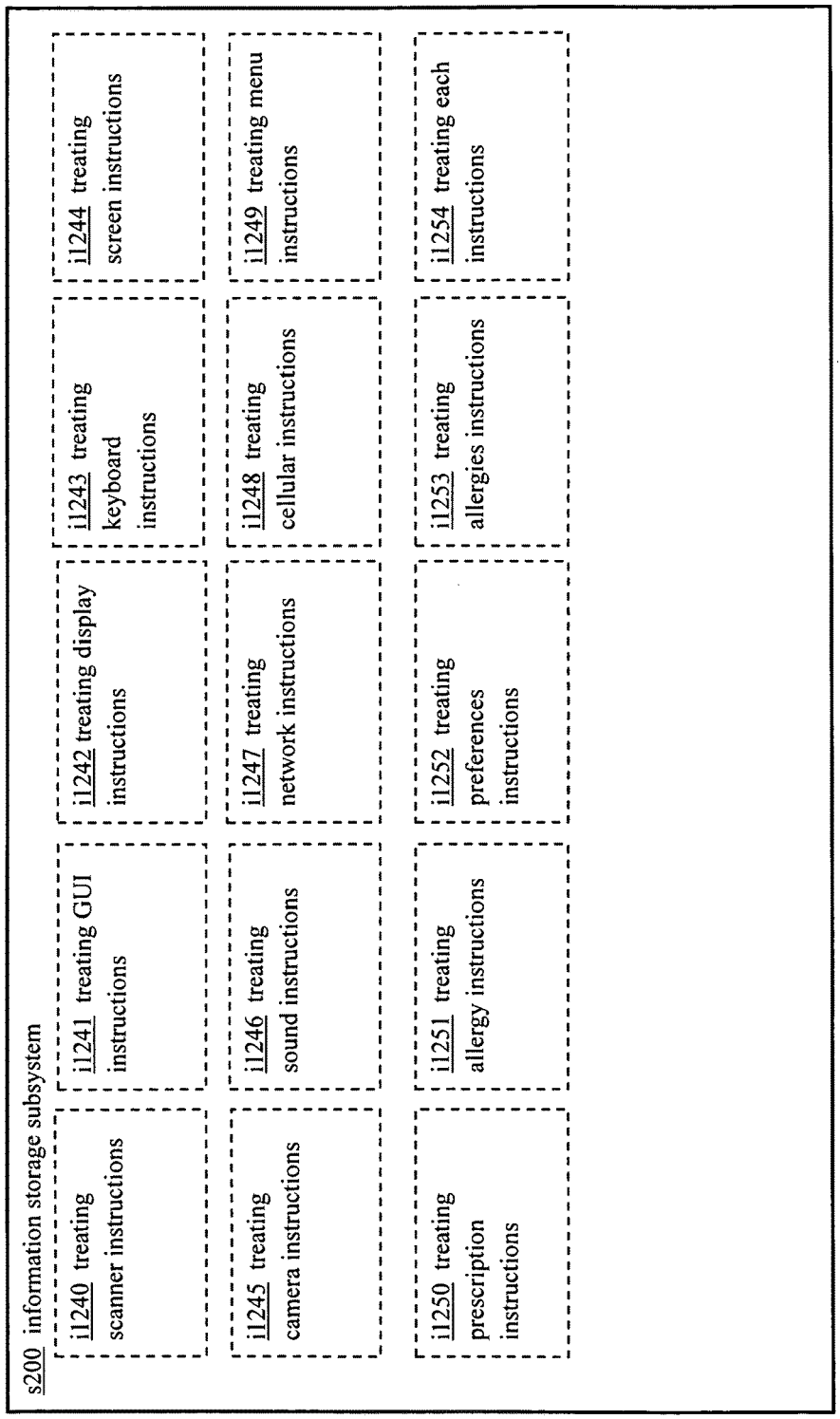
FIG. 30 is a block diagram depicting one or more exemplary instructions of the information storage subsystem s200 of the ingestible product dispensing system 10 of FIG. 1.

One or more exemplary instructions depicted in FIG. 30 as being borne in an exemplary version of a non-transitory signal bearing medium of information storage subsystem s200 include one or more treating scanner instructions i1240, one or more treating GUI instructions i1241, one or more treating display instructions i1242, one or more treating keyboard instructions i1243, one or more treating screen instructions i1244, one or more treating camera instructions i1245, one or more treating sound instructions i1246, one or more treating network instructions i1247, one or more treating cellular instructions i1248, one or more treating menu instructions i1249, one or more treating prescription instructions i1250, one or more treating allergy instructions i1251, one or more treating preferences instructions i1252, one or more treating allergies instructions i1253, and one or more treating each instructions i1254.

Figure 31:
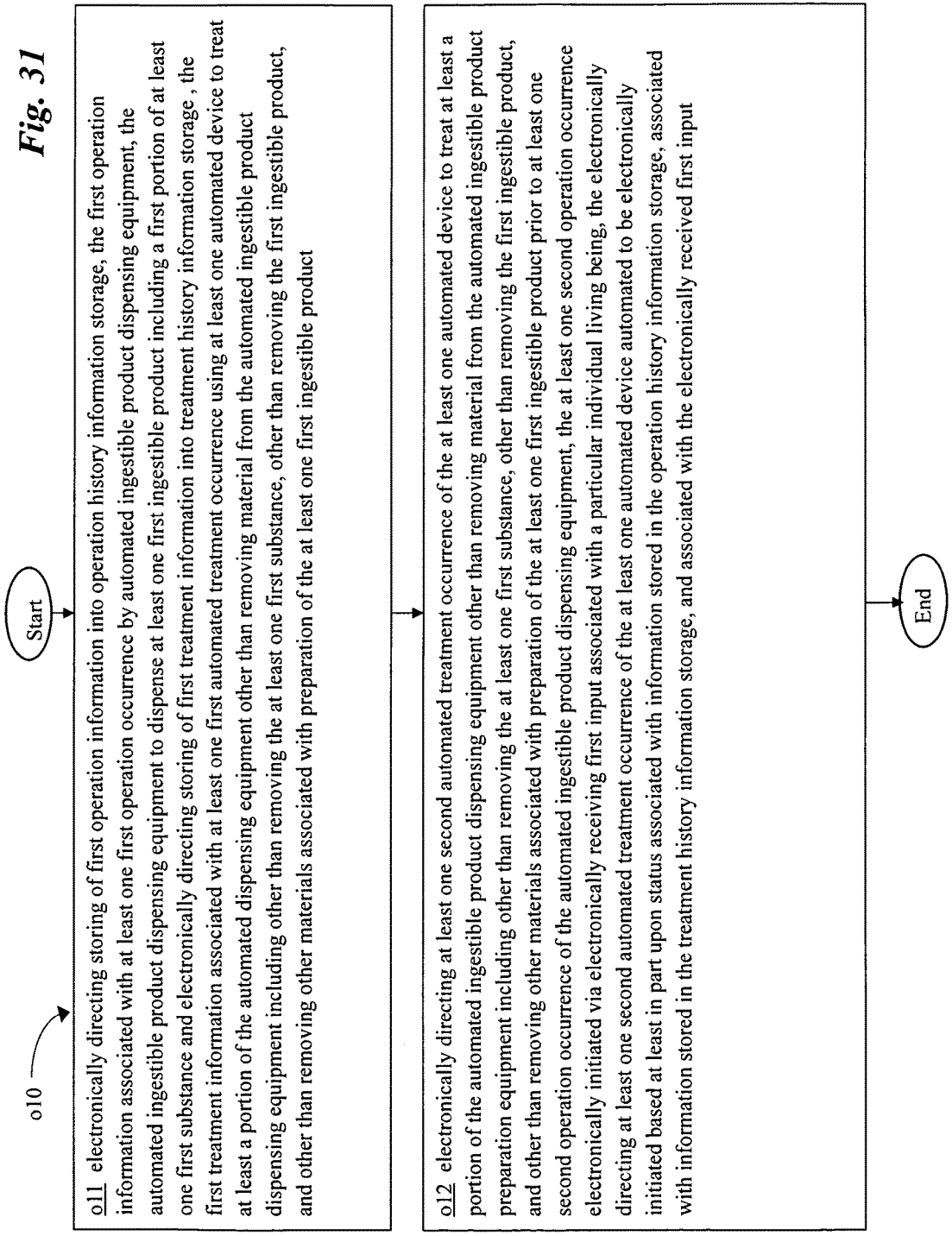
FIG. 31 is a high-level flowchart illustrating an operational flow o10 representing exemplary operations related to electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product, and electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input at least associated with the depicted exemplary implementations of the system.

An operational flow o10 as shown in FIG. 31 represents example operations related to electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product and electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input.

FIG. 31 and those figures that follow may have various examples of operational flows, and explanation may be provided with respect to the above-described examples of FIGS. 1-7 and/or with respect to other examples and contexts. Nonetheless, it should be understood that the operational flows may be executed in a number of other environments and contexts, and/or in modified versions of FIGS. 1-7. Furthermore, although the various operational flows are presented in the sequence(s) illustrated, it should be understood that the various operations may be performed in other orders than those which are illustrated, or may be performed concurrently.

In FIG. 31 and those figures that follow, various operations may be depicted in a box-within-a-box manner. Such depictions may indicate that an operation in an internal box may comprise an optional exemplary implementation of the operational step illustrated in one or more external boxes. However, it should be understood that internal box operations may be viewed as independent operations separate from any associated external boxes and may be performed in any sequence with respect to all other illustrated operations, or may be performed concurrently.

As shown in FIG. 31, the operational flow o10 proceeds to operation o11 for electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product. An exemplary version of a non-transitory signal bearing medium of information storage subsystem s200 is depicted as bearing one or more store and first treating instructions i11 that when executed will direct performance of the operation o11. In an implementation, the one or more store and first treating instructions i11 when executed direct electronically directing storing of first operation information into operation history information storage (e.g. one or more of the microprocessor components s102 of the control and information processing subsystem s100 can direct storing the first operation information into one or more instances of the disk cluster component s226 via the network cable component s502, etc.), the first operation information associated with at least one first operation occurrence by automated ingestible product dispensing equipment, the automated ingestible product dispensing equipment to dispense at least one first ingestible product including a first portion of at least one first substance (e.g. the first operation information contains recorded log information of when the ingestible product treatment system 10 warmed internal surfaces using devices including one or more instances of heating component s702) and electronically directing storing of first treatment information into treatment history information storage (e.g. one or more of the microprocessor components s102 of the control and information processing subsystem s100 can direct storing the first operation information into one or more instances of the other volatile memory component s206, etc.), the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with dispensing of the at least one first ingestible product (e.g. after the internal surfaces are warmed as the first operation occurrence, portions of the ingestible product treatment system 10 are chemically treated using one or more instances of the chemical component s832 as part of the first automated treatment operation occurrence, etc.). Furthermore, the store and first treating electrical circuitry arrangement ("elec circ arrange") e11 when activated will perform the operation o11. In an implementation, the store and first treating electrical circuitry arrangement e11, when activated performs electronically directing storing of first operation information into operation history information storage (e.g. one or more of the microprocessor components s102 of the control and information processing subsystem s100 can direct storing the first operation information into one or more instances of the disk cluster component s226 via the network cable component s502, etc.), the first operation information associated with at least one first operation occurrence by automated ingestible product dispensing equipment, the automated ingestible product dispensing equipment to dispense at least one first ingestible product including a first portion of at least one first substance (e.g. the first operation information contains recorded log information of when the ingestible product treatment system 10 warmed internal surfaces using devices including one or more instances of heating component s702) and electronically directing storing of first treatment information into treatment history information storage (e.g. one or more of the microprocessor components s102 of the control and information processing subsystem s100 can direct storing the first operation information into one or more instances of the other volatile memory component s206, etc.), the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with dispensing of the at least one first ingestible product (e.g. after the internal surfaces are warmed as the first operation occurrence, portions of the ingestible product treatment system 10 are chemically treated using one or more instances of the chemical component s832 as part of the first automated treatment operation occurrence, etc.). In an implementation, the electronically directing storing of first operation information into operation history information storage, the first operation information associated with at least one first operation occurrence by automated ingestible product dispensing equipment, the automated ingestible product dispensing equipment to dispense at least one first ingestible product including a first portion of at least one first substance and electronically directing storing of first treatment information into treatment history information storage, the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with preparation of the at least one first ingestible product is carried out by electronically directing storing of first operation information into operation history information storage (e.g. one or more of the microprocessor components s102 of the control and information processing subsystem s100 can direct storing the first operation information into one or more instances of the disk cluster component s226 via the network cable component s502, etc.), the first operation information associated with at least one first operation occurrence by automated ingestible product dispensing equipment, the automated ingestible product dispensing equipment to dispense at least one first ingestible product including a first portion of at least one first substance (e.g. the first operation information contains recorded log information of when the ingestible product treatment system 10 warmed internal surfaces using devices including one or more instances of heating component s702) and electronically directing storing of first treatment information into treatment history information storage (e.g. one or more of the microprocessor components s102 of the control and information processing subsystem s100 can direct storing the first operation information into one or more instances of the other volatile memory component s206, etc.), the first treatment information associated with at least one first automated treatment occurrence using at least one automated device to treat at least a portion of the automated dispensing equipment other than removing material from the automated ingestible product dispensing equipment including other than removing the at least one first substance, other than removing the first ingestible product, and other than removing other materials associated with dispensing of the at least one first ingestible product (e.g. after the internal surfaces are warmed as the first operation occurrence, portions of the ingestible product treatment system 10 are chemically treated using one or more instances of the chemical component s832 as part of the first automated treatment operation occurrence, etc.).

Figure 32:
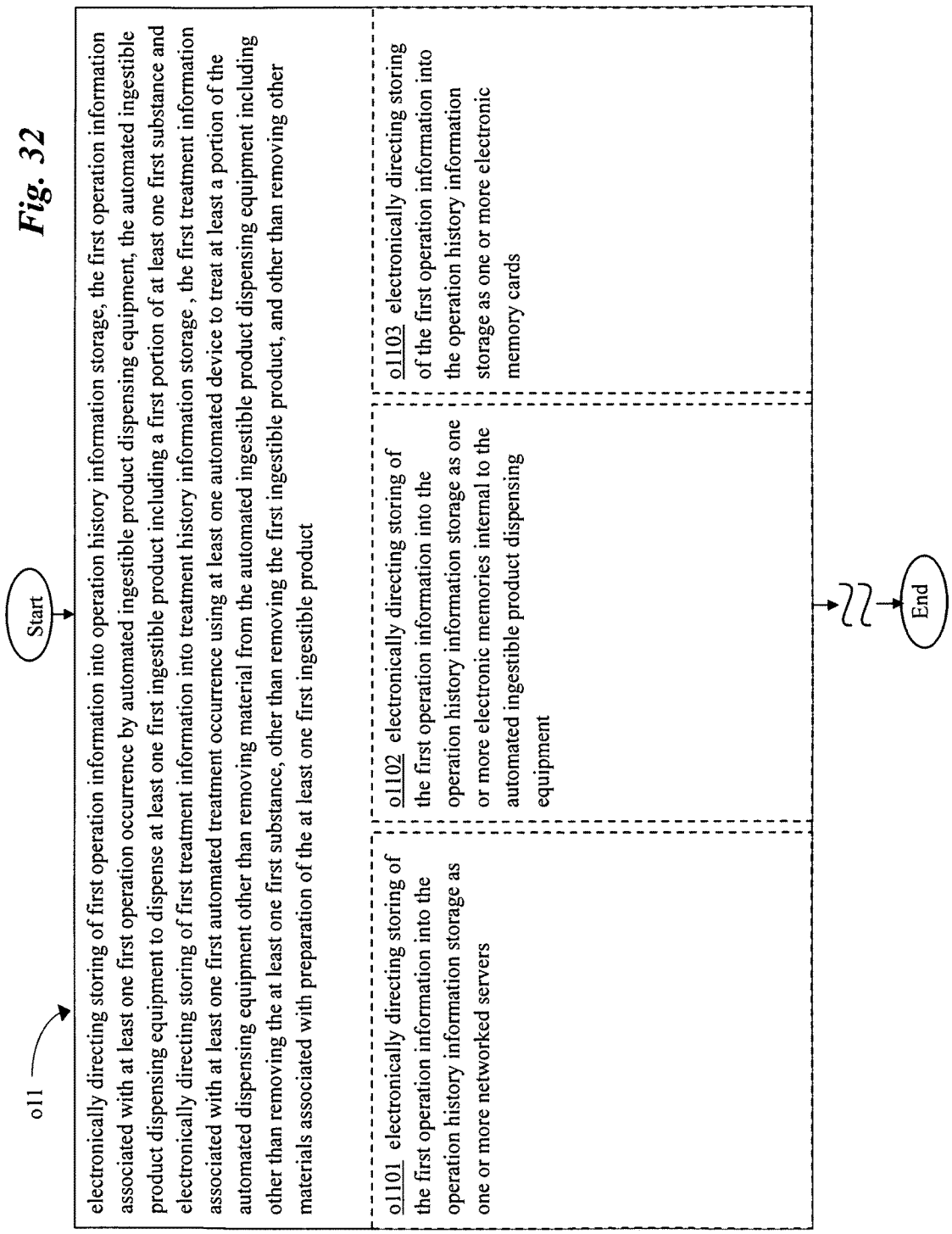
FIG. 32 is a high-level flowchart including exemplary implementations of operation O11 of FIG. 31.

In one or more implementations, as shown in FIG. 32, operation o11 includes an operation o1101 for electronically directing storing of the first operation information into the operation history information storage as one or more networked servers. An exemplary version of a non-transitory signal bearing medium of information storage subsystem s200 is depicted as bearing one or more store servers instructions i1101 that when executed will direct performance of the operation o1101. In an implementation, the one or more store servers instructions i1101 when executed direct electronically directing storing of the first operation information into the operation history information storage as one or more networked servers (e.g. one or more of the microprocessor components s102 of the control and information processing subsystem s100 can direct storing the first operation information into one or more instances of the server component s230 via the wide area network component s512, etc.). Furthermore, the store servers electrical circuitry arrangement ("elec circ arrange") e1101 when activated will perform the operation o1101. In an implementation, the store servers electrical circuitry arrangement e1101, when activated performs electronically directing storing of the first operation information into the operation history information storage as one or more networked servers (e.g. one or more of the microprocessor components s102 of the control and information processing subsystem s100 can direct storing the first operation information into one or more instances of the server component s230 via the wide area network component s512, etc.). In an implementation, the electronically directing storing of the first operation information into the operation history information storage as one or more networked servers is carried out by electronically directing storing of the first operation information into the operation history information storage as one or more networked servers (e.g. one or more of the microprocessor components s102 of the control and information processing subsystem s100 can direct storing the first operation information into one or more instances of the server component s230 via the wide area network component s512, etc.).

In one or more implementations, operation o11 includes an operation o1102 for electronically directing storing of the first operation information into the operation history information storage as one or more electronic memories internal to the automated ingestible product dispensing equipment. An exemplary version of a non-transitory signal bearing medium of information storage subsystem s200 is depicted as bearing one or more store first operation instructions i1102 that when executed will direct performance of the operation o1102. In an implementation, the one or more store first operation instructions i1102 when executed direct electronically directing storing of the first operation information into the operation history information storage as one or more electronic memories internal to the automated ingestible product dispensing equipment (e.g. one or more instances of the central processing unit (CPU) component s104 of the control and information processing subsystem s100 can direct storing the first operation information into one or more instances of the persistent memory component s208, etc.). Furthermore, the store first operation electrical circuitry arrangement e1102 when activated will perform the operation o1102. In an implementation, the store first operation electrical circuitry arrangement e1102, when activated performs electronically directing storing of the first operation information into the operation history information storage as one or more electronic memories internal to the automated ingestible product dispensing equipment (e.g. one or more instances of the central processing unit (CPU) component s104 of the control and information processing subsystem s100 can direct storing the first operation information into one or more instances of the persistent memory component s208, etc.). In an implementation, the electronically directing storing of the first operation information into the operation history information storage as one or more electronic memories internal to the automated ingestible product dispensing equipment is carried out by electronically directing storing of the first operation information into the operation history information storage as one or more electronic memories internal to the automated ingestible product dispensing equipment (e.g. one or more instances of the central processing unit (CPU) component s104 of the control and information processing subsystem s100 can direct storing the first operation information into one or more instances of the persistent memory component s208, etc.).

In one or more implementations, operation o11 includes an operation o1103 for electronically directing storing of the first operation information into the operation history information storage as one or more electronic memory cards. An exemplary version of a non-transitory signal bearing medium of information storage subsystem s200 is depicted as bearing one or more store memory card instructions i1103 that when executed will direct performance of the operation o1103. In an implementation, the one or more store memory card instructions i1103 when executed direct electronically directing storing of the first operation information into the operation history information storage as one or more electronic memory cards (e.g. one or more instances of the digital signal processor (DSP) component s106 of the control and information processing subsystem s100 can direct storing the first operation information into one or more instances of the flash memory component s218 fashioned as memory cards, etc.). Furthermore, the store memory card electrical circuitry arrangement e1103 when activated will perform the operation o1103. In an implementation, the store memory card electrical circuitry arrangement e1103, when activated performs electronically directing storing of the first operation information into the operation history information storage as one or more electronic memory cards (e.g. one or more instances of the digital signal processor (DSP) component s106 of the control and information processing subsystem s100 can direct storing the first operation information into one or more instances of the flash memory component s218 fashioned as memory cards, etc.). In an implementation, the is electronically directing storing of the first operation information into the operation history information storage as one or more electronic memory cards carried out by electronically directing storing of the first operation information into the operation history information storage as one or more electronic memory cards (e.g. one or more instances of the digital signal processor (DSP) component s106 of the control and information processing subsystem s100 can direct storing the first operation information into one or more instances of the flash memory component s218 fashioned as memory cards, etc.).

Figure 33:
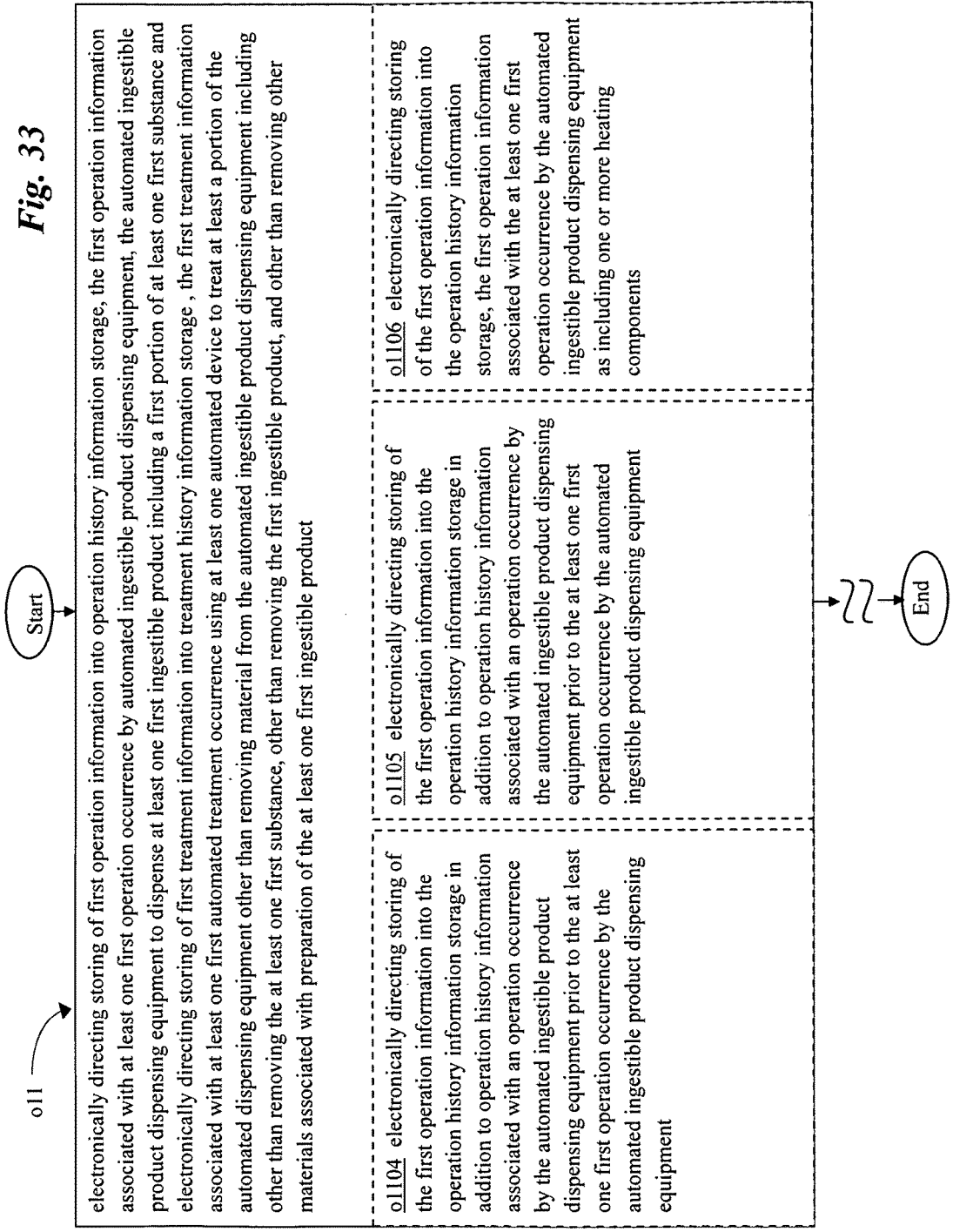
FIG. 33 is a high-level flowchart including exemplary implementations of operation O11 of FIG. 31.

In one or more implementations, as shown in FIG. 33, operation o11 includes an operation o1104 for electronically directing storing of the first operation information into the operation history information storage in addition to operation history information associated with an operation occurrence by the automated ingestible product dispensing equipment prior to the at least one first operation occurrence by the automated ingestible product dispensing equipment. An exemplary version of a non-transitory signal bearing medium of information storage subsystem s200 is depicted as bearing one or more store first prior instructions i1104 that when executed will direct performance of the operation o1104. In an implementation, the one or more store first prior instructions i1104 when executed direct electronically directing storing of the first operation information into the operation history information storage in addition to operation history information associated with an operation occurrence by the automated ingestible product dispensing equipment of the at least one first ingestible product prior to the at least one first operation occurrence by the automated ingestible product dispensing equipment of the at least one first ingestible product (e.g. one or more instances of the application specific integrated circuit (ASIC) component s108 of the control and information processing subsystem s100 can direct storing the first operation information into one or more instances of the random access memory (RAM) component s202 along with information about other operation prior to the first operation information, etc.). Furthermore, the store first prior electrical circuitry arrangement e1104 when activated will perform the operation o1104. In an implementation, the store first prior electrical circuitry arrangement e1104, when activated performs electronically directing storing of the first operation information into the operation history information storage in addition to operation history information associated with an operation occurrence by the automated ingestible product dispensing equipment of the at least one first ingestible product prior to the at least one first operation occurrence by the automated ingestible product dispensing equipment of the at least one first ingestible product (e.g. one or more instances of the application specific integrated circuit (ASIC) component s108 of the control and information processing subsystem s100 can direct storing the first operation information into one or more instances of the random access memory (RAM) component s202 along with information about other operation prior to the first operation information, etc.). In an implementation, the is electronically directing storing of the first operation information into the operation history information storage in addition to operation history information associated with an operation occurrence by the automated ingestible product dispensing equipment prior to the at least one first operation occurrence by the automated ingestible product dispensing equipment carried out by electronically directing storing of the first operation information into the operation history information storage in addition to operation history information associated with an operation occurrence by the automated ingestible product dispensing equipment of the at least one first ingestible product prior to the at least one first operation occurrence by the automated ingestible product dispensing equipment of the at least one first ingestible product (e.g. one or more instances of the application specific integrated circuit (ASIC) component s108 of the control and information processing subsystem s100 can direct storing the first operation information into one or more instances of the random access memory (RAM) component s202 along with information about other operation prior to the first operation information, etc.).

In one or more implementations, operation o11 includes an operation o1105 for electronically directing storing of the first operation information into the operation history information storage in addition to operation history information associated with an operation occurrence by the automated ingestible product dispensing equipment prior to the at least one first operation occurrence by the automated ingestible product dispensing equipment. An exemplary version of a non-transitory signal bearing medium of information storage subsystem s200 is depicted as bearing one or more store prior other instructions i1105 that when executed will direct performance of the operation o1105. In an implementation, the one or more store prior other instructions i1105 when executed direct electronically directing storing of the first operation information into the operation history information storage in addition to operation history information associated with an operation occurrence by the automated ingestible product dispensing equipment of the at least one first ingestible product prior to the at least one first operation occurrence by the automated ingestible product dispensing equipment of the at least one first ingestible product (e.g. one or more instances of the field programmable gate array (FPGA) component s110 of the control and information processing subsystem s100 can direct storing the first operation information into one or more instances of the dynamic random access memory (DRAM) component s204 along with information about operations such as restocking operations prior to the first operation information, etc.). Furthermore, the store prior other electrical circuitry arrangement e1105 when activated will perform the operation o1105. In an implementation, the store prior other electrical circuitry arrangement e1105, when activated performs electronically directing storing of the first operation information into the operation history information storage in addition to operation history information associated with an operation occurrence by the automated ingestible product dispensing equipment of the at least one first ingestible product prior to the at least one first operation occurrence by the automated ingestible product dispensing equipment of the at least one first ingestible product (e.g. one or more instances of the field programmable gate array (FPGA) component s110 of the control and information processing subsystem s100 can direct storing the first operation information into one or more instances of the dynamic random access memory (DRAM) component s204 along with information about operations such as restocking operations prior to the first operation information, etc.). In an implementation, the electronically directing storing of the first operation information into the operation history information storage in addition to operation history information associated with an operation occurrence by the automated ingestible product dispensing equipment prior to the at least one first operation occurrence by the automated ingestible product dispensing equipment is carried out by electronically directing storing of the first operation information into the operation history information storage in addition to operation history information associated with an operation occurrence by the automated ingestible product dispensing equipment of the at least one first ingestible product prior to the at least one first operation occurrence by the automated ingestible product dispensing equipment of the at least one first ingestible product (e.g. one or more instances of the field programmable gate array (FPGA) component s110 of the control and information processing subsystem s100 can direct storing the first operation information into one or more instances of the dynamic random access memory (DRAM) component s204 along with information about operations such as restocking operations prior to the first operation information, etc.).

In one or more implementations, operation o11 includes an operation o1106 for electronically directing storing of the first operation information into the operation history information storage, the first operation information associated with the at least one first operation occurrence by the automated ingestible product dispensing equipment as including one or more heating components. An exemplary version of a non-transitory signal bearing medium of information storage subsystem s200 is depicted as bearing one or more equipment heating instructions i1106 that when executed will direct performance of the operation o1106. In an implementation, the one or more equipment heating instructions i1106 when executed direct electronically directing storing of the first operation information into the operation history information storage, the first operation information associated with the at least one first operation occurrence by the automated ingestible product dispensing equipment of the at least one first ingestible product as including one or more heating components (e.g. one or more of instances of the multiprocessor component s112 of the control and information processing subsystem s100 can direct storing the first operation information into one or more instances of the other volatile memory component s206, the first operation occurrence involving one or more instances of the heating component s702, etc.). Furthermore, the equipment heating electrical circuitry arrangement e1106 when activated will perform the operation o1106. In an implementation, the equipment heating electrical circuitry arrangement e1106, when activated performs electronically directing storing of the first operation information into the operation history information storage, the first operation information associated with the at least one first operation occurrence by the automated ingestible product dispensing equipment of the at least one first ingestible product as including one or more heating components (e.g. one or more of instances of the multiprocessor component s112 of the control and information processing subsystem s100 can direct storing the first operation information into one or more instances of the other volatile memory component s206, the first operation occurrence involving one or more instances of the heating component s702, etc.). In an implementation, the electronically directing storing of the first operation information into the operation history information storage, the first operation information associated with the at least one first operation occurrence by the automated ingestible product dispensing equipment as including one or more heating components is carried out by electronically directing storing of the first operation information into the operation history information storage, the first operation information associated with the at least one first operation occurrence by the automated ingestible product dispensing equipment of the at least one first ingestible product as including one or more heating components (e.g. one or more of instances of the multiprocessor component s112 of the control and information processing subsystem s100 can direct storing the first operation information into one or more instances of the other volatile memory component s206, the first operation occurrence involving one or more instances of the heating component s702, etc.).

Figure 34:
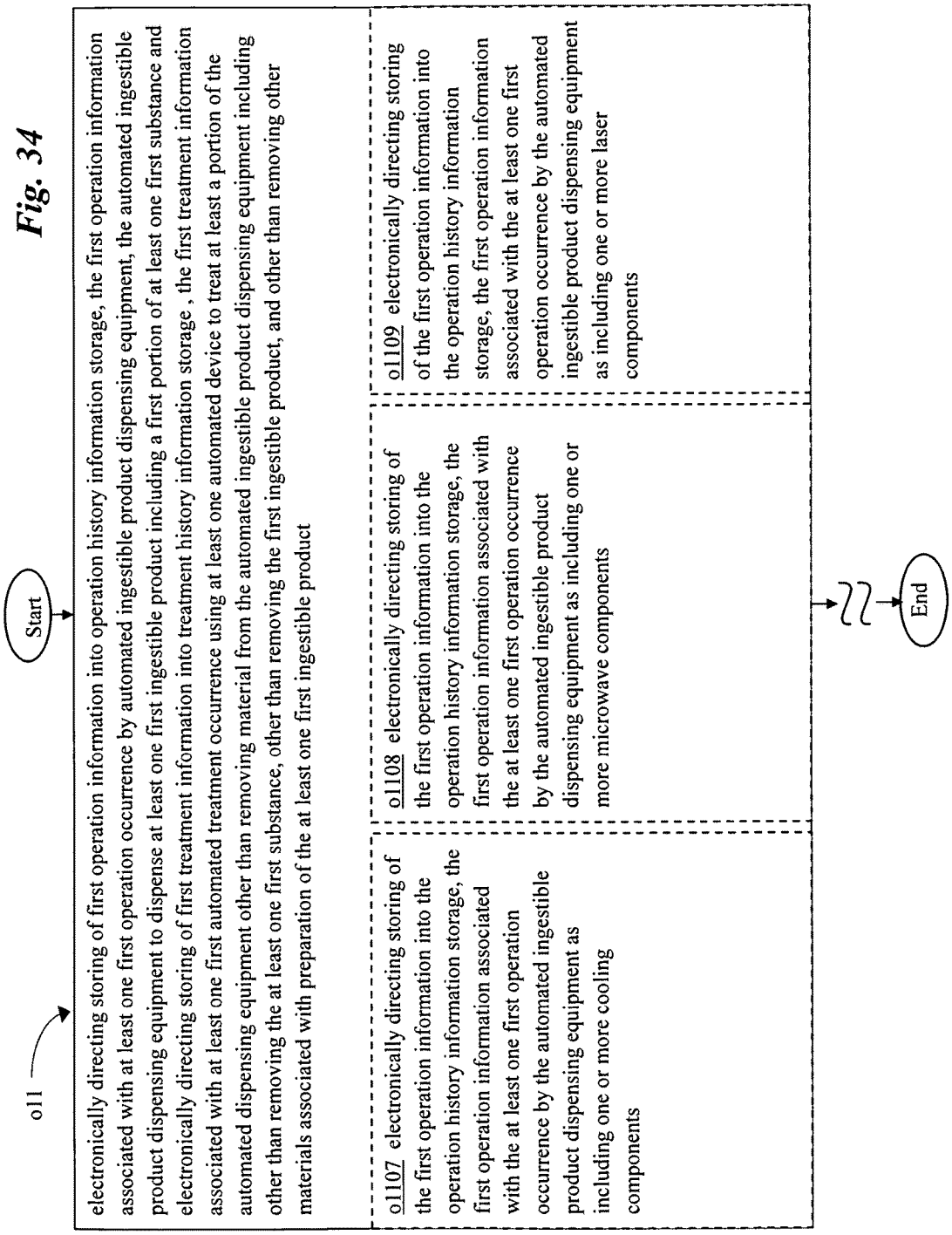
FIG. 34 is a high-level flowchart including exemplary implementations of operation O11 of FIG. 31.

In one or more implementations, as shown in FIG. 34, operation o11 includes an operation o1107 for electronically directing storing of the first operation information into the operation history information storage, the first operation information associated with the at least one first operation occurrence by the automated ingestible product dispensing equipment as including one or more cooling components. An exemplary version of a non-transitory signal bearing medium of information storage subsystem s200 is depicted as bearing one or more equipment cooling instructions i1107 that when executed will direct performance of the operation o1107. In an implementation, the one or more equipment cooling instructions i1107 when executed direct electronically directing storing of the first operation information into the operation history information storage, the first operation information associated with the at least one first operation occurrence by the automated ingestible product dispensing equipment of the at least one first ingestible product as including one or more cooling components (e.g. one or more of instances of the optical processing component s114 of the control and information processing subsystem s100 can direct storing the first operation information into one or more instances of the persistent memory component s208, the first operation occurrence involving one or more instances of the cooling component s704, etc.). Furthermore, the equipment cooling electrical circuitry arrangement e1107 when activated will perform the operation o1107. In an implementation, the equipment cooling electrical circuitry arrangement e1107, when activated performs electronically directing storing of the first operation information into the operation history information storage, the first operation information associated with the at least one first operation occurrence by the automated ingestible product dispensing equipment of the at least one first ingestible product as including one or more cooling components (e.g. one or more of instances of the optical processing component s114 of the control and information processing subsystem s100 can direct storing the first operation information into one or more instances of the persistent memory component s208, the first operation occurrence involving one or more instances of the cooling component s704, etc.). In an implementation, the electronically directing storing of the first operation information into the operation history information storage, the first operation information associated with the at least one first operation occurrence by the automated ingestible product dispensing equipment as including one or more cooling components is carried out by electronically directing storing of the first operation information into the operation history information storage, the first operation information associated with the at least one first operation occurrence by the automated ingestible product dispensing equipment of the at least one first ingestible product as including one or more cooling components (e.g. one or more of instances of the optical processing component s114 of the control and information processing subsystem s100 can direct storing the first operation information into one or more instances of the persistent memory component s208, the first operation occurrence involving one or more instances of the cooling component s704, etc.).

In one or more implementations, operation o11 includes an operation o1108 for electronically directing storing of the first operation information into the operation history information storage, the first operation information associated with the at least one first operation occurrence by the automated ingestible product dispensing equipment as including one or more microwave components. An exemplary version of a non-transitory signal bearing medium of information storage subsystem s200 is depicted as bearing one or more equipment microwave instructions i1108 that when executed will direct performance of the operation o1108. In an implementation, the one or more equipment microwave instructions i1108 when executed direct electronically directing storing of the first operation information into the operation history information storage, the first operation information associated with the at least one first operation occurrence by the automated ingestible product dispensing equipment of the at least one first ingestible product as including one or more microwave components (e.g. one or more of instances of the microprocessor component s102 of the control and information processing subsystem s100 can direct storing the first operation information into one or more instances of the read only memory (ROM) component s210, the first operation occurrence involving one or more instances of the microwave component s706, etc.). Furthermore, the equipment microwave electrical circuitry arrangement e1108 when activated will perform the operation o1108. In an implementation, the equipment microwave electrical circuitry arrangement e1108, when activated performs electronically directing storing of the first operation information into the operation history information storage, the first operation information associated with the at least one first operation occurrence by the automated ingestible product dispensing equipment of the at least one first ingestible product as including one or more microwave components (e.g. one or more of instances of the microprocessor component s102 of the control and information processing subsystem s100 can direct storing the first operation information into one or more instances of the read only memory (ROM) component s210, the first operation occurrence involving one or more instances of the microwave component s706, etc.). In an implementation, the electronically directing storing of the first operation information into the operation history information storage, the first operation information associated with the at least one first operation occurrence by the automated ingestible product dispensing equipment as including one or more microwave components is carried out by electronically directing storing of the first operation information into the operation history information storage, the first operation information associated with the at least one first operation occurrence by the automated ingestible product dispensing equipment of the at least one first ingestible product as including one or more microwave components (e.g. one or more of instances of the microprocessor component s102 of the control and information processing subsystem s100 can direct storing the first operation information into one or more instances of the read only memory (ROM) component s210, the first operation occurrence involving one or more instances of the microwave component s706, etc.).

In one or more implementations, operation o11 includes an operation o1109 for electronically directing storing of the first operation information into the operation history information storage, the first operation information associated with the at least one first operation occurrence by the automated ingestible product dispensing equipment as including one or more laser components. An exemplary version of a non-transitory signal bearing medium of information storage subsystem s200 is depicted as bearing one or more equipment laser instructions i1109 that when executed will direct performance of the operation o1109. In an implementation, the one or more equipment laser instructions i1109 when executed direct electronically directing storing of the first operation information into the operation history information storage, the first operation information associated with the at least one first operation occurrence by the automated ingestible product dispensing equipment of the at least one first ingestible product as including one or more laser components (e.g. one or more of instances of the central processing unit (CPU) component s104 of the control and information processing subsystem s100 can direct storing the first operation information into one or more instances of the electrically erasable programmable read only memory (EEPROM) component s212, the first operation occurrence involving one or more instances of the laser component s708, etc.). Furthermore, the equipment laser electrical circuitry arrangement e1109 when activated will perform the operation o1109. In an implementation, the equipment laser electrical circuitry arrangement e1109, when activated performs electronically directing storing of the first operation information into the operation history information storage, the first operation information associated with the at least one first operation occurrence by the automated ingestible product dispensing equipment of the at least one first ingestible product as including one or more laser components (e.g. one or more of instances of the central processing unit (CPU) component s104 of the control and information processing subsystem s100 can direct storing the first operation information into one or more instances of the electrically erasable programmable read only memory (EEPROM) component s212, the first operation occurrence involving one or more instances of the laser component s708, etc.). In an implementation, the electronically directing storing of the first operation information into the operation history information storage, the first operation information associated with the at least one first operation occurrence by the automated ingestible product dispensing equipment as including one or more laser components is carried out by electronically directing storing of the first operation information into the operation history information storage, the first operation information associated with the at least one first operation occurrence by the automated ingestible product dispensing equipment of the at least one first ingestible product as including one or more laser components (e.g. one or more of instances of the central processing unit (CPU) component s104 of the control and information processing subsystem s100 can direct storing the first operation information into one or more instances of the electrically erasable programmable read only memory (EEPROM) component s212, the first operation occurrence involving one or more instances of the laser component s708, etc.).

Figure 35:
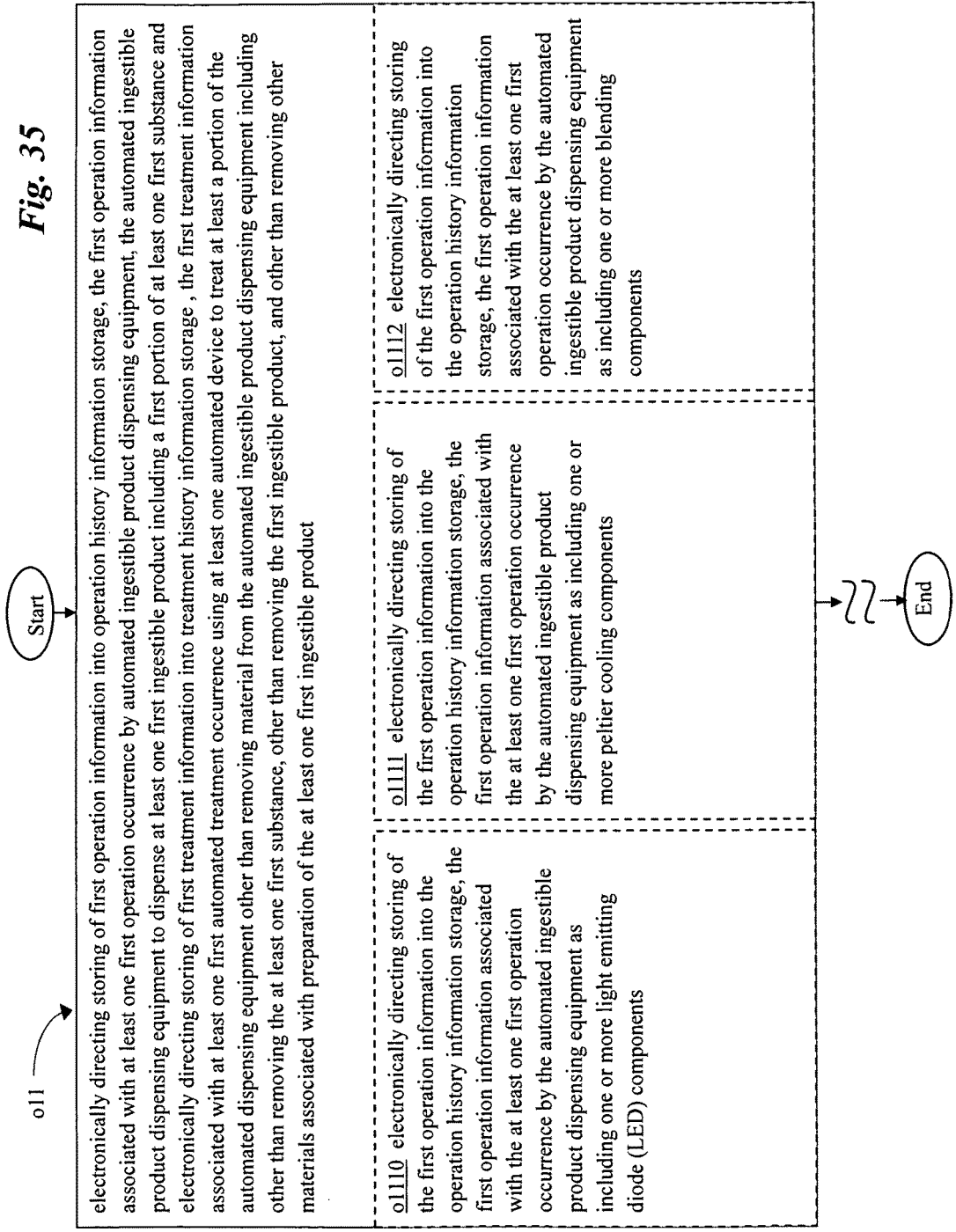
FIG. 35 is a high-level flowchart including exemplary implementations of operation O11 of FIG. 31.

In one or more implementations, as shown in FIG. 35, operation o11 includes an operation o1110 for electronically directing storing of the first operation information into the operation history information storage, the first operation information associated with the at least one first operation occurrence by the automated ingestible product dispensing equipment as including one or more light emitting diode (LED) components. An exemplary version of a non-transitory signal bearing medium of information storage subsystem s200 is depicted as bearing one or more equipment LED instructions i1110 that when executed will direct performance of the operation o1110. In an implementation, the one or more equipment LED instructions i1110 when executed direct electronically directing storing of the first operation information into the operation history information storage, the first operation information associated with the at least one first operation occurrence by the automated ingestible product dispensing equipment of the at least one first ingestible product as including one or more light emitting diode (LED) components (e.g. one or more of instances of the digital signal processor (DSP) component s106 of the control and information processing subsystem s100 can direct storing the first operation information into one or more instances of the compact disk (CD) component s214, the first operation occurrence involving one or more instances of the light emitting diode (LED) component s710, etc.). Furthermore, the equipment LED electrical circuitry arrangement e1110 when activated will perform the operation o1110. In an implementation, the equipment LED electrical circuitry arrangement e1110, when activated performs electronically directing storing of the first operation information into the operation history information storage, the first operation information associated with the at least one first operation occurrence by the automated ingestible product dispensing equipment of the at least one first ingestible product as including one or more light emitting diode (LED) components (e.g. one or more of instances of the digital signal processor (DSP) component s106 of the control and information processing subsystem s100 can direct storing the first operation information into one or more instances of the compact disk (CD) component s214, the first operation occurrence involving one or more instances of the light emitting diode (LED) component s710, etc.). In an implementation, the electronically directing storing of the first operation information into the operation history information storage, the first operation information associated with the at least one first operation occurrence by the automated ingestible product dispensing equipment as including one or more light emitting diode (LED) components is carried out by electronically directing storing of the first operation information into the operation history information storage, the first operation information associated with the at least one first operation occurrence by the automated ingestible product dispensing equipment of the at least one first ingestible product as including one or more light emitting diode (LED) components (e.g. one or more of instances of the digital signal processor (DSP) component s106 of the control and information processing subsystem s100 can direct storing the first operation information into one or more instances of the compact disk (CD) component s214, the first operation occurrence involving one or more instances of the light emitting diode (LED) component s710, etc.).

In one or more implementations, operation o11 includes an operation o1111 for electronically directing storing of the first operation information into the operation history information storage, the first operation information associated with the at least one first operation occurrence by the automated ingestible product dispensing equipment as including one or more peltier cooling components. An exemplary version of a non-transitory signal bearing medium of information storage subsystem s200 is depicted as bearing one or more equipment peltier instructions i1111 that when executed will direct performance of the operation o1111. In an implementation, the one or more equipment peltier instructions i1111 when executed direct electronically directing storing of the first operation information into the operation history information storage, the first operation information associated with the at least one first operation occurrence by the automated ingestible product dispensing equipment of the at least one first ingestible product as including one or more peltier cooling components (e.g. one or more of instances of the application specific integrated circuit (ASIC) component s108 of the control and information processing subsystem s100 can direct storing the first operation information into one or more instances of the digital versatile disk (DVD) component s216, the first operation occurrence involving one or more instances of the peltier cooling component s712, etc.). Furthermore, equipment peltier electrical circuitry arrangement e1111 when activated will perform the operation o1111. In an implementation, the equipment peltier electrical circuitry arrangement e1111, when activated performs electronically directing storing of the first operation information into the operation history information storage, the first operation information associated with the at least one first operation occurrence by the automated ingestible product dispensing equipment of the at least one first ingestible product as including one or more peltier cooling components (e.g. one or more of instances of the application specific integrated circuit (ASIC) component s108 of the control and information processing subsystem s100 can direct storing the first operation information into one or more instances of the digital versatile disk (DVD) component s216, the first operation occurrence involving one or more instances of the peltier cooling component s712, etc.). In an implementation, the electronically directing storing of the first operation information into the operation history information storage, the first operation information associated with the at least one first operation occurrence by the automated ingestible product dispensing equipment of the at least one first ingestible product as including one or more peltier cooling components is carried out by electronically directing storing of the first operation information into the operation history information storage, the first operation information associated with the at least one first operation occurrence by the automated ingestible product dispensing equipment of the at least one first ingestible product as including one or more peltier cooling components (e.g. one or more of instances of the application specific integrated circuit (ASIC) component s108 of the control and information processing subsystem s100 can direct storing the first operation information into one or more instances of the digital versatile disk (DVD) component s216, the first operation occurrence involving one or more instances of the peltier cooling component s712, etc.).

In one or more implementations, operation o11 includes an operation o1112 for electronically directing storing of the first operation information into the operation history information storage, the first operation information associated with the at least one first operation occurrence by the automated ingestible product dispensing equipment as including one or more blending components. An exemplary version of a non-transitory signal bearing medium of information storage subsystem s200 is depicted as bearing one or more equipment blending instructions i1112 that when executed will direct performance of the operation o1112. In an implementation, the one or more equipment blending instructions i1112 when executed direct electronically directing storing of the first operation information into the operation history information storage, the first operation information associated with the at least one first operation occurrence by the automated ingestible product dispensing equipment of the at least one first ingestible product as including one or more blending components (e.g. one or more of instances of the application specific integrated circuit (ASIC) component s108 of the control and information processing subsystem s100 can direct storing the first operation information into one or more instances of the flash memory component s218, the first operation occurrence involving one or more instances of the blending component s714, etc.). Furthermore, the equipment blending electrical circuitry arrangement e1112 when activated will perform the operation o1112. In an implementation, the equipment blending electrical circuitry arrangement e1112, when activated performs electronically directing storing of the first operation information into the operation history information storage, the first operation information associated with the at least one first operation occurrence by the automated ingestible product dispensing equipment of the at least one first ingestible product as including one or more blending components (e.g. one or more of instances of the application specific integrated circuit (ASIC) component s108 of the control and information processing subsystem s100 can direct storing the first operation information into one or more instances of the flash memory component s218, the first operation occurrence involving one or more instances of the blending component s714, etc.). In an implementation, the electronically directing storing of the first operation information into the operation history information storage, the first operation information associated with the at least one first operation occurrence by the automated ingestible product dispensing equipment as including one or more blending components is carried out by electronically directing storing of the first operation information into the operation history information storage, the first operation information associated with the at least one first operation occurrence by the automated ingestible product dispensing equipment of the at least one first ingestible product as including one or more blending components (e.g. one or more of instances of the application specific integrated circuit (ASIC) component s108 of the control and information processing subsystem s100 can direct storing the first operation information into one or more instances of the flash memory component s218, the first operation occurrence involving one or more instances of the blending component s714, etc.).

Figure 36:
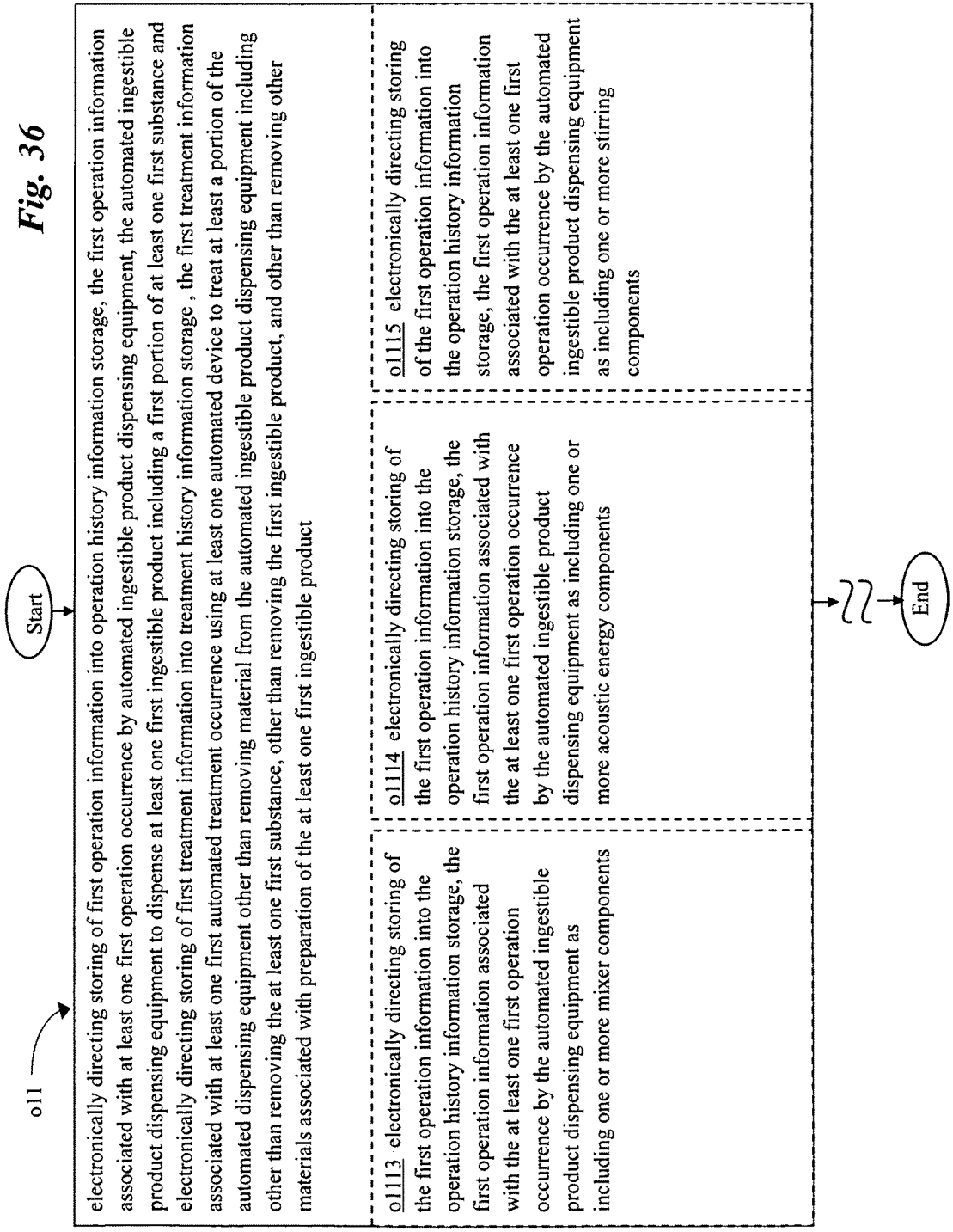
FIG. 36 is a high-level flowchart including exemplary implementations of operation O11 of FIG. 31.

In one or more implementations, as shown in FIG. 36, operation o11 includes an operation o1113 for electronically directing storing of the first operation information into the operation history information storage, the first operation information associated with the at least one first operation occurrence by the automated ingestible product dispensing equipment as including one or more mixer components. An exemplary version of a non-transitory signal bearing medium of information storage subsystem s200 is depicted as bearing one or more equipment mixer instructions i1113 that when executed will direct performance of the operation o1113. In an implementation, the one or more equipment mixer instructions i1113 when executed direct electronically directing storing of the first operation information into the operation history information storage, the first operation information associated with the at least one first operation occurrence by the automated ingestible product dispensing equipment of the at least one first ingestible product as including one or more mixer components (e.g. one or more of instances of the field programmable gate array (FPGA) component s110 of the control and information processing subsystem s100 can direct storing the first operation information into one or more instances of the other nonvolatile memory component s220, the first operation occurrence involving one or more instances of the mixer component s716, etc.). Furthermore, the equipment mixer electrical circuitry arrangement e1113 when activated will perform the operation o1113. In an implementation, the equipment mixer electrical circuitry arrangement e1113, when activated performs electronically directing storing of the first operation information into the operation history information storage, the first operation information associated with the at least one first operation occurrence by the automated ingestible product dispensing equipment of the at least one first ingestible product as including one or more mixer components (e.g. one or more of instances of the field programmable gate array (FPGA) component s110 of the control and information processing subsystem s100 can direct storing the first operation information into one or more instances of the other nonvolatile memory component s220, the first operation occurrence involving one or more instances of the mixer component s716, etc.). In an implementation, the electronically directing storing of the first operation information into the operation history information storage, the first operation information associated with the at least one first operation occurrence by the automated ingestible product dispensing equipment as including one or more mixer components is carried out by electronically directing storing of the first operation information into the operation history information storage, the first operation information associated with the at least one first operation occurrence by the automated ingestible product dispensing equipment of the at least one first ingestible product as including one or more mixer components (e.g. one or more of instances of the field programmable gate array (FPGA) component s110 of the control and information processing subsystem s100 can direct storing the first operation information into one or more instances of the other nonvolatile memory component s220, the first operation occurrence involving one or more instances of the mixer component s716, etc.).

In one or more implementations, operation o11 includes an operation o1114 for electronically directing storing of the first operation information into the operation history information storage, the first operation information associated with the at least one first operation occurrence by the automated ingestible product dispensing equipment as including one or more acoustic energy components. An exemplary version of a non-transitory signal bearing medium of information storage subsystem s200 is depicted as bearing one or more equipment acoustic instructions i1114 that when executed will direct performance of the operation o1114. In an implementation, the one or more equipment acoustic instructions i1114 when executed direct electronically directing storing of the first operation information into the operation history information storage, the first operation information associated with the at least one first operation occurrence by the automated ingestible product dispensing equipment of the at least one first ingestible product as including one or more acoustic energy components (e.g. one or more of instances of the multiprocessor component s112 of the control and information processing subsystem s100 can direct storing the first operation information into one or more instances of the hard drive component s222, the first operation occurrence involving one or more instances of the acoustic energy component s718, etc.). Furthermore, the equipment acoustic electrical circuitry arrangement e1114 when activated will perform the operation o1114. In an implementation, the equipment acoustic electrical circuitry arrangement e1114, when activated performs electronically directing storing of the first operation information into the operation history information storage, the first operation information associated with the at least one first operation occurrence by the automated ingestible product dispensing equipment of the at least one first ingestible product as including one or more acoustic energy components (e.g. one or more of instances of the multiprocessor component s112 of the control and information processing subsystem s100 can direct storing the first operation information into one or more instances of the hard drive component s222, the first operation occurrence involving one or more instances of the acoustic energy component s718, etc.). In an implementation, the electronically directing storing of the first operation information into the operation history information storage, the first operation information associated with the at least one first operation occurrence by the automated ingestible product dispensing equipment as including one or more acoustic energy components is carried out by electronically directing storing of the first operation information into the operation history information storage, the first operation information associated with the at least one first operation occurrence by the automated ingestible product dispensing equipment of the at least one first ingestible product as including one or more acoustic energy components (e.g. one or more of instances of the multiprocessor component s112 of the control and information processing subsystem s100 can direct storing the first operation information into one or more instances of the hard drive component s222, the first operation occurrence involving one or more instances of the acoustic energy component s718, etc.).

In one or more implementations, operation o11 includes an operation o1115 for electronically directing storing of the first operation information into the operation history information storage, the first operation information associated with the at least one first operation occurrence by the automated ingestible product dispensing equipment as including one or more stirring components. An exemplary version of a non-transitory signal bearing medium of information storage subsystem s200 is depicted as bearing one or more equipment stirring instructions i1115 that when executed will direct performance of the operation o1115. In an implementation, the one or more equipment stirring instructions i1115 when executed direct electronically directing storing of the first operation information into the operation history information storage, the first operation information associated with the at least one first operation occurrence by the automated ingestible product dispensing equipment of the at least one first ingestible product as including one or more stirring components (e.g. one or more of instances of the optical processing component s114 of the control and information processing subsystem s100 can direct storing the first operation information into one or more instances of the disk farm component s224, the first operation occurrence involving one or more instances of the stirring component s720, etc.). Furthermore, the equipment stirring electrical circuitry arrangement e1115 when activated will perform the operation o1115. In an implementation, the equipment stirring electrical circuitry arrangement e1115, when activated performs electronically directing storing of the first operation information into the operation history information storage, the first operation information associated with the at least one first operation occurrence by the automated ingestible product dispensing equipment of the at least one first ingestible product as including one or more stirring components (e.g. one or more of instances of the optical processing component s114 of the control and information processing subsystem s100 can direct storing the first operation information into one or more instances of the disk farm component s224, the first operation occurrence involving one or more instances of the stirring component s720, etc.). In an implementation, the electronically directing storing of the first operation information into the operation history information storage, the first operation information associated with the at least one first operation occurrence by the automated ingestible product dispensing equipment as including one or more stirring components is carried out by electronically directing storing of the first operation information into the operation history information storage, the first operation information associated with the at least one first operation occurrence by the automated ingestible product dispensing equipment of the at least one first ingestible product as including one or more stirring components (e.g. one or more of instances of the optical processing component s114 of the control and information processing subsystem s100 can direct storing the first operation information into one or more instances of the disk farm component s224, the first operation occurrence involving one or more instances of the stirring component s720, etc.).

Figure 37:
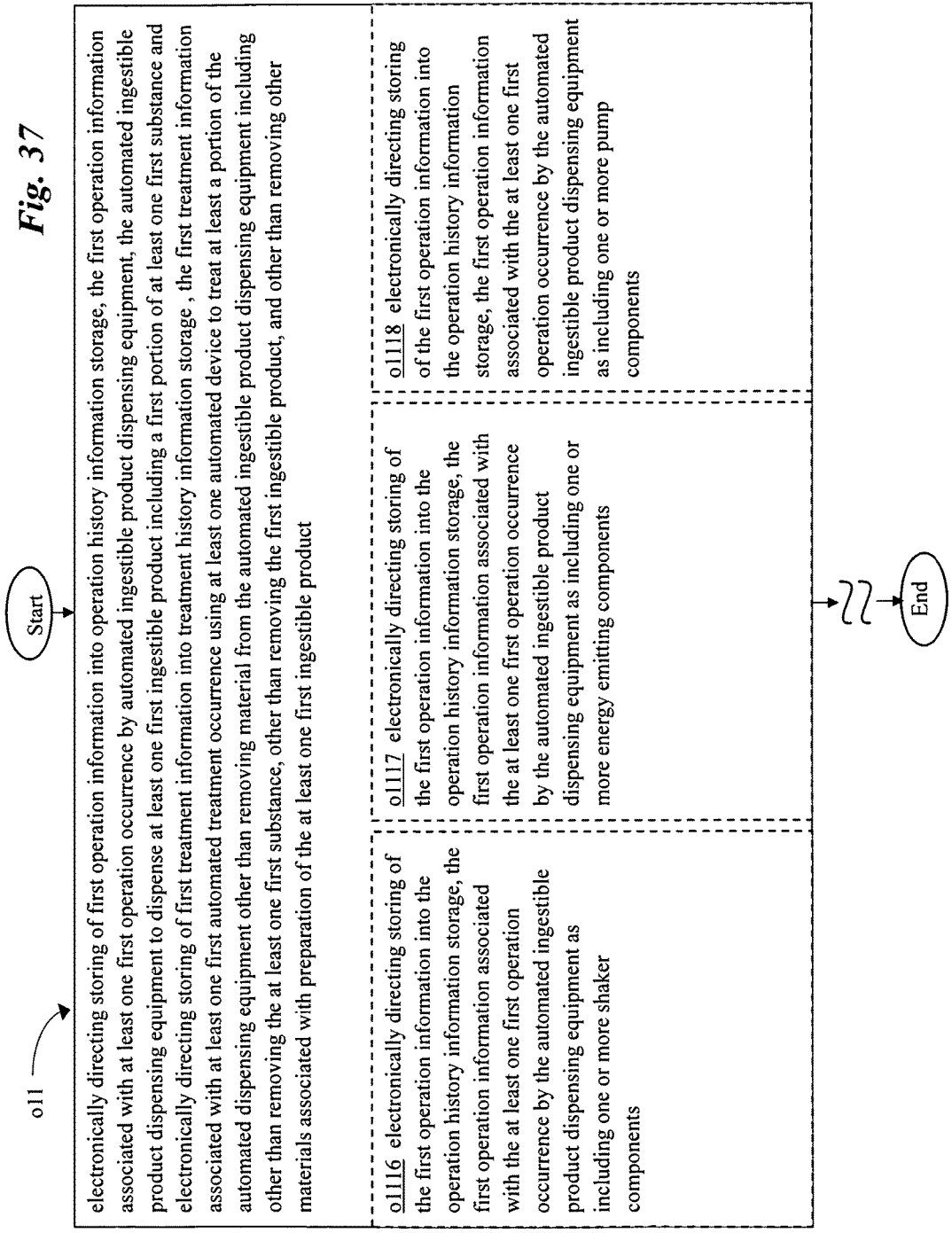
FIG. 37 is a high-level flowchart including exemplary implementations of operation O11 of FIG. 31.

In one or more implementations, as shown in FIG. 37, operation o11 includes an operation o1116 for electronically directing storing of the first operation information into the operation history information storage, the first operation information associated with the at least one first operation occurrence by the automated ingestible product dispensing equipment as including one or more shaker components. An exemplary version of a non-transitory signal bearing medium of information storage subsystem s200 is depicted as bearing one or more equipment shaker instructions i1116 that when executed will direct performance of the operation o1116. In an implementation, the one or more equipment shaker instructions i1116 when executed direct electronically directing storing of the first operation information into the operation history information storage, the first operation information associated with the at least one first operation occurrence by the automated ingestible product dispensing equipment of the at least one first ingestible product as including one or more shaker components (e.g. one or more of instances of the microprocessor component s102 of the control and information processing subsystem s100 can direct storing the first operation information into one or more instances of the disk cluster component s226, the first operation occurrence involving one or more instances of the shaker component s722, etc.). Furthermore, the equipment shaker electrical circuitry arrangement e1116 when activated will perform the operation o1116. In an implementation, the equipment shaker electrical circuitry arrangement e1116, when activated performs electronically directing storing of the first operation information into the operation history information storage, the first operation information associated with the at least one first operation occurrence by the automated ingestible product dispensing equipment of the at least one first ingestible product as including one or more shaker components (e.g. one or more of instances of the microprocessor component s102 of the control and information processing subsystem s100 can direct storing the first operation information into one or more instances of the disk cluster component s226, the first operation occurrence involving one or more instances of the shaker component s722, etc.). In an implementation, the electronically directing storing of the first operation information into the operation history information storage, the first operation information associated with the at least one first operation occurrence by the automated ingestible product dispensing equipment as including one or more shaker components is carried out by electronically directing storing of the first operation information into the operation history information storage, the first operation information associated with the at least one first operation occurrence by the automated ingestible product dispensing equipment of the at least one first ingestible product as including one or more shaker components (e.g. one or more of instances of the microprocessor component s102 of the control and information processing subsystem s100 can direct storing the first operation information into one or more instances of the disk cluster component s226, the first operation occurrence involving one or more instances of the shaker component s722, etc.).

In one or more implementations, operation o11 includes an operation o1117 for electronically directing storing of the first operation information into the operation history information storage, the first operation information associated with the at least one first operation occurrence by the automated ingestible product dispensing equipment as including one or more energy emitting components. An exemplary version of a non-transitory signal bearing medium of information storage subsystem s200 is depicted as bearing one or more equipment energy instructions i1117 that when executed will direct performance of the operation o1117. In an implementation, the one or more equipment energy instructions i1117 when executed direct electronically directing storing of the first operation information into the operation history information storage, the first operation information associated with the at least one first operation occurrence by the automated ingestible product dispensing equipment of the at least one first ingestible product as including one or more energy emitting components (e.g. one or more of instances of the central processing unit (CPU) component s104 of the control and information processing subsystem s100 can direct storing the first operation information into one or more instances of the remote backup component s228, the first operation occurrence involving one or more instances of the energy emitting component s724, etc.). Furthermore, the equipment energy electrical circuitry arrangement e1117 when activated will perform the operation o1117. In an implementation, the equipment energy electrical circuitry arrangement e1117, when activated performs electronically directing storing of the first operation information into the operation history information storage, the first operation information associated with the at least one first operation occurrence by the automated ingestible product dispensing equipment of the at least one first ingestible product as including one or more energy emitting components (e.g. one or more of instances of the central processing unit (CPU) component s104 of the control and information processing subsystem s100 can direct storing the first operation information into one or more instances of the remote backup component s228, the first operation occurrence involving one or more instances of the energy emitting component s724, etc.). In an implementation, the electronically directing storing of the first operation information into the operation history information storage, the first operation information associated with the at least one first operation occurrence by the automated ingestible product dispensing equipment as including one or more energy emitting components is carried out by electronically directing storing of the first operation information into the operation history information storage, the first operation information associated with the at least one first operation occurrence by the automated ingestible product dispensing equipment of the at least one first ingestible product as including one or more energy emitting components (e.g. one or more of instances of the central processing unit (CPU) component s104 of the control and information processing subsystem s100 can direct storing the first operation information into one or more instances of the remote backup component s228, the first operation occurrence involving one or more instances of the energy emitting component s724, etc.).

In one or more implementations, operation o11 includes an operation o1118 for electronically directing storing of the first operation information into the operation history information storage, the first operation information associated with the at least one first operation occurrence by the automated ingestible product dispensing equipment as including one or more pump components. An exemplary version of a non-transitory signal bearing medium of information storage subsystem s200 is depicted as bearing one or more equipment pump instructions i1118 that when executed will direct performance of the operation o1118. In an implementation, the one or more equipment pump instructions i1118 when executed direct electronically directing storing of the first operation information into the operation history information storage, the first operation information associated with the at least one first operation occurrence by the automated ingestible product dispensing equipment of the at least one first ingestible product as including one or more pump components (e.g. one or more of instances of the digital signal processor (DSP) component s106 of the control and information processing subsystem s100 can direct storing the first operation information into one or more instances of the server component s230, the first operation occurrence involving one or more instances of the pump component s726, etc.). Furthermore, the equipment pump electrical circuitry arrangement e1118 when activated will perform the operation o1118. In an implementation, the equipment pump electrical circuitry arrangement e1118, when activated performs electronically directing storing of the first operation information into the operation history information storage, the first operation information associated with the at least one first operation occurrence by the automated ingestible product dispensing equipment of the at least one first ingestible product as including one or more pump components (e.g. one or more of instances of the digital signal processor (DSP) component s106 of the control and information processing subsystem s100 can direct storing the first operation information into one or more instances of the server component s230, the first operation occurrence involving one or more instances of the pump component s726, etc.). In an implementation, the electronically directing storing of the first operation information into the operation history information storage, the first operation information associated with the at least one first operation occurrence by the automated ingestible product dispensing equipment as including one or more pump components is carried out by electronically directing storing of the first operation information into the operation history information storage, the first operation information associated with the at least one first operation occurrence by the automated ingestible product dispensing equipment of the at least one first ingestible product as including one or more pump components (e.g. one or more of instances of the digital signal processor (DSP) component s106 of the control and information processing subsystem s100 can direct storing the first operation information into one or more instances of the server component s230, the first operation occurrence involving one or more instances of the pump component s726, etc.).

Figure 38:
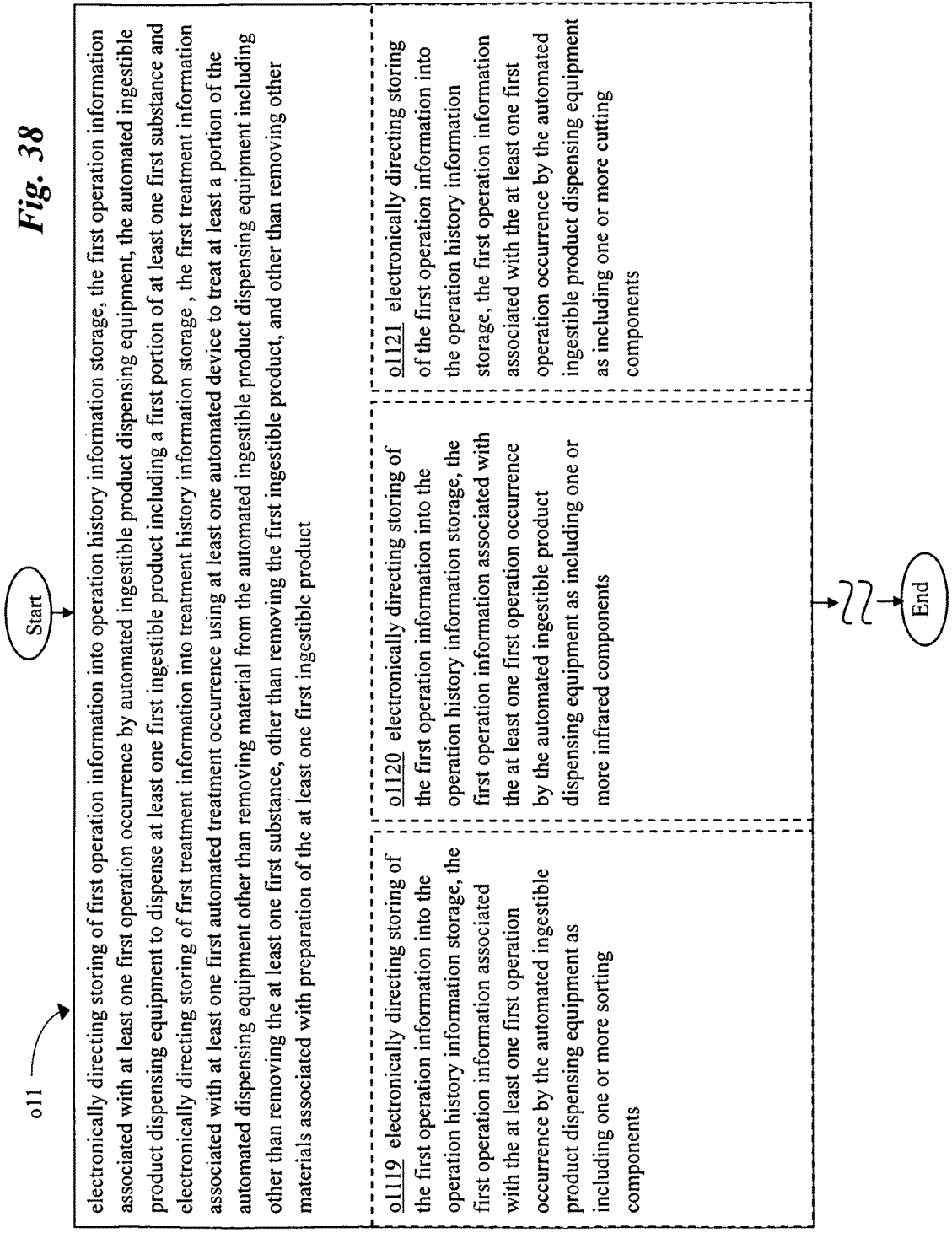
FIG. 38 is a high-level flowchart including exemplary implementations of operation O11 of FIG. 31.

In one or more implementations, as shown in FIG. 38, operation o11 includes an operation o1119 for electronically directing storing of the first operation information into the operation history information storage, the first operation information associated with the at least one first operation occurrence by the automated ingestible product dispensing equipment as including one or more sorting components. An exemplary version of a non-transitory signal bearing medium of information storage subsystem s200 is depicted as bearing one or more equipment sorting instructions i1119 that when executed will direct performance of the operation o1119. In an implementation, the one or more equipment sorting instructions i1119 when executed direct electronically directing storing of the first operation information into the operation history information storage, the first operation information associated with the at least one first operation occurrence by the automated ingestible product dispensing equipment of the at least one first ingestible product as including one or more sorting components (e.g. one or more of instances of the application specific integrated circuit (ASIC) component s108 of the control and information processing subsystem s100 can direct storing the first operation information into one or more instances of the digital tape component s232, the first operation occurrence involving one or more instances of the sorting component s728, etc.). Furthermore, the equipment sorting electrical circuitry arrangement e1119 when activated will perform the operation o1119. In an implementation, the equipment sorting electrical circuitry arrangement e1119, when activated performs electronically directing storing of the first operation information into the operation history information storage, the first operation information associated with the at least one first operation occurrence by the automated ingestible product dispensing equipment of the at least one first ingestible product as including one or more sorting components (e.g. one or more of instances of the application specific integrated circuit (ASIC) component s108 of the control and information processing subsystem s100 can direct storing the first operation information into one or more instances of the digital tape component s232, the first operation occurrence involving one or more instances of the sorting component s728, etc.). In an implementation, the electronically directing storing of the first operation information into the operation history information storage, the first operation information associated with the at least one first operation occurrence by the automated ingestible product dispensing equipment as including one or more sorting components is carried out by electronically directing storing of the first operation information into the operation history information storage, the first operation information associated with the at least one first operation occurrence by the automated ingestible product dispensing equipment of the at least one first ingestible product as including one or more sorting components (e.g. one or more of instances of the application specific integrated circuit (ASIC) component s108 of the control and information processing subsystem s100 can direct storing the first operation information into one or more instances of the digital tape component s232, the first operation occurrence involving one or more instances of the sorting component s728, etc.).

In one or more implementations, operation o11 includes an operation o1120 for electronically directing storing of the first operation information into the operation history information storage, the first operation information associated with the at least one first operation occurrence by the automated ingestible product dispensing equipment as including one or more infrared components. An exemplary version of a non-transitory signal bearing medium of information storage subsystem s200 is depicted as bearing one or more equipment infrared instructions i1120 that when executed will direct performance of the operation o1120. In an implementation, the one or more equipment infrared instructions i1120 when executed direct electronically directing storing of the first operation information into the operation history information storage, the first operation information associated with the at least one first operation occurrence by the automated ingestible product dispensing equipment of the at least one first ingestible product as including one or more infrared components (e.g. one or more of instances of the field programmable gate array (FPGA) component s110 of the control and information processing subsystem s100 can direct storing the first operation information into one or more instances of the optical storage component s234, the first operation occurrence involving one or more instances of the infrared component s730, etc.). Furthermore, the equipment infrared electrical circuitry arrangement e1120 when activated will perform the operation electronically directing storing of the first operation information into the operation history information storage, the first operation information associated with the at least one first operation occurrence by the automated ingestible product dispensing equipment as including one or more infrared components. In an implementation, the equipment infrared electrical circuitry arrangement e1120, when activated performs electronically directing storing of the first operation information into the operation history information storage, the first operation information associated with the at least one first operation occurrence by the automated ingestible product dispensing equipment of the at least one first ingestible product as including one or more infrared components (e.g. one or more of instances of the field programmable gate array (FPGA) component s110 of the control and information processing subsystem s100 can direct storing the first operation information into one or more instances of the optical storage component s234, the first operation occurrence involving one or more instances of the infrared component s730, etc.). In an implementation, the electronically directing storing of the first operation information into the operation history information storage, the first operation information associated with the at least one first operation occurrence by the automated ingestible product dispensing equipment as including one or more infrared components is carried out by electronically directing storing of the first operation information into the operation history information storage, the first operation information associated with the at least one first operation occurrence by the automated ingestible product dispensing equipment of the at least one first ingestible product as including one or more infrared components (e.g. one or more of instances of the field programmable gate array (FPGA) component s110 of the control and information processing subsystem s100 can direct storing the first operation information into one or more instances of the optical storage component s234, the first operation occurrence involving one or more instances of the infrared component s730, etc.).

In one or more implementations, operation o11 includes an operation o1121 for electronically directing storing of the first operation information into the operation history information storage, the first operation information associated with the at least one first operation occurrence by the automated ingestible product dispensing equipment as including one or more cutting components. An exemplary version of a non-transitory signal bearing medium of information storage subsystem s200 is depicted as bearing one or more equipment cutting instructions i1121 that when executed will direct performance of the operation o1121. In an implementation, the one or more equipment cutting instructions i1121 when executed direct electronically directing storing of the first operation information into the operation history information storage, the first operation information associated with the at least one first operation occurrence by the automated ingestible product dispensing equipment of the at least one first ingestible product as including one or more cutting components (e.g. one or more of instances of the multiprocessor component s112 of the control and information processing subsystem s100 can direct storing the first operation information into one or more instances of the optical storage component s236, the first operation occurrence involving one or more instances of the cutting component s732, etc.). Furthermore, the equipment cutting electrical circuitry arrangement e1121 when activated will perform the operation o1121. In an implementation, the equipment cutting electrical circuitry arrangement e1121, when activated performs electronically directing storing of the first operation information into the operation history information storage, the first operation information associated with the at least one first operation occurrence by the automated ingestible product dispensing equipment of the at least one first ingestible product as including one or more cutting components (e.g. one or more of instances of the multiprocessor component s112 of the control and information processing subsystem s100 can direct storing the first operation information into one or more instances of the optical storage component s236, the first operation occurrence involving one or more instances of the cutting component s732, etc.). In an implementation, the electronically directing storing of the first operation information into the operation history information storage, the first operation information associated with the at least one first operation occurrence by the automated ingestible product dispensing equipment as including one or more cutting components is carried out by electronically directing storing of the first operation information into the operation history information storage, the first operation information associated with the at least one first operation occurrence by the automated ingestible product dispensing equipment of the at least one first ingestible product as including one or more cutting components (e.g. one or more of instances of the multiprocessor component s112 of the control and information processing subsystem s100 can direct storing the first operation information into one or more instances of the optical storage component s236, the first operation occurrence involving one or more instances of the cutting component s732, etc.).

Figure 39:
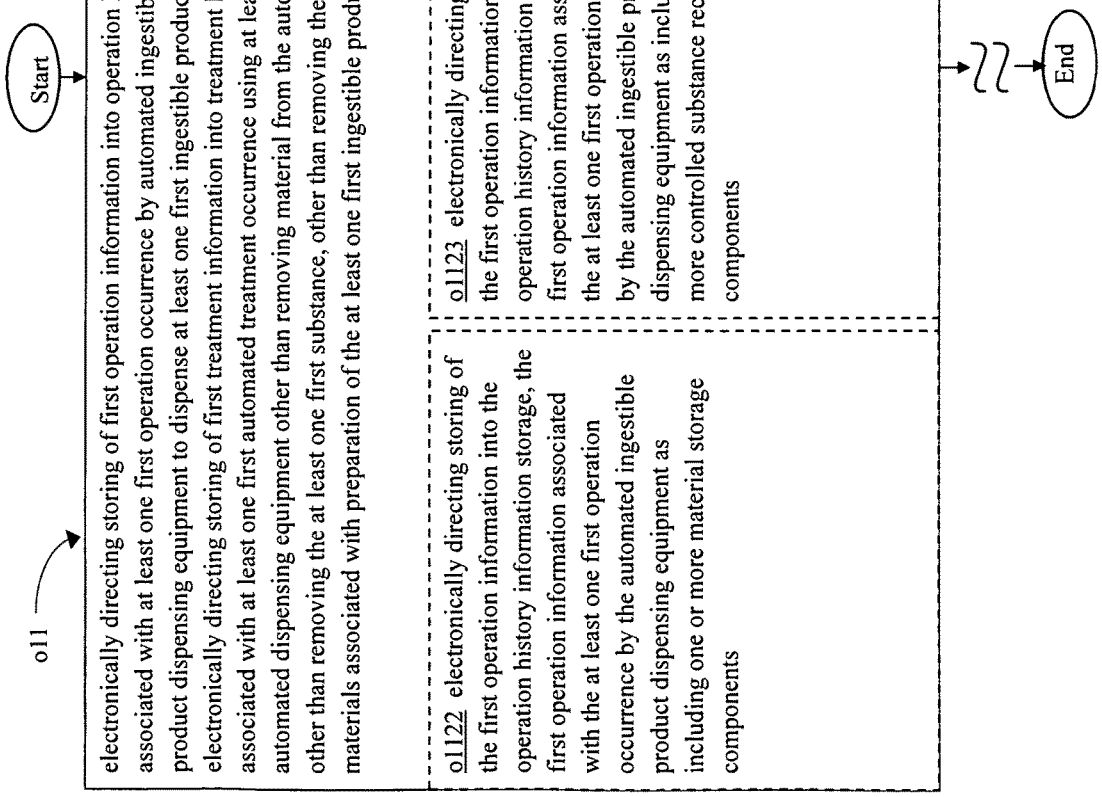
FIG. 39 is a high-level flowchart including exemplary implementations of operation O11 of FIG. 31.

In one or more implementations, as shown in FIG. 39, operation o11 includes an operation o1122 for electronically directing storing of the first operation information into the operation history information storage, the first operation information associated with the at least one first operation occurrence by the automated ingestible product dispensing equipment as including one or more material storage components. An exemplary version of a non-transitory signal bearing medium of information storage subsystem s200 is depicted as bearing one or more equipment material instructions i1122 that when executed will direct performance of the operation o1122. In an implementation, the one or more equipment material instructions i1122 when executed direct electronically directing storing of the first operation information into the operation history information storage, the first operation information associated with the at least one first operation occurrence by the automated ingestible product dispensing equipment of the at least one first ingestible product as including one or more material storage components (e.g. one or more of instances of the optical processing component s114 of the control and information processing subsystem s100 can direct storing the first operation information into one or more instances of the computer readable signal bearing medium s238, the first operation occurrence involving one or more instances of the material storage component s734, etc.). Furthermore, the equipment material electrical circuitry arrangement e1122 when activated will perform the operation o1122. In an implementation, the equipment material electrical circuitry arrangement e1122, when activated performs electronically directing storing of the first operation information into the operation history information storage, the first operation information associated with the at least one first operation occurrence by the automated ingestible product dispensing equipment of the at least one first ingestible product as including one or more material storage components (e.g. one or more of instances of the optical processing component s114 of the control and information processing subsystem s100 can direct storing the first operation information into one or more instances of the computer readable signal bearing medium s238, the first operation occurrence involving one or more instances of the material storage component s734, etc.). In an implementation, the electronically directing storing of the first operation information into the operation history information storage, the first operation information associated with the at least one first operation occurrence by the automated ingestible product dispensing equipment as including one or more material storage components is carried out by electronically directing storing of the first operation information into the operation history information storage, the first operation information associated with the at least one first operation occurrence by the automated ingestible product dispensing equipment of the at least one first ingestible product as including one or more material storage components (e.g. one or more of instances of the optical processing component s114 of the control and information processing subsystem s100 can direct storing the first operation information into one or more instances of the computer readable signal bearing medium s238, the first operation occurrence involving one or more instances of the material storage component s734, etc.).

In one or more implementations, operation o11 includes an operation o1123 for electronically directing storing of the first operation information into the operation history information storage, the first operation information associated with the at least one first operation occurrence by the automated ingestible product dispensing equipment as including one or more controlled substance receiving components. An exemplary version of a non-transitory signal bearing medium of information storage subsystem s200 is depicted as bearing one or more equipment receiving instructions i1123 that when executed will direct performance of the operation o1123. In an implementation, the one or more equipment receiving instructions i1123 when executed direct electronically directing storing of the first operation information into the operation history information storage, the first operation information associated with the at least one first operation occurrence by the automated ingestible product dispensing equipment of the at least one first ingestible product as including one or more controlled substance receiving components (e.g. one or more of instances of the logic component s116 of the control and information processing subsystem s100 can direct storing the first operation information into one or more instances of the Blu Ray disk component s240, the first operation occurrence involving one or more instances of the controlled substance receiving assembly s736, etc.). Furthermore, the equipment receiving electrical circuitry arrangement e1123 when activated will perform the operation o1123. In an implementation, the equipment receiving electrical circuitry arrangement e1123, when activated performs electronically directing storing of the first operation information into the operation history information storage, the first operation information associated with the at least one first operation occurrence by the automated ingestible product dispensing equipment of the at least one first ingestible product as including one or more controlled substance receiving components (e.g. one or more of instances of the logic component s116 of the control and information processing subsystem s100 can direct storing the first operation information into one or more instances of the Blu Ray disk component s240, the first operation occurrence involving one or more instances of the controlled substance receiving assembly s736, etc.). In an implementation, the electronically directing storing of the first operation information into the operation history information storage, the first operation information associated with the at least one first operation occurrence by the automated ingestible product dispensing equipment as including one or more controlled substance receiving components is carried out by electronically directing storing of the first operation information into the operation history information storage, the first operation information associated with the at least one first operation occurrence by the automated ingestible product dispensing equipment of the at least one first ingestible product as including one or more controlled substance receiving components (e.g. one or more of instances of the logic component s116 of the control and information processing subsystem s100 can direct storing the first operation information into one or more instances of the Blu Ray disk component s240, the first operation occurrence involving one or more instances of the controlled substance receiving assembly s736, etc.).

In one or more implementations, operation o11 includes an operation o1124 for electronically directing storing of the first operation information into the operation history information storage, the first operation information associated with the at least one first operation occurrence by the automated ingestible product dispensing equipment as including one or more controlled substance containing components. An exemplary version of a non-transitory signal bearing medium of information storage subsystem s200 is depicted as bearing one or more equipment containing instructions i1124 that when executed will direct performance of the operation o1124. In an implementation, the one or more equipment containing instructions i1124 when executed direct electronically directing storing of the first operation information into the operation history information storage, the first operation information associated with the at least one first operation occurrence by the automated ingestible product dispensing equipment of the at least one first ingestible product as including one or more controlled substance containing components (e.g. one or more of instances of the microprocessor component s102 of the control and information processing subsystem s100 can direct storing the first operation information into one or more instances of the random access memory (RAM) component s202, the first operation occurrence involving one or more instances of the controlled substance containing assembly s738, etc.). Furthermore, the equipment containing electrical circuitry arrangement e1124 when activated will perform the operation o1124. In an implementation, the equipment containing electrical circuitry arrangement e1124, when activated performs electronically directing storing of the first operation information into the operation history information storage, the first operation information associated with the at least one first operation occurrence by the automated ingestible product dispensing equipment of the at least one first ingestible product as including one or more controlled substance containing components (e.g. one or more of instances of the microprocessor component s102 of the control and information processing subsystem s100 can direct storing the first operation information into one or more instances of the random access memory (RAM) component s202, the first operation occurrence involving one or more instances of the controlled substance containing assembly s738, etc.). In an implementation, the electronically directing storing of the first operation information into the operation history information storage, the first operation information associated with the at least one first operation occurrence by the automated ingestible product dispensing equipment as including one or more controlled substance containing components is carried out by electronically directing storing of the first operation information into the operation history information storage, the first operation information associated with the at least one first operation occurrence by the automated ingestible product dispensing equipment of the at least one first ingestible product as including one or more controlled substance containing components (e.g. one or more of instances of the microprocessor component s102 of the control and information processing subsystem s100 can direct storing the first operation information into one or more instances of the random access memory (RAM) component s202, the first operation occurrence involving one or more instances of the controlled substance containing assembly s738, etc.).

Figure 40:
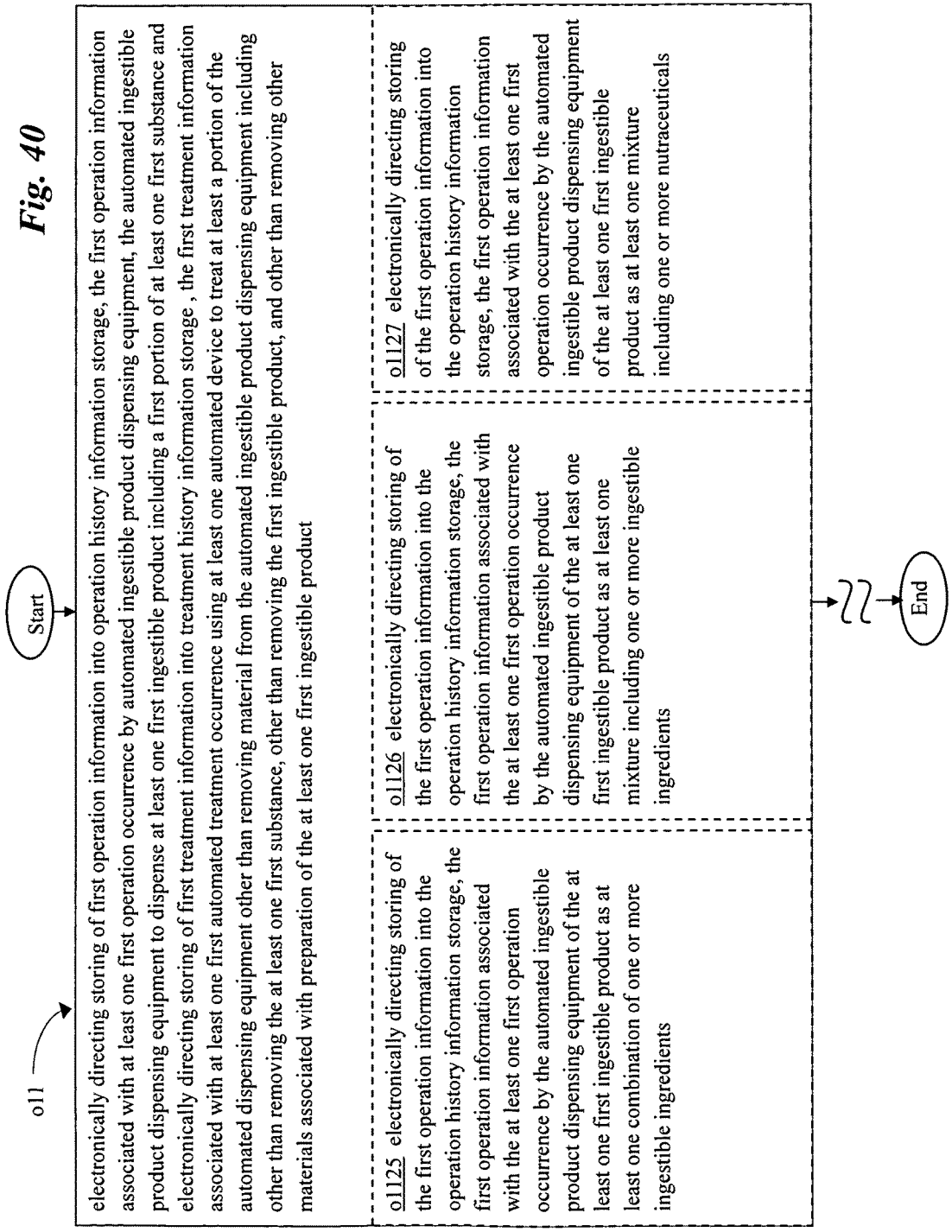
FIG. 40 is a high-level flowchart including exemplary implementations of operation O11 of FIG. 31.

In one or more implementations, as shown in FIG. 40, operation o11 includes an operation o1125 for electronically directing storing of the first operation information into the operation history information storage, the first operation information associated with the at least one first operation occurrence by the automated ingestible product dispensing equipment of the at least one first ingestible product as at least one combination of one or more ingestible ingredients. An exemplary version of a non-transitory signal bearing medium of information storage subsystem s200 is depicted as bearing one or more combination ingredients instructions i1125 that when executed will direct performance of the operation o1125. In an implementation, the one or more combination ingredients instructions i1125 when executed direct electronically directing storing of the first operation information into the operation history information storage, the first operation information associated with the at least one first operation occurrence by the automated ingestible product dispensing equipment of the at least one first ingestible product as at least one combination of one or more ingestible ingredients (e.g. one or more of instances of the microprocessor component s102 of the control and information processing subsystem s100 can direct storing the first operation information into one or more instances of the dynamic random access memory (DRAM) component s204, involving dispensing of one or more pizzas, etc.). Furthermore, the combination ingredients electrical circuitry arrangement e1125 when activated will perform the operation o1125. In an implementation, the combination ingredients electrical circuitry arrangement e1125, when activated performs electronically directing storing of the first operation information into the operation history information storage, the first operation information associated with the at least one first operation occurrence by the automated ingestible product dispensing equipment of the at least one first ingestible product as at least one combination of one or more ingestible ingredients (e.g. one or more of instances of the microprocessor component s102 of the control and information processing subsystem s100 can direct storing the first operation information into one or more instances of the dynamic random access memory (DRAM) component s204, involving dispensing of one or more pizzas, etc.). In an implementation, the electronically directing storing of the first operation information into the operation history information storage, the first operation information associated with the at least one first operation occurrence by the automated ingestible product dispensing equipment of the at least one first ingestible product as at least one combination of one or more ingestible ingredients is carried out by electronically directing storing of the first operation information into the operation history information storage, the first operation information associated with the at least one first operation occurrence by the automated ingestible product dispensing equipment of the at least one first ingestible product as at least one combination of one or more ingestible ingredients (e.g. one or more of instances of the microprocessor component s102 of the control and information processing subsystem s100 can direct storing the first operation information into one or more instances of the dynamic random access memory (DRAM) component s204, involving dispensing of one or more pizzas, etc.).

In one or more implementations, operation o11 includes an operation o1126 for electronically directing storing of the first operation information into the operation history information storage, the first operation information associated with the at least one first operation occurrence by the automated ingestible product dispensing equipment of the at least one first ingestible product as at least one mixture including one or more ingestible ingredients. An exemplary version of a non-transitory signal bearing medium of information storage subsystem s200 is depicted as bearing one or more mixture ingredients instructions i1126 that when executed will direct performance of the operation o1126. In an implementation, the one or more mixture ingredients instructions i1126 when executed direct electronically directing storing of the first operation information into the operation history information storage, the first operation information associated with the at least one first operation occurrence by the automated ingestible product dispensing equipment of the at least one first ingestible product as at least one mixture including one or more ingestible ingredients (e.g. one or more of instances of the logic component s116 of the control and information processing subsystem s100 can direct storing the first operation information into one or more instances of the other volatile memory component s206, involving dispensing of one or more salad mixes, etc.). Furthermore, the mixture ingredients electrical circuitry arrangement e1126 when activated will perform the operation o1126. In an implementation, the mixture ingredients electrical circuitry arrangement e1126, when activated performs electronically directing storing of the first operation information into the operation history information storage, the first operation information associated with the at least one first operation occurrence by the automated ingestible product dispensing equipment of the at least one first ingestible product as at least one mixture including one or more ingestible ingredients (e.g. one or more of instances of the logic component s116 of the control and information processing subsystem s100 can direct storing the first operation information into one or more instances of the other volatile memory component s206, involving dispensing of one or more salad mixes, etc.). In an implementation, the electronically directing storing of the first operation information into the operation history information storage, the first operation information associated with the at least one first operation occurrence by the automated ingestible product dispensing equipment of the at least one first ingestible product as at least one mixture including one or more ingestible ingredients is carried out by electronically directing storing of the first operation information into the operation history information storage, the first operation information associated with the at least one first operation occurrence by the automated ingestible product dispensing equipment of the at least one first ingestible product as at least one mixture including one or more ingestible ingredients (e.g. one or more of instances of the logic component s116 of the control and information processing subsystem s100 can direct storing the first operation information into one or more instances of the other volatile memory component s206, involving dispensing of one or more salad mixes, etc.).

In one or more implementations, operation o11 includes an operation o1127 for electronically directing storing of the first operation information into the operation history information storage, the first operation information associated with the at least one first operation occurrence by the automated ingestible product dispensing equipment of the at least one first ingestible product as at least one mixture including one or more nutraceuticals. An exemplary version of a non-transitory signal bearing medium of information storage subsystem s200 is depicted as bearing one or more mixture nutraceuticals instructions i1127 that when executed will direct performance of the operation o1127. In an implementation, the one or more mixture nutraceuticals instructions i1127 when executed direct electronically directing storing of the first operation information into the operation history information storage, the first operation information associated with the at least one first operation occurrence by the automated ingestible product dispensing equipment of the at least one first ingestible product as at least one mixture including one or more nutraceuticals (e.g. one or more of instances of the central processing unit (CPU) component s104 of the control and information processing subsystem s100 can direct storing the first operation information into one or more instances of the persistent memory component s208, involving dispensing of one or more sports drinks, etc.). Furthermore, the mixture nutraceuticals electrical circuitry arrangement e1127 when activated will perform the operation o1127. In an implementation, the mixture nutraceuticals electrical circuitry arrangement e1127, when activated performs electronically directing storing of the first operation information into the operation history information storage, the first operation information associated with the at least one first operation occurrence by the automated ingestible product dispensing equipment of the at least one first ingestible product as at least one mixture including one or more nutraceuticals (e.g. one or more of instances of the central processing unit (CPU) component s104 of the control and information processing subsystem s100 can direct storing the first operation information into one or more instances of the persistent memory component s208, involving dispensing of one or more sports drinks, etc.). In an implementation, the electronically directing storing of the first operation information into the operation history information storage, the first operation information associated with the at least one first operation occurrence by the automated ingestible product dispensing equipment of the at least one first ingestible product as at least one mixture including one or more nutraceuticals is carried out by electronically directing storing of the first operation information into the operation history information storage, the first operation information associated with the at least one first operation occurrence by the automated ingestible product dispensing equipment of the at least one first ingestible product as at least one mixture including one or more nutraceuticals (e.g. one or more of instances of the central processing unit (CPU) component s104 of the control and information processing subsystem s100 can direct storing the first operation information into one or more instances of the persistent memory component s208, involving dispensing of one or more sports drinks, etc.).

Figure 41:
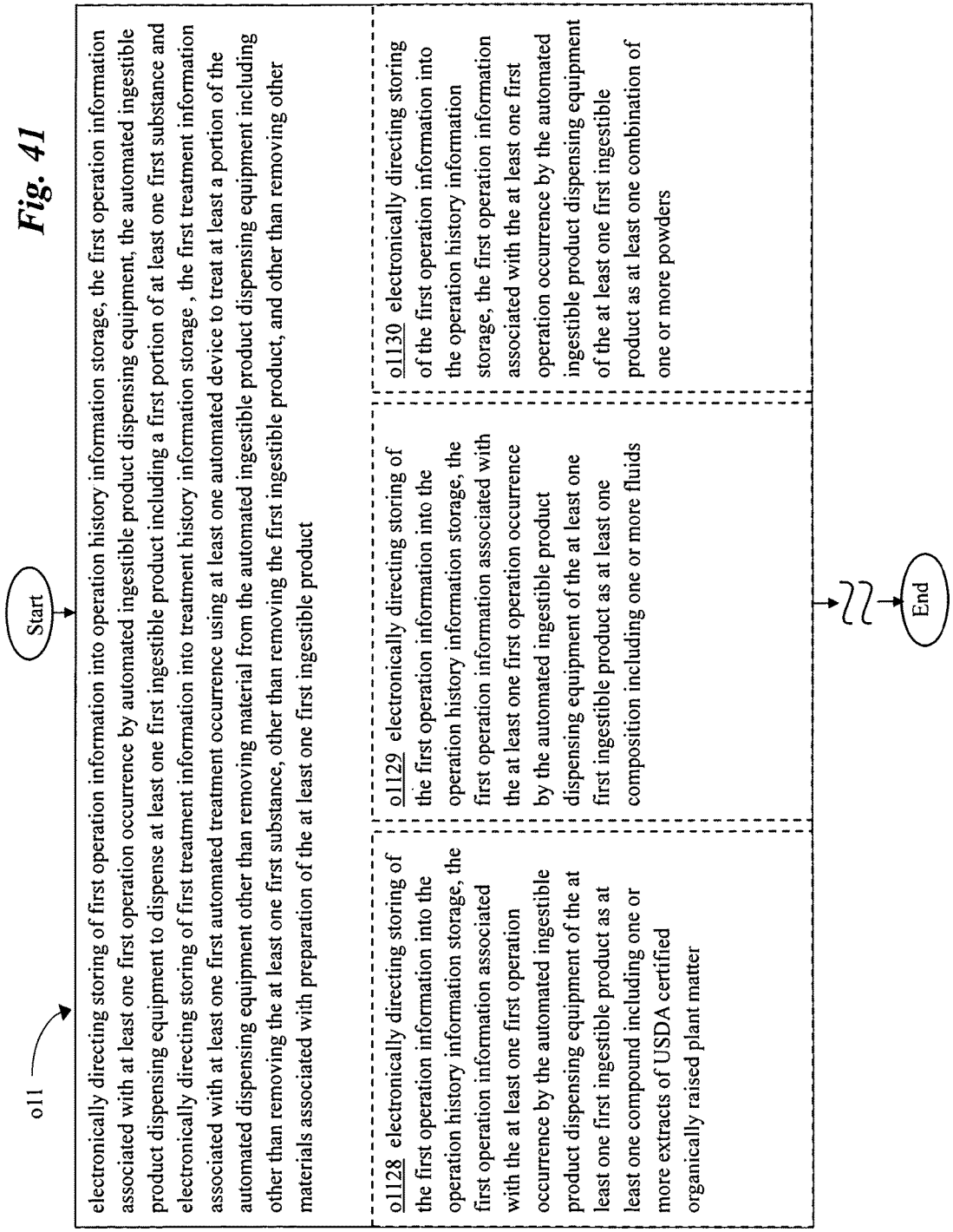
FIG. 41 is a high-level flowchart including exemplary implementations of operation O11 of FIG. 31.

In one or more implementations, as shown in FIG. 41, operation o11 includes an operation o1128 for electronically directing storing of the first operation information into the operation history information storage, the first operation information associated with the at least one first operation occurrence by the automated ingestible product dispensing equipment of the at least one first ingestible product as at least one compound including one or more extracts of USDA certified organically raised plant matter. An exemplary version of a non-transitory signal bearing medium of information storage subsystem s200 is depicted as bearing one or more compound organic instructions i1128 that when executed will direct performance of the operation o1128. In an implementation, the one or more compound organic instructions i1128 when executed direct electronically directing storing of the first operation information into the operation history information storage, the first operation information associated with the at least one first operation occurrence by the automated ingestible product dispensing equipment of the at least one first ingestible product as at least one compound including one or more extracts of USDA certified organically raised plant matter (e.g. one or more of instances of the digital signal processor (DSP) component s106 of the control and information processing subsystem s100 can direct storing the first operation information into one or more instances of the read only memory (ROM) component s210, involving dispensing of one or more fruit smoothies, etc.). Furthermore, the compound organic electrical circuitry arrangement e1128 when activated will perform the operation o1128. In an implementation, the compound organic electrical circuitry arrangement e1128, when activated performs electronically directing storing of the first operation information into the operation history information storage, the first operation information associated with the at least one first operation occurrence by the automated ingestible product dispensing equipment of the at least one first ingestible product as at least one compound including one or more extracts of USDA certified organically raised plant matter (e.g. one or more of instances of the digital signal processor (DSP) component s106 of the control and information processing subsystem s100 can direct storing the first operation information into one or more instances of the read only memory (ROM) component s210, involving dispensing of one or more fruit smoothies, etc.). In an implementation, the electronically directing storing of the first operation information into the operation history information storage, the first operation information associated with the at least one first operation occurrence by the automated ingestible product dispensing equipment of the at least one first ingestible product as at least one compound including one or more extracts of USDA certified organically raised plant matter is carried out by electronically directing storing of the first operation information into the operation history information storage, the first operation information associated with the at least one first operation occurrence by the automated ingestible product dispensing equipment of the at least one first ingestible product as at least one compound including one or more extracts of USDA certified organically raised plant matter (e.g. one or more of instances of the digital signal processor (DSP) component s106 of the control and information processing subsystem s100 can direct storing the first operation information into one or more instances of the read only memory (ROM) component s210, involving dispensing of one or more fruit smoothies, etc.).

In one or more implementations, operation o11 includes an operation o1129 for electronically directing storing of the first operation information into the operation history information storage, the first operation information associated with the at least one first operation occurrence by the automated ingestible product dispensing equipment of the at least one first ingestible product as at least one composition including one or more fluids. An exemplary version of a non-transitory signal bearing medium of information storage subsystem s200 is depicted as bearing one or more composition fluids instructions i1129 that when executed will direct performance of the operation o1129. In an implementation, the one or more composition fluids instructions i1129 when executed direct electronically directing storing of the first operation information into the operation history information storage, the first operation information associated with the at least one first operation occurrence by the automated ingestible product dispensing equipment of the at least one first ingestible product as at least one composition including one or more fluids (e.g. one or more of instances of the application specific integrated circuit (ASIC) component s108 of the control and information processing subsystem s100 can direct storing the first operation information into one or more instances of the electrically erasable programmable read only memory (EEPROM) component s212, involving dispensing of one or more soft drinks, etc.). Furthermore, the composition fluids electrical circuitry arrangement e1129 when activated will perform the operation o1129. In an implementation, the composition fluids electrical circuitry arrangement e1129, when activated performs electronically directing storing of the first operation information into the operation history information storage, the first operation information associated with the at least one first operation occurrence by the automated ingestible product dispensing equipment of the at least one first ingestible product as at least one composition including one or more fluids (e.g. one or more of instances of the application specific integrated circuit (ASIC) component s108 of the control and information processing subsystem s100 can direct storing the first operation information into one or more instances of the electrically erasable programmable read only memory (EEPROM) component s212, involving dispensing of one or more soft drinks, etc.). In an implementation, the electronically directing storing of the first operation information into the operation history information storage, the first operation information associated with the at least one first operation occurrence by the automated ingestible product dispensing equipment of the at least one first ingestible product as at least one composition including one or more fluids is carried out by electronically directing storing of the first operation information into the operation history information storage, the first operation information associated with the at least one first operation occurrence by the automated ingestible product dispensing equipment of the at least one first ingestible product as at least one composition including one or more fluids (e.g. one or more of instances of the application specific integrated circuit (ASIC) component s108 of the control and information processing subsystem s100 can direct storing the first operation information into one or more instances of the electrically erasable programmable read only memory (EEPROM) component s212, involving dispensing of one or more soft drinks, etc.).

In one or more implementations, operation o11 includes an operation o1130 for electronically directing storing of the first operation information into the operation history information storage, the first operation information associated with the at least one first operation occurrence by the automated ingestible product dispensing equipment of the at least one first ingestible product as at least one combination of one or more powders. An exemplary version of a non-transitory signal bearing medium of information storage subsystem s200 is depicted as bearing one or more combination powders instructions i1130 that when executed will direct performance of the operation o1130. In an implementation, the one or more combination powders instructions i1130 when executed direct electronically directing storing of the first operation information into the operation history information storage, the first operation information associated with the at least one first operation occurrence by the automated ingestible product dispensing equipment of the at least one first ingestible product as at least one combination of one or more powders (e.g. one or more of instances of the field programmable gate array (FPGA) component s110 of the control and information processing subsystem s100 can direct storing the first operation information into one or more instances of the compact disk (CD) component s214, involving one or more skin treatments, etc.). Furthermore, the combination powders electrical circuitry arrangement e1130 when activated will perform the operation o1130. In an implementation, the combination powders electrical circuitry arrangement e1130, when activated performs electronically directing storing of the first operation information into the operation history information storage, the first operation information associated with the at least one first operation occurrence by the automated ingestible product dispensing equipment of the at least one first ingestible product as at least one combination of one or more powders (e.g. one or more of instances of the field programmable gate array (FPGA) component s110 of the control and information processing subsystem s100 can direct storing the first operation information into one or more instances of the compact disk (CD) component s214, involving one or more skin treatments, etc.). In an implementation, the electronically directing storing of the first operation information into the operation history information storage, the first operation information associated with the at least one first operation occurrence by the automated ingestible product dispensing equipment of the at least one first ingestible product as at least one combination of one or more powders is carried out by electronically directing storing of the first operation information into the operation history information storage, the first operation information associated with the at least one first operation occurrence by the automated ingestible product dispensing equipment of the at least one first ingestible product as at least one combination of one or more powders (e.g. one or more of instances of the field programmable gate array (FPGA) component s110 of the control and information processing subsystem s100 can direct storing the first operation information into one or more instances of the compact disk (CD) component s214, involving one or more skin treatments, etc.).

Figure 42:
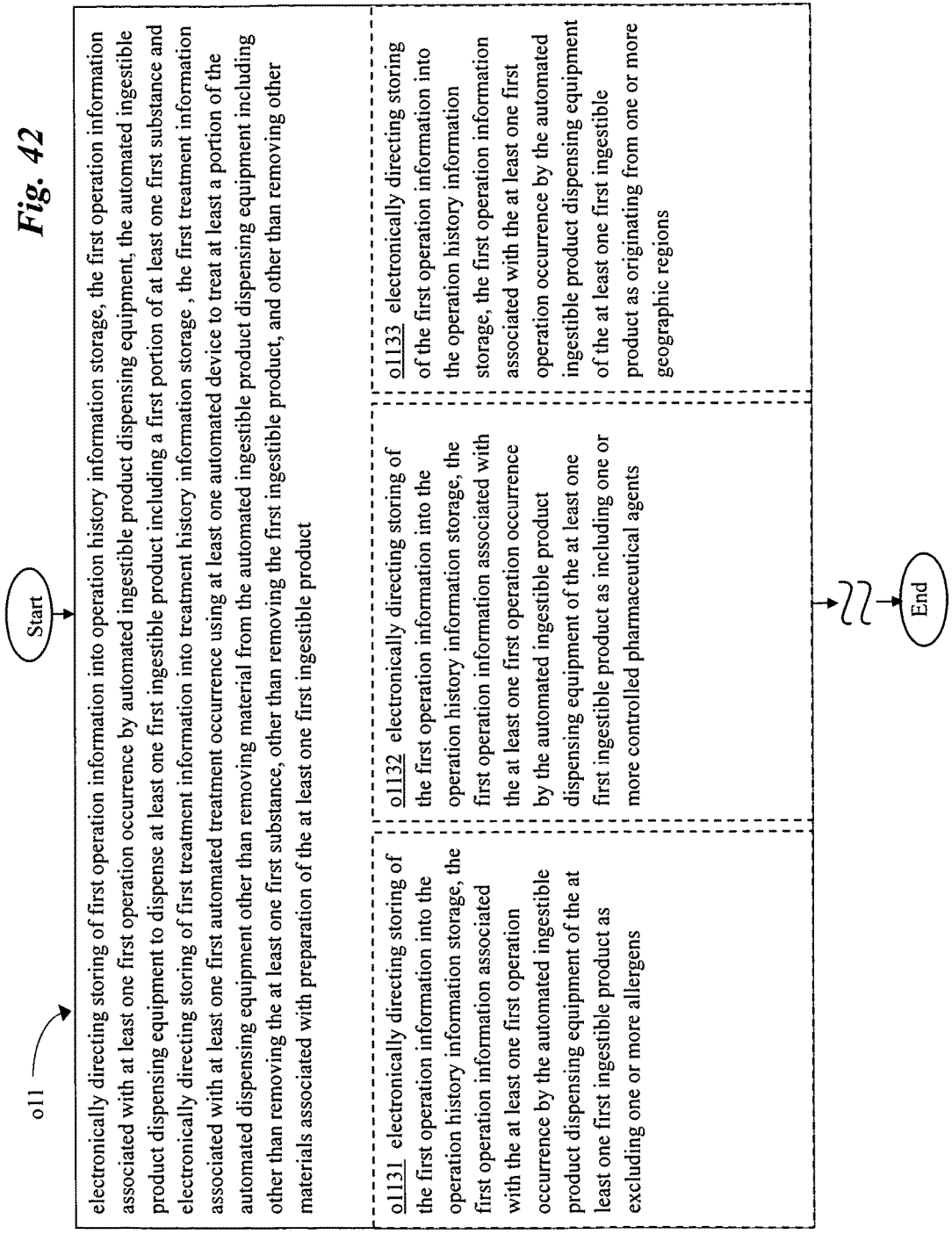
FIG. 42 is a high-level flowchart including exemplary implementations of operation O11 of FIG. 31.

In one or more implementations, as shown in FIG. 42, operation o11 includes an operation o1131 for electronically directing storing of the first operation information into the operation history information storage, the first operation information associated with the at least one first operation occurrence by the automated ingestible product dispensing equipment of the at least one first ingestible product as excluding one or more allergens. An exemplary version of a non-transitory signal bearing medium of information storage subsystem s200 is depicted as bearing one or more excluding allergens instructions i1131 that when executed will direct performance of the operation o1131. In an implementation, the one or more excluding allergens instructions i1131 when executed direct electronically directing storing of the first operation information into the operation history information storage, the first operation information associated with the at least one first operation occurrence by the automated ingestible product dispensing equipment of the at least one first ingestible product as excluding one or more allergens (e.g. one or more of instances of the multiprocessor component s112 of the control and information processing subsystem s100 can direct storing the first operation information into one or more instances of the digital versatile disk (DVD) component s216, involving dispensing other than soybeans and peanuts due to user allergies, etc.). Furthermore, the excluding allergens electrical circuitry arrangement e1131 when activated will perform the operation o1131. In an implementation, the excluding allergens electrical circuitry arrangement e1131, when activated performs electronically directing storing of the first operation information into the operation history information storage, the first operation information associated with the at least one first operation occurrence by the automated ingestible product dispensing equipment of the at least one first ingestible product as excluding one or more allergens (e.g. one or more of instances of the multiprocessor component s112 of the control and information processing subsystem s100 can direct storing the first operation information into one or more instances of the digital versatile disk (DVD) component s216, involving dispensing other than soybeans and peanuts due to user allergies, etc.). In an implementation, the electronically directing storing of the first operation information into the operation history information storage, the first operation information associated with the at least one first operation occurrence by the automated ingestible product dispensing equipment of the at least one first ingestible product as excluding one or more allergens is carried out by electronically directing storing of the first operation information into the operation history information storage, the first operation information associated with the at least one first operation occurrence by the automated ingestible product dispensing equipment of the at least one first ingestible product as excluding one or more allergens (e.g. one or more of instances of the multiprocessor component s112 of the control and information processing subsystem s100 can direct storing the first operation information into one or more instances of the digital versatile disk (DVD) component s216, involving dispensing other than soybeans and peanuts due to user allergies, etc.).

In one or more implementations, operation o11 includes an operation o1132 for electronically directing storing of the first operation information into the operation history information storage, the first operation information associated with the at least one first operation occurrence by the automated ingestible product dispensing equipment of the at least one first ingestible product as including one or more controlled pharmaceutical agents. An exemplary version of a non-transitory signal bearing medium of information storage subsystem s200 is depicted as bearing one or more pharmaceutical agents instructions i1132 that when executed will direct performance of the operation o1132. In an implementation, the one or more pharmaceutical agents instructions i1132 when executed direct electronically directing storing of the first operation information into the operation history information storage, the first operation information associated with the at least one first operation occurrence by the automated ingestible product dispensing equipment of the at least one first ingestible product as including one or more controlled pharmaceutical agents (e.g. one or more of instances of the optical processing component s114 of the control and information processing subsystem s100 can direct storing the first operation information into one or more instances of the flash memory component s218, involving dispensing including the first operation occurrence involving one or more instances of the heating component s702, involving dispensing including acetaminophen and diazepam, etc.). Furthermore, the pharmaceutical agents electrical circuitry arrangement e1132 when activated will perform the operation o1132. In an implementation, the pharmaceutical agents electrical circuitry arrangement e1132, when activated performs electronically directing storing of the first operation information into the operation history information storage, the first operation information associated with the at least one first operation occurrence by the automated ingestible product dispensing equipment of the at least one first ingestible product as including one or more controlled pharmaceutical agents (e.g. one or more of instances of the optical processing component s114 of the control and information processing subsystem s100 can direct storing the first operation information into one or more instances of the flash memory component s218, involving dispensing including the first operation occurrence involving one or more instances of the heating component s702, involving dispensing including acetaminophen and diazepam, etc.). In an implementation, the electronically directing storing of the first operation information into the operation history information storage, the first operation information associated with the at least one first operation occurrence by the automated ingestible product dispensing equipment of the at least one first ingestible product as including one or more controlled pharmaceutical agents is carried out by electronically directing storing of the first operation information into the operation history information storage, the first operation information associated with the at least one first operation occurrence by the automated ingestible product dispensing equipment of the at least one first ingestible product as including one or more controlled pharmaceutical agents (e.g. one or more of instances of the optical processing component s114 of the control and information processing subsystem s100 can direct storing the first operation information into one or more instances of the flash memory component s218, involving dispensing including the first operation occurrence involving one or more instances of the heating component s702, involving dispensing including acetaminophen and diazepam, etc.).

In one or more implementations, operation o11 includes an operation o1133 for electronically directing storing of the first operation information into the operation history information storage, the first operation information associated with the at least one first operation occurrence by the automated ingestible product dispensing equipment of the at least one first ingestible product as originating from one or more geographic regions. An exemplary version of a non-transitory signal bearing medium of information storage subsystem s200 is depicted as bearing one or more geographic regions instructions i1133 that when executed will direct performance of the operation o1133. In an implementation, the one or more geographic regions instructions i1133 when executed direct electronically directing storing of the first operation information into the operation history information storage, the first operation information associated with the at least one first operation occurrence by the automated ingestible product dispensing equipment of the at least one first ingestible product as originating from one or more geographic regions (e.g. one or more of instances of the logic component s116 of the control and information processing subsystem s100 can direct storing the first operation information into one or more instances of the other nonvolatile memory component s220, involving dispensing using ingredients only from the western United States, etc.). Furthermore, the geographic regions electrical circuitry arrangement e1133 when activated will perform the operation o1133. In an implementation, the geographic regions electrical circuitry arrangement e1133, when activated performs electronically directing storing of the first operation information into the operation history information storage, the first operation information associated with the at least one first operation occurrence by the automated ingestible product dispensing equipment of the at least one first ingestible product as originating from one or more geographic regions (e.g. one or more of instances of the logic component s116 of the control and information processing subsystem s100 can direct storing the first operation information into one or more instances of the other nonvolatile memory component s220, involving dispensing using ingredients only from the western United States, etc.). In an implementation, the electronically directing storing of the first operation information into the operation history information storage, the first operation information associated with the at least one first operation occurrence by the automated ingestible product dispensing equipment of the at least one first ingestible product as originating from one or more geographic regions is carried out by electronically directing storing of the first operation information into the operation history information storage, the first operation information associated with the at least one first operation occurrence by the automated ingestible product dispensing equipment of the at least one first ingestible product as originating from one or more geographic regions (e.g. one or more of instances of the logic component s116 of the control and information processing subsystem s100 can direct storing the first operation information into one or more instances of the other nonvolatile memory component s220, involving dispensing using ingredients only from the western United States, etc.).

Figure 43:
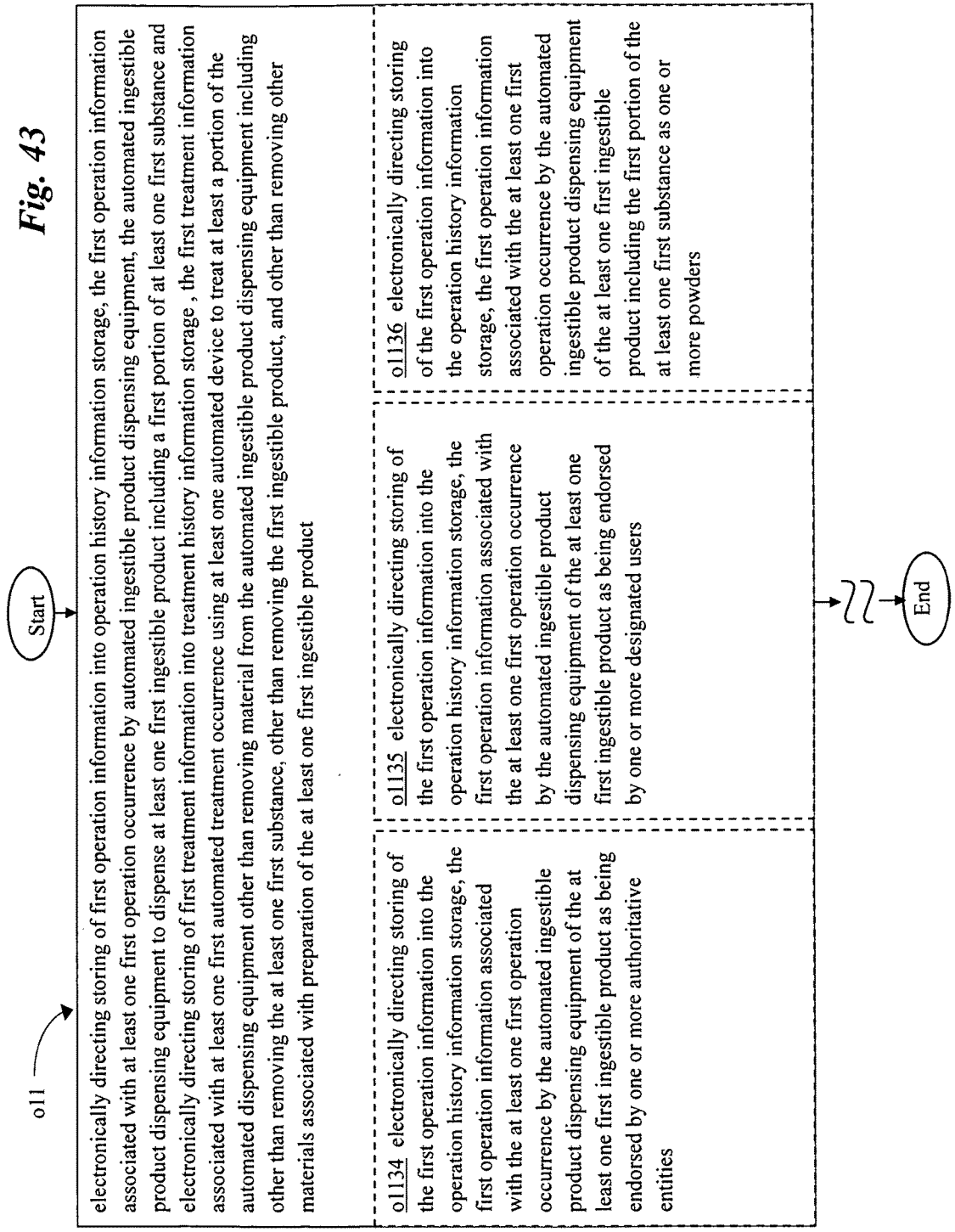
FIG. 43 is a high-level flowchart including exemplary implementations of operation O11 of FIG. 31.

In one or more implementations, as shown in FIG. 43, operation o11 includes an operation o1134 for electronically directing storing of the first operation information into the operation history information storage, the first operation information associated with the at least one first operation occurrence by the automated ingestible product dispensing equipment of the at least one first ingestible product as being endorsed by one or more authoritative entities. An exemplary version of a non-transitory signal bearing medium of information storage subsystem s200 is depicted as bearing one or more authoritative entities instructions i1134 that when executed will direct performance of the operation o1134. In an implementation, the one or more authoritative entities instructions i1134 when executed direct electronically directing storing of the first operation information into the operation history information storage, the first operation information associated with the at least one first operation occurrence by the automated ingestible product dispensing equipment of the at least one first ingestible product as being endorsed by one or more authoritative entities (e.g. one or more of instances of the microprocessor component s102 of the control and information processing subsystem s100 can direct storing the first operation information into one or more instances of the hard drive component s222, involving dispensing being endorsed by five major league baseball players, etc.). Furthermore, the authoritative entities electrical circuitry arrangement e1134 when activated will perform the operation o1134. In an implementation, the authoritative entities electrical circuitry arrangement e1134, when activated performs electronically directing storing of the first operation information into the operation history information storage, the first operation information associated with the at least one first operation occurrence by the automated ingestible product dispensing equipment of the at least one first ingestible product as being endorsed by one or more authoritative entities (e.g. one or more of instances of the microprocessor component s102 of the control and information processing subsystem s100 can direct storing the first operation information into one or more instances of the hard drive component s222, involving dispensing being endorsed by five major league baseball players, etc.). In an implementation, the electronically directing storing of the first operation information into the operation history information storage, the first operation information associated with the at least one first operation occurrence by the automated ingestible product dispensing equipment of the at least one first ingestible product as being endorsed by one or more authoritative entities is carried out by electronically directing storing of the first operation information into the operation history information storage, the first operation information associated with the at least one first operation occurrence by the automated ingestible product dispensing equipment of the at least one first ingestible product as being endorsed by one or more authoritative entities (e.g. one or more of instances of the microprocessor component s102 of the control and information processing subsystem s100 can direct storing the first operation information into one or more instances of the hard drive component s222, involving dispensing being endorsed by five major league baseball players, etc.).

In one or more implementations, operation o11 includes an operation o1135 for electronically directing storing of the first operation information into the operation history information storage, the first operation information associated with the at least one first operation occurrence by the automated ingestible product dispensing equipment of the at least one first ingestible product as being endorsed by one or more designated users. An exemplary version of a non-transitory signal bearing medium of information storage subsystem s200 is depicted as bearing one or more designated users instructions i1135 that when executed will direct performance of the operation o1135. In an implementation, the one or more designated users instructions i1135 when executed direct electronically directing storing of the first operation information into the operation history information storage, the first operation information associated with the at least one first operation occurrence by the automated ingestible product dispensing equipment of the at least one first ingestible product as being endorsed by one or more designated users (e.g. one or more of instances of the logic component s116 of the control and information processing subsystem s100 can direct storing the first operation information into one or more instances of the disk farm component s224, involving dispensing ingestible products used for and endorsed by famous actors that suffer migraine headaches, etc.). Furthermore, the designated users electrical circuitry arrangement e1135 when activated will perform the operation o1135. In an implementation, the designated users electrical circuitry arrangement e1135, when activated performs electronically directing storing of the first operation information into the operation history information storage, the first operation information associated with the at least one first operation occurrence by the automated ingestible product dispensing equipment of the at least one first ingestible product as being endorsed by one or more designated users (e.g. one or more of instances of the logic component s116 of the control and information processing subsystem s100 can direct storing the first operation information into one or more instances of the disk farm component s224, involving dispensing ingestible products used for and endorsed by famous actors that suffer migraine headaches, etc.). In an implementation, the electronically directing storing of the first operation information into the operation history information storage, the first operation information associated with the at least one first operation occurrence by the automated ingestible product dispensing equipment of the at least one first ingestible product as being endorsed by one or more designated users is carried out by electronically directing storing of the first operation information into the operation history information storage, the first operation information associated with the at least one first operation occurrence by the automated ingestible product dispensing equipment of the at least one first ingestible product as being endorsed by one or more designated users (e.g. one or more of instances of the logic component s116 of the control and information processing subsystem s100 can direct storing the first operation information into one or more instances of the disk farm component s224, involving dispensing ingestible products used for and endorsed by famous actors that suffer migraine headaches, etc.).

In one or more implementations, operation o11 includes an operation o1136 for electronically directing storing of the first operation information into the operation history information storage, the first operation information associated with the at least one first operation occurrence by the automated ingestible product dispensing equipment of the at least one first ingestible product including the first portion of the at least one first substance as one or more powders. An exemplary version of a non-transitory signal bearing medium of information storage subsystem s200 is depicted as bearing one or more substance powders instructions i1136 that when executed will direct performance of the operation o1136. In an implementation, the one or more substance powders instructions i1136 when executed direct electronically directing storing of the first operation information into the operation history information storage, the first operation information associated with the at least one first operation occurrence by the automated ingestible product dispensing equipment of the at least one first ingestible product including the first portion of the at least one first substance as one or more powders (e.g. one or more of instances of the central processing unit (CPU) component s104 of the control and information processing subsystem s100 can direct storing the first operation information into one or more instances of the disk cluster component s226, involving dispensing ingredients including one or more powdered bulking agents, etc.). Furthermore, the substance powders electrical circuitry arrangement e1136 when activated will perform the operation o1136. In an implementation, the substance powders electrical circuitry arrangement e1136, when activated performs electronically directing storing of the first operation information into the operation history information storage, the first operation information associated with the at least one first operation occurrence by the automated ingestible product dispensing equipment of the at least one first ingestible product including the first portion of the at least one first substance as one or more powders (e.g. one or more of instances of the central processing unit (CPU) component s104 of the control and information processing subsystem s100 can direct storing the first operation information into one or more instances of the disk cluster component s226, involving dispensing ingredients including one or more powdered bulking agents, etc.). In an implementation, the electronically directing storing of the first operation information into the operation history information storage, the first operation information associated with the at least one first operation occurrence by the automated ingestible product dispensing equipment of the at least one first ingestible product including the first portion of the at least one first substance as one or more powders is carried out by electronically directing storing of the first operation information into the operation history information storage, the first operation information associated with the at least one first operation occurrence by the automated ingestible product dispensing equipment of the at least one first ingestible product including the first portion of the at least one first substance as one or more powders (e.g. one or more of instances of the central processing unit (CPU) component s104 of the control and information processing subsystem s100 can direct storing the first operation information into one or more instances of the disk cluster component s226, involving dispensing ingredients including one or more powdered bulking agents, etc.).

Figure 44:
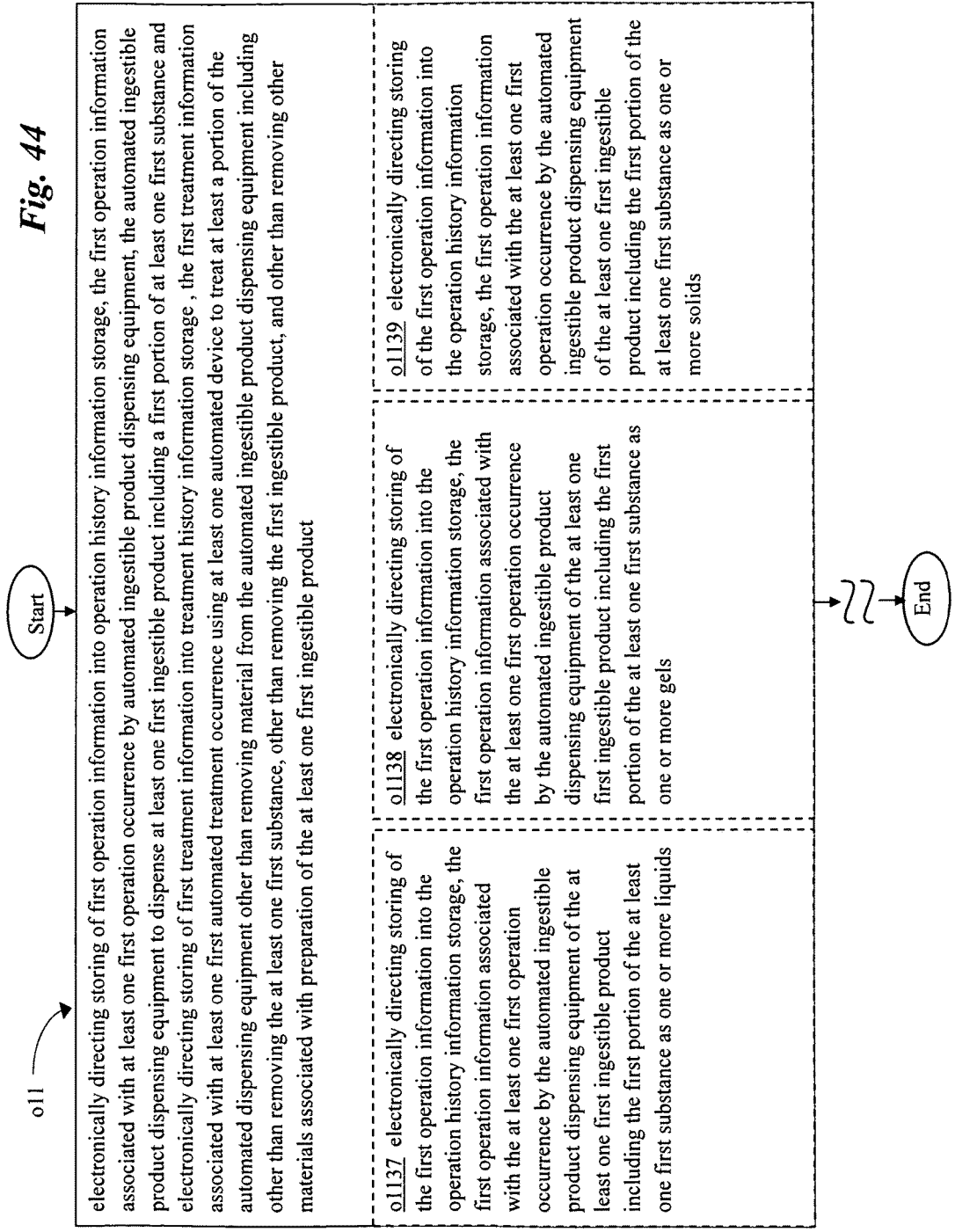
FIG. 44 is a high-level flowchart including exemplary implementations of operation O11 of FIG. 31.

In one or more implementations, as shown in FIG. 44, operation o11 includes an operation o1137 for electronically directing storing of the first operation information into the operation history information storage, the first operation information associated with the at least one first operation occurrence by the automated ingestible product dispensing equipment of the at least one first ingestible product including the first portion of the at least one first substance as one or more liquids. An exemplary version of a non-transitory signal bearing medium of information storage subsystem s200 is depicted as bearing one or more substance liquids instructions i1137 that when executed will direct performance of the operation o1137. In an implementation, the one or more substance liquids instructions i1137 when executed direct electronically directing storing of the first operation information into the operation history information storage, the first operation information associated with the at least one first operation occurrence by the automated ingestible product dispensing equipment of the at least one first ingestible product including the first portion of the at least one first substance as one or more liquids (e.g. one or more of instances of the digital signal processor (DSP) component s106 of the control and information processing subsystem s100 can direct storing the first operation information into one or more instances of the remote backup component s228, involving dispensing ingredients including water and apple juice, etc.). Furthermore, the substance liquids electrical circuitry arrangement e1137 when activated will perform the operation o1137. In an implementation, the substance liquids electrical circuitry arrangement e1137, when activated performs electronically directing storing of the first operation information into the operation history information storage, the first operation information associated with the at least one first operation occurrence by the automated ingestible product dispensing equipment of the at least one first ingestible product including the first portion of the at least one first substance as one or more liquids (e.g. one or more of instances of the digital signal processor (DSP) component s106 of the control and information processing subsystem s100 can direct storing the first operation information into one or more instances of the remote backup component s228, involving dispensing ingredients including water and apple juice, etc.). In an implementation, the electronically directing storing of the first operation information into the operation history information storage, the first operation information associated with the at least one first operation occurrence by the automated ingestible product dispensing equipment of the at least one first ingestible product including the first portion of the at least one first substance as one or more liquids (e.g. one or more of instances of the digital signal processor (DSP) component s106 of the control and information processing subsystem s100 can direct storing the first operation information into one or more instances of the remote backup component s228, involving dispensing ingredients including water and apple juice, etc.).

In one or more implementations, operation o11 includes an operation o1138 for electronically directing storing of the first operation information into the operation history information storage, the first operation information associated with the at least one first operation occurrence by the automated ingestible product dispensing equipment of the at least one first ingestible product including the first portion of the at least one first substance as one or more gels. An exemplary version of a non-transitory signal bearing medium of information storage subsystem s200 is depicted as bearing one or more substance gel instructions i1138 that when executed will direct performance of the operation o1138. In an implementation, the one or more substance gel instructions i1138 when executed direct electronically directing storing of the first operation information into the operation history information storage, the first operation information associated with the at least one first operation occurrence by the automated ingestible product dispensing equipment of the at least one first ingestible product including the first portion of the at least one first substance as one or more gels (e.g. one or more of instances of the application specific integrated circuit (ASIC) component s108 of the control and information processing subsystem s100 can direct storing the first operation information into one or more instances of the server component s230, involving dispensing ingredients including glycerol, etc.). Furthermore, the substance gel electrical circuitry arrangement e1138 when activated will perform the operation o1138. In an implementation, the substance gel electrical circuitry arrangement e1138, when activated performs electronically directing storing of the first operation information into the operation history information storage, the first operation information associated with the at least one first operation occurrence by the automated ingestible product dispensing equipment of the at least one first ingestible product including the first portion of the at least one first substance as one or more gels (e.g. one or more of instances of the application specific integrated circuit (ASIC) component s108 of the control and information processing subsystem s100 can direct storing the first operation information into one or more instances of the server component s230, involving dispensing ingredients including glycerol, etc.). In an implementation, the electronically directing storing of the first operation information into the operation history information storage, the first operation information associated with the at least one first operation occurrence by the automated ingestible product dispensing equipment of the at least one first ingestible product including the first portion of the at least one first substance as one or more gels is carried out by electronically directing storing of the first operation information into the operation history information storage, the first operation information associated with the at least one first operation occurrence by the automated ingestible product dispensing equipment of the at least one first ingestible product including the first portion of the at least one first substance as one or more gels (e.g. one or more of instances of the application specific integrated circuit (ASIC) component s108 of the control and information processing subsystem s100 can direct storing the first operation information into one or more instances of the server component s230, involving dispensing ingredients including glycerol, etc.).

In one or more implementations, operation o11 includes an operation o1139 for electronically directing storing of the first operation information into the operation history information storage, the first operation information associated with the at least one first operation occurrence by the automated ingestible product dispensing equipment of the at least one first ingestible product including the first portion of the at least one first substance as one or more solids. An exemplary version of a non-transitory signal bearing medium of information storage subsystem s200 is depicted as bearing one or more substance solids instructions i1139 that when executed will direct performance of the operation o1139. In an implementation, the one or more substance solids instructions i1139 when executed direct electronically directing storing of the first operation information into the operation history information storage, the first operation information associated with the at least one first operation occurrence by the automated ingestible product dispensing equipment of the at least one first ingestible product including the first portion of the at least one first substance as one or more solids (e.g. one or more of instances of the field programmable gate array (FPGA) component s110 of the control and information processing subsystem s100 can direct storing the first operation information into one or more instances of the digital tape component s232, involving dispensing ingredients including frozen coconut oil, etc.). Furthermore, the substance solids electrical circuitry arrangement e1139 when activated will perform the operation o1139. In an implementation, the substance solids electrical circuitry arrangement e1139, when activated performs electronically directing storing of the first operation information into the operation history information storage, the first operation information associated with the at least one first operation occurrence by the automated ingestible product dispensing equipment of the at least one first ingestible product including the first portion of the at least one first substance as one or more solids (e.g. one or more of instances of the field programmable gate array (FPGA) component s110 of the control and information processing subsystem s100 can direct storing the first operation information into one or more instances of the digital tape component s232, involving dispensing ingredients including frozen coconut oil, etc.). In an implementation, the electronically directing storing of the first operation information into the operation history information storage, the first operation information associated with the at least one first operation occurrence by the automated ingestible product dispensing equipment of the at least one first ingestible product including the first portion of the at least one first substance as one or more solids is carried out by electronically directing storing of the first operation information into the operation history information storage, the first operation information associated with the at least one first operation occurrence by the automated ingestible product dispensing equipment of the at least one first ingestible product including the first portion of the at least one first substance as one or more solids (e.g. one or more of instances of the field programmable gate array (FPGA) component s110 of the control and information processing subsystem s100 can direct storing the first operation information into one or more instances of the digital tape component s232, involving dispensing ingredients including frozen coconut oil, etc.).

Figure 45:
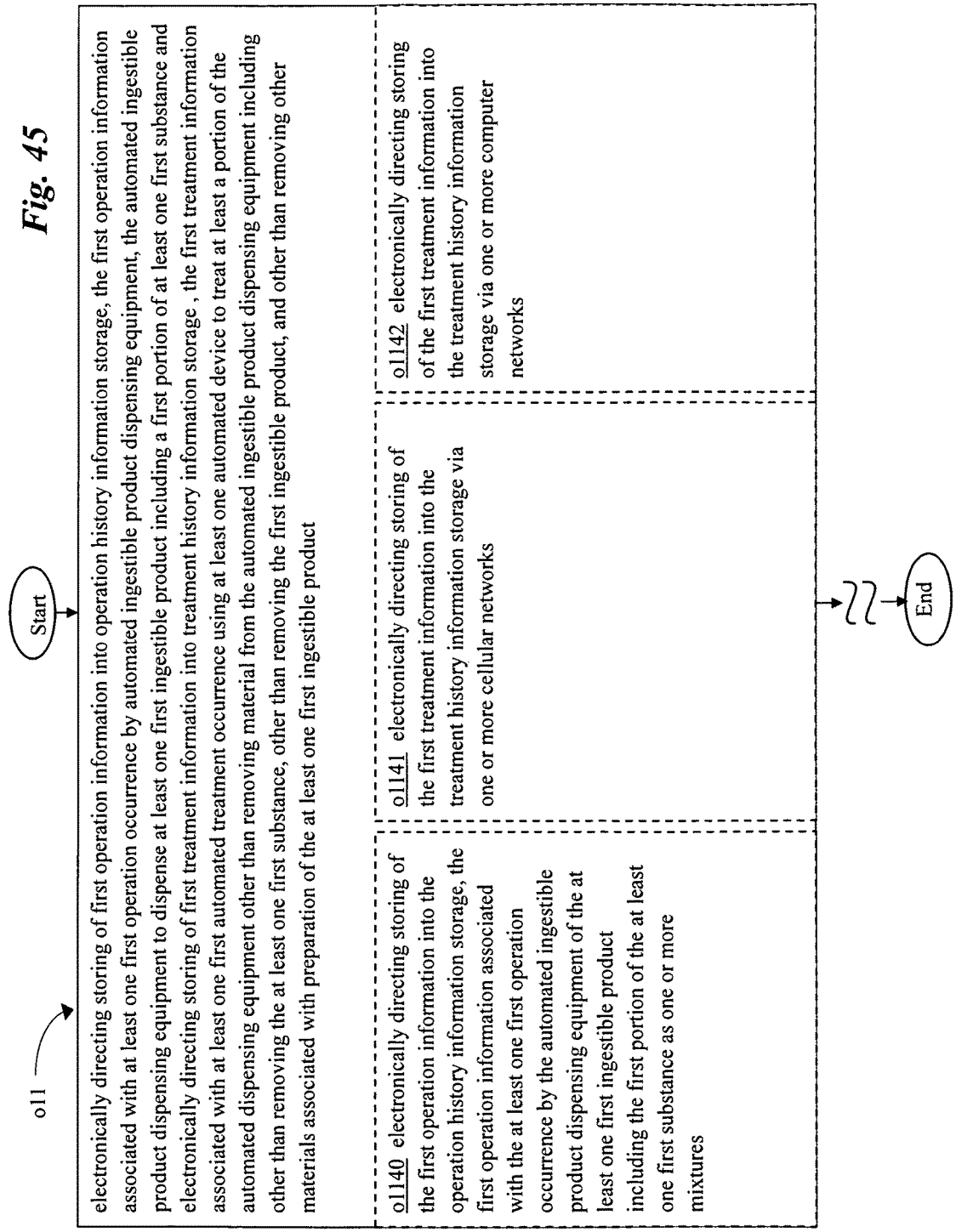
FIG. 45 is a high-level flowchart including exemplary implementations of operation O11 of FIG. 31.

In one or more implementations, as shown in FIG. 45, operation o11 includes an operation o1140 for electronically directing storing of the first operation information into the operation history information storage, the first operation information associated with the at least one first operation occurrence by the automated ingestible product dispensing equipment of the at least one first ingestible product including the first portion of the at least one first substance as one or more mixtures. An exemplary version of a non-transitory signal bearing medium of information storage subsystem s200 is depicted as bearing one or more substance mixtures instructions i1140 that when executed will direct performance of the operation o1140. In an implementation, the one or more substance mixtures instructions i1140 when executed direct electronically directing storing of the first operation information into the operation history information storage, the first operation information associated with the at least one first operation occurrence by the automated ingestible product dispensing equipment of the at least one first ingestible product including the first portion of the at least one first substance as one or more mixtures (e.g. one or more of instances of the multiprocessor component s112 of the control and information processing subsystem s100 can direct storing the first operation information into one or more instances of the optical storage component s234, involving dispensing ingredients including a multivitamin formula, etc.). Furthermore, the substance mixtures electrical circuitry arrangement e1140 when activated will perform the operation o1140. In an implementation, the substance mixtures electrical circuitry arrangement e1140, when activated performs electronically directing storing of the first operation information into the operation history information storage, the first operation information associated with the at least one first operation occurrence by the automated ingestible product dispensing equipment of the at least one first ingestible product including the first portion of the at least one first substance as one or more mixtures (e.g. one or more of instances of the multiprocessor component s112 of the control and information processing subsystem s100 can direct storing the first operation information into one or more instances of the optical storage component s234, involving dispensing ingredients including a multivitamin formula, etc.). In an implementation, the electronically directing storing of the first operation information into the operation history information storage, the first operation information associated with the at least one first operation occurrence by the automated ingestible product dispensing equipment of the at least one first ingestible product including the first portion of the at least one first substance as one or more mixtures is carried out by electronically directing storing of the first operation information into the operation history information storage, the first operation information associated with the at least one first operation occurrence by the automated ingestible product dispensing equipment of the at least one first ingestible product including the first portion of the at least one first substance as one or more mixtures (e.g. one or more of instances of the multiprocessor component s112 of the control and information processing subsystem s100 can direct storing the first operation information into one or more instances of the optical storage component s234, involving dispensing ingredients including a multivitamin formula, etc.).

In one or more implementations, operation o11 includes an operation o1141 for electronically directing storing of the first treatment information into the treatment history information storage via one or more cellular networks. An exemplary version of a non-transitory signal bearing medium of information storage subsystem s200 is depicted as bearing one or more treating cellular instructions i1141 that when executed will direct performance of the operation o1141. In an implementation, the one or more treating cellular instructions i1141 when executed direct electronically directing storing of the first treatment information into the treatment history information storage via one or more cellular networks (e.g. one or more of instances of the optical processing component s114 of the control and information processing subsystem s100 can direct storing the first treatment information into one or more instances of the optical storage component s236, via one or more instances of the cellular network component s514, etc.). Furthermore, the treating cellular electrical circuitry arrangement e1141 when activated will perform the operation o1141. In an implementation, the treating cellular electrical circuitry arrangement e1141, when activated performs electronically directing storing of the first treatment information into the treatment history information storage via one or more cellular networks (e.g. one or more of instances of the optical processing component s114 of the control and information processing subsystem s100 can direct storing the first treatment information into one or more instances of the optical storage component s236, via one or more instances of the cellular network component s514, etc.). In an implementation, the electronically directing storing of the first treatment information into the treatment history information storage via one or more cellular networks is carried out by electronically directing storing of the first treatment information into the treatment history information storage via one or more cellular networks (e.g. one or more of instances of the optical processing component s114 of the control and information processing subsystem s100 can direct storing the first treatment information into one or more instances of the optical storage component s236, via one or more instances of the cellular network component s514, etc.).

In one or more implementations, operation o11 includes an operation o1142 for electronically directing storing of the first treatment information into the treatment history information storage via one or more computer networks. An exemplary version of a non-transitory signal bearing medium of information storage subsystem s200 is depicted as bearing one or more treating network instructions i1142 that when executed will direct performance of the operation o1142. In an implementation, the one or more treating network instructions i1142 when executed direct electronically directing storing of the first treatment information into the treatment history information storage via one or more computer networks (e.g. one or more of instances of the logic component s116 of the control and information processing subsystem s100 can direct storing the first treatment information into one or more instances of the computer readable signal bearing medium s238, via one or more instances of the network cable component s502, etc.). Furthermore, the treating network electrical circuitry arrangement e1142 when activated will perform the operation o1142. In an implementation, the treating network electrical circuitry arrangement e1142, when activated performs electronically directing storing of the first treatment information into the treatment history information storage via one or more computer networks (e.g. one or more of instances of the logic component s116 of the control and information processing subsystem s100 can direct storing the first treatment information into one or more instances of the computer readable signal bearing medium s238, via one or more instances of the network cable component s502, etc.). In an implementation, the electronically directing storing of the first treatment information into the treatment history information storage via one or more computer networks is carried out by electronically directing storing of the first treatment information into the treatment history information storage via one or more computer networks (e.g. one or more of instances of the logic component s116 of the control and information processing subsystem s100 can direct storing the first treatment information into one or more instances of the computer readable signal bearing medium s238, via one or more instances of the network cable component s502, etc.).

Figure 46:
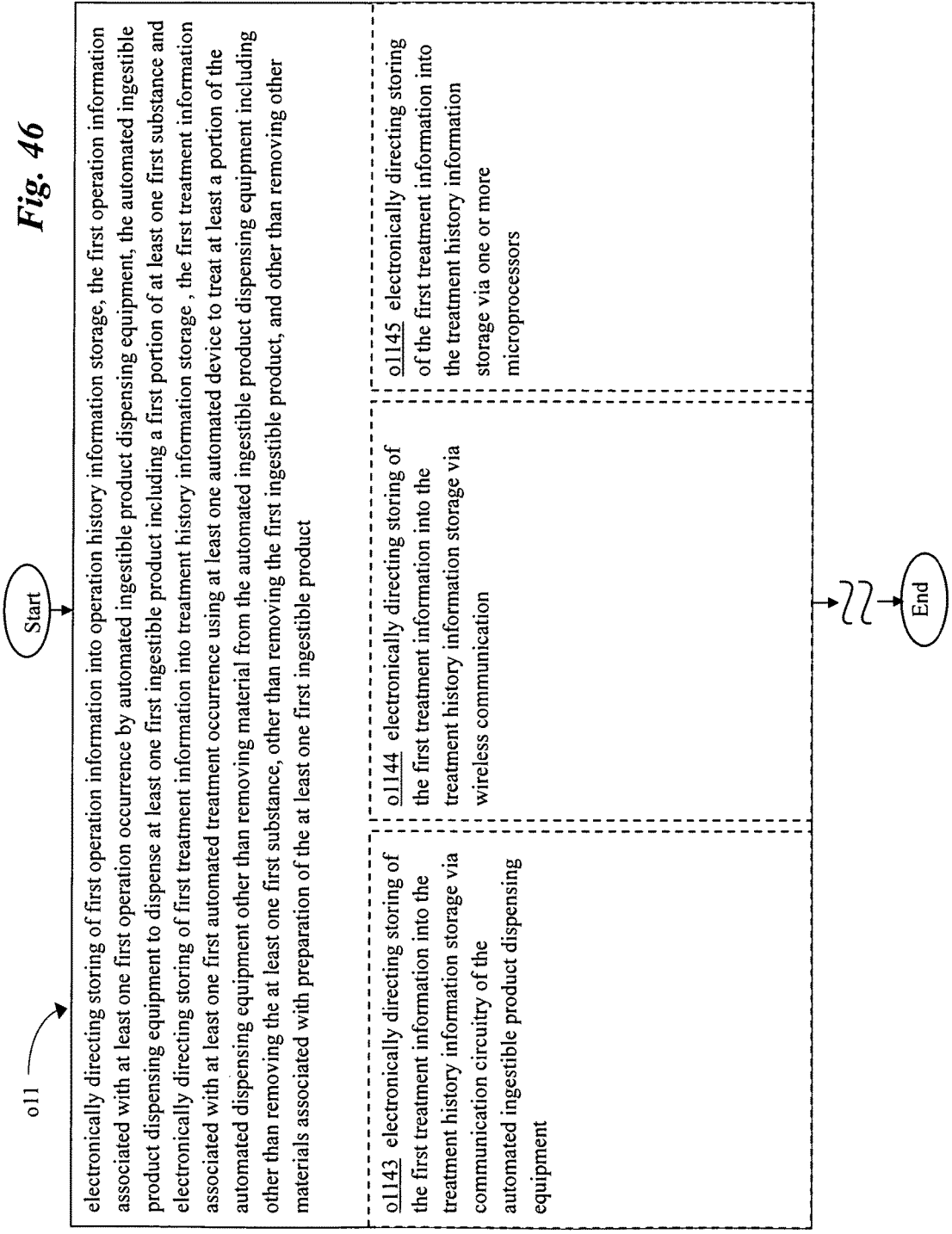
FIG. 46 is a high-level flowchart including exemplary implementations of operation O11 of FIG. 31.

In one or more implementations, as shown in FIG. 46, operation o11 includes an operation o1143 for electronically directing storing of the first treatment information into the treatment history information storage via communication circuitry of the automated ingestible product dispensing equipment. An exemplary version of a non-transitory signal bearing medium of information storage subsystem s200 is depicted as bearing one or more treating circuitry instructions i1143 that when executed will direct performance of the operation o1143. In an implementation, the one or more treating circuitry instructions i1143 when executed direct electronically directing storing of the first treatment information into the treatment history information storage via communication circuitry of the automated ingestible product dispensing equipment (e.g. one or more of instances of the microprocessor component s102 of the control and information processing subsystem s100 can direct storing the first treatment information into one or more instances of the Blu Ray disk component s240, via one or more instances of the transceiver component s522, etc.). Furthermore, the treating circuitry electrical circuitry arrangement e1143 when activated will perform the operation o1143. In an implementation, the treating circuitry electrical circuitry arrangement e1143, when activated performs electronically directing storing of the first treatment information into the treatment history information storage via communication circuitry of the automated ingestible product dispensing equipment (e.g. one or more of instances of the microprocessor component s102 of the control and information processing subsystem s100 can direct storing the first treatment information into one or more instances of the Blu Ray disk component s240, via one or more instances of the transceiver component s522, etc.). In an implementation, the electronically directing storing of the first treatment information into the treatment history information storage via communication circuitry of the automated ingestible product dispensing equipment is carried out by electronically directing storing of the first treatment information into the treatment history information storage via communication circuitry of the automated ingestible product dispensing equipment (e.g. one or more of instances of the microprocessor component s102 of the control and information processing subsystem s100 can direct storing the first treatment information into one or more instances of the Blu Ray disk component s240, via one or more instances of the transceiver component s522, etc.).

In one or more implementations, operation o11 includes an operation o1144 for electronically directing storing of the first treatment information into the treatment history information storage via wireless communication. An exemplary version of a non-transitory signal bearing medium of information storage subsystem s200 is depicted as bearing one or more treating wireless instructions i1144 that when executed will direct performance of the operation o1144. In an implementation, the one or more treating wireless instructions i1144 when executed direct electronically directing storing of the first treatment information into the treatment history information storage via wireless communication (e.g. one or more of instances of the central processing unit (CPU) component s104 of the control and information processing subsystem s100 can direct storing the first treatment information into one or more instances of the random access memory (RAM) component s202, via one or more instances of the wireless network component s510, etc.). Furthermore, the treating wireless electrical circuitry arrangement e1144 when activated will perform the operation o1144. In an implementation, the treating wireless electrical circuitry arrangement e1144, when activated performs electronically directing storing of the first treatment information into the treatment history information storage via wireless communication (e.g. one or more of instances of the central processing unit (CPU) component s104 of the control and information processing subsystem s100 can direct storing the first treatment information into one or more instances of the random access memory (RAM) component s202, via one or more instances of the wireless network component s510, etc.). In an implementation, the electronically directing storing of the first treatment information into the treatment history information storage via wireless communication is carried out by electronically directing storing of the first treatment information into the treatment history information storage via wireless communication (e.g. one or more of instances of the central processing unit (CPU) component s104 of the control and information processing subsystem s100 can direct storing the first treatment information into one or more instances of the random access memory (RAM) component s202, via one or more instances of the wireless network component s510, etc.).

In one or more implementations, operation o11 includes an operation o1145 for electronically directing storing of the first treatment information into the treatment history information storage via one or more microprocessors. An exemplary version of a non-transitory signal bearing medium of information storage subsystem s200 is depicted as bearing one or more treating microprocessor instructions i1145 that when executed will direct performance of the operation o1145. In an implementation, the one or more treating microprocessor instructions i1145 when executed direct electronically directing storing of the first treatment information into the treatment history information storage via one or more microprocessors (e.g. one or more of instances of the digital signal processor (DSP) component s106 of the control and information processing subsystem s100 can direct storing the first treatment information into one or more instances of the dynamic random access memory (DRAM) component s204, via one or more instances of the encrypted communication component s520, etc.). Furthermore, the treating microprocessor electrical circuitry arrangement e1145 when activated will perform the operation o1145. In an implementation, the treating microprocessor electrical circuitry arrangement e1145, when activated performs electronically directing storing of the first treatment information into the treatment history information storage via one or more microprocessors (e.g. one or more of instances of the digital signal processor (DSP) component s106 of the control and information processing subsystem s100 can direct storing the first treatment information into one or more instances of the dynamic random access memory (DRAM) component s204, via one or more instances of the encrypted communication component s520, etc.). In an implementation, the electronically directing storing of the first treatment information into the treatment history information storage via one or more microprocessors is carried out by electronically directing storing of the first treatment information into the treatment history information storage via one or more microprocessors (e.g. one or more of instances of the digital signal processor (DSP) component s106 of the control and information processing subsystem s100 can direct storing the first treatment information into one or more instances of the dynamic random access memory (DRAM) component s204, via one or more instances of the encrypted communication component s520, etc.).

Figure 47:
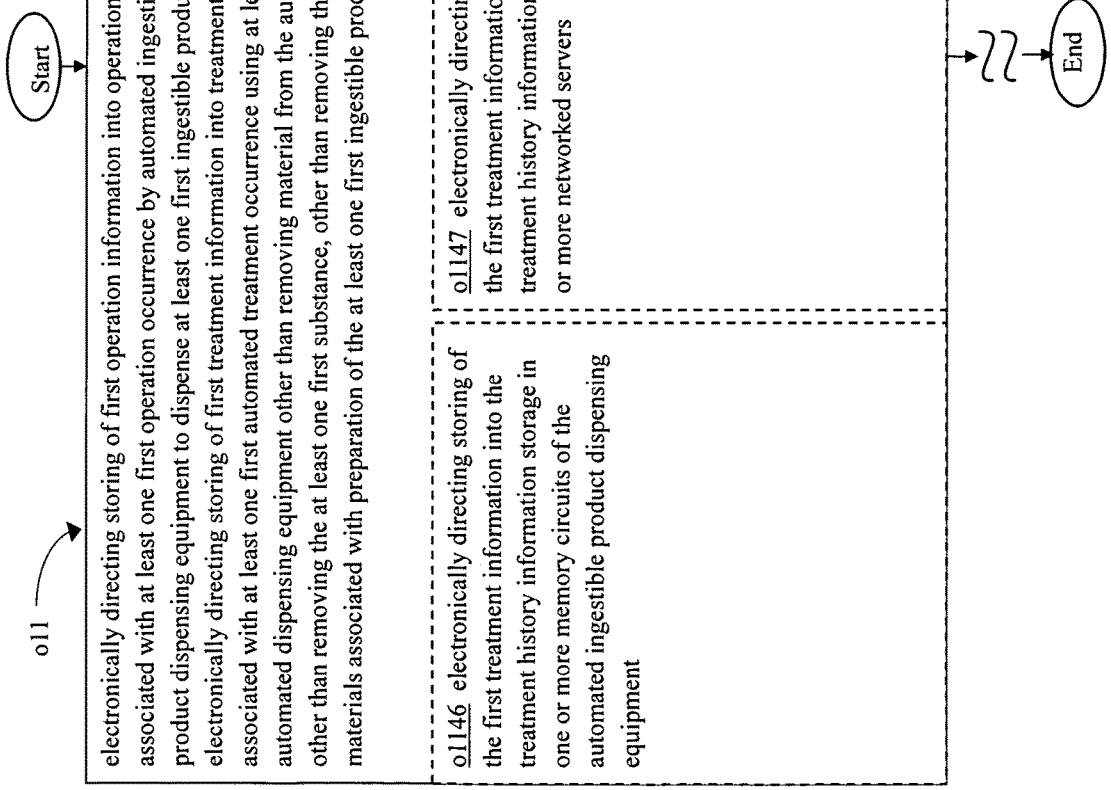
FIG. 47 is a high-level flowchart including exemplary implementations of operation O11 of FIG. 31.

In one or more implementations, as shown in FIG. 47, operation o11 includes an operation o1146 for electronically directing storing of the first treatment information into the treatment history information storage in one or more memory circuits of the automated ingestible product dispensing equipment. An exemplary version of a non-transitory signal bearing medium of information storage subsystem s200 is depicted as bearing one or more treating memory instructions i1146 that when executed will direct performance of the operation o1146. In an implementation, the one or more treating memory instructions i1146 when executed direct electronically directing storing of the first treatment information into the treatment history information storage in one or more memory circuits of the automated ingestible product dispensing equipment (e.g. one or more of instances of the application specific integrated circuit (ASIC) component s108 of the control and information processing subsystem s100 can direct storing the first treatment information into one or more instances of the other volatile memory component s206, via one or more instances of the transmitter component s526, etc.). Furthermore, the treating memory electrical circuitry arrangement e1146 when activated will perform the operation o1146. In an implementation, the treating memory electrical circuitry arrangement e1146, when activated performs electronically directing storing of the first treatment information into the treatment history information storage in one or more memory circuits of the automated ingestible product dispensing equipment (e.g. one or more of instances of the application specific integrated circuit (ASIC) component s108 of the control and information processing subsystem s100 can direct storing the first treatment information into one or more instances of the other volatile memory component s206, via one or more instances of the transmitter component s526, etc.). In an implementation, the electronically directing storing of the first treatment information into the treatment history information storage in one or more memory circuits of the automated ingestible product dispensing equipment is carried out by electronically directing storing of the first treatment information into the treatment history information storage in one or more memory circuits of the automated ingestible product dispensing equipment (e.g. one or more of instances of the application specific integrated circuit (ASIC) component s108 of the control and information processing subsystem s100 can direct storing the first treatment information into one or more instances of the other volatile memory component s206, via one or more instances of the transmitter component s526, etc.).

In one or more implementations, operation o11 includes an operation o1147 for electronically directing storing of the first treatment information into the treatment history information storage in one or more networked servers. An exemplary version of a non-transitory signal bearing medium of information storage subsystem s200 is depicted as bearing one or more treating servers instructions i1147 that when executed will direct performance of the operation o1147. In an implementation, the one or more treating servers instructions i1147 when executed direct electronically directing storing of the first treatment information into the treatment history information storage in one or more networked servers (e.g. one or more of instances of the field programmable gate array (FPGA) component s110 of the control and information processing subsystem s100 can direct storing the first treatment information into one or more instances of the server component s230, etc.). Furthermore, the treating servers electrical circuitry arrangement e1147 when activated will perform the operation o1147. In an implementation, the treating servers electrical circuitry arrangement e1147, when activated performs electronically directing storing of the first treatment information into the treatment history information storage in one or more networked servers (e.g. one or more of instances of the field programmable gate array (FPGA) component s110 of the control and information processing subsystem s100 can direct storing the first treatment information into one or more instances of the server component s230, etc.). In an implementation, the electronically directing storing of the first treatment information into the treatment history information storage in one or more networked servers is carried out by electronically directing storing of the first treatment information into the treatment history information storage in one or more networked servers (e.g. one or more of instances of the field programmable gate array (FPGA) component s110 of the control and information processing subsystem s100 can direct storing the first treatment information into one or more instances of the server component s230, etc.).

In one or more implementations, operation o11 includes an operation o1148 for electronically directing storing of the first treatment information into the treatment history information storage in one or more electronic memory cards. An exemplary version of a non-transitory signal bearing medium of information storage subsystem s200 is depicted as bearing one or more treating card instructions i1148 that when executed will direct performance of the operation o1148. In an implementation, the one or more treating card instructions i1148 when executed direct electronically directing storing of the first treatment information into the treatment history information storage in one or more electronic memory cards (e.g. one or more of instances of the multiprocessor component s112 of the control and information processing subsystem s100 can direct storing the first treatment information into one or more instances of the read only memory (ROM) component s210, etc.). Furthermore, the treating card electrical circuitry arrangement e1148 when activated will perform the operation o1148. In an implementation, the treating card electrical circuitry arrangement e1148, when activated performs electronically directing storing of the first treatment information into the treatment history information storage in one or more electronic memory cards (e.g. one or more of instances of the multiprocessor component s112 of the control and information processing subsystem s100 can direct storing the first treatment information into one or more instances of the read only memory (ROM) component s210, etc.). In an implementation, the electronically directing storing of the first treatment information into the treatment history information storage in one or more electronic memory cards is carried out by electronically directing storing of the first treatment information into the treatment history information storage in one or more electronic memory cards (e.g. one or more of instances of the multiprocessor component s112 of the control and information processing subsystem s100 can direct storing the first treatment information into one or more instances of the read only memory (ROM) component s210, etc.).

Figure 48:
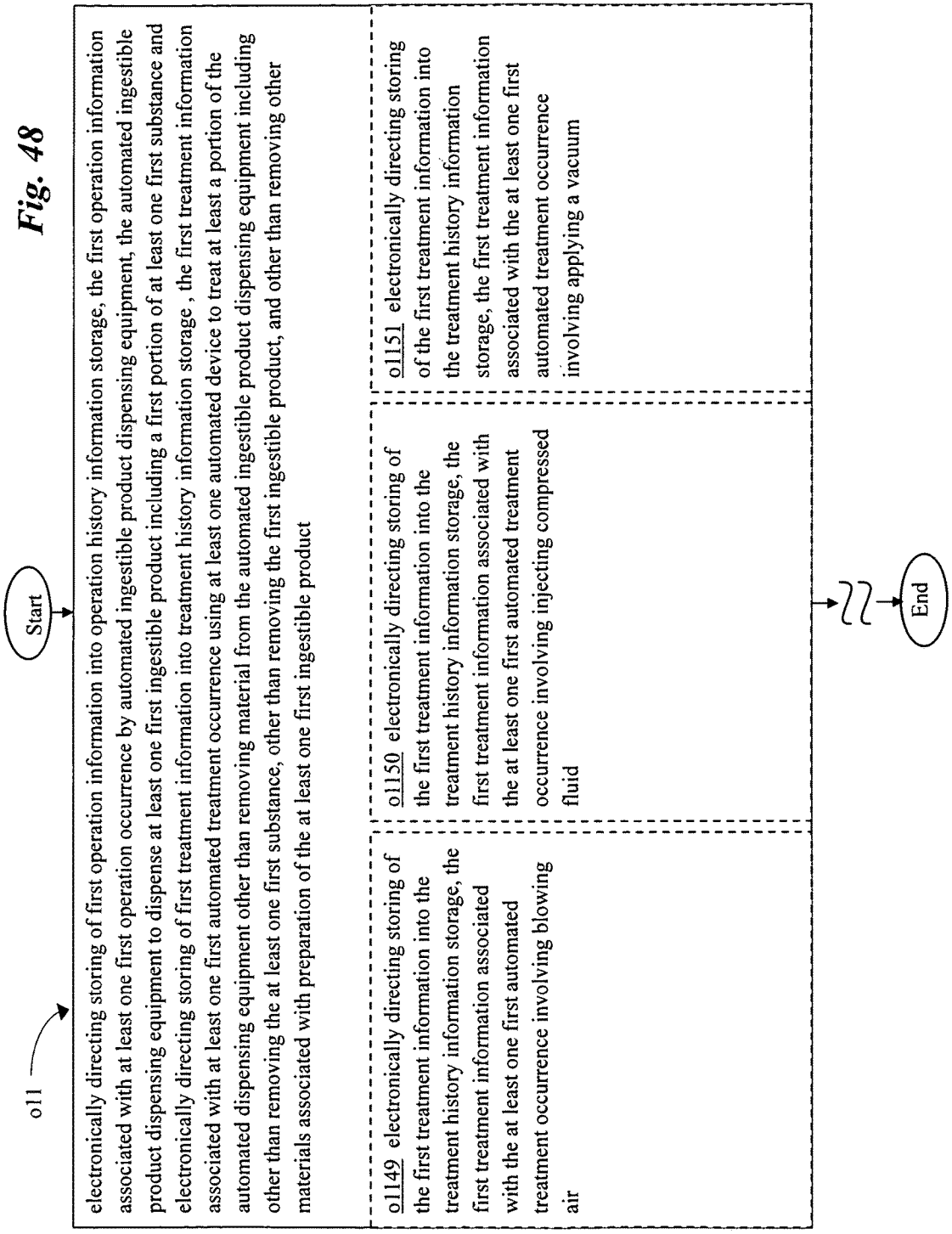
FIG. 48 is a high-level flowchart including exemplary implementations of operation O11 of FIG. 31.

In one or more implementations, as shown in FIG. 48, operation o11 includes an operation o1149 for electronically directing storing of the first treatment information into the treatment history information storage, the first treatment information associated with the at least one first automated treatment occurrence involving blowing air. An exemplary version of a non-transitory signal bearing medium of information storage subsystem s200 is depicted as bearing one or more treating blowing instructions i1149 that when executed will direct performance of the operation o1149. In an implementation, the one or more treating blowing instructions i1149 when executed direct electronically directing storing of the first treatment information into the treatment history information storage, the first treatment information associated with the at least one first automated treatment operation occurrence involving blowing air (e.g. one or more of instances of the optical processing component s114 of the control and information processing subsystem s100 can direct storing the first treatment information into one or more instances of the electrically erasable programmable read only memory (EEPROM) component s212, involving use of one or more instances of the air blower component 802, etc.). Furthermore, the treating blowing electrical circuitry arrangement e1149 when activated will perform the operation o1149. In an implementation, the treating blowing electrical circuitry arrangement e1149, when activated performs electronically directing storing of the first treatment information into the treatment history information storage, the first treatment information associated with the at least one first automated treatment operation occurrence involving blowing air (e.g. one or more of instances of the optical processing component s114 of the control and information processing subsystem s100 can direct storing the first treatment information into one or more instances of the electrically erasable programmable read only memory (EEPROM) component s212, involving use of one or more instances of the air blower component 802, etc.). In an implementation, the electronically directing storing of the first treatment information into the treatment history information storage, the first treatment information associated with the at least one first automated treatment occurrence involving blowing air is carried out by electronically directing storing of the first treatment information into the treatment history information storage, the first treatment information associated with the at least one first automated treatment operation occurrence involving blowing air (e.g. one or more of instances of the optical processing component s114 of the control and information processing subsystem s100 can direct storing the first treatment information into one or more instances of the electrically erasable programmable read only memory (EEPROM) component s212, involving use of one or more instances of the air blower component 802, etc.).

In one or more implementations, operation o11 includes an operation o1150 for electronically directing storing of the first treatment information into the treatment history information storage, the first treatment information associated with the at least one first automated treatment occurrence involving injecting compressed fluid. An exemplary version of a non-transitory signal bearing medium of information storage subsystem s200 is depicted as bearing one or more treating compressed instructions i1150 that when executed will direct performance of the operation o1150. In an implementation, the one or more treating compressed instructions i1150 when executed direct electronically directing storing of the first treatment information into the treatment history information storage, the first treatment information associated with the at least one first automated treatment operation occurrence involving injecting compressed fluid (e.g. one or more of instances of the logic component s116 of the control and information processing subsystem s100 can direct storing the first treatment information into one or more instances of the compact disk (CD) component s214, involving use of one or more instances of the compressed water fluid component s830, etc.). Furthermore, the treating compressed electrical circuitry arrangement e1150 when activated will perform the operation o1150. In an implementation, the treating compressed electrical circuitry arrangement e1150, when activated performs electronically directing storing of the first treatment information into the treatment history information storage, the first treatment information associated with the at least one first automated treatment operation occurrence involving injecting compressed fluid (e.g. one or more of instances of the logic component s116 of the control and information processing subsystem s100 can direct storing the first treatment information into one or more instances of the compact disk (CD) component s214, involving use of one or more instances of the compressed water fluid component s830, etc.). In an implementation, the electronically directing storing of the first treatment information into the treatment history information storage, the first treatment information associated with the at least one first automated treatment occurrence involving injecting compressed fluid is carried out by electronically directing storing of the first treatment information into the treatment history information storage, the first treatment information associated with the at least one first automated treatment operation occurrence involving injecting compressed fluid (e.g. one or more of instances of the logic component s116 of the control and information processing subsystem s100 can direct storing the first treatment information into one or more instances of the compact disk (CD) component s214, involving use of one or more instances of the compressed water fluid component s830, etc.).

In one or more implementations, operation o11 includes an operation o1151 for electronically directing storing of the first treatment information into the treatment history information storage, the first treatment information associated with the at least one first automated treatment occurrence involving applying a vacuum. An exemplary version of a non-transitory signal bearing medium of information storage subsystem s200 is depicted as bearing one or more treating vacuum instructions i1151 that when executed will direct performance of the operation o1151. In an implementation, the one or more treating vacuum instructions i1151 when executed direct electronically directing storing of the first treatment information into the treatment history information storage, the first treatment information associated with the at least one first automated treatment operation occurrence involving applying a vacuum (e.g. one or more of instances of the microprocessor component s102 of the control and information processing subsystem s100 can direct storing the first treatment information into one or more instances of the digital versatile disk (DVD) component s216, involving use of one or more instances of the vacuum component s806, etc.). Furthermore, the treating vacuum electrical circuitry arrangement e1151 when activated will perform the operation o1151. In an implementation, the treating vacuum electrical circuitry arrangement e1151, when activated performs electronically directing storing of the first treatment information into the treatment history information storage, the first treatment information associated with the at least one first automated treatment operation occurrence involving applying a vacuum (e.g. one or more of instances of the microprocessor component s102 of the control and information processing subsystem s100 can direct storing the first treatment information into one or more instances of the digital versatile disk (DVD) component s216, involving use of one or more instances of the vacuum component s806, etc.). In an implementation, the electronically directing storing of the first treatment information into the treatment history information storage, the first treatment information associated with the at least one first automated treatment occurrence involving applying a vacuum is carried out by electronically directing storing of the first treatment information into the treatment history information storage, the first treatment information associated with the at least one first automated treatment operation occurrence involving applying a vacuum (e.g. one or more of instances of the microprocessor component s102 of the control and information processing subsystem s100 can direct storing the first treatment information into one or more instances of the digital versatile disk (DVD) component s216, involving use of one or more instances of the vacuum component s806, etc.).

Figure 49:
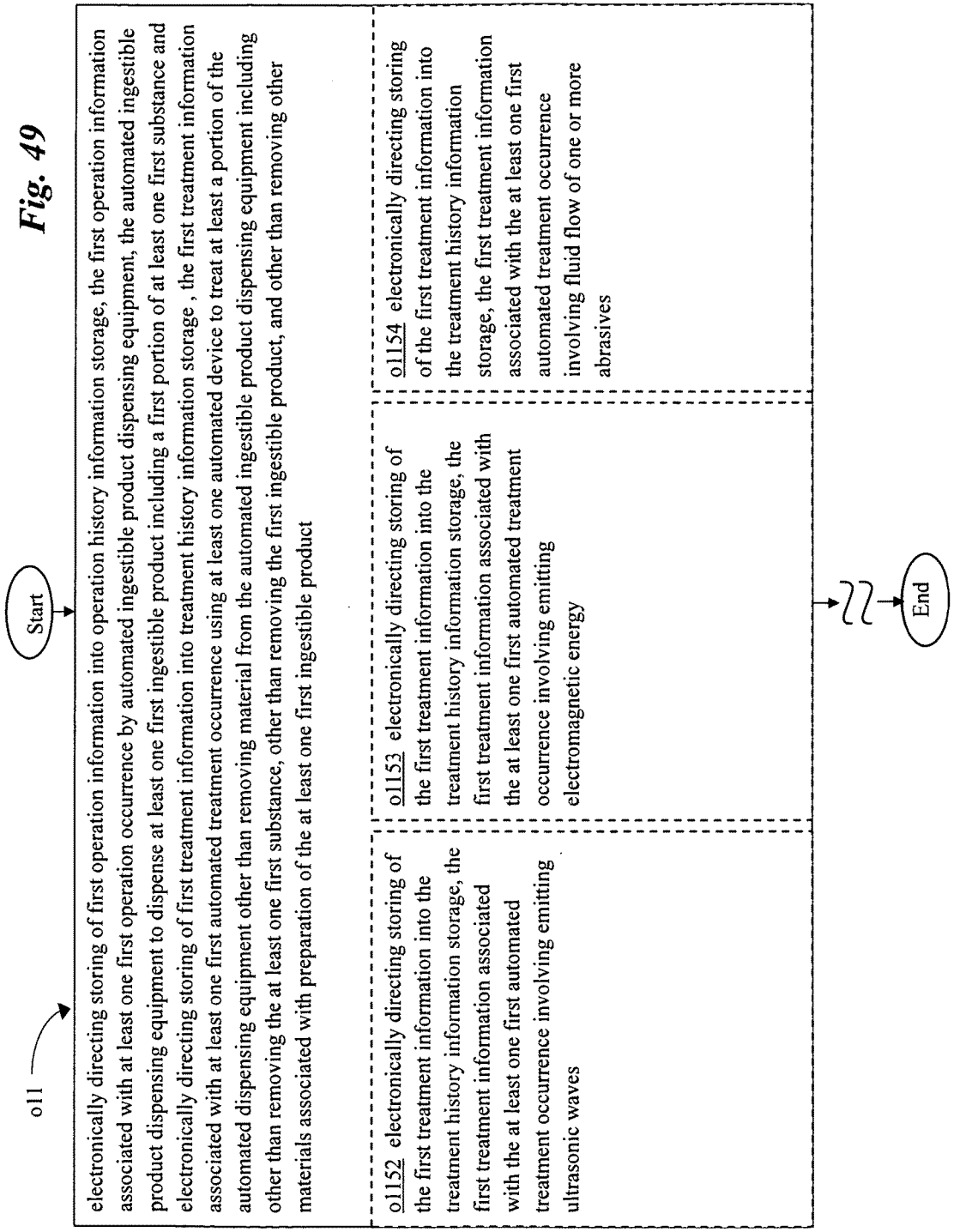
FIG. 49 is a high-level flowchart including exemplary implementations of operation O11 of FIG. 31.

In one or more implementations, as shown in FIG. 49, operation o11 includes an operation o1152 for electronically directing storing of the first treatment information into the treatment history information storage, the first treatment information associated with the at least one first automated treatment occurrence involving emitting ultrasonic waves. An exemplary version of a non-transitory signal bearing medium of information storage subsystem s200 is depicted as bearing one or more treating ultrasonic instructions i1152 that when executed will direct performance of the operation o1152. In an implementation, the one or more treating ultrasonic instructions i1152 when executed direct electronically directing storing of the first treatment information into the treatment history information storage, the first treatment information associated with the at least one first automated treatment operation occurrence involving emitting ultrasonic waves (e.g. one or more of instances of the central processing unit (CPU) component s104 of the control and information processing subsystem s100 can direct storing the first treatment information into one or more instances of the flash memory component s218, involving use of one or more instances of the ultrasonic component s808, etc.). Furthermore, the treating ultrasonic electrical circuitry arrangement e1152 when activated will perform the operation o1152. In an implementation, the treating ultrasonic electrical circuitry arrangement e1152, when activated performs electronically directing storing of the first treatment information into the treatment history information storage, the first treatment information associated with the at least one first automated treatment operation occurrence involving emitting ultrasonic waves (e.g. one or more of instances of the central processing unit (CPU) component s104 of the control and information processing subsystem s100 can direct storing the first treatment information into one or more instances of the flash memory component s218, involving use of one or more instances of the ultrasonic component s808, etc.). In an implementation, the electronically directing storing of the first treatment information into the treatment history information storage, the first treatment information associated with the at least one first automated treatment occurrence involving emitting ultrasonic waves is carried out by electronically directing storing of the first treatment information into the treatment history information storage, the first treatment information associated with the at least one first automated treatment operation occurrence involving emitting ultrasonic waves (e.g. one or more of instances of the central processing unit (CPU) component s104 of the control and information processing subsystem s100 can direct storing the first treatment information into one or more instances of the flash memory component s218, involving use of one or more instances of the ultrasonic component s808, etc.).

In one or more implementations, operation o11 includes an operation o1153 for electronically directing storing of the first treatment information into the treatment history information storage, the first treatment information associated with the at least one first automated treatment occurrence involving emitting electromagnetic energy. An exemplary version of a non-transitory signal bearing medium of information storage subsystem s200 is depicted as bearing one or more treating electromagnetic instructions i1153 that when executed will direct performance of the operation o1153. In an implementation, the one or more treating electromagnetic instructions i1153 when executed direct electronically directing storing of the first treatment information into the treatment history information storage, the first treatment information associated with the at least one first automated treatment operation occurrence involving emitting electromagnetic energy (e.g. one or more of instances of the digital signal processor (DSP) component s106 of the control and information processing subsystem s100 can direct storing the first treatment information into one or more instances of the other nonvolatile memory component s220, involving use of one or more instances of the radiant energy component s810, etc.). Furthermore, the treating electromagnetic electrical circuitry arrangement e1153 when activated will perform the operation o1153. In an implementation, the treating electromagnetic electrical circuitry arrangement e1153, when activated performs electronically directing storing of the first treatment information into the treatment history information storage, the first treatment information associated with the at least one first automated treatment operation occurrence involving emitting electromagnetic energy (e.g. one or more of instances of the digital signal processor (DSP) component s106 of the control and information processing subsystem s100 can direct storing the first treatment information into one or more instances of the other nonvolatile memory component s220, involving use of one or more instances of the radiant energy component s810, etc.). In an implementation, the electronically directing storing of the first treatment information into the treatment history information storage, the first treatment information associated with the at least one first automated treatment occurrence involving emitting electromagnetic energy is carried out by electronically directing storing of the first treatment information into the treatment history information storage, the first treatment information associated with the at least one first automated treatment operation occurrence involving emitting electromagnetic energy (e.g. one or more of instances of the digital signal processor (DSP) component s106 of the control and information processing subsystem s100 can direct storing the first treatment information into one or more instances of the other nonvolatile memory component s220, involving use of one or more instances of the radiant energy component s810, etc.).

In one or more implementations, operation o11 includes an operation o1154 for electronically directing storing of the first treatment information into the treatment history information storage, the first treatment information associated with the at least one first automated treatment occurrence involving fluid flow of one or more abrasives. An exemplary version of a non-transitory signal bearing medium of information storage subsystem s200 is depicted as bearing one or more treating abrasives instructions i1154 that when executed will direct performance of the operation o1154. In an implementation, the one or more treating abrasives instructions i1154 when executed direct electronically directing storing of the first treatment information into the treatment history information storage, the first treatment information associated with the at least one first automated treatment operation occurrence involving fluid flow of one or more abrasives (e.g. one or more of instances of the application specific integrated circuit (ASIC) component s108 of the control and information processing subsystem s100 can direct storing the first treatment information into one or more instances of the hard drive component s222, involving use of one or more instances of the material flush abrasive component s820, etc.). Furthermore, the treating abrasives electrical circuitry arrangement e1154 when activated will perform the operation o1154. In an implementation, the treating abrasives electrical circuitry arrangement e1154, when activated performs electronically directing storing of the first treatment information into the treatment history information storage, the first treatment information associated with the at least one first automated treatment operation occurrence involving fluid flow of one or more abrasives (e.g. one or more of instances of the application specific integrated circuit (ASIC) component s108 of the control and information processing subsystem s100 can direct storing the first treatment information into one or more instances of the hard drive component s222, involving use of one or more instances of the material flush abrasive component s820, etc.). In an implementation, the electronically directing storing of the first treatment information into the treatment history information storage, the first treatment information associated with the at least one first automated treatment occurrence involving fluid flow of one or more abrasives is carried out by electronically directing storing of the first treatment information into the treatment history information storage, the first treatment information associated with the at least one first automated treatment operation occurrence involving fluid flow of one or more abrasives (e.g. one or more of instances of the application specific integrated circuit (ASIC) component s108 of the control and information processing subsystem s100 can direct storing the first treatment information into one or more instances of the hard drive component s222, involving use of one or more instances of the material flush abrasive component s820, etc.).

In one or more implementations, as shown in FIG. 50, operation o11 includes an operation o1155 for electronically directing storing of the first treatment information into the treatment history information storage, the first treatment information associated with the at least one first automated treatment occurrence involving brush contact. An exemplary version of a non-transitory signal bearing medium of information storage subsystem s200 is depicted as bearing one or more treating brush instructions i1155 that when executed will direct performance of the operation o1155. In an implementation, the one or more treating brush instructions i1155 when executed direct electronically directing storing of the first treatment information into the treatment history information storage, the first treatment information associated with the at least one first automated treatment operation occurrence involving brush contact (e.g. one or more of instances of the field programmable gate array (FPGA) component s110 of the control and information processing subsystem s100 can direct storing the first treatment information into one or more instances of the disk farm component s224, involving use of one or more instances of the brush component s814, etc.). Furthermore, the treating brush electrical circuitry arrangement e1155 when activated will perform the operation o1155. In an implementation, the treating brush electrical circuitry arrangement e1155, when activated performs electronically directing storing of the first treatment information into the treatment history information storage, the first treatment information associated with the at least one first automated treatment operation occurrence involving brush contact (e.g. one or more of instances of the field programmable gate array (FPGA) component s110 of the control and information processing subsystem s100 can direct storing the first treatment information into one or more instances of the disk farm component s224, involving use of one or more instances of the brush component s814, etc.). In an implementation, the electronically directing storing of the first treatment information into the treatment history information storage, the first treatment information associated with the at least one first automated treatment occurrence involving brush contact is carried out by electronically directing storing of the first treatment information into the treatment history information storage, the first treatment information associated with the at least one first automated treatment operation occurrence involving brush contact (e.g. one or more of instances of the field programmable gate array (FPGA) component s110 of the control and information processing subsystem s100 can direct storing the first treatment information into one or more instances of the disk farm component s224, involving use of one or more instances of the brush component s814, etc.).

In one or more implementations, operation o11 includes an operation o1156 for electronically directing storing of the first treatment information into the treatment history information storage, the first treatment information associated with the at least one first automated treatment occurrence involving chemical action. An exemplary version of a non-transitory signal bearing medium of information storage subsystem s200 is depicted as bearing one or more treating chemical instructions i1156 that when executed will direct performance of the operation o1156. In an implementation, the one or more treating chemical instructions i1156 when executed direct electronically directing storing of the first treatment information into the treatment history information storage, the first treatment information associated with the at least one first automated treatment operation occurrence involving chemical action (e.g. one or more of instances of the multiprocessor component s112 of the control and information processing subsystem s100 can direct storing the first treatment information into one or more instances of the disk cluster component s226, involving use of one or more instances of the chemical component s832, etc.). Furthermore, the treating chemical electrical circuitry arrangement e1156 when activated will perform the operation o1156. In an implementation, the treating chemical electrical circuitry arrangement e1156, when activated performs electronically directing storing of the first treatment information into the treatment history information storage, the first treatment information associated with the at least one first automated treatment operation occurrence involving chemical action (e.g. one or more of instances of the multiprocessor component s112 of the control and information processing subsystem s100 can direct storing the first treatment information into one or more instances of the disk cluster component s226, involving use of one or more instances of the chemical component s832, etc.). In an implementation, the electronically directing storing of the first treatment information into the treatment history information storage, the first treatment information associated with the at least one first automated treatment occurrence involving chemical action is carried out by electronically directing storing of the first treatment information into the treatment history information storage, the first treatment information associated with the at least one first automated treatment operation occurrence involving chemical action (e.g. one or more of instances of the multiprocessor component s112 of the control and information processing subsystem s100 can direct storing the first treatment information into one or more instances of the disk cluster component s226, involving use of one or more instances of the chemical component s832, etc.).

In one or more implementations, operation o11 includes an operation o1157 for electronically directing storing of the first treatment information into the treatment history information storage, the first treatment information associated with the at least one first automated treatment occurrence to treat at least a portion of the automated ingestible product dispensing equipment as one or more manifolds of tubes. An exemplary version of a non-transitory signal bearing medium of information storage subsystem s200 is depicted as bearing one or more treating tubes instructions i1157 that when executed will direct performance of the operation o1157. In an implementation, the one or more treating tubes instructions i1157 when executed direct electronically directing storing of the first treatment information into the treatment history information storage, the first treatment information associated with the at least one first automated treatment operation occurrence to treat at least a portion of the automated ingestible product dispensing equipment as one or more manifolds of tubes (e.g. one or more of instances of the optical processing component s114 of the control and information processing subsystem s100 can direct storing the first treatment information into one or more instances of the remote backup component s228, involving use of one or more instances of the compressed water fluid component s830, etc.). Furthermore, the treating tubes electrical circuitry arrangement e1157 when activated will perform the operation o1157. In an implementation, the treating tubes electrical circuitry arrangement e1157, when activated performs electronically directing storing of the first treatment information into the treatment history information storage, the first treatment information associated with the at least one first automated treatment operation occurrence to treat at least a portion of the automated ingestible product dispensing equipment as one or more manifolds of tubes (e.g. one or more of instances of the optical processing component s114 of the control and information processing subsystem s100 can direct storing the first treatment information into one or more instances of the remote backup component s228, involving use of one or more instances of the compressed water fluid component s830, etc.). In an implementation, the electronically directing storing of the first treatment information into the treatment history information storage, the first treatment information associated with the at least one first automated treatment occurrence to treat at least a portion of the automated ingestible product dispensing equipment as one or more manifolds of tubes is carried out by electronically directing storing of the first treatment information into the treatment history information storage, the first treatment information associated with the at least one first automated treatment operation occurrence to treat at least a portion of the automated ingestible product dispensing equipment as one or more manifolds of tubes (e.g. one or more of instances of the optical processing component s114 of the control and information processing subsystem s100 can direct storing the first treatment information into one or more instances of the remote backup component s228, involving use of one or more instances of the compressed water fluid component s830, etc.).

In one or more implementations, as shown in FIG. 51, operation o11 includes an operation o1158 for electronically directing storing of the first treatment information into the treatment history information storage, the first treatment information associated with the at least one first automated treatment occurrence to treat at least a portion of the automated ingestible product dispensing equipment as one or more nozzles. An exemplary version of a non-transitory signal bearing medium of information storage subsystem s200 is depicted as bearing one or more treating nozzles instructions i1158 that when executed will direct performance of the operation o1158. In an implementation, the one or more treating nozzles instructions i1158 when executed direct electronically directing storing of the first treatment information into the treatment history information storage, the first treatment information associated with the at least one first automated treatment operation occurrence to treat at least a portion of the automated ingestible product dispensing equipment as one or more nozzles (e.g. one or more of instances of the logic component s116 of the control and information processing subsystem s100 can direct storing the first treatment information into one or more instances of the server component s230, involving one or more nozzles as part of one or more instances of the blending component s714, etc.). Furthermore, the treating nozzles electrical circuitry arrangement e1158 when activated will perform the operation o1158. In an implementation, the treating nozzles electrical circuitry arrangement e1158, when activated performs electronically directing storing of the first treatment information into the treatment history information storage, the first treatment information associated with the at least one first automated treatment operation occurrence to treat at least a portion of the automated ingestible product dispensing equipment as one or more nozzles (e.g. one or more of instances of the logic component s116 of the control and information processing subsystem s100 can direct storing the first treatment information into one or more instances of the server component s230, involving one or more nozzles as part of one or more instances of the blending component s714, etc.). In an implementation, the electronically directing storing of the first treatment information into the treatment history information storage, the first treatment information associated with the at least one first automated treatment occurrence to treat at least a portion of the automated ingestible product dispensing equipment as one or more nozzles is carried out by electronically directing storing of the first treatment information into the treatment history information storage, the first treatment information associated with the at least one first automated treatment operation occurrence to treat at least a portion of the automated ingestible product dispensing equipment as one or more nozzles (e.g. one or more of instances of the logic component s116 of the control and information processing subsystem s100 can direct storing the first treatment information into one or more instances of the server component s230, involving one or more nozzles as part of one or more instances of the blending component s714, etc.).

In one or more implementations, operation o11 includes an operation o1159 for electronically directing storing of the first treatment information into the treatment history information storage, the first treatment information associated with the at least one first automated treatment occurrence to treat at least a portion of the automated ingestible product dispensing equipment as one or more heating chambers. An exemplary version of a non-transitory signal bearing medium of information storage subsystem s200 is depicted as bearing one or more treating heating instructions i1159 that when executed will direct performance of the operation o1159. In an implementation, the one or more treating heating instructions i1159 when executed direct electronically directing storing of the first treatment information into the treatment history information storage, the first treatment information associated with the at least one first automated treatment operation occurrence to treat at least a portion of the automated ingestible product dispensing equipment as one or more heating chambers (e.g. one or more of instances of the microprocessor component s102 of the control and information processing subsystem s100 can direct storing the first treatment information into one or more instances of the digital tape component s232, involving one or more heating chambers as part of one or more instances of the heating component s702, etc.). Furthermore, the treating heating electrical circuitry arrangement e1159 when activated will perform the operation o1159. In an implementation, the treating heating electrical circuitry arrangement e1159, when activated performs electronically directing storing of the first treatment information into the treatment history information storage, the first treatment information associated with the at least one first automated treatment operation occurrence to treat at least a portion of the automated ingestible product dispensing equipment as one or more heating chambers (e.g. one or more of instances of the microprocessor component s102 of the control and information processing subsystem s100 can direct storing the first treatment information into one or more instances of the digital tape component s232, involving one or more heating chambers as part of one or more instances of the heating component s702, etc.). In an implementation, the electronically directing storing of the first treatment information into the treatment history information storage, the first treatment information associated with the at least one first automated treatment occurrence to treat at least a portion of the automated ingestible product dispensing equipment as one or more heating chambers is carried out by electronically directing storing of the first treatment information into the treatment history information storage, the first treatment information associated with the at least one first automated treatment operation occurrence to treat at least a portion of the automated ingestible product dispensing equipment as one or more heating chambers (e.g. one or more of instances of the microprocessor component s102 of the control and information processing subsystem s100 can direct storing the first treatment information into one or more instances of the digital tape component s232, involving one or more heating chambers as part of one or more instances of the heating component s702, etc.).

In one or more implementations, operation o11 includes an operation o1160 for electronically directing storing of the first treatment information into the treatment history information storage, the first treatment information associated with the at least one first automated treatment occurrence to treat at least a portion of the automated ingestible product dispensing equipment as one or more blender compartments. An exemplary version of a non-transitory signal bearing medium of information storage subsystem s200 is depicted as bearing one or more treating blender instructions i1160 that when executed will direct performance of the operation o1160. In an implementation, the one or more treating blender instructions i1160 when executed direct electronically directing storing of the first treatment information into the treatment history information storage, the first treatment information associated with the at least one first automated treatment operation occurrence to treat at least a portion of the automated ingestible product dispensing equipment as one or more blender compartments (e.g. one or more of instances of the central processing unit (CPU) component s104 of the control and information processing subsystem s100 can direct storing the first treatment information into one or more instances of the optical storage component s234, involving one or more blender compartments as part of one or more instances of the blending component s714, etc.). Furthermore, the treating blender electrical circuitry arrangement e1160 when activated will perform the operation o1160. In an implementation, the treating blender electrical circuitry arrangement e1160, when activated performs electronically directing storing of the first treatment information into the treatment history information storage, the first treatment information associated with the at least one first automated treatment operation occurrence to treat at least a portion of the automated ingestible product dispensing equipment as one or more blender compartments (e.g. one or more of instances of the central processing unit (CPU) component s104 of the control and information processing subsystem s100 can direct storing the first treatment information into one or more instances of the optical storage component s234, involving one or more blender compartments as part of one or more instances of the blending component s714, etc.). In an implementation, the electronically directing storing of the first treatment information into the treatment history information storage, the first treatment information associated with the at least one first automated treatment occurrence to treat at least a portion of the automated ingestible product dispensing equipment as one or more blender compartments is carried out by electronically directing storing of the first treatment information into the treatment history information storage, the first treatment information associated with the at least one first automated treatment operation occurrence to treat at least a portion of the automated ingestible product dispensing equipment as one or more blender compartments (e.g. one or more of instances of the central processing unit (CPU) component s104 of the control and information processing subsystem s100 can direct storing the first treatment information into one or more instances of the optical storage component s234, involving one or more blender compartments as part of one or more instances of the blending component s714, etc.).

Figure 52:
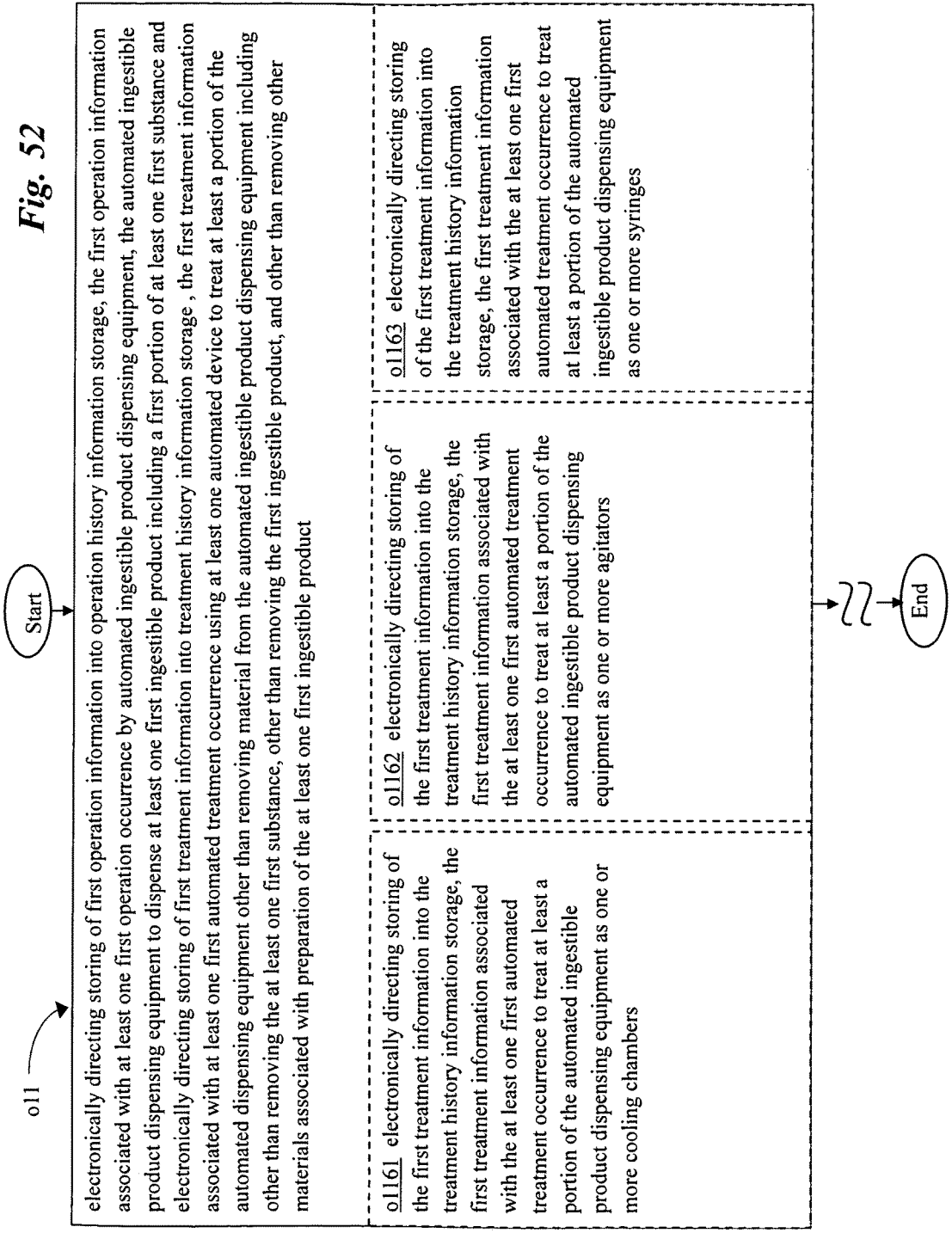
FIG. 52 is a high-level flowchart including exemplary implementations of operation O11 of FIG. 31.

In one or more implementations, as shown in FIG. 52, operation o11 includes an operation o1161 for electronically directing storing of the first treatment information into the treatment history information storage, the first treatment information associated with the at least one first automated treatment occurrence to treat at least a portion of the automated ingestible product dispensing equipment as one or more cooling chambers. An exemplary version of a non-transitory signal bearing medium of information storage subsystem s200 is depicted as bearing one or more treating cooling instructions i1161 that when executed will direct performance of the operation o1161. In an implementation, the one or more treating cooling instructions i1161 when executed direct electronically directing storing of the first treatment information into the treatment history information storage, the first treatment information associated with the at least one first automated treatment operation occurrence to treat at least a portion of the automated ingestible product dispensing equipment as one or more cooling chambers (e.g. one or more of instances of the digital signal processor (DSP) component s106 of the control and information processing subsystem s100 can direct storing the first treatment information into one or more instances of the optical storage component s236, involving one or more cooling chambers as part of one or more instances of the cooling component s704, etc.). Furthermore, the treating cooling electrical circuitry arrangement e1161 when activated will perform the operation o1161. In an implementation, the treating cooling electrical circuitry arrangement e1161, when activated performs electronically directing storing of the first treatment information into the treatment history information storage, the first treatment information associated with the at least one first automated treatment operation occurrence to treat at least a portion of the automated ingestible product dispensing equipment as one or more cooling chambers (e.g. one or more of instances of the digital signal processor (DSP) component s106 of the control and information processing subsystem s100 can direct storing the first treatment information into one or more instances of the optical storage component s236, involving one or more cooling chambers as part of one or more instances of the cooling component s704, etc.). In an implementation, the electronically directing storing of the first treatment information into the treatment history information storage, the first treatment information associated with the at least one first automated treatment occurrence to treat at least a portion of the automated ingestible product dispensing equipment as one or more cooling chambers is carried out by electronically directing storing of the first treatment information into the treatment history information storage, the first treatment information associated with the at least one first automated treatment operation occurrence to treat at least a portion of the automated ingestible product dispensing equipment as one or more cooling chambers (e.g. one or more of instances of the digital signal processor (DSP) component s106 of the control and information processing subsystem s100 can direct storing the first treatment information into one or more instances of the optical storage component s236, involving one or more cooling chambers as part of one or more instances of the cooling component s704, etc.).

In one or more implementations, operation o11 includes an operation o1162 for electronically directing storing of the first treatment information into the treatment history information storage, the first treatment information associated with the at least one first automated treatment occurrence to treat at least a portion of the automated ingestible product dispensing equipment as one or more agitators. An exemplary version of a non-transitory signal bearing medium of information storage subsystem s200 is depicted as bearing one or more treating agitator instructions i1162 that when executed will direct performance of the operation o1162. In an implementation, the one or more treating agitator instructions i1162 when executed direct electronically directing storing of the first treatment information into the treatment history information storage, the first treatment information associated with the at least one first automated treatment operation occurrence to treat at least a portion of the automated ingestible product dispensing equipment as one or more agitators (e.g. one or more of instances of the application specific integrated circuit (ASIC) component s108 of the control and information processing subsystem s100 can direct storing the first treatment information into one or more instances of the computer readable signal bearing medium s238, involving one or more agitators as part of one or more instances of the mixer component s716, etc.). Furthermore, the treating agitator electrical circuitry arrangement e1162 when activated will perform the operation o1162. In an implementation, the treating agitator electrical circuitry arrangement e1162, when activated performs electronically directing storing of the first treatment information into the treatment history information storage, the first treatment information associated with the at least one first automated treatment operation occurrence to treat at least a portion of the automated ingestible product dispensing equipment as one or more agitators (e.g. one or more of instances of the application specific integrated circuit (ASIC) component s108 of the control and information processing subsystem s100 can direct storing the first treatment information into one or more instances of the computer readable signal bearing medium s238, involving one or more agitators as part of one or more instances of the mixer component s716, etc.). In an implementation, the electronically directing storing of the first treatment information into the treatment history information storage, the first treatment information associated with the at least one first automated treatment occurrence to treat at least a portion of the automated ingestible product dispensing equipment as one or more agitators is carried out by electronically directing storing of the first treatment information into the treatment history information storage, the first treatment information associated with the at least one first automated treatment operation occurrence to treat at least a portion of the automated ingestible product dispensing equipment as one or more agitators (e.g. one or more of instances of the application specific integrated circuit (ASIC) component s108 of the control and information processing subsystem s100 can direct storing the first treatment information into one or more instances of the computer readable signal bearing medium s238, involving one or more agitators as part of one or more instances of the mixer component s716, etc.).

In one or more implementations, operation o11 includes an operation o1163 for electronically directing storing of the first treatment information into the treatment history information storage, the first treatment information associated with the at least one first automated treatment occurrence to treat at least a portion of the automated ingestible product dispensing equipment as one or more syringes. An exemplary version of a non-transitory signal bearing medium of information storage subsystem s200 is depicted as bearing one or more treating syringe instructions i1163 that when executed will direct performance of the operation o1163. In an implementation, the one or more treating syringe instructions i1163 when executed direct electronically directing storing of the first treatment information into the treatment history information storage, the first treatment information associated with the at least one first automated treatment operation occurrence to treat at least a portion of the automated ingestible product dispensing equipment as one or more syringes (e.g. one or more of instances of the field programmable gate array (FPGA) component s110 of the control and information processing subsystem s100 can direct storing the first treatment information into one or more instances of the Blu Ray disk component s240, involving one or more syringes as part of one or more instances of the deposition component s740, etc.). Furthermore, the treating syringe electrical circuitry arrangement e1163 when activated will perform the operation o1163. In an implementation, the treating syringe electrical circuitry arrangement e1163, when activated performs electronically directing storing of the first treatment information into the treatment history information storage, the first treatment information associated with the at least one first automated treatment operation occurrence to treat at least a portion of the automated ingestible product dispensing equipment as one or more syringes (e.g. one or more of instances of the field programmable gate array (FPGA) component s110 of the control and information processing subsystem s100 can direct storing the first treatment information into one or more instances of the Blu Ray disk component s240, involving one or more syringes as part of one or more instances of the deposition component s740, etc.). In an implementation, the electronically directing storing of the first treatment information into the treatment history information storage, the first treatment information associated with the at least one first automated treatment occurrence to treat at least a portion of the automated ingestible product dispensing equipment as one or more syringes is carried out by electronically directing storing of the first treatment information into the treatment history information storage, the first treatment information associated with the at least one first automated treatment operation occurrence to treat at least a portion of the automated ingestible product dispensing equipment as one or more syringes (e.g. one or more of instances of the field programmable gate array (FPGA) component s110 of the control and information processing subsystem s100 can direct storing the first treatment information into one or more instances of the Blu Ray disk component s240, involving one or more syringes as part of one or more instances of the deposition component s740, etc.).

Figure 53:
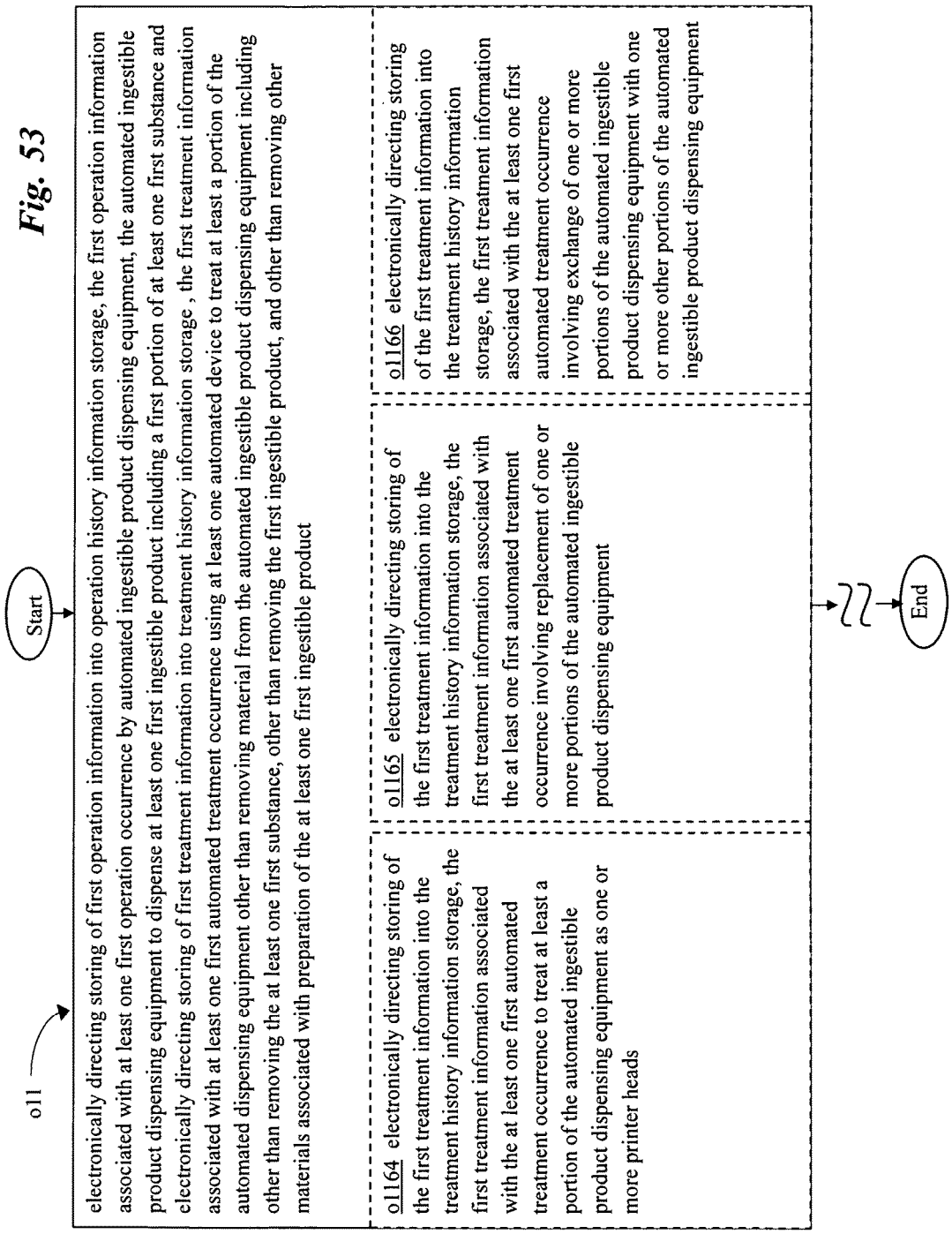
FIG. 53 is a high-level flowchart including exemplary implementations of operation O11 of FIG. 31.

In one or more implementations, as shown in FIG. 53, operation o11 includes an operation o1164 for electronically directing storing of the first treatment information into the treatment history information storage, the first treatment information associated with the at least one first automated treatment occurrence to treat at least a portion of the automated ingestible product dispensing equipment as one or more printer heads. An exemplary version of a non-transitory signal bearing medium of information storage subsystem s200 is depicted as bearing one or more treating head instructions i1164 that when executed will direct performance of the operation o1164. In an implementation, the one or more treating head instructions i1164 when executed direct electronically directing storing of the first treatment information into the treatment history information storage, the first treatment information associated with the at least one first automated treatment operation occurrence to treat at least a portion of the automated ingestible product dispensing equipment as one or more printer heads (e.g. one or more of instances of the multiprocessor component s112 of the control and information processing subsystem s100 can direct storing the first treatment information into one or more instances of the random access memory (RAM) component s202, involving one or more printer heads as part of one or more instances of the deposition component s740, etc.). Furthermore, the treating head electrical circuitry arrangement e1164 when activated will perform the operation o1164. In an implementation, the treating head electrical circuitry arrangement e1164, when activated performs electronically directing storing of the first treatment information into the treatment history information storage, the first treatment information associated with the at least one first automated treatment operation occurrence to treat at least a portion of the automated ingestible product dispensing equipment as one or more printer heads (e.g. one or more of instances of the multiprocessor component s112 of the control and information processing subsystem s100 can direct storing the first treatment information into one or more instances of the random access memory (RAM) component s202, involving one or more printer heads as part of one or more instances of the deposition component s740, etc.). In an implementation, the electronically directing storing of the first treatment information into the treatment history information storage, the first treatment information associated with the at least one first automated treatment occurrence to treat at least a portion of the automated ingestible product dispensing equipment as one or more printer heads is carried out by electronically directing storing of the first treatment information into the treatment history information storage, the first treatment information associated with the at least one first automated treatment operation occurrence to treat at least a portion of the automated ingestible product dispensing equipment as one or more printer heads (e.g. one or more of instances of the multiprocessor component s112 of the control and information processing subsystem s100 can direct storing the first treatment information into one or more instances of the random access memory (RAM) component s202, involving one or more printer heads as part of one or more instances of the deposition component s740, etc.).

In one or more implementations, operation o11 includes an operation o1165 for electronically directing storing of the first treatment information into the treatment history information storage, the first treatment information associated with the at least one first automated treatment occurrence involving replacement of one or more portions of the automated ingestible product dispensing equipment. A non-transitory signal bearing medium includes one or more treating replacement instructions i1165 that when executed will direct performance of the operation o1165. In an implementation, the one or more treating replacement instructions i1165 when executed direct electronically directing storing of the first treatment information into the treatment history information storage, the first treatment information associated with the at least one first automated treatment operation occurrence involving replacement of one or more portions of the automated ingestible product dispensing equipment (e.g. one or more of instances of the optical processing component s114 of the control and information processing subsystem s100 can direct storing the first treatment information into one or more instances of the dynamic random access memory (DRAM) component s204, involving the parts replacement component replacing one or more printer heads with new print heads as part of one or more instances of the deposition component s740, etc.). Furthermore, the treating replacement electrical circuitry arrangement e1165 when activated will perform the operation o1165. In an implementation, the treating replacement electrical circuitry arrangement e1165, when activated performs electronically directing storing of the first treatment information into the treatment history information storage, the first treatment information associated with the at least one first automated treatment operation occurrence involving replacement of one or more portions of the automated ingestible product dispensing equipment (e.g. one or more of instances of the optical processing component s114 of the control and information processing subsystem s100 can direct storing the first treatment information into one or more instances of the dynamic random access memory (DRAM) component s204, involving the parts replacement component replacing one or more printer heads with new print heads as part of one or more instances of the deposition component s740, etc.). In an implementation, the electronically directing storing of the first treatment information into the treatment history information storage, the first treatment information associated with the at least one first automated treatment occurrence involving replacement of one or more portions of the automated ingestible product dispensing equipment is carried out by electronically directing storing of the first treatment information into the treatment history information storage, the first treatment information associated with the at least one first automated treatment operation occurrence involving replacement of one or more portions of the automated ingestible product dispensing equipment (e.g. one or more of instances of the optical processing component s114 of the control and information processing subsystem s100 can direct storing the first treatment information into one or more instances of the dynamic random access memory (DRAM) component s204, involving the parts replacement component replacing one or more printer heads with new print heads as part of one or more instances of the deposition component s740, etc.).

In one or more implementations, operation o11 includes an operation o1166 for electronically directing storing of the first treatment information into the treatment history information storage, the first treatment information associated with the at least one first automated treatment occurrence involving exchange of one or more portions of the automated ingestible product dispensing equipment with one or more other portions of the automated ingestible product dispensing equipment. A non-transitory signal bearing medium includes one or more treating exchange instructions i1166 that when executed will direct performance of the operation o1166. In an implementation, the one or more treating exchange instructions i1166 when executed direct electronically directing storing of the first treatment information into the treatment history information storage, the first treatment information associated with the at least one first automated treatment operation occurrence involving exchange of one or more portions of the automated ingestible product dispensing equipment with one or more other portions of the automated ingestible product dispensing equipment (e.g. one or more of instances of the logic component s116 of the control and information processing subsystem s100 can direct storing the first treatment information into one or more instances of the other volatile memory component s206, involving exchanging one or more printer heads with one or more other printer heads as part of one or more instances of the deposition component s740, etc.). Furthermore, the treating exchange electrical circuitry arrangement e1166 when activated will perform the operation o1166. In an implementation, the treating exchange electrical circuitry arrangement e1166, when activated performs electronically directing storing of the first treatment information into the treatment history information storage, the first treatment information associated with the at least one first automated treatment operation occurrence involving exchange of one or more portions of the automated ingestible product dispensing equipment with one or more other portions of the automated ingestible product dispensing equipment (e.g. one or more of instances of the logic component s116 of the control and information processing subsystem s100 can direct storing the first treatment information into one or more instances of the other volatile memory component s206, involving exchanging one or more printer heads with one or more other printer heads as part of one or more instances of the deposition component s740, etc.). In an implementation, the electronically directing storing of the first treatment information into the treatment history information storage, the first treatment information associated with the at least one first automated treatment occurrence involving exchange of one or more portions of the automated ingestible product dispensing equipment with one or more other portions of the automated ingestible product dispensing equipment is carried out by electronically directing storing of the first treatment information into the treatment history information storage, the first treatment information associated with the at least one first automated treatment operation occurrence involving exchange of one or more portions of the automated ingestible product dispensing equipment with one or more other portions of the automated ingestible product dispensing equipment (e.g. one or more of instances of the logic component s116 of the control and information processing subsystem s100 can direct storing the first treatment information into one or more instances of the other volatile memory component s206, involving exchanging one or more printer heads with one or more other printer heads as part of one or more instances of the deposition component s740, etc.).

As shown in FIG. 31, the operational flow o10 proceeds to operation o12 for electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input. An exemplary version of a non-transitory signal bearing medium of information storage subsystem s200 is depicted as bearing one or more second treating instructions i12 that when executed will direct performance of the operation o12. In an implementation, the one or more second treating instructions i12 when executed direct electronically directing at least one second automated treatment occurrence of the at least one automated device to treat at least a portion of the automated ingestible product dispensing equipment other than removing material from the automated ingestible product dispensing equipment including other than removing the at least one first substance, other than removing the first ingestible product, and other than removing other materials associated with dispensing of the at least one first ingestible product prior to at least one second operation occurrence of the automated ingestible product dispensing equipment, (e.g. one or more instances of the multiprocessor component s112 of the control and information processing subsystem s100 can direct, via one or more instances of the waveguide network component s506, one or more instances of the abrasive component s812 to treat one or more portions of the ingestible product treatment system 10, etc.), the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input (e.g. one or more instances of the multiprocessor component s112 of the control and information processing subsystem s100 can direct one or more instances of the parts replacement component s826 as an operation prior to the second operation occurrence based upon status determined to be that the ingestible product treatment system 10 had not been treated after a ingredient replacement operation by the part replacement component s826 and the user inputting preferences to have treatment such as a sanitation treatment by the radiant energy component s810 occur after any ingredient replacement operations, as the second operation occurrence being initiated by user input through one or more instances of the cellular network component s514, etc.). Furthermore, the second treating electrical circuitry arrangement e12 when activated will perform the operation o12. In an implementation, the second treating electrical circuitry arrangement e12, when activated performs electronically directing at least one second automated treatment occurrence of the at least one automated device to treat at least a portion of the automated ingestible product dispensing equipment other than removing material from the automated ingestible product dispensing equipment including other than removing the at least one first substance, other than removing the first ingestible product, and other than removing other materials associated with dispensing of the at least one first ingestible product prior to at least one second operation occurrence of the automated ingestible product dispensing equipment, (e.g. one or more instances of the multiprocessor component s112 of the control and information processing subsystem s100 can direct, via one or more instances of the waveguide network component s506, one or more instances of the abrasive component s812 to treat one or more portions of the ingestible product treatment system 10, etc.), the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input (e.g. one or more instances of the multiprocessor component s112 of the control and information processing subsystem s100 can direct one or more instances of the parts replacement component s826 as an operation prior to the second operation occurrence based upon status determined to be that the ingestible product treatment system 10 had not been treated after a ingredient replacement operation by the part replacement component s826 and the user inputting preferences to have treatment such as a sanitation treatment by the radiant energy component s810 occur after any ingredient replacement operations, as the second operation occurrence being initiated by user input through one or more instances of the cellular network component s514, etc.). In an implementation, the electronically directing at least one second automated treatment occurrence of the at least one automated device to treat at least a portion of the automated ingestible product dispensing equipment other than removing material from the automated ingestible product preparation equipment including other than removing the at least one first substance, other than removing the first ingestible product, and other than removing other materials associated with preparation of the at least one first ingestible product prior to at least one second operation occurrence of the automated ingestible product dispensing equipment, the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input is carried out by electronically directing at least one second automated treatment occurrence of the at least one automated device to treat at least a portion of the automated ingestible product dispensing equipment other than removing material from the automated ingestible product dispensing equipment including other than removing the at least one first substance, other than removing the first ingestible product, and other than removing other materials associated with dispensing of the at least one first ingestible product prior to at least one second operation occurrence of the automated ingestible product dispensing equipment, (e.g. one or more instances of the multiprocessor component s112 of the control and information processing subsystem s100 can direct, via one or more instances of the waveguide network component s506, one or more instances of the abrasive component s812 to treat one or more portions of the ingestible product treatment system 10, etc.), the at least one second operation occurrence electronically initiated via electronically receiving first input associated with a particular individual living being, the electronically directing at least one second automated treatment occurrence of the at least one automated device automated to be electronically initiated based at least in part upon status associated with information stored in the operation history information storage, associated with information stored in the treatment history information storage, and associated with the electronically received first input (e.g. one or more instances of the multiprocessor component s112 of the control and information processing subsystem s100 can direct one or more instances of the parts replacement component s826 as an operation prior to the second operation occurrence based upon status determined to be that the ingestible product treatment system 10 had not been treated after a ingredient replacement operation by the part replacement component s826 and the user inputting preferences to have treatment such as a sanitation treatment by the radiant energy component s810 occur after any ingredient replacement operations, as the second operation occurrence being initiated by user input through one or more instances of the cellular network component s514, etc.).

Figure 54:
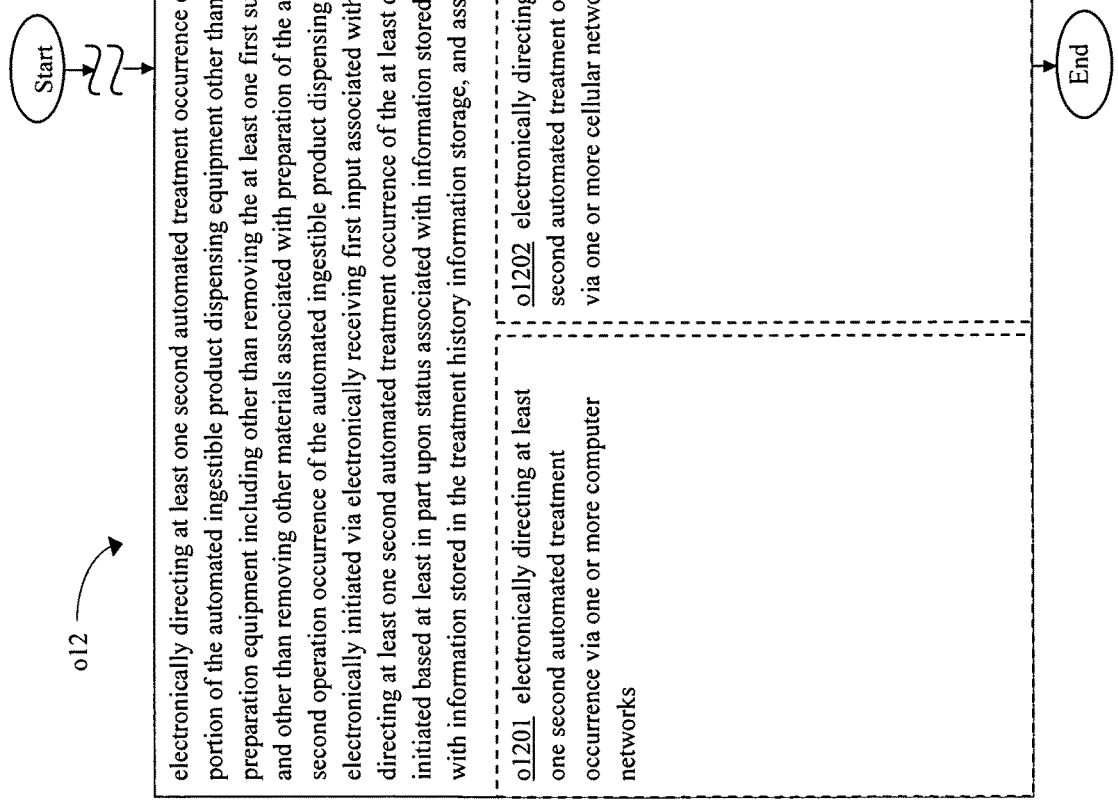
FIG. 54 is a high-level flowchart including exemplary implementations of operation O12 of FIG. 31.

In one or more implementations, as shown in FIG. 54, operation o12 includes an operation o1201 for electronically directing at least one second automated treatment occurrence via one or more computer networks. An exemplary version of a non-transitory signal bearing medium of information storage subsystem s200 is depicted as bearing one or more treating network instructions i1201 that when executed will direct performance of the operation o1201. In an implementation, the one or more treating network instructions i1201 when executed direct electronically directing at least one second automated treatment occurrence via one or more computer networks (e.g. one or more instances of the microprocessor component s102 of the control and information processing subsystem s100 can direct, via one or more instances of the wide area network component s516, one or more instances of the air blower component s802, etc.). Furthermore, the treating network electrical circuitry arrangement e1201 when activated will perform the operation o1201. In an implementation, the treating network electrical circuitry arrangement e1201, when activated performs electronically directing at least one second automated treatment occurrence via one or more computer networks (e.g. one or more instances of the microprocessor component s102 of the control and information processing subsystem s100 can direct, via one or more instances of the wide area network component s516, one or more instances of the air blower component s802, etc.). In an implementation, the electronically directing at least one second automated treatment occurrence via one or more computer networks is carried out by electronically directing at least one second automated treatment occurrence via one or more computer networks (e.g. one or more instances of the microprocessor component s102 of the control and information processing subsystem s100 can direct, via one or more instances of the wide area network component s516, one or more instances of the air blower component s802, etc.).

In one or more implementations, operation o12 includes an operation o1202 for electronically directing at least one second automated treatment occurrence via one or more cellular networks. An exemplary version of a non-transitory signal bearing medium of information storage subsystem s200 is depicted as bearing one or more treating cellular instructions i1202 that when executed will direct performance of the operation o1202. In an implementation, the one or more treating cellular instructions i1202 when executed direct electronically directing at least one second automated treatment occurrence via one or more cellular networks (e.g. one or more instances of the central processing unit (CPU) component s104 of the control and information processing subsystem s100 can direct via, one or more instances of the cellular network component s514, one or more instances of the compressed fluid component s804, etc.). Furthermore, the treating cellular electrical circuitry arrangement e1202 when activated will perform the operation o1202. In an implementation, the treating cellular electrical circuitry arrangement e1202, when activated performs electronically directing at least one second automated treatment occurrence via one or more cellular networks (e.g. one or more instances of the central processing unit (CPU) component s104 of the control and information processing subsystem s100 can direct via, one or more instances of the cellular network component s514, one or more instances of the compressed fluid component s804, etc.). In an implementation, the electronically directing at least one second automated treatment occurrence via one or more cellular networks is carried out by electronically directing at least one second automated treatment occurrence via one or more cellular networks (e.g. one or more instances of the central processing unit (CPU) component s104 of the control and information processing subsystem s100 can direct via, one or more instances of the cellular network component s514, one or more instances of the compressed fluid component s804, etc.).

In one or more implementations, operation o12 includes an operation o1203 for electronically directing at least one second automated treatment occurrence via electrical circuitry internal to the automated ingestible product dispensing equipment. An exemplary version of a non-transitory signal bearing medium of information storage subsystem s200 is depicted as bearing one or more treating circuitry instructions i1203 that when executed will direct performance of the operation o1203. In an implementation, the one or more treating circuitry instructions i1203 when executed direct electronically directing at least one second automated treatment occurrence via electrical circuitry internal to the automated ingestible product dispensing equipment (e.g. one or more instances of the digital signal processor (DSP) component s106 of the control and information processing subsystem s100 can direct, via one or more instances of the wired network component s512, one or more instances of the vacuum component s806, etc.). Furthermore, the treating circuitry electrical circuitry arrangement e1203 when activated will perform the operation o1203. In an implementation, the treating circuitry electrical circuitry arrangement e1203, when activated performs electronically directing at least one second automated treatment occurrence via electrical circuitry internal to the automated ingestible product dispensing equipment (e.g. one or more instances of the digital signal processor (DSP) component s106 of the control and information processing subsystem s100 can direct, via one or more instances of the wired network component s512, one or more instances of the vacuum component s806, etc.). In an implementation, the electronically directing at least one second automated treatment occurrence via electrical circuitry internal to the automated ingestible product dispensing equipment is carried out by electronically directing at least one second automated treatment occurrence via electrical circuitry internal to the automated ingestible product dispensing equipment (e.g. one or more instances of the digital signal processor (DSP) component s106 of the control and information processing subsystem s100 can direct, via one or more instances of the wired network component s512, one or more instances of the vacuum component s806, etc.).

Figure 55:
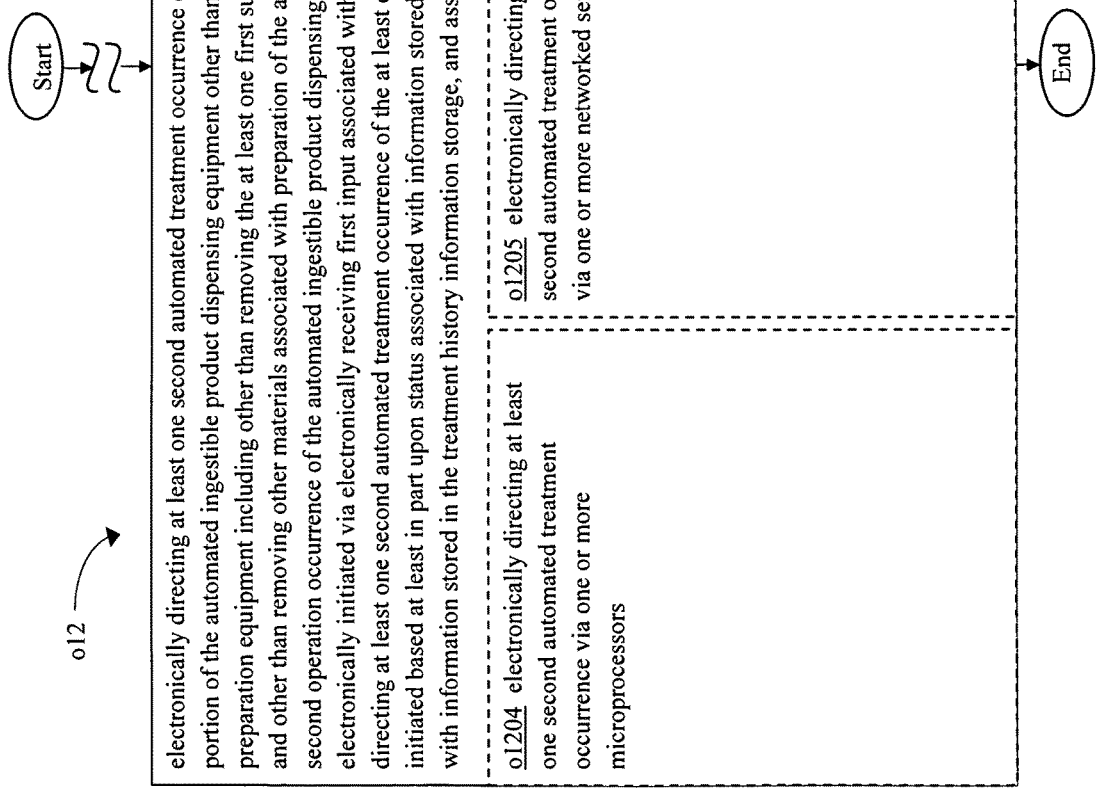
FIG. 55 is a high-level flowchart including exemplary implementations of operation O12 of FIG. 31.

In one or more implementations, as shown in FIG. 55, operation o12 includes an operation o1204 for electronically directing at least one second automated treatment occurrence via one or more microprocessors. An exemplary version of a non-transitory signal bearing medium of information storage subsystem s200 is depicted as bearing one or more treating microprocessors instructions i1204 that when executed will direct performance of the operation o1204. In an implementation, the one or more treating microprocessors instructions i1204 when executed direct electronically directing at least one second automated treatment occurrence via one or more microprocessors (e.g. one or more instances of the application specific integrated circuit (ASIC) component s108 of the control and information processing subsystem s100 can direct, via one or more instances of the microprocessor component s102, one or more instances of the ultrasonic component s808, etc.). Furthermore, the treating network electrical circuitry arrangement e1204 when activated will perform the operation o1204. In an implementation, the treating microprocessors electrical circuitry arrangement e1204, when activated performs electronically directing at least one second automated treatment occurrence via one or more microprocessors (e.g. one or more instances of the application specific integrated circuit (ASIC) component s108 of the control and information processing subsystem s100 can direct, via one or more instances of the microprocessor component s102, one or more instances of the ultrasonic component s808, etc.). In an implementation, the electronically directing at least one second automated treatment occurrence via one or more microprocessors is carried out by electronically directing at least one second automated treatment occurrence via one or more microprocessors (e.g. one or more instances of the application specific integrated circuit (ASIC) component s108 of the control and information processing subsystem s100 can direct, via one or more instances of the microprocessor component s102, one or more instances of the ultrasonic component s808, etc.).

In one or more implementations, operation o12 includes an operation o1205 for electronically directing at least one second automated treatment occurrence via one or more networked servers. An exemplary version of a non-transitory signal bearing medium of information storage subsystem s200 is depicted as bearing one or more treating servers instructions i1205 that when executed will direct performance of the operation o1205. In an implementation, the one or more treating servers instructions i1205 when executed direct electronically directing at least one second automated treatment occurrence via one or more networked servers (e.g. one or more instances of the field programmable gate array (FPGA) component s102 of the control and information processing subsystem s100 can direct, via one or more instances of the server component s230, one or more instances of the radiant energy component s810, etc.). Furthermore, the treating servers electrical circuitry arrangement e1205 when activated will perform the operation o1205. In an implementation, the treating servers electrical circuitry arrangement e1205, when activated performs electronically directing at least one second automated treatment occurrence via one or more networked servers (e.g. one or more instances of the field programmable gate array (FPGA) component s102 of the control and information processing subsystem s100 can direct, via one or more instances of the server component s230, one or more instances of the radiant energy component s810, etc.). In an implementation, the electronically directing at least one second automated treatment occurrence via one or more networked servers is carried out by electronically directing at least one second automated treatment occurrence via one or more networked servers (e.g. one or more instances of the field programmable gate array (FPGA) component s102 of the control and information processing subsystem s100 can direct, via one or more instances of the server component s230, one or more instances of the radiant energy component s810, etc.).

In one or more implementations, operation o12 includes an operation o1206 for electronically directing the at least one second automated treatment occurrence of a portion of the at least one automated device other than the portion of the at least one automated device treated by the at least one first automated treatment occurrence. An exemplary version of a non-transitory signal bearing medium of information storage subsystem s200 is depicted as bearing one or more treating other instructions i1206 that when executed will direct performance of the operation o1206. In an implementation, the one or more treating other instructions i1206 when executed direct electronically directing the at least one second automated treatment occurrence of a portion of the at least one automated device other than the portion of the at least one automated device treated by the at least one first automated treatment occurrence (e.g. one or more instances of the multiprocessor component s112 of the control and information processing subsystem s100 can direct one or more instances of the abrasive component s812, etc.). Furthermore, the treating other electrical circuitry arrangement e1206 when activated will perform the operation o1205. In an implementation, the treating other electrical circuitry arrangement e1206, when activated performs electronically directing the at least one second automated treatment occurrence of a portion of the at least one automated device other than the portion of the at least one automated device treated by the at least one first automated treatment occurrence (e.g. one or more instances of the multiprocessor component s112 of the control and information processing subsystem s100 can direct one or more instances of the abrasive component s812, etc.). In an implementation, the electronically directing the at least one second automated treatment occurrence of a portion of the at least one automated device other than the portion of the at least one automated device treated by the at least one first automated treatment occurrence is carried out by electronically directing the at least one second automated treatment occurrence of a portion of the at least one automated device other than the portion of the at least one automated device treated by the at least one first automated treatment occurrence (e.g. one or more instances of the multiprocessor component s112 of the control and information processing subsystem s100 can direct one or more instances of the abrasive component s812, etc.).

Figure 56:
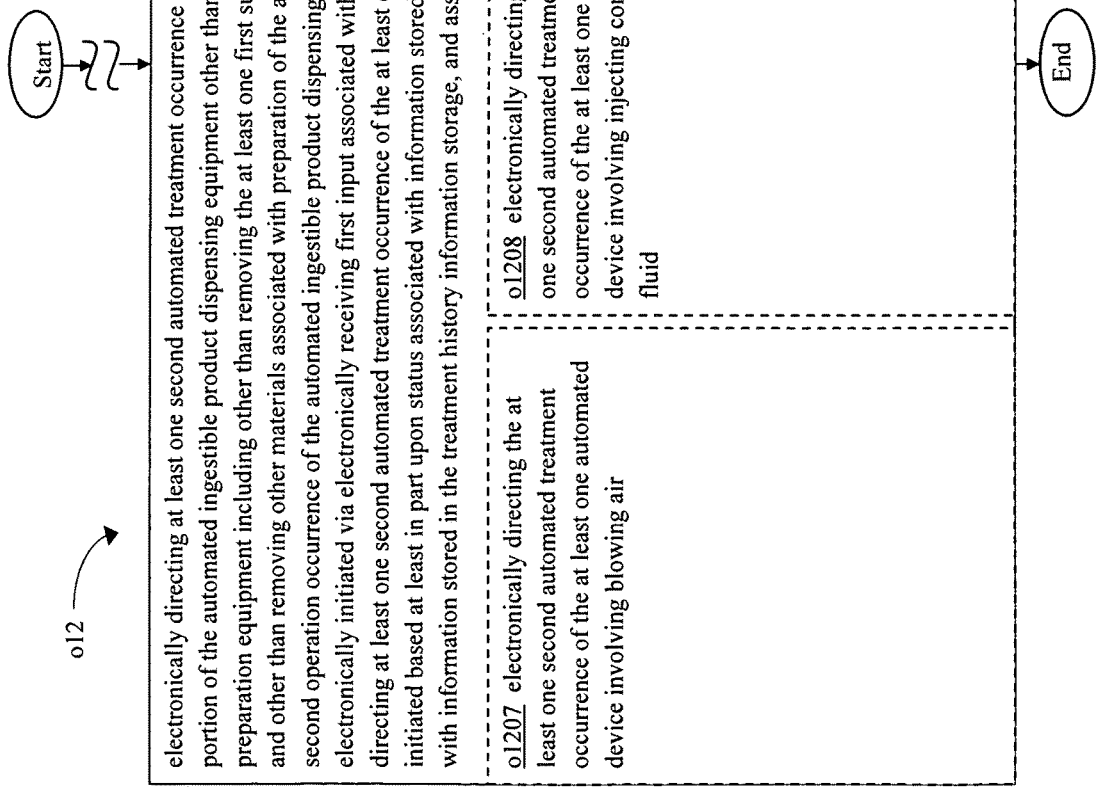
FIG. 56 is a high-level flowchart including exemplary implementations of operation O12 of FIG. 31.

In one or more implementations, as shown in FIG. 56, operation o12 includes an operation o1207 for electronically directing the at least one second automated treatment occurrence of the at least one automated device involving blowing air. An exemplary version of a non-transitory signal bearing medium of information storage subsystem s200 is depicted as bearing one or more treating blowing instructions i1207 that when executed will direct performance of the operation o1207. In an implementation, the one or more treating blowing instructions i1207 when executed direct electronically directing the at least one second automated treatment occurrence of the at least one automated device involving blowing air (e.g. one or more instances of the optical processing component s114 of the control and information processing subsystem s100 can direct one or more instances of the air blower component s802, etc.). Furthermore, the treating blowing electrical circuitry arrangement e1207 when activated will perform the operation o1207. In an implementation, the treating blowing electrical circuitry arrangement e1207, when activated performs electronically directing the at least one second automated treatment occurrence of the at least one automated device involving blowing air (e.g. one or more instances of the optical processing component s114 of the control and information processing subsystem s100 can direct one or more instances of the air blower component s802, etc.). In an implementation, the electronically directing the at least one second automated treatment occurrence of the at least one automated device involving blowing air is carried out by electronically directing the at least one second automated treatment occurrence of the at least one automated device involving blowing air (e.g. one or more instances of the optical processing component s114 of the control and information processing subsystem s100 can direct one or more instances of the air blower component s802, etc.).

In one or more implementations, operation o12 includes an operation o1208 for electronically directing the at least one second automated treatment occurrence of the at least one automated device involving injecting compressed fluid. An exemplary version of a non-transitory signal bearing medium of information storage subsystem s200 is depicted as bearing one or more treating compressed instructions i1208 that when executed will direct performance of the operation o1208. In an implementation, the one or more treating compressed instructions i1208 when executed direct electronically directing the at least one second automated treatment occurrence of the at least one automated device involving injecting compressed fluid (e.g. one or more instances of the logic component s116 of the control and information processing subsystem s100 can direct one or more instances of the compressed fluid component s804, etc.). Furthermore, the treating compressed electrical circuitry arrangement e1208 when activated will perform the operation o1208. In an implementation, the treating compressed electrical circuitry arrangement e1208, when activated performs electronically directing the at least one second automated treatment occurrence of the at least one automated device involving injecting compressed fluid (e.g. one or more instances of the logic component s116 of the control and information processing subsystem s100 can direct one or more instances of the compressed fluid component s804, etc.). In an implementation, the electronically directing the at least one second automated treatment occurrence of the at least one automated device involving injecting compressed fluid is carried out by electronically directing the at least one second automated treatment occurrence of the at least one automated device involving injecting compressed fluid (e.g. one or more instances of the logic component s116 of the control and information processing subsystem s100 can direct one or more instances of the compressed fluid component s804, etc.).

In one or more implementations, operation o12 includes an operation o1209 for electronically directing the at least one second automated treatment occurrence of the at least one automated device involving applying a vacuum. An exemplary version of a non-transitory signal bearing medium of information storage subsystem s200 is depicted as bearing one or more treating vacuum instructions i1209 that when executed will direct performance of the operation o1209. In an implementation, the one or more treating vacuum instructions i1209 when executed direct electronically directing the at least one second automated treatment occurrence of the at least one automated device involving applying a vacuum (e.g. one or more instances of the microprocessor component s102 of the control and information processing subsystem s100 can direct one or more instances of the vacuum component s806, etc.). Furthermore, the treating vacuum electrical circuitry arrangement e1209 when activated will perform the operation o1209. In an implementation, the treating vacuum electrical circuitry arrangement e1209, when activated performs electronically directing the at least one second automated treatment occurrence of the at least one automated device involving applying a vacuum (e.g. one or more instances of the microprocessor component s102 of the control and information processing subsystem s100 can direct one or more instances of the vacuum component s806, etc.). In an implementation, the electronically directing the at least one second automated treatment occurrence of the at least one automated device involving applying a vacuum is carried out by electronically directing the at least one second automated treatment occurrence of the at least one automated device involving applying a vacuum (e.g. one or more instances of the microprocessor component s102 of the control and information processing subsystem s100 can direct one or more instances of the vacuum component s806, etc.).

Figure 57:
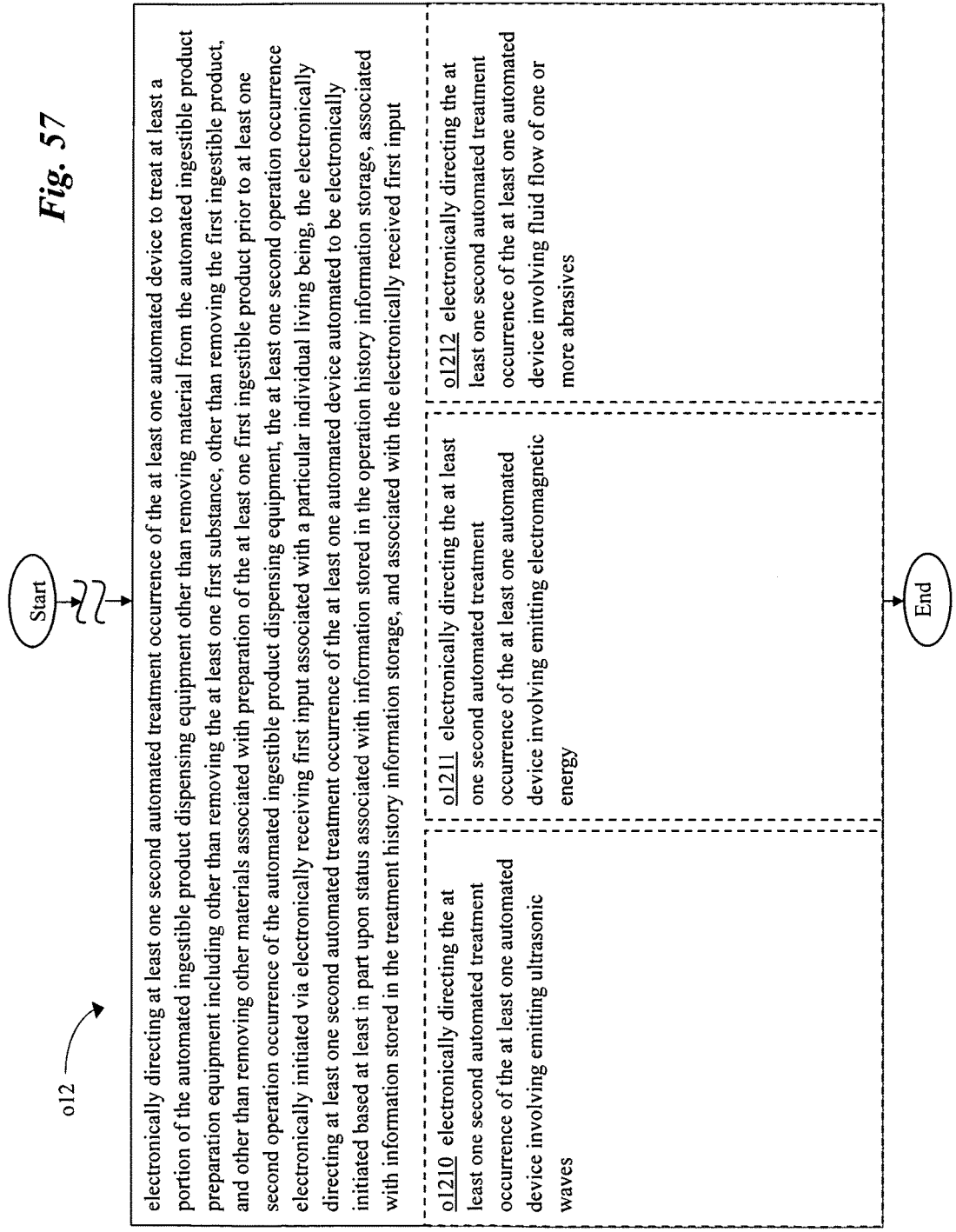
FIG. 57 is a high-level flowchart including exemplary implementations of operation O12 of FIG. 31.

In one or more implementations, as shown in FIG. 57, operation o12 includes an operation o1210 for electronically directing the at least one second automated treatment occurrence of the at least one automated device involving emitting ultrasonic waves. An exemplary version of a non-transitory signal bearing medium of information storage subsystem s200 is depicted as bearing one or more treating ultrasonic instructions i1210 that when executed will direct performance of the operation o1210. In an implementation, the one or more treating ultrasonic instructions i1210 when executed direct electronically directing the at least one second automated treatment occurrence of the at least one automated device involving emitting ultrasonic waves (e.g. one or more instances of the central processing unit (CPU) component s104 of the control and information processing subsystem s100 can direct one or more instances of the ultrasonic component s808, etc.). Furthermore, the treating ultrasonic electrical circuitry arrangement e1210 when activated will perform the operation o1210. In an implementation, the treating ultrasonic electrical circuitry arrangement e1210, when activated performs electronically directing the at least one second automated treatment occurrence of the at least one automated device involving emitting ultrasonic waves (e.g. one or more instances of the central processing unit (CPU) component s104 of the control and information processing subsystem s100 can direct one or more instances of the ultrasonic component s808, etc.). In an implementation, the electronically directing the at least one second automated treatment occurrence of the at least one automated device involving emitting ultrasonic waves is carried out by electronically directing the at least one second automated treatment occurrence of the at least one automated device involving emitting ultrasonic waves (e.g. one or more instances of the central processing unit (CPU) component s104 of the control and information processing subsystem s100 can direct one or more instances of the ultrasonic component s808, etc.).

In one or more implementations, operation o12 includes an operation o1211 for electronically directing the at least one second automated treatment occurrence of the at least one automated device involving emitting electromagnetic energy. An exemplary version of a non-transitory signal bearing medium of information storage subsystem s200 is depicted as bearing one or more treating electromagnetic instructions i1211 that when executed will direct performance of the operation o1211. In an implementation, the one or more treating electromagnetic instructions i1211 when executed direct electronically directing the at least one second automated treatment occurrence of the at least one automated device involving emitting electromagnetic energy (e.g. one or more instances of the digital signal processor (DSP) component s106 of the control and information processing subsystem s100 can direct one or more instances of the radiant energy component s810, etc.). Furthermore, the treating electromagnetic electrical circuitry arrangement e1211 when activated will perform the operation o1211. In an implementation, the treating electromagnetic electrical circuitry arrangement e1211, when activated performs electronically directing the at least one second automated treatment occurrence of the at least one automated device involving emitting electromagnetic energy (e.g. one or more instances of the digital signal processor (DSP) component s106 of the control and information processing subsystem s100 can direct one or more instances of the radiant energy component s810, etc.). In an implementation, the electronically directing the at least one second automated treatment occurrence of the at least one automated device involving emitting electromagnetic energy is carried out by electronically directing the at least one second automated treatment occurrence of the at least one automated device involving emitting electromagnetic energy (e.g. one or more instances of the digital signal processor (DSP) component s106 of the control and information processing subsystem s100 can direct one or more instances of the radiant energy component s810, etc.).

In one or more implementations, operation o12 includes an operation o1212 for electronically directing the at least one second automated treatment occurrence of the at least one automated device involving fluid flow of one or more abrasives. An exemplary version of a non-transitory signal bearing medium of information storage subsystem s200 is depicted as bearing one or more treating abrasives instructions i1212 that when executed will direct performance of the operation o1212. In an implementation, the one or more treating abrasives instructions i1212 when executed direct electronically directing the at least one second automated treatment occurrence of the at least one automated device involving fluid flow of one or more abrasives (e.g. one or more instances of the application specific integrated circuit (ASIC) component s108 of the control and information processing subsystem s100 can direct one or more instances of the abrasive component s812, etc.). Furthermore, the treating abrasives electrical circuitry arrangement e1212 when activated will perform the operation o1212. In an implementation, the treating abrasives electrical circuitry arrangement e1212, when activated performs electronically directing the at least one second automated treatment occurrence of the at least one automated device involving fluid flow of one or more abrasives (e.g. one or more instances of the application specific integrated circuit (ASIC) component s108 of the control and information processing subsystem s100 can direct one or more instances of the abrasive component s812, etc.). In an implementation, the electronically directing the at least one second automated treatment occurrence of the at least one automated device involving fluid flow of one or more abrasives is carried out by electronically directing the at least one second automated treatment occurrence of the at least one automated device involving fluid flow of one or more abrasives (e.g. one or more instances of the application specific integrated circuit (ASIC) component s108 of the control and information processing subsystem s100 can direct one or more instances of the abrasive component s812, etc.).

Figure 58:
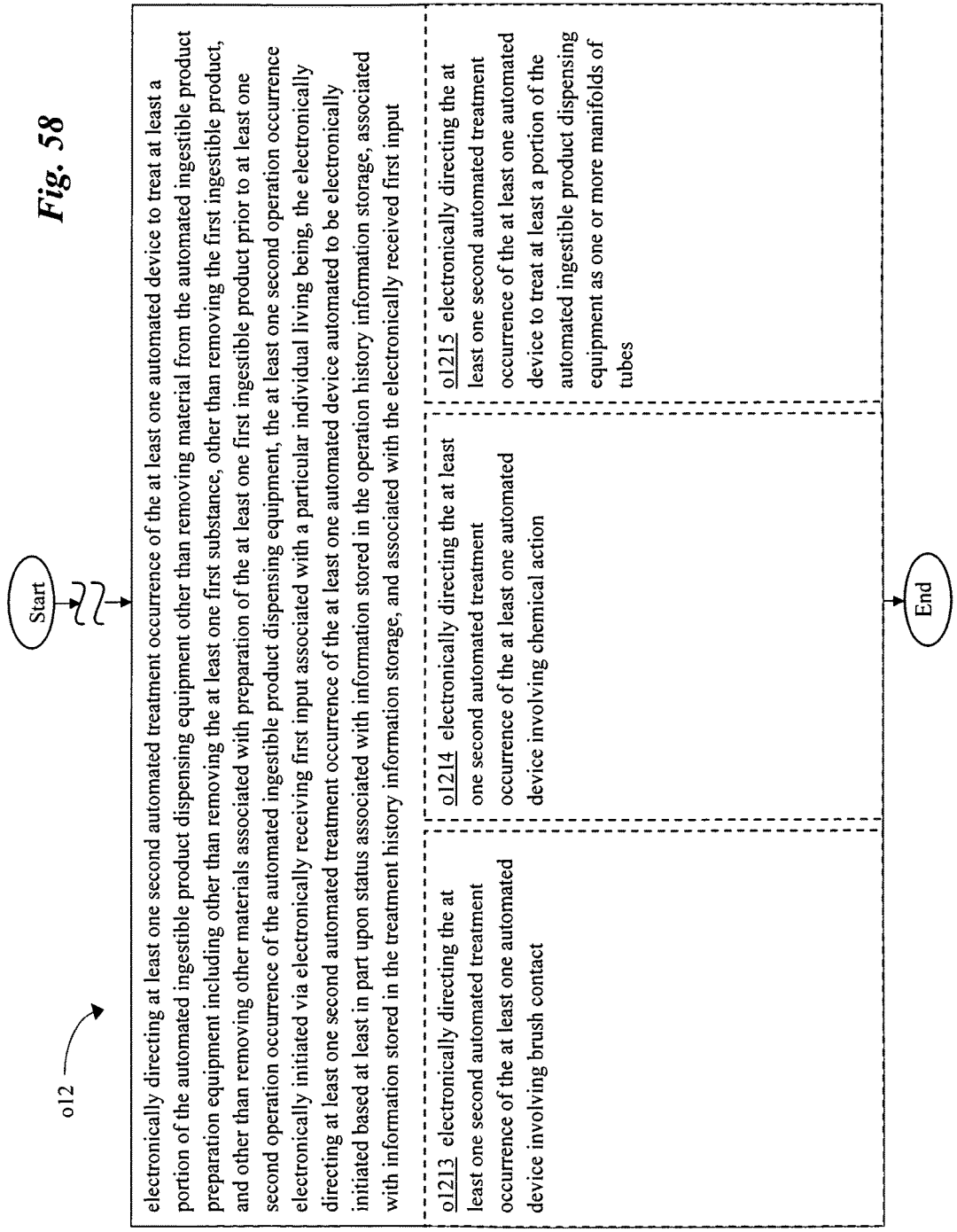
FIG. 58 is a high-level flowchart including exemplary implementations of operation O12 of FIG. 31.

In one or more implementations, as shown in FIG. 58, operation o12 includes an operation o1213 for electronically directing the at least one second automated treatment occurrence of the at least one automated device involving brush contact. An exemplary version of a non-transitory signal bearing medium of information storage subsystem s200 is depicted as bearing one or more treating brush instructions i1213 that when executed will direct performance of the operation o1213. In an implementation, the one or more treating brush instructions i1213 when executed direct electronically directing the at least one second automated treatment occurrence of the at least one automated device involving brush contact (e.g. one or more instances of the field programmable gate array (FPGA) component s110 of the control and information processing subsystem s100 can direct one or more instances of the brush component s814, etc.). Furthermore, the treating brush electrical circuitry arrangement e1213 when activated will perform the operation o1213. In an implementation, the treating brush electrical circuitry arrangement e1213, when activated performs electronically directing the at least one second automated treatment occurrence of the at least one automated device involving brush contact (e.g. one or more instances of the field programmable gate array (FPGA) component s110 of the control and information processing subsystem s100 can direct one or more instances of the brush component s814, etc.). In an implementation, the electronically directing the at least one second automated treatment occurrence of the at least one automated device involving brush contact is carried out by electronically directing the at least one second automated treatment occurrence of the at least one automated device involving brush contact (e.g. one or more instances of the field programmable gate array (FPGA) component s110 of the control and information processing subsystem s100 can direct one or more instances of the brush component s814, etc.).

In one or more implementations, operation o12 includes an operation o1214 for electronically directing the at least one second automated treatment occurrence of the at least one automated device involving chemical action. An exemplary version of a non-transitory signal bearing medium of information storage subsystem s200 is depicted as bearing one or more treating chemical instructions i1214 that when executed will direct performance of the operation o1214. In an implementation, the one or more treating chemical instructions i1214 when executed direct electronically directing the at least one second automated treatment occurrence of the at least one automated device involving chemical action (e.g. one or more instances of the multiprocessor component s112 of the control and information processing subsystem s100 can direct one or more instances of the chemical component s832, etc.). Furthermore, the treating chemical electrical circuitry arrangement e1214 when activated will perform the operation o1214. In an implementation, the treating chemical electrical circuitry arrangement e1214, when activated performs electronically directing the at least one second automated treatment occurrence of the at least one automated device involving chemical action (e.g. one or more instances of the multiprocessor component s112 of the control and information processing subsystem s100 can direct one or more instances of the chemical component s832, etc.). In an implementation, the electronically directing the at least one second automated treatment occurrence of the at least one automated device involving chemical action is carried out by electronically directing the at least one second automated treatment occurrence of the at least one automated device involving chemical action (e.g. one or more instances of the multiprocessor component s112 of the control and information processing subsystem s100 can direct one or more instances of the chemical component s832, etc.).

In one or more implementations, operation o12 includes an operation o1215 for electronically directing the at least one second automated treatment occurrence of the at least one automated device to treat at least a portion of the automated ingestible product dispensing equipment as one or more manifolds of tubes. An exemplary version of a non-transitory signal bearing medium of information storage subsystem s200 is depicted as bearing one or more treating tubes instructions i1215 that when executed will direct performance of the operation o1215. In an implementation, the one or more treating tubes instructions i1215 when executed direct electronically directing the at least one second automated treatment occurrence of the at least one automated device to treat at least a portion of the automated ingestible product dispensing equipment as one or more manifolds of tubes (e.g. one or more instances of the optical processing component s114 of the control and information processing subsystem s100 can direct one or more instances of the squeegee brush component s816 to treat the one or more manifolds of tubes of the mixer component s716, etc.). Furthermore, the treating tubes electrical circuitry arrangement e1215 when activated will perform the operation o1215. In an implementation, the treating tubes electrical circuitry arrangement e1215, when activated performs electronically directing the at least one second automated treatment occurrence of the at least one automated device to treat at least a portion of the automated ingestible product dispensing equipment as one or more manifolds of tubes (e.g. one or more instances of the optical processing component s114 of the control and information processing subsystem s100 can direct one or more instances of the squeegee brush component s816 to treat the one or more manifolds of tubes of the mixer component s716, etc.). In an implementation, the electronically directing the at least one second automated treatment occurrence of the at least one automated device to treat at least a portion of the automated ingestible product dispensing equipment as one or more manifolds of tubes is carried out by electronically directing the at least one second automated treatment occurrence of the at least one automated device to treat at least a portion of the automated ingestible product dispensing equipment as one or more manifolds of tubes (e.g. one or more instances of the optical processing component s114 of the control and information processing subsystem s100 can direct one or more instances of the squeegee brush component s816 to treat the one or more manifolds of tubes of the mixer component s716, etc.).

In one or more implementations, as shown in FIG. 59, operation o12 includes an operation o1216 for electronically directing the at least one second automated treatment occurrence of the at least one automated device to treat at least a portion of the automated ingestible product dispensing equipment as one or more nozzles. An exemplary version of a non-transitory signal bearing medium of information storage subsystem s200 is depicted as bearing one or more treating nozzles instructions i1216 that when executed will direct performance of the operation o1216. In an implementation, the one or more treating nozzles instructions i1216 when executed direct electronically directing the at least one second automated treatment occurrence of the at least one automated device to treat at least a portion of the automated ingestible product dispensing equipment as one or more nozzles (e.g. one or more instances of the logic component s116 of the control and information processing subsystem s100 can direct one or more instances of the pipe cleaner brush component s818 to treat the one or more nozzles of the blending component s718, etc.). Furthermore, the treating nozzles electrical circuitry arrangement e1216 when activated will perform the operation o1216. In an implementation, the treating nozzles electrical circuitry arrangement e1216, when activated performs electronically directing the at least one second automated treatment occurrence of the at least one automated device to treat at least a portion of the automated ingestible product dispensing equipment as one or more nozzles (e.g. one or more instances of the logic component s116 of the control and information processing subsystem s100 can direct one or more instances of the pipe cleaner brush component s818 to treat the one or more nozzles of the blending component s718, etc.). In an implementation, the electronically directing the at least one second automated treatment occurrence of the at least one automated device to treat at least a portion of the automated ingestible product dispensing equipment as one or more nozzles is carried out by electronically directing the at least one second automated treatment occurrence of the at least one automated device to treat at least a portion of the automated ingestible product dispensing equipment as one or more nozzles (e.g. one or more instances of the logic component s116 of the control and information processing subsystem s100 can direct one or more instances of the pipe cleaner brush component s818 to treat the one or more nozzles of the blending component s718, etc.).

In one or more implementations, operation o12 includes an operation o1217 for electronically directing the at least one second automated treatment occurrence of the at least one automated device to treat at least a portion of the automated ingestible product dispensing equipment as one or more heating chambers. An exemplary version of a non-transitory signal bearing medium of information storage subsystem s200 is depicted as bearing one or more treating heating instructions i1217 that when executed will direct performance of the operation o1217. In an implementation, the one or more treating heating instructions i1217 when executed direct electronically directing the at least one second automated treatment occurrence of the at least one automated device to treat at least a portion of the automated ingestible product dispensing equipment as one or more heating chambers (e.g. one or more instances of the microprocessor component s102 of the control and information processing subsystem s100 can direct one or more instances of the material flush abrasive component s820 to treat the one or more heating chambers of the heating component s702, etc.). Furthermore, the treating heating electrical circuitry arrangement e1217 when activated will perform the operation o1217. In an implementation, the treating heating electrical circuitry arrangement e1217, when activated performs electronically directing the at least one second automated treatment occurrence of the at least one automated device to treat at least a portion of the automated ingestible product dispensing equipment as one or more heating chambers (e.g. one or more instances of the microprocessor component s102 of the control and information processing subsystem s100 can direct one or more instances of the material flush abrasive component s820 to treat the one or more heating chambers of the heating component s702, etc.). In an implementation, the electronically directing the at least one second automated treatment occurrence of the at least one automated device to treat at least a portion of the automated ingestible product dispensing equipment as one or more heating chambers is carried out by electronically directing the at least one second automated treatment occurrence of the at least one automated device to treat at least a portion of the automated ingestible product dispensing equipment as one or more heating chambers (e.g. one or more instances of the microprocessor component s102 of the control and information processing subsystem s100 can direct one or more instances of the material flush abrasive component s820 to treat the one or more heating chambers of the heating component s702, etc.).

In one or more implementations, operation o12 includes an operation o1218 for electronically directing the at least one second automated treatment occurrence of the at least one automated device to treat at least a portion of the automated ingestible product dispensing equipment as one or more blender compartments. An exemplary version of a non-transitory signal bearing medium of information storage subsystem s200 is depicted as bearing one or more treating blender instructions i1218 that when executed will direct performance of the operation o1218. In an implementation, the one or more treating blender instructions i1218 when executed direct electronically directing the at least one second automated treatment occurrence of the at least one automated device to treat at least a portion of the automated ingestible product dispensing equipment as one or more blender compartments (e.g. one or more instances of the central processing unit (CPU) component s104 of the control and information processing subsystem s100 can direct one or more instances of the fish tape system brush component s822 to treat one or more compartments of the blender component s714, etc.). Furthermore, the treating blender electrical circuitry arrangement e1218 when activated will perform the operation o1218. In an implementation, the treating blender electrical circuitry arrangement e1218, when activated performs electronically directing the at least one second automated treatment occurrence of the at least one automated device to treat at least a portion of the automated ingestible product dispensing equipment as one or more blender compartments (e.g. one or more instances of the central processing unit (CPU) component s104 of the control and information processing subsystem s100 can direct one or more instances of the fish tape system brush component s822 to treat one or more compartments of the blender component s714, etc.). In an implementation, the electronically directing the at least one second automated treatment occurrence of the at least one automated device to treat at least a portion of the automated ingestible product dispensing equipment as one or more blender compartments is carried out by electronically directing the at least one second automated treatment occurrence of the at least one automated device to treat at least a portion of the automated ingestible product dispensing equipment as one or more blender compartments (e.g. one or more instances of the central processing unit (CPU) component s104 of the control and information processing subsystem s100 can direct one or more instances of the fish tape system brush component s822 to treat one or more compartments of the blender component s714, etc.).

Figure 60:
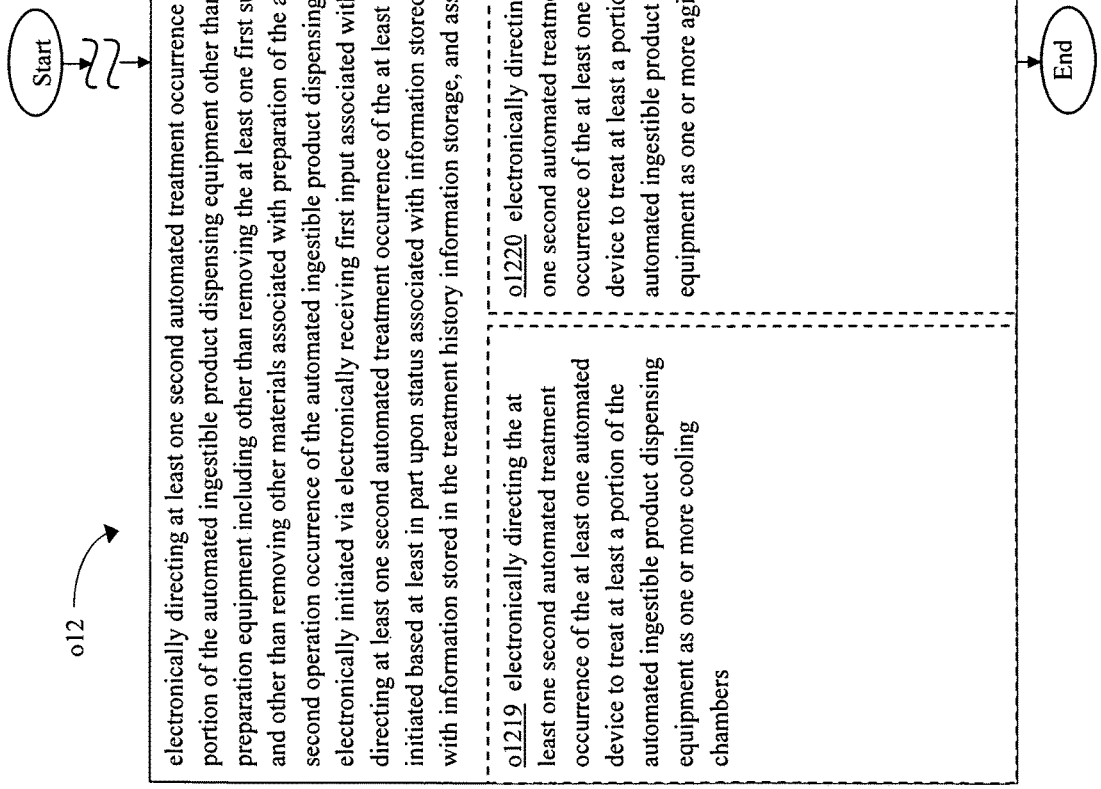
FIG. 60 is a high-level flowchart including exemplary implementations of operation O12 of FIG. 31.

In one or more implementations, as shown in FIG. 60, operation o12 includes an operation o1219 for electronically directing the at least one second automated treatment occurrence of the at least one automated device to treat at least a portion of the automated ingestible product dispensing equipment as one or more cooling chambers. An exemplary version of a non-transitory signal bearing medium of information storage subsystem s200 is depicted as bearing one or more treating cooling instructions i1219 that when executed will direct performance of the operation o1219. In an implementation, the one or more treating cooling instructions i1219 when executed direct electronically directing the at least one second automated treatment occurrence of the at least one automated device to treat at least a portion of the automated ingestible product dispensing equipment as one or more cooling chambers (e.g. one or more instances of the digital signal processor (DSP) component s106 of the control and information processing subsystem s100 can direct one or more instances of the abrasive component s812 to treat the one or more cooling chambers of the cooling component s704, etc.). Furthermore, the treating cooling electrical circuitry arrangement e1219 when activated will perform the operation o1219. In an implementation, the treating cooling electrical circuitry arrangement e1219, when activated performs electronically directing the at least one second automated treatment occurrence of the at least one automated device to treat at least a portion of the automated ingestible product dispensing equipment as one or more cooling chambers (e.g. one or more instances of the digital signal processor (DSP) component s106 of the control and information processing subsystem s100 can direct one or more instances of the abrasive component s812 to treat the one or more cooling chambers of the cooling component s704, etc.). In an implementation, the electronically directing the at least one second automated treatment occurrence of the at least one automated device to treat at least a portion of the automated ingestible product dispensing equipment as one or more cooling chambers is carried out by electronically directing the at least one second automated treatment occurrence of the at least one automated device to treat at least a portion of the automated ingestible product dispensing equipment as one or more cooling chambers (e.g. one or more instances of the digital signal processor (DSP) component s106 of the control and information processing subsystem s100 can direct one or more instances of the abrasive component s812 to treat the one or more cooling chambers of the cooling component s704, etc.).

In one or more implementations, operation o12 includes an operation o1220 for electronically directing the at least one second automated treatment occurrence of the at least one automated device to treat at least a portion of the automated ingestible product dispensing equipment as one or more agitators. An exemplary version of a non-transitory signal bearing medium of information storage subsystem s200 is depicted as bearing one or more treating agitator instructions i1220 that when executed will direct performance of the operation o1220. In an implementation, the one or more treating agitator instructions i1220 when executed direct electronically directing the at least one second automated treatment occurrence of the at least one automated device to treat at least a portion of the automated ingestible product dispensing equipment as one or more agitators (e.g. one or more instances of the application specific integrated circuit (ASIC) component s108 of the control and information processing subsystem s100 can direct one or more instances of the chemical component s832 to treat the one or more agitators of the mixer component s716, etc.). Furthermore, the treating agitator electrical circuitry arrangement e1220 when activated will perform the operation o1220. In an implementation, the treating agitator electrical circuitry arrangement e1220, when activated performs electronically directing the at least one second automated treatment occurrence of the at least one automated device to treat at least a portion of the automated ingestible product dispensing equipment as one or more agitators (e.g. one or more instances of the application specific integrated circuit (ASIC) component s108 of the control and information processing subsystem s100 can direct one or more instances of the chemical component s832 to treat the one or more agitators of the mixer component s716, etc.). In an implementation, the electronically directing the at least one second automated treatment occurrence of the at least one automated device to treat at least a portion of the automated ingestible product dispensing equipment as one or more agitators is carried out by electronically directing the at least one second automated treatment occurrence of the at least one automated device to treat at least a portion of the automated ingestible product dispensing equipment as one or more agitators (e.g. one or more instances of the application specific integrated circuit (ASIC) component s108 of the control and information processing subsystem s100 can direct one or more instances of the chemical component s832 to treat the one or more agitators of the mixer component s716, etc.).

In one or more implementations, operation o12 includes an operation o1221 for electronically directing the at least one second automated treatment occurrence of the at least one automated device to treat at least a portion of the automated ingestible product dispensing equipment as one or more syringes. An exemplary version of a non-transitory signal bearing medium of information storage subsystem s200 is depicted as bearing one or more treating syringe instructions i1221 that when executed will direct performance of the operation o1221. In an implementation, the one or more treating syringe instructions i1221 when executed direct electronically directing the at least one second automated treatment occurrence of the at least one automated device to treat at least a portion of the automated ingestible product dispensing equipment as one or more syringes (e.g. one or more instances of the field programmable gate array (FPGA) component s110 of the control and information processing subsystem s100 can direct one or more instances of the compressed air fluid component s828 to t to treat the one or more syringes of the deposition component s740, etc.). Furthermore, the treating syringe electrical circuitry arrangement e1221 when activated will perform the operation o1221. In an implementation, the treating syringe electrical circuitry arrangement e1221, when activated performs electronically directing the at least one second automated treatment occurrence of the at least one automated device to treat at least a portion of the automated ingestible product dispensing equipment as one or more syringes (e.g. one or more instances of the field programmable gate array (FPGA) component s110 of the control and information processing subsystem s100 can direct one or more instances of the compressed air fluid component s828 to t to treat the one or more syringes of the deposition component s740, etc.). In an implementation, the electronically directing the at least one second automated treatment occurrence of the at least one automated device to treat at least a portion of the automated ingestible product dispensing equipment as one or more syringes is carried out by electronically directing the at least one second automated treatment occurrence of the at least one automated device to treat at least a portion of the automated ingestible product dispensing equipment as one or more syringes (e.g. one or more instances of the field programmable gate array (FPGA) component s110 of the control and information processing subsystem s100 can direct one or more instances of the compressed air fluid component s828 to t to treat the one or more syringes of the deposition component s740, etc.).

Figure 61:
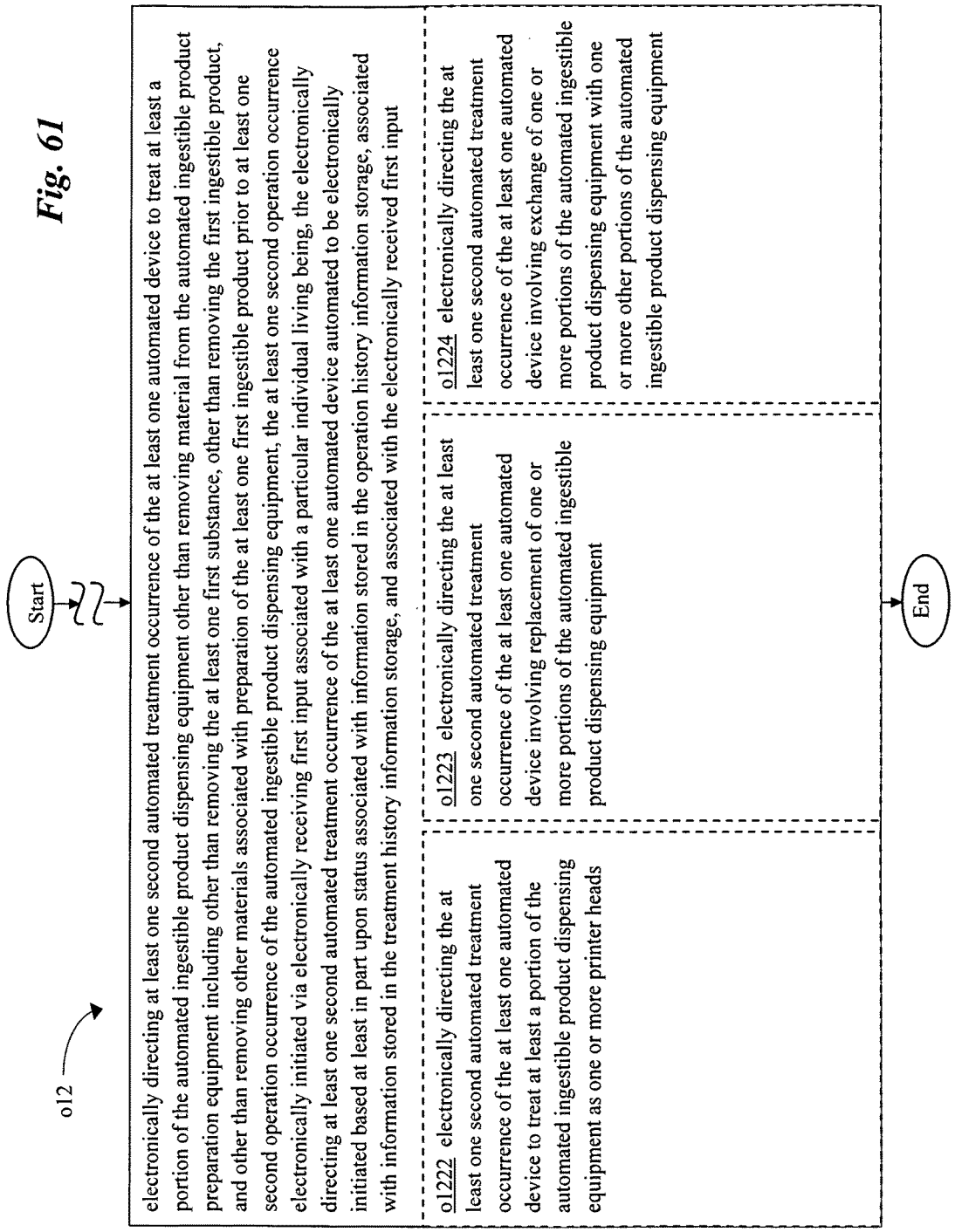
FIG. 61 is a high-level flowchart including exemplary implementations of operation O12 of FIG. 31.

In one or more implementations, as shown in FIG. 61, operation o12 includes an operation o1222 for electronically directing the at least one second automated treatment occurrence of the at least one automated device to treat at least a portion of the automated ingestible product dispensing equipment as one or more printer heads. An exemplary version of a non-transitory signal bearing medium of information storage subsystem s200 is depicted as bearing one or more treating head instructions i1222 that when executed will direct performance of the operation o1222. In an implementation, the one or more treating head instructions i1222 when executed direct electronically directing the at least one second automated treatment occurrence of the at least one automated device to treat at least a portion of the automated ingestible product dispensing equipment as one or more printer heads (e.g. one or more instances of the multiprocessor component s112 of the control and information processing subsystem s100 can direct one or more instances of the compressed water fluid component s830 to the one or more printer heads of one or more instances of the deposition component s740, etc.). Furthermore, the treating head electrical circuitry arrangement e1222 when activated will perform the operation o1222. In an implementation, the treating head electrical circuitry arrangement e1222, when activated performs electronically directing the at least one second automated treatment occurrence of the at least one automated device to treat at least a portion of the automated ingestible product dispensing equipment as one or more printer heads (e.g. one or more instances of the multiprocessor component s112 of the control and information processing subsystem s100 can direct one or more instances of the compressed water fluid component s830 to the one or more printer heads of one or more instances of the deposition component s740, etc.). In an implementation, the electronically directing the at least one second automated treatment occurrence of the at least one automated device to treat at least a portion of the automated ingestible product dispensing equipment as one or more printer heads is carried out by electronically directing the at least one second automated treatment occurrence of the at least one automated device to treat at least a portion of the automated ingestible product dispensing equipment as one or more printer heads (e.g. one or more instances of the multiprocessor component s112 of the control and information processing subsystem s100 can direct one or more instances of the compressed water fluid component s830 to the one or more printer heads of one or more instances of the deposition component s740, etc.).

In one or more implementations, operation o12 includes an operation o1223 for electronically directing the at least one second automated treatment occurrence of the at least one automated device involving replacement of one or more portions of the automated ingestible product dispensing equipment. An exemplary version of a non-transitory signal bearing medium of information storage subsystem s200 is depicted as bearing one or more treating replacement instructions i1223 that when executed will direct performance of the operation o1223. In an implementation, the one or more treating replacement instructions i1223 when executed direct electronically directing the at least one second automated treatment occurrence of the at least one automated device involving replacement of one or more portions of the automated ingestible product dispensing equipment (e.g. one or more instances of the optical processing component s114 of the control and information processing subsystem s100 can direct one or more instances of the parts replacement component s826 to treat via replacement of one or more printer heads of one or more instances of the deposition component s740, etc.). Furthermore, the treating replacement electrical circuitry arrangement e1223 when activated will perform the operation o1223. In an implementation, the treating replacement electrical circuitry arrangement e1223, when activated performs electronically directing the at least one second automated treatment occurrence of the at least one automated device involving replacement of one or more portions of the automated ingestible product dispensing equipment (e.g. one or more instances of the optical processing component s114 of the control and information processing subsystem s100 can direct one or more instances of the parts replacement component s826 to treat via replacement of one or more printer heads of one or more instances of the deposition component s740, etc.). In an implementation, the electronically directing the at least one second automated treatment occurrence of the at least one automated device involving replacement of one or more portions of the automated ingestible product dispensing equipment is carried out by electronically directing the at least one second automated treatment occurrence of the at least one automated device involving replacement of one or more portions of the automated ingestible product dispensing equipment (e.g. one or more instances of the optical processing component s114 of the control and information processing subsystem s100 can direct one or more instances of the parts replacement component s826 to treat via replacement of one or more printer heads of one or more instances of the deposition component s740, etc.).

In one or more implementations, operation o12 includes an operation o1224 for electronically directing the at least one second automated treatment occurrence of the at least one automated device involving exchange of one or more portions of the automated ingestible product dispensing equipment with one or more other portions of the automated ingestible product dispensing equipment. An exemplary version of a non-transitory signal bearing medium of information storage subsystem s200 is depicted as bearing one or more treating exchange instructions i1224 that when executed will direct performance of the operation o1224. In an implementation, the one or more treating exchange instructions i1224 when executed direct electronically directing the at least one second automated treatment occurrence of the at least one automated device involving exchange of one or more portions of the automated ingestible product dispensing equipment with one or more other portions of the automated ingestible product dispensing equipment (e.g. one or more instances of the logic component s116 of the control and information processing subsystem s100 can direct one or more instances of the parts exchange component s824 to treat via exchange of one or more printer heads of one or more instances of the deposition component s740, etc. Furthermore, the treating exchange electrical circuitry arrangement e1224 when activated will perform the operation o1224. In an implementation, the treating exchange electrical circuitry arrangement e1224, when activated performs electronically directing the at least one second automated treatment occurrence of the at least one automated device involving exchange of one or more portions of the automated ingestible product dispensing equipment with one or more other portions of the automated ingestible product dispensing equipment (e.g. one or more instances of the logic component s116 of the control and information processing subsystem s100 can direct one or more instances of the parts exchange component s824 to treat via exchange of one or more printer heads of one or more instances of the deposition component s740, etc. In an implementation, the electronically directing the at least one second automated treatment occurrence of the at least one automated device involving exchange of one or more portions of the automated ingestible product dispensing equipment with one or more other portions of the automated ingestible product dispensing equipment is carried out by electronically directing the at least one second automated treatment occurrence of the at least one automated device involving exchange of one or more portions of the automated ingestible product dispensing equipment with one or more other portions of the automated ingestible product dispensing equipment (e.g. one or more instances of the logic component s116 of the control and information processing subsystem s100 can direct one or more instances of the parts exchange component s824 to treat via exchange of one or more printer heads of one or more instances of the deposition component s740, etc.

Figure 62:
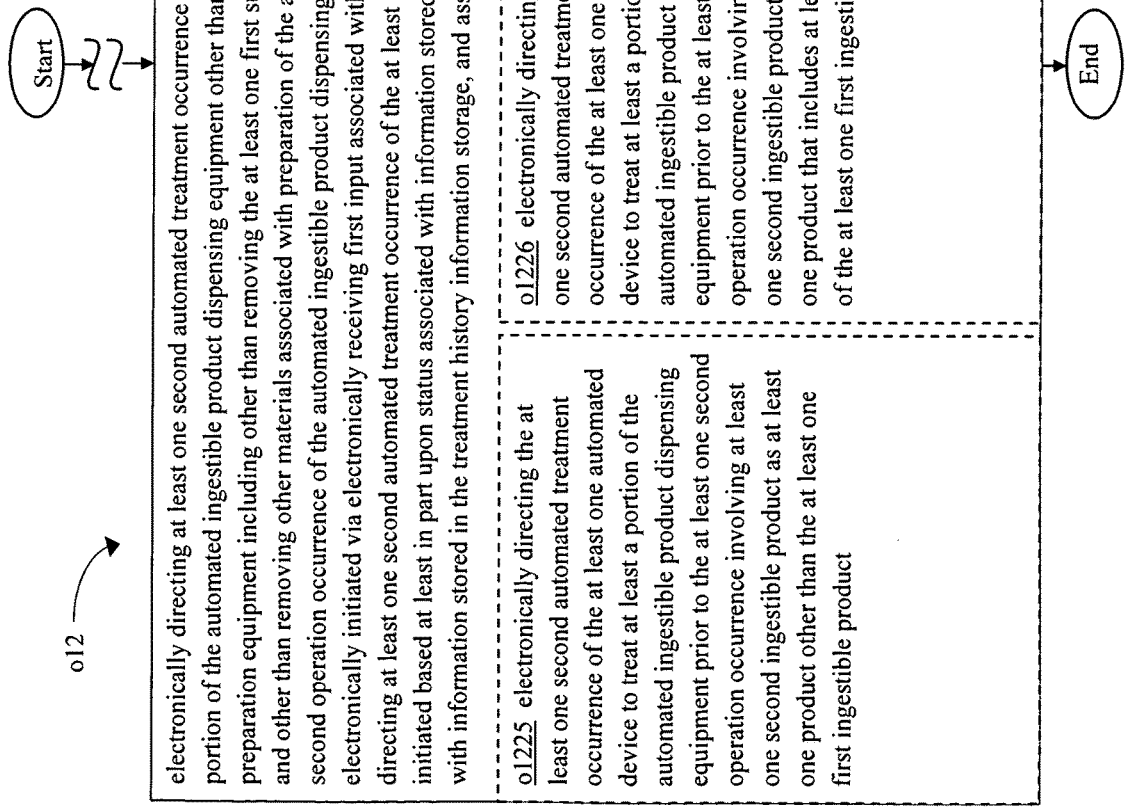
FIG. 62 is a high-level flowchart including exemplary implementations of operation O12 of FIG. 31.

In one or more implementations, as shown in FIG. 62, operation o12 includes an operation o1225 for electronically directing the at least one second automated treatment occurrence of the at least one automated device to treat at least a portion of the automated ingestible product dispensing equipment prior to the at least one second operation occurrence involving at least one second ingestible product as at least one product other than the at least one first ingestible product. An exemplary version of a non-transitory signal bearing medium of information storage subsystem s200 is depicted as bearing one or more treating other instructions i1225 that when executed will direct performance of the operation o1225. In an implementation, the one or more treating other instructions i1225 when executed direct electronically directing the at least one second automated treatment occurrence of the at least one automated device to treat at least a portion of the automated ingestible product dispensing equipment prior to the at least one second operation occurrence involving least one second ingestible product as at least one product other than the at least one first ingestible product (e.g. one or more instances of the microprocessor component s102 of the control and information processing subsystem s100 can direct one or more instances of the compressed water fluid component s830 to treat at least a portion of the ingestible product dispensing system 10 prior to the second operation occurrence, etc.). Furthermore, the treating other electrical circuitry arrangement e1225 when activated will perform the operation o1225. In an implementation, the treating other electrical circuitry arrangement e1225, when activated performs electronically directing the at least one second automated treatment occurrence of the at least one automated device to treat at least a portion of the automated ingestible product dispensing equipment prior to the at least one second operation occurrence involving least one second ingestible product as at least one product other than the at least one first ingestible product (e.g. one or more instances of the microprocessor component s102 of the control and information processing subsystem s100 can direct one or more instances of the compressed water fluid component s830 to treat at least a portion of the ingestible product dispensing system 10 prior to the second operation occurrence, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one product other than the at least one first ingestible product is carried out by electronically directing the at least one second automated treatment occurrence of the at least one automated device to treat at least a portion of the automated ingestible product dispensing equipment prior to the at least one second operation occurrence involving least one second ingestible product as at least one product other than the at least one first ingestible product (e.g. one or more instances of the microprocessor component s102 of the control and information processing subsystem s100 can direct one or more instances of the compressed water fluid component s830 to treat at least a portion of the ingestible product dispensing system 10 prior to the second operation occurrence, etc.).

In one or more implementations, operation o12 includes an operation o1226 for electronically directing the at least one second automated treatment occurrence of the at least one automated device to treat at least a portion of the automated ingestible product dispensing equipment prior to the at least one second operation occurrence involving at least one second ingestible product as at least one product that includes at least a portion of the at least one first ingestible product. An exemplary version of a non-transitory signal bearing medium of information storage subsystem s200 is depicted as bearing one or more treating includes instructions i1226 that when executed will direct performance of the operation o1226. In an implementation, the one or more treating includes instructions i1226 when executed direct electronically directing the at least one second automated treatment occurrence of the at least one automated device to treat at least a portion of the automated ingestible product dispensing equipment prior to the at least one second operation occurrence of involving at least one second ingestible product as at least one product that includes at least a portion of the at least one first ingestible product (e.g. one or more instances of the central processing unit (CPU) component s104 of the control and information processing subsystem s100 can direct one or more instances of the air blower component s802 to treat at least a portion of the automated ingestible product dispensing equipment prior to the second operation occurrence involving the second ingestible product that includes at least a portion of the first ingestible product, etc.). Furthermore, the treating includes electrical circuitry arrangement e1226 when activated will perform the operation o1226. In an implementation, the treating includes electrical circuitry arrangement e1226, when activated performs electronically directing the at least one second automated treatment occurrence of the at least one automated device to treat at least a portion of the automated ingestible product dispensing equipment prior to the at least one second operation occurrence of involving at least one second ingestible product as at least one product that includes at least a portion of the at least one first ingestible product (e.g. one or more instances of the central processing unit (CPU) component s104 of the control and information processing subsystem s100 can direct one or more instances of the air blower component s802 to treat at least a portion of the automated ingestible product dispensing equipment prior to the second operation occurrence involving the second ingestible product that includes at least a portion of the first ingestible product, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one product that includes at least a portion of the at least one first ingestible product is carried out by electronically directing the at least one second automated treatment occurrence of the at least one automated device to treat at least a portion of the automated ingestible product dispensing equipment prior to the at least one second operation occurrence of involving at least one second ingestible product as at least one product that includes at least a portion of the at least one first ingestible product (e.g. one or more instances of the central processing unit (CPU) component s104 of the control and information processing subsystem s100 can direct one or more instances of the air blower component s802 to treat at least a portion of the automated ingestible product dispensing equipment prior to the second operation occurrence involving the second ingestible product that includes at least a portion of the first ingestible product, etc.).

In one or more implementations, operation o12 includes an operation o1227 for electronically directing the at least one second automated treatment occurrence of the at least one automated device to treat at least a portion of the automated ingestible product dispensing equipment prior to the at least one second operation occurrence involving at least one second ingestible product as at least one product that is the at least one first ingestible product. An exemplary version of a non-transitory signal bearing medium of information storage subsystem s200 is depicted as bearing one or more treating first instructions i1227 that when executed will direct performance of the operation o1227. In an implementation, the one or more treating first instructions i1227 when executed direct electronically directing the at least one second automated treatment occurrence of the at least one automated device to treat at least a portion of the automated ingestible product dispensing equipment prior to the at least one second operation occurrence involving at least one second ingestible product as at least one product that is the at least one first ingestible product (e.g. one or more instances of the digital signal processor (DSP) component s106 of the control and information processing subsystem s100 can direct one or more instances of the compressed fluid component s804 to treat one or more portions of the ingestible product dispensing system 10 prior to the second operation occurrence, etc.). Furthermore, the treating first electrical circuitry arrangement e1227 when activated will perform the operation o1227. In an implementation, the treating first electrical circuitry arrangement e1227, when activated performs electronically directing the at least one second automated treatment occurrence of the at least one automated device to treat at least a portion of the automated ingestible product dispensing equipment prior to the at least one second operation occurrence involving at least one second ingestible product as at least one product that is the at least one first ingestible product (e.g. one or more instances of the digital signal processor (DSP) component s106 of the control and information processing subsystem s100 can direct one or more instances of the compressed fluid component s804 to treat one or more portions of the ingestible product dispensing system 10 prior to the second operation occurrence, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one product that is the at least one first ingestible product is carried out by electronically directing the at least one second automated treatment occurrence of the at least one automated device to treat at least a portion of the automated ingestible product dispensing equipment prior to the at least one second operation occurrence involving at least one second ingestible product as at least one product that is the at least one first ingestible product (e.g. one or more instances of the digital signal processor (DSP) component s106 of the control and information processing subsystem s100 can direct one or more instances of the compressed fluid component s804 to treat one or more portions of the ingestible product dispensing system 10 prior to the second operation occurrence, etc.).

Figure 63:
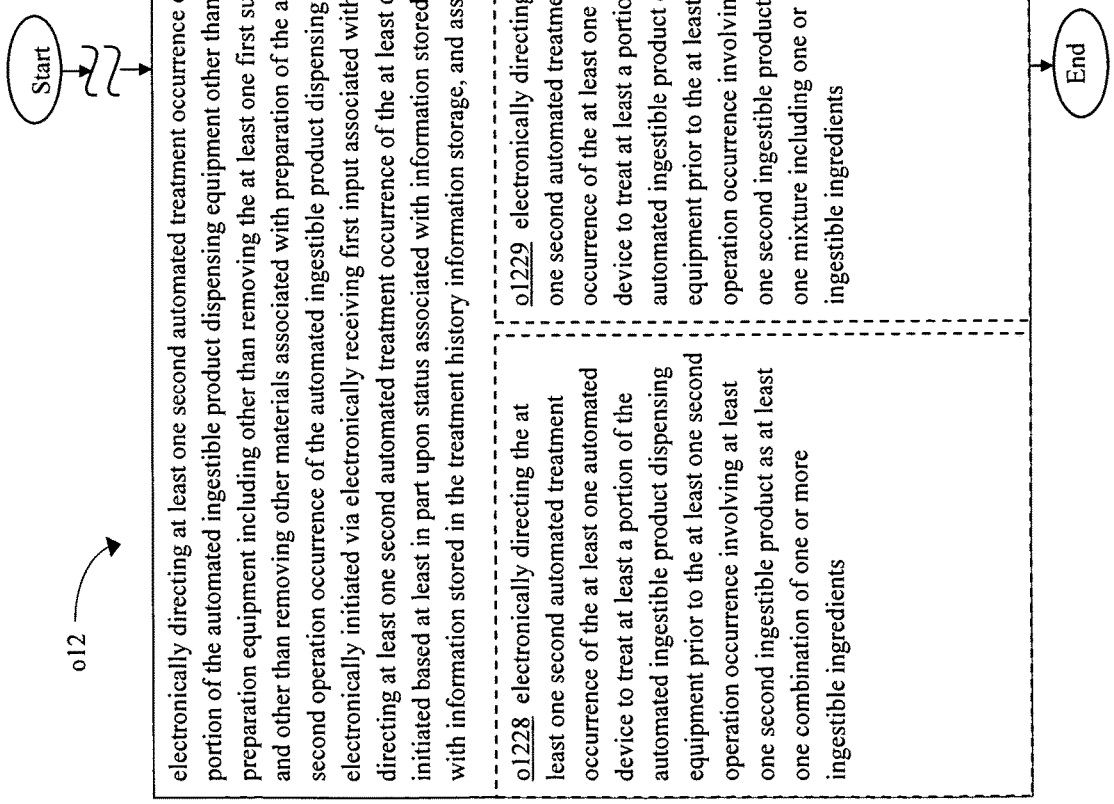
FIG. 63 is a high-level flowchart including exemplary implementations of operation O12 of FIG. 31.

In one or more implementations, as shown in FIG. 63, operation o12 includes an operation o1228 for electronically directing the at least one second automated treatment occurrence of the at least one automated device to treat at least a portion of the automated ingestible product dispensing equipment prior to the at least one second operation occurrence involving at least one second ingestible product as at least one combination of one or more ingestible ingredients. An exemplary version of a non-transitory signal bearing medium of information storage subsystem s200 is depicted as bearing one or more treating combination instructions i1228 that when executed will direct performance of the operation o1228. In an implementation, the one or more treating combination instructions i1228 when executed direct electronically directing the at least one second automated treatment occurrence of the at least one automated device to treat at least a portion of the automated ingestible product dispensing equipment prior to the at least one second operation occurrence involving at least one second ingestible product as at least one combination of one or more ingestible ingredients (e.g. one or more instances of the application specific integrated circuit (ASIC) component s108 of the control and information processing subsystem s100 can direct one or more instances of the vacuum component s806 to treat the ingestible product dispensing system 10 prior to the second operation, etc.). Furthermore, the treating combination electrical circuitry arrangement e1228 when activated will perform the operation o1228. In an implementation, the treating combination electrical circuitry arrangement e1228, when activated performs electronically directing the at least one second automated treatment occurrence of the at least one automated device to treat at least a portion of the automated ingestible product dispensing equipment prior to the at least one second operation occurrence involving at least one second ingestible product as at least one combination of one or more ingestible ingredients (e.g. one or more instances of the application specific integrated circuit (ASIC) component s108 of the control and information processing subsystem s100 can direct one or more instances of the vacuum component s806 to treat the ingestible product dispensing system 10 prior to the second operation, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one combination of one or more ingestible ingredients is carried out by electronically directing the at least one second automated treatment occurrence of the at least one automated device to treat at least a portion of the automated ingestible product dispensing equipment prior to the at least one second operation occurrence involving at least one second ingestible product as at least one combination of one or more ingestible ingredients (e.g. one or more instances of the application specific integrated circuit (ASIC) component s108 of the control and information processing subsystem s100 can direct one or more instances of the vacuum component s806 to treat the ingestible product dispensing system 10 prior to the second operation, etc.).

In one or more implementations, operation o12 includes an operation o1229 for electronically directing the at least one second automated treatment occurrence of the at least one automated device to treat at least a portion of the automated ingestible product dispensing equipment prior to the at least one second operation occurrence involving at least one second ingestible product as at least one mixture including one or more ingestible ingredients. An exemplary version of a non-transitory signal bearing medium of information storage subsystem s200 is depicted as bearing one or more treating mixture instructions i1229 that when executed will direct performance of the operation o1229. In an implementation, the one or more treating mixture instructions i1229 when executed direct electronically directing the at least one second automated treatment occurrence of the at least one automated device to treat at least a portion of the automated ingestible product dispensing equipment prior to the at least one second operation occurrence involving at least one second ingestible product as at least one mixture including one or more ingestible ingredients (e.g. one or more instances of the field programmable gate array (FPGA) component s110 of the control and information processing subsystem s100 can direct one or more instances of the ultrasonic component s808 to treat at least a portion of the automated ingestible product dispensing equipment prior to the at least one second operation occurrence involving at least one second ingestible product as at least one mixture including one or more ingestible ingredients of trail mix, etc.). Furthermore, the treating mixture electrical circuitry arrangement e1229 when activated will perform the operation o1229. In an implementation, the treating mixture electrical circuitry arrangement e1229, when activated performs electronically directing the at least one second automated treatment occurrence of the at least one automated device to treat at least a portion of the automated ingestible product dispensing equipment prior to the at least one second operation occurrence involving at least one second ingestible product as at least one mixture including one or more ingestible ingredients (e.g. one or more instances of the field programmable gate array (FPGA) component s110 of the control and information processing subsystem s100 can direct one or more instances of the ultrasonic component s808 to treat at least a portion of the automated ingestible product dispensing equipment prior to the at least one second operation occurrence involving at least one second ingestible product as at least one mixture including one or more ingestible ingredients of trail mix, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one mixture including one or more ingestible ingredients is carried out by electronically directing the at least one second automated treatment occurrence of the at least one automated device to treat at least a portion of the automated ingestible product dispensing equipment prior to the at least one second operation occurrence involving at least one second ingestible product as at least one mixture including one or more ingestible ingredients (e.g. one or more instances of the field programmable gate array (FPGA) component s110 of the control and information processing subsystem s100 can direct one or more instances of the ultrasonic component s808 to treat at least a portion of the automated ingestible product dispensing equipment prior to the at least one second operation occurrence involving at least one second ingestible product as at least one mixture including one or more ingestible ingredients of trail mix, etc.).

In one or more implementations, operation o12 includes an operation o1230 for electronically directing the at least one second automated treatment occurrence of the at least one automated device to treat at least a portion of the automated ingestible product dispensing equipment prior to the at least one second operation occurrence involving at least one second ingestible product as at least one mixture including one or more nutraceuticals. An exemplary version of a non-transitory signal bearing medium of information storage subsystem s200 is depicted as bearing one or more treating nutraceuticals instructions i1230 that when executed will direct performance of the operation o1230. In an implementation, the one or more treating nutraceuticals instructions i1230 when executed direct electronically directing the at least one second automated treatment occurrence of the at least one automated device to treat at least a portion of the automated ingestible product dispensing equipment prior to the at least one second operation occurrence involving at least one second ingestible product as at least one mixture including one or more nutraceuticals (e.g. one or more instances of the multiprocessor component s112 of the control and information processing subsystem s100 can direct one or more instances of the radiant energy component s810 to treat at least a portion of the automated ingestible product dispensing equipment prior to the at least one second operation occurrence involving at least one second ingestible product as a daily supplement mix including vitamin B12 and calcium citrate prior to the second operation occurrence involving a sports drink containing amino acids and magnesium citrate, etc.). Furthermore, the treating nutraceuticals electrical circuitry arrangement e1230 when activated will perform the operation o1230. In an implementation, the treating nutraceuticals electrical circuitry arrangement e1230, when activated performs electronically directing the at least one second automated treatment occurrence of the at least one automated device to treat at least a portion of the automated ingestible product dispensing equipment prior to the at least one second operation occurrence involving at least one second ingestible product as at least one mixture including one or more nutraceuticals (e.g. one or more instances of the multiprocessor component s112 of the control and information processing subsystem s100 can direct one or more instances of the radiant energy component s810 to treat at least a portion of the automated ingestible product dispensing equipment prior to the at least one second operation occurrence involving at least one second ingestible product as a daily supplement mix including vitamin B12 and calcium citrate prior to the second operation occurrence involving a sports drink containing amino acids and magnesium citrate, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one mixture including one or more nutraceuticals is carried out by electronically directing the at least one second automated treatment occurrence of the at least one automated device to treat at least a portion of the automated ingestible product dispensing equipment prior to the at least one second operation occurrence involving at least one second ingestible product as at least one mixture including one or more nutraceuticals (e.g. one or more instances of the multiprocessor component s112 of the control and information processing subsystem s100 can direct one or more instances of the radiant energy component s810 to treat at least a portion of the automated ingestible product dispensing equipment prior to the at least one second operation occurrence involving at least one second ingestible product as a daily supplement mix including vitamin B12 and calcium citrate prior to the second operation occurrence involving a sports drink containing amino acids and magnesium citrate, etc.).

Figure 64:
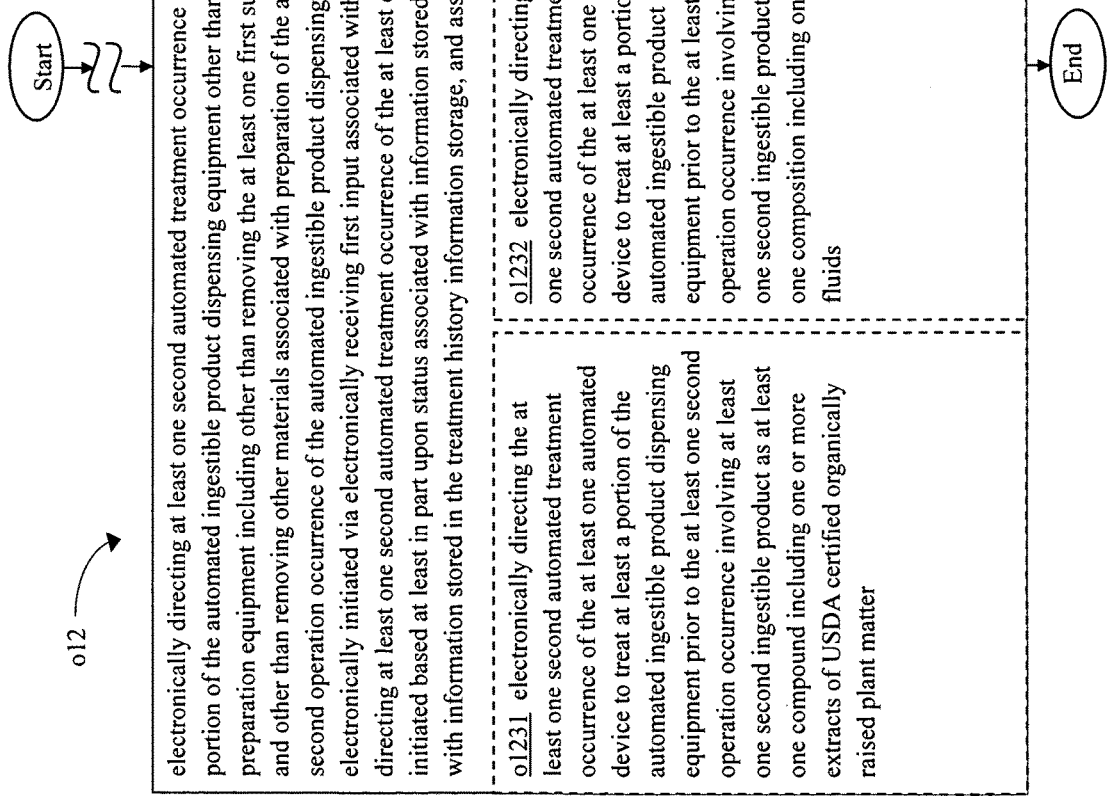
FIG. 64 is a high-level flowchart including exemplary implementations of operation O12 of FIG. 31.

In one or more implementations, as shown in FIG. 64, operation o12 includes an operation o1231 for electronically directing the at least one second automated treatment occurrence of the at least one automated device to treat at least a portion of the automated ingestible product dispensing equipment prior to the at least one second operation occurrence involving at least one second ingestible product as at least one compound including one or more extracts of USDA certified organically raised plant matter. An exemplary version of a non-transitory signal bearing medium of information storage subsystem s200 is depicted as bearing one or more treating organic instructions i1231 that when executed will direct performance of the operation o1231. In an implementation, the one or more treating organic instructions i1231 when executed direct electronically directing the at least one second automated treatment occurrence of the at least one automated device to treat at least a portion of the automated ingestible product dispensing equipment prior to the at least one second operation occurrence involving at least one second ingestible product as at least one compound including one or more extracts of USDA certified organically raised plant matter (e.g. one or more instances of the optical processing component s114 of the control and information processing subsystem s100 can direct one or more instances of the abrasive component s812 to treat at least a portion of the automated ingestible product dispensing equipment prior to the second operation occurrence involving the second ingestible product as a organic fruit drink, etc.). Furthermore, the treating organic electrical circuitry arrangement e1231 when activated will perform the operation o1231. In an implementation, the treating organic electrical circuitry arrangement e1231, when activated performs electronically directing the at least one second automated treatment occurrence of the at least one automated device to treat at least a portion of the automated ingestible product dispensing equipment prior to the at least one second operation occurrence involving at least one second ingestible product as at least one compound including one or more extracts of USDA certified organically raised plant matter (e.g. one or more instances of the optical processing component s114 of the control and information processing subsystem s100 can direct one or more instances of the abrasive component s812 to treat at least a portion of the automated ingestible product dispensing equipment prior to the second operation occurrence involving the second ingestible product as a organic fruit drink, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one compound including one or more extracts of USDA certified organically raised plant matter is carried out by electronically directing the at least one second automated treatment occurrence of the at least one automated device to treat at least a portion of the automated ingestible product dispensing equipment prior to the at least one second operation occurrence involving at least one second ingestible product as at least one compound including one or more extracts of USDA certified organically raised plant matter (e.g. one or more instances of the optical processing component s114 of the control and information processing subsystem s100 can direct one or more instances of the abrasive component s812 to treat at least a portion of the automated ingestible product dispensing equipment prior to the second operation occurrence involving the second ingestible product as a organic fruit drink, etc.).

In one or more implementations, operation o12 includes an operation o1232 for electronically directing the at least one second automated treatment occurrence of the at least one automated device to treat at least a portion of the automated ingestible product dispensing equipment prior to the at least one second operation occurrence involving at least one second ingestible product as at least one composition including one or more fluids. An exemplary version of a non-transitory signal bearing medium of information storage subsystem s200 is depicted as bearing one or more treating fluids instructions i1232 that when executed will direct performance of the operation o1232. In an implementation, the one or more treating fluids instructions i1232 when executed direct electronically directing the at least one second automated treatment occurrence of the at least one automated device to treat at least a portion of the automated ingestible product dispensing equipment prior to the at least one second operation occurrence involving at least one second ingestible product as at least one composition including one or more fluids (e.g. one or more instances of the logic component s116 of the control and information processing subsystem s100 can direct one or more instances of the brush component s814 to treat at least a portion of the automated ingestible product dispensing equipment prior to the second operation occurrence involving the second ingestible product as a milk shake, etc.). Furthermore, the treating fluids electrical circuitry arrangement e1232 when activated will perform the operation o1232. In an implementation, the treating fluids electrical circuitry arrangement e1232, when activated performs electronically directing the at least one second automated treatment occurrence of the at least one automated device to treat at least a portion of the automated ingestible product dispensing equipment prior to the at least one second operation occurrence involving at least one second ingestible product as at least one composition including one or more fluids (e.g. one or more instances of the logic component s116 of the control and information processing subsystem s100 can direct one or more instances of the brush component s814 to treat at least a portion of the automated ingestible product dispensing equipment prior to the second operation occurrence involving the second ingestible product as a milk shake, etc.). In an implementation, the electronically directing the at least one second automated treatment occurrence of the at least one automated device to treat at least a portion of the automated ingestible product dispensing equipment prior to the at least one second operation occurrence involving at least one second ingestible product as at least one composition including one or more fluids is carried out by electronically directing the at least one second automated treatment occurrence of the at least one automated device to treat at least a portion of the automated ingestible product dispensing equipment prior to the at least one second operation occurrence involving at least one second ingestible product as at least one composition including one or more fluids (e.g. one or more instances of the logic component s116 of the control and information processing subsystem s100 can direct one or more instances of the brush component s814 to treat at least a portion of the automated ingestible product dispensing equipment prior to the second operation occurrence involving the second ingestible product as a milk shake, etc.).

In one or more implementations, operation o12 includes an operation o1233 for electronically directing the at least one second automated treatment occurrence of the at least one automated device to treat at least a portion of the automated ingestible product dispensing equipment prior to the at least one second operation occurrence involving at least one second ingestible product as at least one combination of one or more powders. An exemplary version of a non-transitory signal bearing medium of information storage subsystem s200 is depicted as bearing one or more treating powders instructions i1233 that when executed will direct performance of the operation o1233. In an implementation, the one or more treating powders instructions i1233 when executed direct electronically directing the at least one second automated treatment occurrence of the at least one automated device to treat at least a portion of the automated ingestible product dispensing equipment prior to the at least one second operation occurrence involving the at least one second ingestible product as at least one combination of one or more powders (e.g. one or more instances of the microprocessor component s102 of the control and information processing subsystem s100 can direct one or more instances of the squeegee brush component s816 to treat at least a portion of the automated ingestible product dispensing equipment prior to the second operation occurrence involving the second ingestible product as a foot powder mix, etc.). Furthermore, the treating powders electrical circuitry arrangement e1233 when activated will perform the operation o1233. In an implementation, the treating powders electrical circuitry arrangement e1233, when activated performs electronically directing the at least one second automated treatment occurrence of the at least one automated device to treat at least a portion of the automated ingestible product dispensing equipment prior to the at least one second operation occurrence involving the at least one second ingestible product as at least one combination of one or more powders (e.g. one or more instances of the microprocessor component s102 of the control and information processing subsystem s100 can direct one or more instances of the squeegee brush component s816 to treat at least a portion of the automated ingestible product dispensing equipment prior to the second operation occurrence involving the second ingestible product as a foot powder mix, etc.). In an implementation, the electronically directing the at least one second automated treatment occurrence of the at least one automated device to treat at least a portion of the automated ingestible product dispensing equipment prior to the at least one second operation occurrence involving the at least one second ingestible product as at least one combination of one or more powders is carried out by electronically directing the at least one second automated treatment occurrence of the at least one automated device to treat at least a portion of the automated ingestible product dispensing equipment prior to the at least one second operation occurrence involving the at least one second ingestible product as at least one combination of one or more powders (e.g. one or more instances of the microprocessor component s102 of the control and information processing subsystem s100 can direct one or more instances of the squeegee brush component s816 to treat at least a portion of the automated ingestible product dispensing equipment prior to the second operation occurrence involving the second ingestible product as a foot powder mix, etc.).

Figure 65:
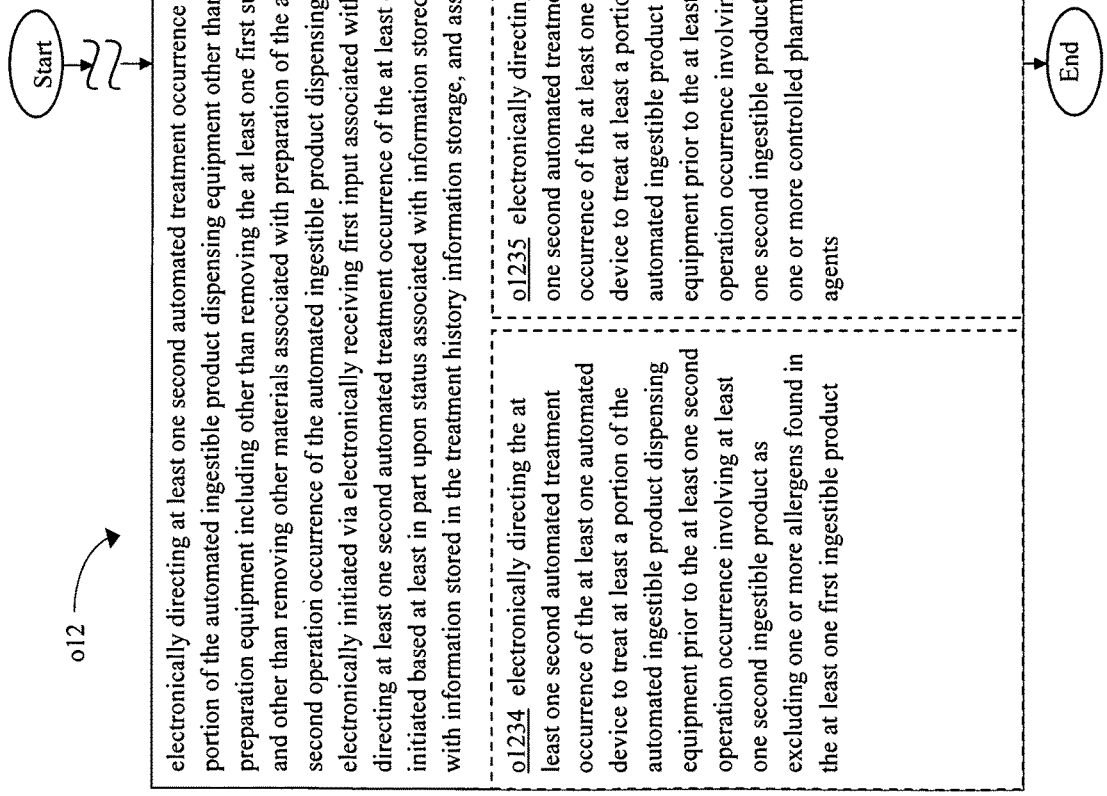
FIG. 65 is a high-level flowchart including exemplary implementations of operation O12 of FIG. 31.

In one or more implementations, as shown in FIG. 65, operation o12 includes an operation o1234 for electronically directing the at least one second automated treatment occurrence of the at least one automated device to treat at least a portion of the automated ingestible product dispensing equipment prior to the at least one second operation occurrence involving at least one second ingestible product as excluding one or more allergens found in the at least one first ingestible product. An exemplary version of a non-transitory signal bearing medium of information storage subsystem s200 is depicted as bearing one or more treating allergens instructions i1234 that when executed will direct performance of the operation o1234. In an implementation, the one or more treating allergens instructions i1234 when executed direct electronically directing the at least one second automated treatment occurrence of the at least one automated device to treat at least a portion of the automated ingestible product dispensing equipment prior to the at least one second operation occurrence involving at least one second ingestible product as excluding one or more allergens found in the at least one first ingestible product (e.g. one or more instances of the central processing unit (CPU) component s104 of the control and information processing subsystem s100 can direct one or more instances of the pipe cleaner brush component s818 to treat at least a portion of the automated ingestible product dispensing equipment prior to the second operation occurrence involving the second ingestible product as a gluten free, diary free pizza pie, etc.). Furthermore, the treating allergens electrical circuitry arrangement e1234 when activated will perform the operation o1234. In an implementation, the treating allergens electrical circuitry arrangement e1234, when activated performs electronically directing the at least one second automated treatment occurrence of the at least one automated device to treat at least a portion of the automated ingestible product dispensing equipment prior to the at least one second operation occurrence involving at least one second ingestible product as excluding one or more allergens found in the at least one first ingestible product (e.g. one or more instances of the central processing unit (CPU) component s104 of the control and information processing subsystem s100 can direct one or more instances of the pipe cleaner brush component s818 to treat at least a portion of the automated ingestible product dispensing equipment prior to the second operation occurrence involving the second ingestible product as a gluten free, diary free pizza pie, etc.). In an implementation, the electronically directing the at least one second automated treatment occurrence of the at least one automated device to treat at least a portion of the automated ingestible product dispensing equipment prior to the at least one second operation occurrence involving at least one second ingestible product as excluding one or more allergens found in the at least one first ingestible product is carried out by electronically directing the at least one second automated treatment occurrence of the at least one automated device to treat at least a portion of the automated ingestible product dispensing equipment prior to the at least one second operation occurrence involving at least one second ingestible product as excluding one or more allergens found in the at least one first ingestible product (e.g. one or more instances of the central processing unit (CPU) component s104 of the control and information processing subsystem s100 can direct one or more instances of the pipe cleaner brush component s818 to treat at least a portion of the automated ingestible product dispensing equipment prior to the second operation occurrence involving the second ingestible product as a gluten free, diary free pizza pie, etc.).

In one or more implementations, operation o12 includes an operation o1235 for electronically directing the at least one second automated treatment occurrence of the at least one automated device to treat at least a portion of the automated ingestible product dispensing equipment prior to the at least one second operation occurrence involving at least one second ingestible product as including one or more controlled pharmaceutical agents. An exemplary version of a non-transitory signal bearing medium of information storage subsystem s200 is depicted as bearing one or more treating agents instructions i1235 that when executed will direct performance of the operation o1235. In an implementation, the one or more treating agents instructions i1235 when executed direct electronically directing the at least one second automated treatment occurrence of the at least one automated device to treat at least a portion of the automated ingestible product dispensing equipment prior to the at least one second operation occurrence involving at least one second ingestible product as including one or more controlled pharmaceutical agents (e.g. one or more instances of the digital signal processor (DSP) component s106 of the control and information processing subsystem s100 can direct one or more instances of the material flush abrasive component s820 to treat at least a portion of the automated ingestible product dispensing equipment prior to the second operation occurrence involving the second ingestible product as a migraine medication, etc.). Furthermore, the treating agents electrical circuitry arrangement e1235 when activated will perform the operation o1235. In an implementation, the treating agents electrical circuitry arrangement e1235, when activated performs electronically directing the at least one second automated treatment occurrence of the at least one automated device to treat at least a portion of the automated ingestible product dispensing equipment prior to the at least one second operation occurrence involving at least one second ingestible product as including one or more controlled pharmaceutical agents (e.g. one or more instances of the digital signal processor (DSP) component s106 of the control and information processing subsystem s100 can direct one or more instances of the material flush abrasive component s820 to treat at least a portion of the automated ingestible product dispensing equipment prior to the second operation occurrence involving the second ingestible product as a migraine medication, etc.). In an implementation, the electronically directing the at least one second automated treatment occurrence of the at least one automated device to treat at least a portion of the automated ingestible product dispensing equipment prior to the at least one second operation occurrence involving at least one second ingestible product as including one or more controlled pharmaceutical agents is carried out by electronically directing the at least one second automated treatment occurrence of the at least one automated device to treat at least a portion of the automated ingestible product dispensing equipment prior to the at least one second operation occurrence involving at least one second ingestible product as including one or more controlled pharmaceutical agents (e.g. one or more instances of the digital signal processor (DSP) component s106 of the control and information processing subsystem s100 can direct one or more instances of the material flush abrasive component s820 to treat at least a portion of the automated ingestible product dispensing equipment prior to the second operation occurrence involving the second ingestible product as a migraine medication, etc.).

In one or more implementations, operation o12 includes an operation o1236 for electronically directing the at least one second automated treatment occurrence of the at least one automated device to treat at least a portion of the automated ingestible product dispensing equipment prior to the at least one second operation occurrence involving at least one second ingestible product as originating from one or more geographic regions. An exemplary version of a non-transitory signal bearing medium of information storage subsystem s200 is depicted as bearing one or more treating regions instructions i1236 that when executed will direct performance of the operation o1236. In an implementation, the one or more treating regions instructions i1236 when executed direct electronically directing the at least one second automated treatment occurrence of the at least one automated device to treat at least a portion of the automated ingestible product dispensing equipment prior to the at least one second operation occurrence involving at least one second ingestible product as originating from one or more geographic regions (e.g. one or more instances of the application specific integrated circuit (ASIC) component s108 of the control and information processing subsystem s100 can direct one or more instances of the fish tape system brush component s822 to treat at least a portion of the automated ingestible product dispensing equipment prior to the second operation occurrence involving the second ingestible product as a milk product from the state of Oregon, etc.). Furthermore, the treating regions electrical circuitry arrangement e1236 when activated will perform the operation o1236. In an implementation, the treating regions electrical circuitry arrangement e1236, when activated performs electronically directing the at least one second automated treatment occurrence of the at least one automated device to treat at least a portion of the automated ingestible product dispensing equipment prior to the at least one second operation occurrence involving at least one second ingestible product as originating from one or more geographic regions (e.g. one or more instances of the application specific integrated circuit (ASIC) component s108 of the control and information processing subsystem s100 can direct one or more instances of the fish tape system brush component s822 to treat at least a portion of the automated ingestible product dispensing equipment prior to the second operation occurrence involving the second ingestible product as a milk product from the state of Oregon, etc.). In an implementation, the electronically directing the at least one second automated treatment occurrence of the at least one automated device to treat at least a portion of the automated ingestible product dispensing equipment prior to the at least one second operation occurrence involving at least one second ingestible product as originating from one or more geographic regions is carried out by electronically directing the at least one second automated treatment occurrence of the at least one automated device to treat at least a portion of the automated ingestible product dispensing equipment prior to the at least one second operation occurrence involving at least one second ingestible product as originating from one or more geographic regions (e.g. one or more instances of the application specific integrated circuit (ASIC) component s108 of the control and information processing subsystem s100 can direct one or more instances of the fish tape system brush component s822 to treat at least a portion of the automated ingestible product dispensing equipment prior to the second operation occurrence involving the second ingestible product as a milk product from the state of Oregon, etc.).

Figure 66:
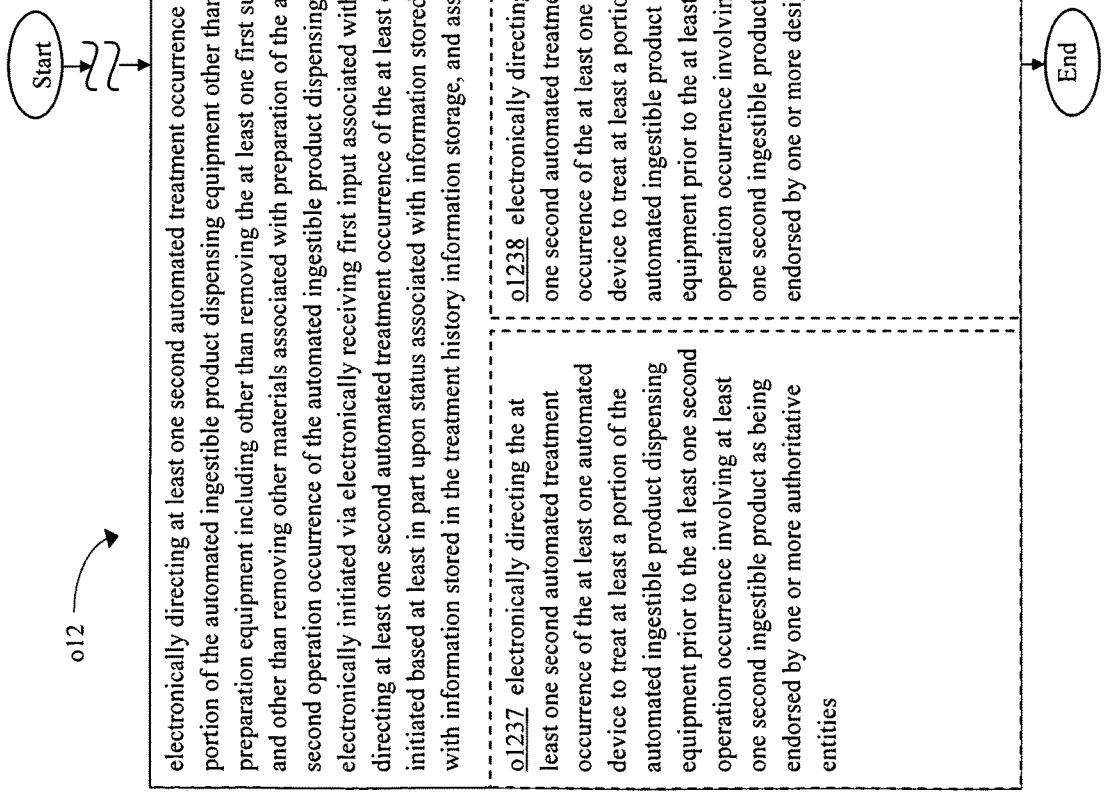
FIG. 66 is a high-level flowchart including exemplary implementations of operation O12 of FIG. 31.

In one or more implementations, as shown in FIG. 66, operation o12 includes an operation o1237 for electronically directing the at least one second automated treatment occurrence of the at least one automated device to treat at least a portion of the automated ingestible product dispensing equipment prior to the at least one second operation occurrence involving at least one second ingestible product as being endorsed by one or more authoritative entities. An exemplary version of a non-transitory signal bearing medium of information storage subsystem s200 is depicted as bearing one or more treating authoritative instructions i1237 that when executed will direct performance of the operation o1237. In an implementation, the one or more treating authoritative instructions i1237 when executed direct electronically directing the at least one second automated treatment occurrence of the at least one automated device to treat at least a portion of the automated ingestible product dispensing equipment prior to the at least one second operation occurrence involving at least one second ingestible product as being endorsed by one or more authoritative entities (e.g. one or more instances of the field programmable gate array (FPGA) component s110 of the control and information processing subsystem s100 can direct one or more instances of the parts exchange component s824 to treat at least a portion of the automated ingestible product dispensing equipment prior to the second operation occurrence involving the second ingestible product, as another sports bar endorsed by six hockey players, etc.). Furthermore, the treating authoritative electrical circuitry arrangement e1237 when activated will perform the operation electronically directing the at least one second automated treatment occurrence of the at least one automated device to treat at least a portion of the automated ingestible product dispensing equipment prior to the at least one second operation occurrence involving at least one second ingestible product as being endorsed by one or more authoritative entities. In an implementation, the treating authoritative electrical circuitry arrangement e1237, when activated performs electronically directing the at least one second automated treatment occurrence of the at least one automated device to treat at least a portion of the automated ingestible product dispensing equipment prior to the at least one second operation occurrence involving at least one second ingestible product as being endorsed by one or more authoritative entities (e.g. one or more instances of the field programmable gate array (FPGA) component s110 of the control and information processing subsystem s100 can direct one or more instances of the parts exchange component s824 to treat at least a portion of the automated ingestible product dispensing equipment prior to the second operation occurrence involving the second ingestible product, as another sports bar endorsed by six hockey players, etc.). In an implementation, the electronically directing the at least one second automated treatment occurrence of the at least one automated device to treat at least a portion of the automated ingestible product dispensing equipment prior to the at least one second operation occurrence involving at least one second ingestible product as being endorsed by one or more authoritative entities is carried out by electronically directing the at least one second automated treatment occurrence of the at least one automated device to treat at least a portion of the automated ingestible product dispensing equipment prior to the at least one second operation occurrence involving at least one second ingestible product as being endorsed by one or more authoritative entities (e.g. one or more instances of the field programmable gate array (FPGA) component s110 of the control and information processing subsystem s100 can direct one or more instances of the parts exchange component s824 to treat at least a portion of the automated ingestible product dispensing equipment prior to the second operation occurrence involving the second ingestible product, as another sports bar endorsed by six hockey players, etc.).

In one or more implementations, operation o12 includes an operation o1238 for electronically directing the at least one second automated treatment occurrence of the at least one automated device to treat at least a portion of the automated ingestible product dispensing equipment prior to the at least one second operation occurrence involving at least one second ingestible product as being endorsed by one or more designated users. An exemplary version of a non-transitory signal bearing medium of information storage subsystem s200 is depicted as bearing one or more treating designated instructions i1238 that when executed will direct performance of the operation o1238. In an implementation, the one or more treating designated instructions i1238 when executed direct electronically directing the at least one second automated treatment occurrence of the at least one automated device to treat at least a portion of the automated ingestible product dispensing equipment prior to the at least one second operation occurrence involving the at least one second ingestible product as being endorsed by one or more designated users (e.g. one or more instances of the multi-processor component s112 of the control and information processing subsystem s100 can direct one or more instances of the parts replacement component s826 to treat at least a portion of the automated ingestible product dispensing equipment prior to the second operation occurrence involving the second ingestible product as a meal replacement weight gain bar endorsed by five body building athletes, etc.). Furthermore, the treating designated electrical circuitry arrangement e1238 when activated will perform the operation o1238. In an implementation, the treating designated electrical circuitry arrangement e1238, when activated performs electronically directing the at least one second automated treatment occurrence of the at least one automated device to treat at least a portion of the automated ingestible product dispensing equipment prior to the at least one second operation occurrence involving the at least one second ingestible product as being endorsed by one or more designated users (e.g. one or more instances of the multiprocessor component s112 of the control and information processing subsystem s100 can direct one or more instances of the parts replacement component s826 to treat at least a portion of the automated ingestible product dispensing equipment prior to the second operation occurrence involving the second ingestible product as a meal replacement weight gain bar endorsed by five body building athletes, etc.). In an implementation, the electronically directing the at least one second automated treatment occurrence of the at least one automated device to treat at least a portion of the automated ingestible product dispensing equipment prior to the at least one second operation occurrence involving at least one second ingestible product as being endorsed by one or more designated users is carried out by electronically directing the at least one second automated treatment occurrence of the at least one automated device to treat at least a portion of the automated ingestible product dispensing equipment prior to the at least one second operation occurrence involving the at least one second ingestible product as being endorsed by one or more designated users (e.g. one or more instances of the multiprocessor component s112 of the control and information processing subsystem s100 can direct one or more instances of the parts replacement component s826 to treat at least a portion of the automated ingestible product dispensing equipment prior to the second operation occurrence involving the second ingestible product as a meal replacement weight gain bar endorsed by five body building athletes, etc.).

In one or more implementations, operation o12 includes an operation o1239 for electronically directing the at least one second automated treatment occurrence of the at least one automated device to treat at least a portion of the automated ingestible product dispensing equipment prior to the at least one second operation occurrence involving at least one second ingestible product as being chemically reactive with the at least one first substance of the at least one first ingestible product. An exemplary version of a non-transitory signal bearing medium of information storage subsystem s200 is depicted as bearing one or more treating reactive instructions i1239 that when executed will direct performance of the operation o1239. In an implementation, the one or more treating reactive instructions i1239 when executed direct electronically directing the at least one second automated treatment occurrence of the at least one automated device to treat at least a portion of the automated ingestible product dispensing equipment prior to the at least one second operation occurrence involving the at least one second ingestible product as being chemically reactive with the at least one first substance of the at least one first ingestible product (e.g. one or more instances of the optical processing component s114 of the control and information processing subsystem s100 can direct one or more instances of the compressed air fluid component s828 to treat at least a portion of the automated ingestible product dispensing equipment prior to the second operation occurrence involving the second ingestible product as the drug cocktail chemically containing the pharmaceuticals that are chemically reactive to the amino acids in the energy drink, etc.). Furthermore, the treating reactive electrical circuitry arrangement e1239 when activated will perform the operation o1239. In an implementation, the treating reactive electrical circuitry arrangement e1239, when activated performs electronically directing the at least one second automated treatment occurrence of the at least one automated device to treat at least a portion of the automated ingestible product dispensing equipment prior to the at least one second operation occurrence involving the at least one second ingestible product as being chemically reactive with the at least one first substance of the at least one first ingestible product (e.g. one or more instances of the optical processing component s114 of the control and information processing subsystem s100 can direct one or more instances of the compressed air fluid component s828 to treat at least a portion of the automated ingestible product dispensing equipment prior to the second operation occurrence involving the second ingestible product as the drug cocktail chemically containing the pharmaceuticals that are chemically reactive to the amino acids in the energy drink, etc.). In an implementation, the electronically directing the at least one second automated treatment occurrence of the at least one automated device to treat at least a portion of the automated ingestible product dispensing equipment prior to the at least one second operation occurrence involving at least one second ingestible product as being chemically reactive with the at least one first substance of the at least one first ingestible product is carried out by electronically directing the at least one second automated treatment occurrence of the at least one automated device to treat at least a portion of the automated ingestible product dispensing equipment prior to the at least one second operation occurrence involving the at least one second ingestible product as being chemically reactive with the at least one first substance of the at least one first ingestible product (e.g. one or more instances of the optical processing component s114 of the control and information processing subsystem s100 can direct one or more instances of the compressed air fluid component s828 to treat at least a portion of the automated ingestible product dispensing equipment prior to the second operation occurrence involving the second ingestible product as the drug cocktail chemically containing the pharmaceuticals that are chemically reactive to the amino acids in the energy drink, etc.).

Figure 67:
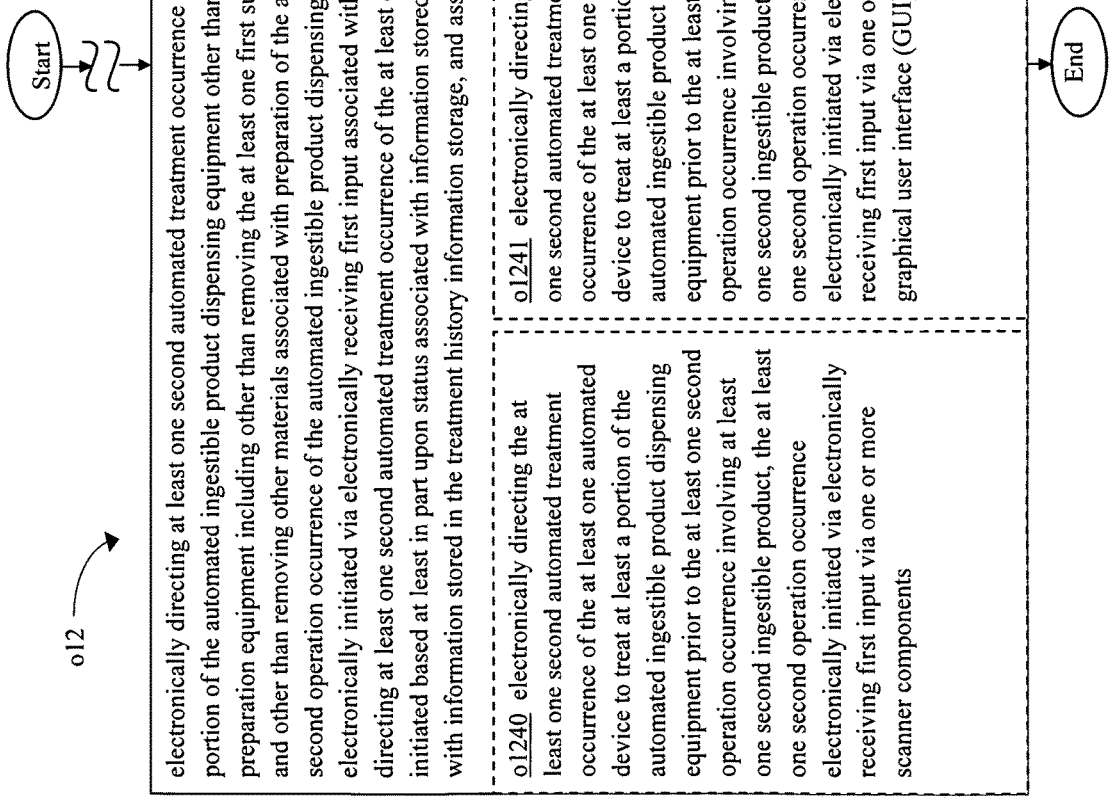
FIG. 67 is a high-level flowchart including exemplary implementations of operation O12 of FIG. 31.

In one or more implementations, as shown in FIG. 67, operation o12 includes an operation o1240 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more scanner components. An exemplary version of a non-transitory signal bearing medium of information storage subsystem s200 is depicted as bearing one or more treating scanner instructions i1240 that when executed will direct performance of the operation o1240. In an implementation, the one or more treating scanner instructions i1240 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more scanner components (e.g. one or more instances of the logic component s116 of the control and information processing subsystem s100 can direct one or more instances of the compressed water fluid component s830 to treat at least a portion of the automated ingestible product dispensing equipment prior to the second operation occurrence involving the second ingestible product as a hamburger initiated by scanning of a user's face by one or more instances of the scanner component s338, etc.). Furthermore, the treating scanner electrical circuitry arrangement e1240 when activated will perform the operation o1240. In an implementation, the treating scanner electrical circuitry arrangement e1240, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more scanner components (e.g. one or more instances of the logic component s116 of the control and information processing subsystem s100 can direct one or more instances of the compressed water fluid component s830 to treat at least a portion of the automated ingestible product dispensing equipment prior to the second operation occurrence involving the second ingestible product as a hamburger initiated by scanning of a user's face by one or more instances of the scanner component s338, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more scanner components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more scanner components (e.g. one or more instances of the logic component s116 of the control and information processing subsystem s100 can direct one or more instances of the compressed water fluid component s830 to treat at least a portion of the automated ingestible product dispensing equipment prior to the second operation occurrence involving the second ingestible product as a hamburger initiated by scanning of a user's face by one or more instances of the scanner component s338, etc.).

In one or more implementations, operation o12 includes an operation o1241 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more graphical user interface (GUI) components. An exemplary version of a non-transitory signal bearing medium of information storage subsystem s200 is depicted as bearing one or more treating GUI instructions i1241 that when executed will direct performance of the operation o1241. In an implementation, the one or more treating GUI instructions i1241 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more graphical user interface (GUI) components (e.g. one or more instances of the microprocessor component s102 of the control and information processing subsystem s100 can direct one or more instances of the chemical component s832 to treat at least a portion of the automated ingestible product dispensing equipment prior to the second operation occurrence involving the second ingestible product as a hotdog sandwich initiated by user input through one or more instances of the graphical user interface (GUI) component s302, etc.). Furthermore, the treating GUI electrical circuitry arrangement e1241 when activated will perform the operation o1241. In an implementation, the treating GUI electrical circuitry arrangement e1241, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more graphical user interface (GUI) components (e.g. one or more instances of the microprocessor component s102 of the control and information processing subsystem s100 can direct one or more instances of the chemical component s832 to treat at least a portion of the automated ingestible product dispensing equipment prior to the second operation occurrence involving the second ingestible product as a hotdog sandwich initiated by user input through one or more instances of the graphical user interface (GUI) component s302, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more graphical user interface (GUI) components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more graphical user interface (GUI) components (e.g. one or more instances of the microprocessor component s102 of the control and information processing subsystem s100 can direct one or more instances of the chemical component s832 to treat at least a portion of the automated ingestible product dispensing equipment prior to the second operation occurrence involving the second ingestible product as a hotdog sandwich initiated by user input through one or more instances of the graphical user interface (GUI) component s302, etc.).

In one or more implementations, operation o12 includes an operation o1242 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more visual display components. An exemplary version of a non-transitory signal bearing medium of information storage subsystem s200 is depicted as bearing one or more treating display instructions i1242 that when executed will direct performance of the operation o1242. In an implementation, the one or more treating display instructions i1242 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more visual display components (e.g. one or more instances of the central processing unit (CPU) component s104 of the control and information processing subsystem s100 can direct one or more instances of the air blower component s802 to treat at least a portion of the automated ingestible product dispensing equipment prior to the second operation occurrence involving the second ingestible product as a sirloin steak initiated by user input through one or more instances of the visual display component s304, etc.). Furthermore, the treating display electrical circuitry arrangement e1242 when activated will perform the operation o1242. In an implementation, the treating display electrical circuitry arrangement e1242, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more visual display components (e.g. one or more instances of the central processing unit (CPU) component s104 of the control and information processing subsystem s100 can direct one or more instances of the air blower component s802 to treat at least a portion of the automated ingestible product dispensing equipment prior to the second operation occurrence involving the second ingestible product as a sirloin steak initiated by user input through one or more instances of the visual display component s304, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more visual display components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more visual display components (e.g. one or more instances of the central processing unit (CPU) component s104 of the control and information processing subsystem s100 can direct one or more instances of the air blower component s802 to treat at least a portion of the automated ingestible product dispensing equipment prior to the second operation occurrence involving the second ingestible product as a sirloin steak initiated by user input through one or more instances of the visual display component s304, etc.).

Figure 68:
FIG. 68 is a high-level flowchart including exemplary implementations of operation O12 of FIG. 31.

In one or more implementations, as shown in FIG. 68, operation o12 includes an operation o1243 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more keyboard components. An exemplary version of a non-transitory signal bearing medium of information storage subsystem s200 is depicted as bearing one or more treating keyboard instructions i1243 that when executed will direct performance of the operation o1243. In an implementation, the one or more treating keyboard instructions i1243 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more keyboard components (e.g. one or more instances of the digital signal processor (DSP) component s106 of the control and information processing subsystem s100 can direct one or more instances of the compressed fluid component s804 to treat at least a portion of the automated ingestible product dispensing equipment prior to the second operation occurrence involving the second ingestible product as a chicken teriyaki initiated by user input through one or more instances of the keyboard component s306, etc.). Furthermore, the treating keyboard electrical circuitry arrangement e1243 when activated will perform the operation o1243. In an implementation, the treating keyboard electrical circuitry arrangement e1243, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more keyboard components (e.g. one or more instances of the digital signal processor (DSP) component s106 of the control and information processing subsystem s100 can direct one or more instances of the compressed fluid component s804 to treat at least a portion of the automated ingestible product dispensing equipment prior to the second operation occurrence involving the second ingestible product as a chicken teriyaki initiated by user input through one or more instances of the keyboard component s306, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more keyboard components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more keyboard components (e.g. one or more instances of the digital signal processor (DSP) component s106 of the control and information processing subsystem s100 can direct one or more instances of the compressed fluid component s804 to treat at least a portion of the automated ingestible product dispensing equipment prior to the second operation occurrence involving the second ingestible product as a chicken teriyaki initiated by user input through one or more instances of the keyboard component s306, etc.).

In one or more implementations, operation o12 includes an operation o1244 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more touch screen components. An exemplary version of a non-transitory signal bearing medium of information storage subsystem s200 is depicted as bearing one or more treating screen instructions i1244 that when executed will direct performance of the operation o1244. In an implementation, the one or more treating screen instructions i1244 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more touch screen components (e.g. one or more instances of the application specific integrated circuit (ASIC) component s108 of the control and information processing subsystem s100 can direct one or more instances of the vacuum component s806 to treat at least a portion of the automated ingestible product dispensing equipment prior to the second operation occurrence involving the second ingestible product as a ravioli initiated by user input through one or more instances of the touch screen component s314, etc.). Furthermore, the treating screen electrical circuitry arrangement e1244 when activated will perform the operation o1244. In an implementation, the treating screen electrical circuitry arrangement e1244, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more touch screen components (e.g. one or more instances of the application specific integrated circuit (ASIC) component s108 of the control and information processing subsystem s100 can direct one or more instances of the vacuum component s806 to treat at least a portion of the automated ingestible product dispensing equipment prior to the second operation occurrence involving the second ingestible product as a ravioli initiated by user input through one or more instances of the touch screen component s314, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more touch screen components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more touch screen components (e.g. one or more instances of the application specific integrated circuit (ASIC) component s108 of the control and information processing subsystem s100 can direct one or more instances of the vacuum component s806 to treat at least a portion of the automated ingestible product dispensing equipment prior to the second operation occurrence involving the second ingestible product as a ravioli initiated by user input through one or more instances of the touch screen component s314, etc.).

In one or more implementations, operation o12 includes an operation o1245 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more camera components. An exemplary version of a non-transitory signal bearing medium of information storage subsystem s200 is depicted as bearing one or more treating camera instructions i1245 that when executed will direct performance of the operation o1245. In an implementation, the one or more treating camera instructions i1245 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more camera components (e.g. one or more instances of the field programmable gate array (FPGA) component s110 of the control and information processing subsystem s100 can direct one or more instances of the ultrasonic component s808 to treat at least a portion of the automated ingestible product dispensing equipment prior to the second operation occurrence involving the second ingestible product as a salmon steak initiated by user input through one or more instances of the camera component s336, etc.). Furthermore, the treating camera electrical circuitry arrangement e1245 when activated will perform the operation o1245. In an implementation, the treating camera electrical circuitry arrangement e1245, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more camera components (e.g. one or more instances of the field programmable gate array (FPGA) component s110 of the control and information processing subsystem s100 can direct one or more instances of the ultrasonic component s808 to treat at least a portion of the automated ingestible product dispensing equipment prior to the second operation occurrence involving the second ingestible product as a salmon steak initiated by user input through one or more instances of the camera component s336, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more camera components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more camera components (e.g. one or more instances of the field programmable gate array (FPGA) component s110 of the control and information processing subsystem s100 can direct one or more instances of the ultrasonic component s808 to treat at least a portion of the automated ingestible product dispensing equipment prior to the second operation occurrence involving the second ingestible product as a salmon steak initiated by user input through one or more instances of the camera component s336, etc.).

In one or more implementations, as shown in FIG. 69, operation o12 includes an operation o1246 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more sound sensing components. An exemplary version of a non-transitory signal bearing medium of information storage subsystem s200 is depicted as bearing one or more treating sound instructions i1246 that when executed will direct performance of the operation o1246. In an implementation, the one or more treating sound instructions i1246 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more sound sensing components (e.g. one or more instances of the multiprocessor component s112 of the control and information processing subsystem s100 can direct one or more instances of the radiant energy component s810 to treat at least a portion of the automated ingestible product dispensing equipment prior to the second operation occurrence involving the second ingestible product as a vegetable juice drink initiated by user input through one or more instances of the sound sensing component s420, etc.). Furthermore, the treating sound electrical circuitry arrangement e1246 when activated will perform the operation o1246. In an implementation, the treating sound electrical circuitry arrangement e1246, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more sound sensing components (e.g. one or more instances of the multiprocessor component s112 of the control and information processing subsystem s100 can direct one or more instances of the radiant energy component s810 to treat at least a portion of the automated ingestible product dispensing equipment prior to the second operation occurrence involving the second ingestible product as a vegetable juice drink initiated by user input through one or more instances of the sound sensing component s420, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more sound sensing components is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more sound sensing components (e.g. one or more instances of the multiprocessor component s112 of the control and information processing subsystem s100 can direct one or more instances of the radiant energy component s810 to treat at least a portion of the automated ingestible product dispensing equipment prior to the second operation occurrence involving the second ingestible product as a vegetable juice drink initiated by user input through one or more instances of the sound sensing component s420, etc.).

In one or more implementations, operation o12 includes an operation o1247 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more computer networks. An exemplary version of a non-transitory signal bearing medium of information storage subsystem s200 is depicted as bearing one or more treating network instructions i1247 that when executed will direct performance of the operation o1247. In an implementation, the one or more treating network instructions i1247 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more computer networks (e.g. one or more instances of the optical processing component s114 of the control and information processing subsystem s100 can direct one or more instances of the abrasive component s812 to treat at least a portion of the automated ingestible product dispensing equipment prior to the second operation occurrence involving the second ingestible product as a fresh made potato chips initiated by user input through one or more instances of the wide area network component s516, etc.). Furthermore, the treating network electrical circuitry arrangement e1247 when activated will perform the operation o1247. In an implementation, the treating network electrical circuitry arrangement e1247, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more computer networks (e.g. one or more instances of the optical processing component s114 of the control and information processing subsystem s100 can direct one or more instances of the abrasive component s812 to treat at least a portion of the automated ingestible product dispensing equipment prior to the second operation occurrence involving the second ingestible product as a fresh made potato chips initiated by user input through one or more instances of the wide area network component s516, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more computer networks is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more computer networks (e.g. one or more instances of the optical processing component s114 of the control and information processing subsystem s100 can direct one or more instances of the abrasive component s812 to treat at least a portion of the automated ingestible product dispensing equipment prior to the second operation occurrence involving the second ingestible product as a fresh made potato chips initiated by user input through one or more instances of the wide area network component s516, etc.).

In one or more implementations, operation o12 includes an operation o1248 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more cellular networks. An exemplary version of a non-transitory signal bearing medium of information storage subsystem s200 is depicted as bearing one or more treating cellular instructions i1248 that when executed will direct performance of the operation o1248. In an implementation, the one or more treating cellular instructions i1248 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more cellular network (e.g. one or more instances of the logic component s116 of the control and information processing subsystem s100 can direct one or more instances of the brush component s814 to treat at least a portion of the automated ingestible product dispensing equipment prior to the second operation occurrence involving the second ingestible product as a sirloin steak initiated by user input through one or more instances of the cellular network component s514, etc.). Furthermore, the treating cellular electrical circuitry arrangement e1248 when activated will perform the operation o1248. In an implementation, the treating cellular electrical circuitry arrangement e1248, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more cellular network (e.g. one or more instances of the logic component s116 of the control and information processing subsystem s100 can direct one or more instances of the brush component s814 to treat at least a portion of the automated ingestible product dispensing equipment prior to the second operation occurrence involving the second ingestible product as a sirloin steak initiated by user input through one or more instances of the cellular network component s514, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more cellular networks is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input via one or more cellular network (e.g. one or more instances of the logic component s116 of the control and information processing subsystem s100 can direct one or more instances of the brush component s814 to treat at least a portion of the automated ingestible product dispensing equipment prior to the second operation occurrence involving the second ingestible product as a sirloin steak initiated by user input through one or more instances of the cellular network component s514, etc.).

Figure 70:
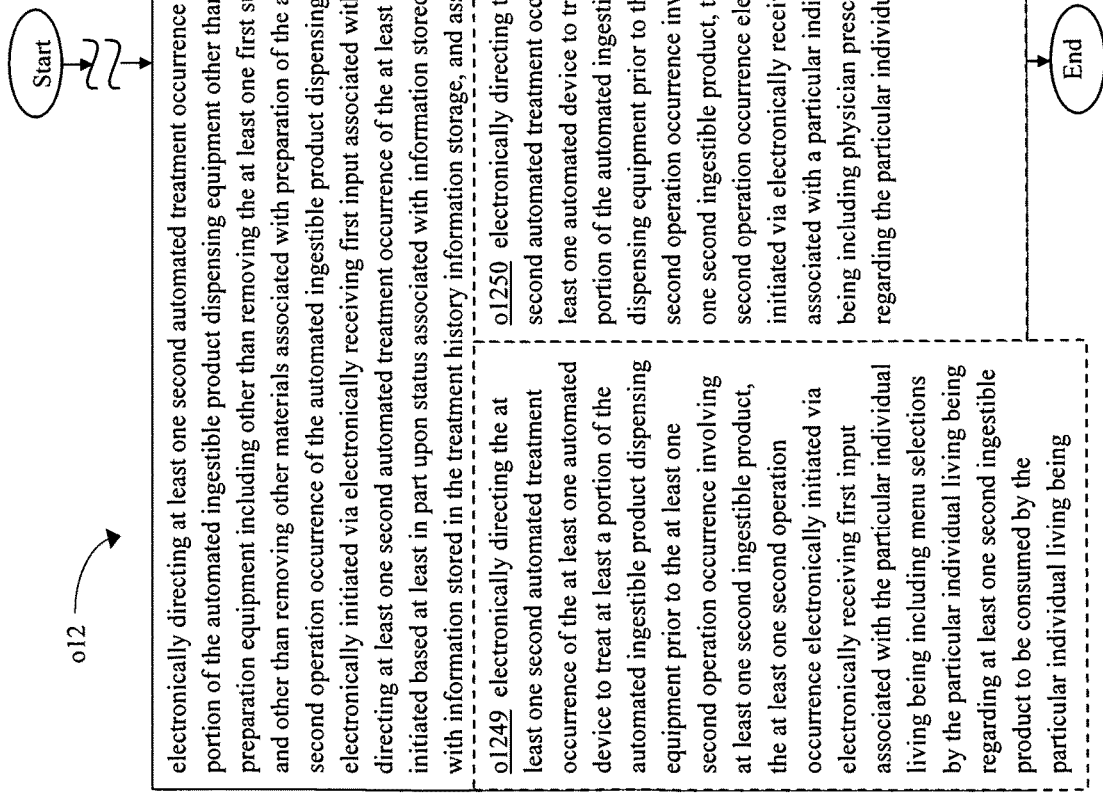
FIG. 70 is a high-level flowchart including exemplary implementations of operation O12 of FIG. 31.

In one or more implementations, as shown in FIG. 70, operation o12 includes an operation o1249 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with the particular individual living being including menu selections by the particular individual living being regarding at least one second ingestible product to be consumed by the particular individual living being. An exemplary version of a non-transitory signal bearing medium of information storage subsystem s200 is depicted as bearing one or more treating menu instructions i1249 that when executed will direct performance of the operation o1249. In an implementation, the one or more treating menu instructions i1249 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including menu selections by the particular individual living being regarding the at least one second ingestible product to be consumed by the particular individual living being (e.g. one or more instances of the microprocessor component s102 of the control and information processing subsystem s100 can direct one or more instances of the squeegee brush component s816 to treat at least a portion of the automated ingestible product dispensing equipment prior to the second operation occurrence involving the second ingestible product as a blue berry pie initiated by user menu selections one or more instances of the graphical user interface (GUI) component s302, etc.). Furthermore, the treating menu electrical circuitry arrangement e1249 when activated will perform the operation o1249. In an implementation, the treating menu electrical circuitry arrangement e1249, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including menu selections by the particular individual living being regarding the at least one second ingestible product to be consumed by the particular individual living being (e.g. one or more instances of the microprocessor component s102 of the control and information processing subsystem s100 can direct one or more instances of the squeegee brush component s816 to treat at least a portion of the automated ingestible product dispensing equipment prior to the second operation occurrence involving the second ingestible product as a blue berry pie initiated by user menu selections one or more instances of the graphical user interface (GUI) component s302, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with the particular individual living being including menu selections by the particular individual living being regarding at least one second ingestible product to be consumed by the particular individual living being is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including menu selections by the particular individual living being regarding the at least one second ingestible product to be consumed by the particular individual living being (e.g. one or more instances of the microprocessor component s102 of the control and information processing subsystem s100 can direct one or more instances of the squeegee brush component s816 to treat at least a portion of the automated ingestible product dispensing equipment prior to the second operation occurrence involving the second ingestible product as a blue berry pie initiated by user menu selections one or more instances of the graphical user interface (GUI) component s302, etc.).

In one or more implementations, operation o12 includes an operation o1250 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including physician prescription directions regarding the particular individual living being. An exemplary version of a non-transitory signal bearing medium of information storage subsystem s200 is depicted as bearing one or more treating prescription instructions i1250 that when executed will direct performance of the operation o1250. In an implementation, the one or more treating prescription instructions i1250 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including physician prescription directions regarding the particular individual living being (e.g. one or more instances of the central processing unit (CPU) component s104 of the control and information processing subsystem s100 can direct one or more instances of the pipe cleaner brush component s818 to treat at least a portion of the automated ingestible product dispensing equipment prior to the second operation occurrence involving the second ingestible product as a fruit punch initiated by user input including pharmaceutical prescription information associated with the user through one or more instances of the scanner component s338, etc.). Furthermore, the treating prescription electrical circuitry arrangement e1250 when activated will perform the operation o1250. In an implementation, the treating prescription electrical circuitry arrangement e1250, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including physician prescription directions regarding the particular individual living being (e.g. one or more instances of the central processing unit (CPU) component s104 of the control and information processing subsystem s100 can direct one or more instances of the pipe cleaner brush component s818 to treat at least a portion of the automated ingestible product dispensing equipment prior to the second operation occurrence involving the second ingestible product as a fruit punch initiated by user input including pharmaceutical prescription information associated with the user through one or more instances of the scanner component s338, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including physician prescription directions regarding the particular individual living being is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including physician prescription directions regarding the particular individual living being (e.g. one or more instances of the central processing unit (CPU) component s104 of the control and information processing subsystem s100 can direct one or more instances of the pipe cleaner brush component s818 to treat at least a portion of the automated ingestible product dispensing equipment prior to the second operation occurrence involving the second ingestible product as a fruit punch initiated by user input including pharmaceutical prescription information associated with the user through one or more instances of the scanner component s338, etc.).

In one or more implementations, operation o12 includes an operation o1251 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including allergy information regarding the particular individual living being. An exemplary version of a non-transitory signal bearing medium of information storage subsystem s200 is depicted as bearing one or more treating allergy instructions i1251 that when executed will direct performance of the operation o1251. In an implementation, the one or more treating allergy instructions i1251 when executed direct electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including allergy information regarding the particular individual living being (e.g. one or more instances of the digital signal processor (DSP) component s106 of the control and information processing subsystem s100 can direct one or more instances of the material flush abrasive component s820 to treat at least a portion of the automated ingestible product dispensing equipment prior to the second operation occurrence involving the second ingestible product as green beans initiated by user input including allergy information associated with the user through one or more instances of the joystick component s312, etc.). Furthermore, the treating allergy electrical circuitry arrangement e1251 when activated will perform the operation o1251. In an implementation, the treating allergy electrical circuitry arrangement e1251, when activated performs electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including allergy information regarding the particular individual living being (e.g. one or more instances of the digital signal processor (DSP) component s106 of the control and information processing subsystem s100 can direct one or more instances of the material flush abrasive component s820 to treat at least a portion of the automated ingestible product dispensing equipment prior to the second operation occurrence involving the second ingestible product as green beans initiated by user input including allergy information associated with the user through one or more instances of the joystick component s312, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including allergy information regarding the particular individual living being is carried out by electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including allergy information regarding the particular individual living being (e.g. one or more instances of the digital signal processor (DSP) component s106 of the control and information processing subsystem s100 can direct one or more instances of the material flush abrasive component s820 to treat at least a portion of the automated ingestible product dispensing equipment prior to the second operation occurrence involving the second ingestible product as green beans initiated by user input including allergy information associated with the user through one or more instances of the joystick component s312, etc.).

In one or more implementations, as shown in FIG. 71, operation o12 includes an operation o1252 for electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including treatment preferences of the particular individual living being. An exemplary version of a non-transitory signal bearing medium of information storage subsystem s200 is depicted as bearing one or more treating preferences instructions i1252 that when executed will direct performance of the operation o1252. In an implementation, the one or more treating preferences instructions i1252 when executed direct electronically directing the at least one second automated treatment occurrence of the at least one automated device to treat at least a portion of the automated ingestible product dispensing equipment prior to the at least one second operation occurrence involving the at least one second ingestible product, the at least one second operation occurrence electronically initiated via electronically receiving first input associated with a particular individual living being including treatment preferences of the particular individual living being (e.g. one or more instances of the application specific integrated circuit (ASIC) component s108 of the control and information processing subsystem s100 can direct one or more instances of the fish tape system brush component s822 to treat at least a portion of the automated ingestible product dispensing equipment prior to the second operation occurrence involving the second ingestible product as chicken soup initiated by user input including user input regarding certain conditions in which the user prefers to have treatment occur through one or more instances of the touch screen component s314, etc.). Furthermore, the treating preferences electrical circuitry arrangement e1252 when activated will perform the operation o1252. In an implementation, the treating preferences electrical circuitry arrangement e1252, when activated performs electronically directing the at least one second automated treatment occurrence of the at least one automated device to treat at least a portion of the automated ingestible product dispensing equipment prior to the at least one second operation occurrence involving the at least one second ingestible product, the at least one second operation occurrence electronically initiated via electronically receiving first input associated with a particular individual living being including treatment preferences of the particular individual living being (e.g. one or more instances of the application specific integrated circuit (ASIC) component s108 of the control and information processing subsystem s100 can direct one or more instances of the fish tape system brush component s822 to treat at least a portion of the automated ingestible product dispensing equipment prior to the second operation occurrence involving the second ingestible product as chicken soup initiated by user input including user input regarding certain conditions in which the user prefers to have treatment occur through one or more instances of the touch screen component s314, etc.). In an implementation, the electronically directing the at least one second automated treatment occurrence of the at least one automated device to treat at least a portion of the automated ingestible product dispensing equipment prior to the at least one second operation occurrence involving at least one second ingestible product, the at least one second operation occurrence electronically initiated via electronically receiving first input associated with a particular individual living being including treatment preferences of the particular individual living being is carried out by electronically directing the at least one second automated treatment occurrence of the at least one automated device to treat at least a portion of the automated ingestible product dispensing equipment prior to the at least one second operation occurrence involving the at least one second ingestible product, the at least one second operation occurrence electronically initiated via electronically receiving first input associated with a particular individual living being including treatment preferences of the particular individual living being (e.g. one or more instances of the application specific integrated circuit (ASIC) component s108 of the control and information processing subsystem s100 can direct one or more instances of the fish tape system brush component s822 to treat at least a portion of the automated ingestible product dispensing equipment prior to the second operation occurrence involving the second ingestible product as chicken soup initiated by user input including user input regarding certain conditions in which the user prefers to have treatment occur through one or more instances of the touch screen component s314, etc.).

In one or more implementations, operation o12 includes an operation o1253 for electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment occurrence did not occur, and the particular individual living being has one or more allergies related to the at least one first substance. An exemplary version of a non-transitory signal bearing medium of information storage subsystem s200 is depicted as bearing one or more treating allergies instructions i1253 that when executed will direct performance of the operation o1253. In an implementation, the one or more treating allergies instructions i1253 when executed direct electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment operation occurrence did not occur, and the particular individual living being has one or more allergies related to the at least one first substance (e.g. one or more instances of the field programmable gate array (FPGA) component s110 of the control and information processing subsystem s100 can direct one or more instances of the parts exchange component s824 to treat at least a portion of the automated ingestible product dispensing equipment prior to the second operation occurrence of the second ingestible product as a hamburger based upon status determined to be that the ingestible product treatment system 10 had not treated one or more portions of the ingestible product dispensing system after a latte was prepared, which the user initiating dispensing of a hamburger was allergic to, etc.). Furthermore, the treating allergies electrical circuitry arrangement e1253 when activated will perform the operation o1253. In an implementation, the treating allergies electrical circuitry arrangement e1253, when activated performs electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment operation occurrence did not occur, and the particular individual living being has one or more allergies related to the at least one first substance (e.g. one or more instances of the field programmable gate array (FPGA) component s110 of the control and information processing subsystem s100 can direct one or more instances of the parts exchange component s824 to treat at least a portion of the automated ingestible product dispensing equipment prior to the second operation occurrence of the second ingestible product as a hamburger based upon status determined to be that the ingestible product treatment system 10 had not treated one or more portions of the ingestible product dispensing system after a latte was prepared, which the user initiating dispensing of a hamburger was allergic to, etc.). In an implementation, the electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment occurrence did not occur, and the particular individual living being has one or more allergies related to the at least one first substance is carried out by electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment operation occurrence did not occur, and the particular individual living being has one or more allergies related to the at least one first substance (e.g. one or more instances of the field programmable gate array (FPGA) component s110 of the control and information processing subsystem s100 can direct one or more instances of the parts exchange component s824 to treat at least a portion of the automated ingestible product dispensing equipment prior to the second operation occurrence of the second ingestible product as a hamburger based upon status determined to be that the ingestible product treatment system 10 had not treated one or more portions of the ingestible product dispensing system after a latte was prepared, which the user initiating dispensing of a hamburger was allergic to, etc.).

In one or more implementations, operation o12 includes an operation o1254 for electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment occurrence did not occur, and the particular individual living being has one or more treatment preferences favoring treating of the at least one automated device each time after an ingestible product is prepared. An exemplary version of a non-transitory signal bearing medium of information storage subsystem s200 is depicted as bearing one or more treating each instructions i1254 that when executed will direct performance of the operation o1254. In an implementation, the one or more treating each instructions i1254 when executed direct electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment operation occurrence did not occur, and the particular individual living being has one or more treatment preferences favoring treating of the at least one automated device each time after an ingestible product is prepared (e.g. one or more instances of the multiprocessor component s112 of the control and information processing subsystem s100 can direct one or more instances of the parts replacement component s826 to treat at least a portion of the automated ingestible product dispensing equipment prior to the second operation occurrence of the second ingestible product as a chicken dinner based upon status determined to be that the ingestible product treatment system 10 had not been treated after an energy drink was prepared and the user preferred to have treatment occur after any drink was prepared, etc.). Furthermore, the treating each electrical circuitry arrangement e1254 when activated will perform the operation o1254. In an implementation, the treating each electrical circuitry arrangement e1254, when activated performs electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment operation occurrence did not occur, and the particular individual living being has one or more treatment preferences favoring treating of the at least one automated device each time after an ingestible product is prepared (e.g. one or more instances of the multiprocessor component s112 of the control and information processing subsystem s100 can direct one or more instances of the parts replacement component s826 to treat at least a portion of the automated ingestible product dispensing equipment prior to the second operation occurrence of the second ingestible product as a chicken dinner based upon status determined to be that the ingestible product treatment system 10 had not been treated after an energy drink was prepared and the user preferred to have treatment occur after any drink was prepared, etc.). In an implementation, the electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment occurrence did not occur, and the particular individual living being has one or more treatment preferences favoring treating of the at least one automated device each time after an ingestible product is prepared is carried out by electronically directing the at least one second automated treatment occurrence of the at least one automated device automated to be electronically initiated based at least in part upon status associated with information stored in the operation history information storage, associated with information stored in the treatment history information storage, and associated with the electronically received first input including status that the at least one first operation occurrence occurred, the at least one first automated treatment operation occurrence did not occur, and the particular individual living being has one or more treatment preferences favoring treating of the at least one automated device each time after an ingestible product is prepared (e.g. one or more instances of the multiprocessor component s112 of the control and information processing subsystem s100 can direct one or more instances of the parts replacement component s826 to treat at least a portion of the automated ingestible product dispensing equipment prior to the second operation occurrence of the second ingestible product as a chicken dinner based upon status determined to be that the ingestible product treatment system 10 had not been treated after an energy drink was prepared and the user preferred to have treatment occur after any drink was prepared, etc.).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware in one or more machines or articles of manufacture), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation that is implemented in one or more machines or articles of manufacture; or, yet again alternatively, the implementer may opt for some combination of hardware, software, and/or firmware in one or more machines or articles of manufacture (limited to patentable subject matter under 35 USC 101). Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware in one or more machines or articles of manufacture.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof (limited to patentable subject matter under 35 U.S.C. 101). In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure (limited to patentable subject matter under 35 USC 101). In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof (limited to patentable subject matter under 35 U.S.C. 101) can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A system, comprising
   a vending machine, including at least:
      an automated dispensing component;
      circuitry configured for controlling preparation of a first ingestible product at least partially via the automated dispensing component;
      circuitry configured for storing information associated with the preparation of the first ingestible product, the information including at least one indication of at least one substance used during the preparation of the first ingestible product;
      circuitry configured for receiving an indication of a directive including at least one request for preparation of a second ingestible product that includes at least one controlled substance and is intended for a particular individual living being;
      circuitry configured for obtaining, from one or more of the directive or at least one user selectable option, at least some allergy information regarding the particular individual living being;
      circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being; and circuitry configured for controlling preparation of the second ingestible product at least partially via the automated dispensing component, including at least treating the at least a portion of the automated dispensing component previous to preparation of the second ingestible product in accordance with the one or more treatment directives.

2. The system of claim 1, wherein circuitry configured for storing information associated with the preparation of the first ingestible product, the information including at least one indication of at least one substance used during the preparation of the first ingestible product comprises:
circuitry configured for storing the information associated with the preparation of the first ingestible product into one or more electronic memory cards.

3. The system of claim 1, wherein circuitry configured for storing information associated with the preparation of the first ingestible product, the information including at least one indication of at least one substance used during the preparation of the first ingestible product comprises:
circuitry configured for storing the information associated with the preparation of the first ingestible product previous to the preparation of the first ingestible product.

4. The system of claim 1, wherein circuitry configured for controlling preparation of a first ingestible product at least partially via the automated dispensing component comprises:
circuitry configured for controlling the preparation of the first ingestible product at least partially via one or more cooling components.

5. The system of claim 1, wherein circuitry configured for controlling preparation of a first ingestible product at least partially via the automated dispensing component comprises:
circuitry configured for controlling the preparation of the first ingestible product at least partially via one or more microwave components.

6. The system of claim 1, wherein circuitry configured for controlling preparation of a first ingestible product at least partially via the automated dispensing component comprises:
circuitry configured for controlling the preparation of the first ingestible product at least partially via one or more light emitting diode (LED) components.

7. The system of claim 1, wherein circuitry configured for controlling preparation of a first ingestible product at least partially via the automated dispensing component comprises:
circuitry configured for controlling the preparation of the first ingestible product at least partially via one or more blending components.

8. The system of claim 1, wherein circuitry configured for controlling preparation of a first ingestible product at least partially via the automated dispensing component comprises:
circuitry configured for controlling the preparation of the first ingestible product at least partially using one or more acoustic energy components.

9. The system of claim 1, wherein circuitry configured for controlling preparation of a first ingestible product at least partially via the automated dispensing component comprises:
circuitry configured for controlling the preparation of the first ingestible product at least partially using one or more stirring components.

10. The system of claim 1, wherein circuitry configured for controlling preparation of a first ingestible product at least partially via the automated dispensing component comprises:
circuitry configured for controlling the preparation of the first ingestible product at least partially using one or more shaker components.

11. The system of claim 1, wherein circuitry configured for controlling preparation of a first ingestible product at least partially via the automated dispensing component comprises:
circuitry configured for controlling the preparation of the first ingestible product at least partially using one or more energy emitting components.

12. The system of claim 1, wherein circuitry configured for controlling preparation of a first ingestible product at least partially via the automated dispensing component comprises:
circuitry configured for controlling the preparation of the first ingestible product at least partially using one or more sorting components.

13. The system of claim 1, wherein circuitry configured for controlling preparation of a first ingestible product at least partially via the automated dispensing component comprises:
circuitry configured for controlling the preparation of the first ingestible product at least partially using one or more cutting components.

14. The system of claim 1, wherein circuitry configured for controlling preparation of a first ingestible product at least partially via the automated dispensing component comprises:
circuitry configured for controlling the preparation of the first ingestible product at least partially using one or more controlled substance receiving components.

15. The system of claim 1, wherein circuitry configured for controlling preparation of a first ingestible product at least partially via the automated dispensing component comprises:
circuitry configured for controlling the preparation of the first ingestible product at least partially using one or more controlled substance containing components.

16. The system of claim 1, wherein circuitry configured for storing information associated with the preparation of the first ingestible product, the information including at least one indication of at least one substance used during the preparation of the first ingestible product comprises:
circuitry configured for storing at least one indication of one or more fluids as the at least one substance used during the preparation of the first ingestible product.

17. The system of claim 1, wherein circuitry configured for storing information associated with the preparation of the first ingestible product, the information including at least one indication of at least one substance used during the preparation of the first ingestible product comprises:
circuitry configured for storing at least one indication of at least one combination of one or more powders as the at least one substance used during the preparation of the first ingestible product.

18. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being comprises:
  circuitry configured for obtaining one or more treatment directives including at one directive associated with excluding one or more allergens from preparation of the second ingestible product, the at least one directive at least partially based on stored information associated with the preparation of the first ingestible product and at least partially based on the at least some allergy information regarding the particular individual living being.

19. The system of claim 1, wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
  circuitry configured for selecting at least one ingredient originating from one or more land-based geographic regions for preparation of the second ingestible product, the selecting at least partially based on the at least some allergy information regarding the particular individual living being.

20. The system of claim 1, wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
  circuitry configured for selecting at least one ingredient endorsed by one or more designated users associated with celebrity and associated with at least one medical condition common to at least one medical condition of the particular individual living being for preparation of the second ingestible product, the selecting at least partially based on the at least some allergy information regarding the particular individual living being.

21. The system of claim 1, wherein circuitry configured for storing information associated with the preparation of the first ingestible product, the information including at least one indication of at least one substance used during the preparation of the first ingestible product comprises:
  circuitry configured for storing at least one indication of one or more liquids used during the preparation of the first ingestible product.

22. The system of claim 1, wherein circuitry configured for storing information associated with the preparation of the first ingestible product, the information including at least one indication of at least one substance used during the preparation of the first ingestible product comprises:
  circuitry configured for storing the information associated with the preparation of the first ingestible product via one or more computer networks.

23. The system of claim 1, wherein circuitry configured for storing information associated with the preparation of the first ingestible product, the information including at least one indication of at least one substance used during the preparation of the first ingestible product comprises:
  circuitry configured for storing the information associated with the preparation of the first ingestible product in one or more networked servers.

24. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
  circuitry configured for treating the at least a portion of the automated dispensing component at least partially via blowing air previous to preparation of second ingestible product in accordance with the one or more treatment directives.

25. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
  circuitry configured for treating the at least a portion of the automated dispensing component at least partially via emitting ultrasonic waves previous to preparation of second ingestible product in accordance with the one or more treatment directives.

26. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
  circuitry configured for treating the at least a portion of the automated dispensing component at least partially via emitting electromagnetic energy previous to preparation of second ingestible product in accordance with the one or more treatment directives.

27. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
  circuitry configured for treating the at least a portion of the automated dispensing component at least partially via at least one brush contact previous to preparation of second ingestible product in accordance with the one or more treatment directives.

28. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
  circuitry configured for treating one or more manifolds of tubes of the automated dispensing component previous to preparation of second ingestible product in accordance with the one or more treatment directives.

29. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:

circuitry configured for treating one or more blender compartments of the automated dispensing component previous to preparation of second ingestible product in accordance with the one or more treatment directives.

30. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
   circuitry configured for treating one or more syringes of the automated dispensing component previous to preparation of second ingestible product in accordance with the one or more treatment directives.

31. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
   circuitry configured for replacing one or more print heads of at least one deposition component of the automated dispensing component with one or more new print heads to treat the one or more print heads of the at least one deposition component of the automated dispensing component previous to preparation of second ingestible product in accordance with the one or more treatment directives.

32. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and least one substance to be used during the preparation of the second ingestible product would be contraindicated at least partially based on the at least some allergy information regarding the particular individual living being comprises:
   circuitry configured for obtaining the one or more treatment directives via one or more computer networks.

33. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the reparation of the first ingestible product and a least one substance to be used during the preparation of the second ingestible product would be contraindicated at least partially based on the at least some allergy information regarding the particular individual living being comprises:
   circuitry configured for obtaining the one or more treatment directives via one or more cellular networks.

34. The system of claim 1, wherein circuitry configured for controlling preparation of the second ingestible product at least partially via the automated dispensing component, including at least treating the at least a portion of the automated dispensing component previous to preparation of second ingestible product in accordance with the one or more treatment directives comprises:
   circuitry configured for controlling preparation of the second ingestible product at least partially via one or more digital signal processors associated with control of temperature of at least one enclosure containing one or more ingredients for use in the preparation of the second ingestible product.

35. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being comprises:
   circuitry configured for obtaining the one or more treatment directives via one or more networked servers.

36. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated least partially based on the at least some allay information regarding the particular individual living being comprises:
   circuitry configured for obtaining one or more treatment directives relating to treatment of the at least a portion of the automated dispensing component involving injecting compressed fluid.

37. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being comprises:
   circuitry configured for obtaining one or more treatment directives relating to treatment of the at least a portion of the automated dispensing component involving applying a vacuum.

38. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being comprises:
circuitry configured for obtaining one or more treatment directives relating to treatment of the at least a portion of the automated dispensing component involving emitting ultrasonic waves.

39. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and a least one substance to be used during the preparation of the second ingestible product would be contraindicated at least partially based on the at least some allergy information regarding the particular individual living being comprises:
circuitry configured for obtaining one or more treatment directives relating to treatment of the at least a portion of the automated dispensing component involving fluid flow of one or more abrasives.

40. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being comprises:
circuitry configured for obtaining one or more treatment directives relating to treatment of one or more manifolds of tubes of the automated dispensing component.

41. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and a least one substance to be used during the preparation of the second ingestible product would be contraindicated at least partially based on the at least some allergy information regarding the particular individual living being comprises:
circuitry configured for obtaining one or more treatment directives relating to treatment of one or more blender compartments of the automated dispensing component.

42. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the reparation of the first ingestible product and a least one substance to be used during the preparation of the second ingestible product would be contraindicated at least partially based on the at least some allergy information regarding the particular individual living being comprises:
circuitry configured for obtaining one or more treatment directives relating to treatment of one or more cooling chambers of the automated dispensing component.

43. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and a least one substance to be used during the preparation of the second ingestible product would be contraindicated at least partially based on the at least some allergy information regarding the particular individual living being comprises:
circuitry configured for obtaining one or more treatment directives relating to exchange of one or more portions of the automated dispensing component with one or more other portions of the automated dispensing component.

44. The system of claim 1, wherein circuitry configured for receiving an indication of a directive including at least one request for preparation of a second ingestible product that includes at least one controlled substance and is intended for a articular individual living being comprises:
circuitry configured for receiving an indication of a directive including at least one request for preparation of a second ingestible product other than the first ingestible product.

45. The system of claim 1, wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
circuitry configured for treating the at least a portion of the automated dispensing component using at least one composition including one or more fluids.

46. The system of claim 1, wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
circuitry configured for treating the at least a portion of the automated dispensing component previous to preparation of the second ingestible product in accordance with at least one treatment directive directing the system to exclude to one or more allergens found in the first ingestible product.

47. The system of claim 1, wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
circuitry configured for treating the at least a portion of the automated dispensing component previous to preparation of the second ingestible product in accordance with at least one treatment directive indicating the at least one substance used during the preparation of the first ingestible product as originating from one or more geographic regions.

48. The system of claim 1, further including wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
circuitry configured for treating the at least a portion of the automated dispensing component previous to preparation of the second ingestible product in accordance with at least one treatment directive indicating the second ingestible product as being endorsed by one or more designated users.

49. The system of claim 1, wherein circuitry configured for controlling preparation of the second ingestible product at least partially via the automated dispensing component, including at least treating the at least a portion of the automated dispensing component previous to preparation of the second ingestible product in accordance with the one or more treatment directives comprises:
circuitry configured for treating the at least a portion of the automated dispensing component previous to preparation of the second ingestible product in accordance with at least one treatment directive indicating the second ingestible product as being chemically reactive with the at least one substance used during the preparation of the first ingestible product.

50. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and a least one substance to be used during the preparation of the second ingestible product would be contraindicated at least partially based on the at least some allergy information regarding the particular individual living being comprises:
circuitry configured for obtaining the one or more treatment directives via one or more keyboard components.

51. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and a least one substance to be used during the preparation of the second ingestible product would be contraindicated at least partially based on the at least some allergy information regarding the particular individual living being comprises:
circuitry configured for obtaining the one or more treatment directives via one or more touch screen components.

52. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being comprises:
circuitry configured for obtaining the one or more treatment directives via one or more cellular networks.

53. The system of claim 1, wherein circuitry configured for obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at last one substance to be used during the preparation of the second ingestible product would be contraindicated at least partially based on the at least some allergy information regarding the particular individual living being comprises:
circuitry configured for determining whether the particular individual living being is allergic to the at least one substance used during the preparation of the first ingestible product, and, if the particular individual living being is allergic to at least one substance used during the preparation of the first ingestible product, providing one or more treatment directives related to cleansing of the at least one substance used during the preparation of the first ingestible product to which the particular individual living being is allergic.

54. The system of claim 1, wherein circuitry configured for obtaining, from one or more of the directive or at least one user selectable option at least some allergy information regarding the particular individual living being comprises:
circuitry configured for displaying, via a user interface of the vending machine, a list of allergens;
circuitry configured for receiving, via the user interface of the vending machine, a selection of one or more allergens, the one or more allergens selected by the particular individual living being in response to a prompt for the particular individual living being to select allergens known to cause allergic reactions in the particular individual living being;
circuitry configured for obtaining a list of substance known to cross-react with the one or more allergens selected by the particular individual living being; and
circuitry configured for requiring a check of the stored information associated with the preparation of the first ingestible product for determining whether the at least one substance used during the preparation of the first ingestible product is on the list of substances known to cross-react with the one or more allergens selected by the particular individual living being.

55. The system of claim 54, wherein circuitry configured for displaying, via a user interface of the vending machine, a list of allergens comprises:
circuitry configured for displaying, in response to receiving the indication of a directive including at least one request for preparation of a second ingestible product that includes at least one controlled substance and is intended for a articular individual living being, a display screen showing content having one or more user selectable options to indicate what sorts of substances or general categories may cause allergies for the particular individual living being to assist in determining if one or more portions of the automated dispensing component should be treated.

56. A method, comprising:
providing a vending machine, the vending machine including at least:
an automated dispensing component;
controlling preparation of a first ingestible product at least partially via the automated dispensing component;
storing information associated with the preparation of the first ingestible product, the information including at least one indication of at least one substance used during the preparation of the first ingestible product;
receiving an indication of a directive including at least one request for preparation of a second ingestible product that includes at least one controlled substance and is intended for a particular individual living being;
obtaining, from one or more of the directive or at least one user selectable option, at least some allergy information regarding the particular individual living being;
obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being; and
controlling preparation of the second ingestible product at least partially via the automated dispensing component, including at least treating the at least a portion of the automated dispensing component previous to preparation of the second ingestible product in accordance with the one or more treatment directives,
wherein at least one of the controlling, storing, receiving, or obtaining is at least partially implemented using at last one processing device.

57. A system, comprising:
an automated dispensing component;
a processing device; and
one or more instructions which, when executed by the processing device, configure the processing device to perform one or more operations including at least:
controlling preparation of a first ingestible product at least partially via the automated dispensing component;
storing information associated with the preparation of the first ingestible product, the information including at least one indication of at least one substance used during the preparation of the first ingestible product;
receiving an indication of a directive including at least one request for preparation of a second ingestible product that includes at least one controlled substance and is intended for a particular individual living being;
obtaining, from one or more of the directive or at least one user selectable option, at least some allergy information regarding the particular individual living being;
obtaining one or more treatment directives, the one or more treatment directives relating to treating at least a portion of the automated dispensing component previous to preparation of the second ingestible product at least partially based on stored information associated with the preparation of the first ingestible product, including at least determining whether a combination of at least one substance used during the preparation of the first ingestible product and at least one substance to be used during the preparation of the second ingestible product would be contraindicated at least partially based on the at least some allergy information regarding the particular individual living being; and
controlling preparation of the second ingestible product at least partially via the automated dispensing component, including at least treating the at least a portion of the automated dispensing component previous to preparation of the second ingestible product in accordance with the one or more treatment directives.

* * * * *

UNITED STATES PATENT AND TRADEMARK OFFICE
CERTIFICATE OF CORRECTION

PATENT NO. : 9,947,167 B2
APPLICATION NO. : 13/200906
DATED : April 17, 2018
INVENTOR(S) : Paul Holman et al.

It is certified that error appears in the above-identified patent and that said Letters Patent is hereby corrected as shown below:

Column 136, Line 34, Claim 36:
"at least some allay information"
Should read:
—at least some allergy information—

Column 137, Line 16, Claim 39:
"and a least one"
Should read:
—and at least one—

Column 137, Line 49, Claim 41:
"and a least one"
Should read:
—and at least one—

Column 137, Line 65, Claim 42:
"the reparation of the first ingestible product and a least one"
Should read:
—the preparation of the first ingestible product and at least one—

Column 138, Line 15, Claim 43:
"and a least one one"
Should read:
—and at least one—

Column 138, Line 29, Claim 44:
"intended for a articular individual"
Should read:
—intended for a particular individual—

Signed and Sealed this
Sixth Day of November, 2018

Andrei Iancu
*Director of the United States Patent and Trademark Office*

CERTIFICATE OF CORRECTION (continued)
U.S. Pat. No. 9,947,167 B2

Column 139, Line 39, Claim 50:
"and a least one"
Should read:
—and at least one—

Column 139, Line 54, Claim 51:
"and a least one"
Should read:
—and at least one—

Column 140, Line 63, Claim 55:
"intended for a articular individual"
Should read:
—intended for a particular individual—